(12) United States Patent
Stinchcomb et al.

(10) Patent No.: US 6,194,150 B1
(45) Date of Patent: Feb. 27, 2001

(54) NUCLEIC ACID BASED INHIBITION OF CD40

(75) Inventors: Dan T. Stinchcomb; Thale Jarvis; James McSwiggen, all of Boulder, CO (US)

(73) Assignee: Ribozyme Pharmaceuticals, Inc., Boulder, CO (US)

(*) Notice: Subject to any disclaimer, the term of this patent is extended or adjusted under 35 U.S.C. 154(b) by 0 days.

(21) Appl. No.: 09/038,073

(22) Filed: Mar. 11, 1998

Related U.S. Application Data

(63) Continuation of application No. 08/585,684, filed on Jan. 12, 1996, now Pat. No. 5,877,021
(60) Provisional application No. 60/000,951, filed on Jul. 7, 1995.

(51) Int. Cl.[7] .............................. C07H 21/04; C12Q 1/68; C12N 15/63; C12N 15/85
(52) U.S. Cl. .................... 435/6; 435/320.1; 435/325; 435/375; 435/366; 536/23.1; 536/245
(58) Field of Search .......................... 435/6, 91.1, 91.31, 435/325, 366, 375, 320.1, 440; 536/23.1, 23.2, 24.5, 24.3; 514/44

(56) References Cited

U.S. PATENT DOCUMENTS

| | | | |
|---|---|---|---|
| 4,987,071 | 1/1991 | Cech et al. | 435/91 |
| 5,149,796 | 9/1992 | Rossi et al. | 536/27 |
| 5,359,051 | 10/1994 | Cook et al. | 536/26.7 |

FOREIGN PATENT DOCUMENTS

| | | |
|---|---|---|
| 0 360 257 | 9/1989 | (EP). |
| 91/03162 | 3/1991 | (WO). |
| 92/00092 | 1/1992 | (WO). |
| 92/07065 | 4/1992 | (WO). |
| 93/15187 | 8/1993 | (WO). |
| 93/23569 | 11/1993 | (WO). |
| 94/01547 | 1/1994 | (WO). |
| 94/02595 | 2/1994 | (WO). |
| 94/11011 | 5/1994 | (WO). |

OTHER PUBLICATIONS

Azuma et al., "B70 Antigen is a Second Ligand for CTLA–4 and CD28" *Nature* 366, 76–79 (1993).
Blazar et al., "In Vivo Blockade of CD28/CTLA4: B7/BB1 Interaction With CTLA4–Ig Reduces Lethal Murine Graft–Versus–Host Disease Across the Major Histocompatibility Complex Barrier in Mice" *Blood* 83(12) 3815–3825 (1994).
Boussiotis et al., "Activated Human B Lymphocytes Express Three CTLA–4 Counter receptors that Costimulate T–Cell Activation" *Proc. Natl. Acad. Sci. USA* 90, 11059–1163 (1993).
Caine, "Immunosuppression for Organ Grafting" *Trans. Proceedings* 24(4) 1260–1262 (1992).
Carlson et al., "Effects of Orally Administered Rapamycin in Animal Models of Arthritis and Other Autoimmune Diseases" *Annals NY Acad. of Sci.* 86–113.
Carter, "Adeno–Associated Virus Vectors" *Curr. Biol.* 3, 533–539 (1992).
Chen et al., "Multitarget–Ribozyme Directed to Cleave at up to Nine Highly Conserved HIV–1 Env RNA Regions Inhibits HIV–1 Replication–Potential Effectiveness Against Most Presently Sequenced HIV–1 Isolates" *Nucl. Acid Res.* 20(17) 4581–4589 (1992).
Chowrira et al., "Extensive Phosphorothioate Substitution Yields Highly Active and Nuclease–Resistant Hairpin Ribozymes" *Nucl. Acids Res.* 20(11) 2835–2840 (1992).
Chowrira et al., "In Vitro and In Vivo Comparison of Hammerhead, Hairpin and Hepatitis Delta Virus Self–Processing Ribozyme Cassettes" *J. of Biol. Chem.* 269(41) 25856–25864 (1994).
Clark et al., "How B and T Cells Talk to Each other" *Nature* 367, 425–428 (1994).
Cohen et al., "New Protein Steals the Show as 'Costimulator' T Cells" *Science* p. 262 (1993).
Collins et al., "Reaction Conditions and Kinetics of Self-–Cleavage of a Cleavage of a Ribozyme Derived for Neurospora VS RNA"*Biochem* 32, 2795–2799 (1992).
Drouplic et al., "Functional Characterization of a U5 Ribozyme: Intracellular Suppression of Human Immunodeficiency Virus Type 1 Expression" *J. of Virology* 66(3) 1432–1441(1992).
Duval–Valentin et al., "Specific Inhibition of Transcription by Triple Helix–Forming Oligonucleotide" *Proc. Natl. Acad. Sci. USA* 89, 504–508 (1992).
Egholm et al., "PNA Hybridizes to Complementary Oligonucleotides Obeying the Watson–Crick Hydrogen–Bonding Rules" *Nature* 365, 566–568 (1993).
Elroy–Stein et al., "Cytoplasmic Expression System Based on Constitutive Synthesis of Bacteriophage T7 RNA Polymerase in Mammalian Cells" *Proc. Natl. Acad. Sci. USA* 87, 6743–6747 (1990).
Finck et al., "Treatment of Murine Lupus with CTLA4lg" *Science* 265, 1225–1227 (1994).
Fodor et al., "Expression of a functional human complement inhibitor in a transgenic pig as a model for the prevention of Xenogeneic Hyperacute Organ Rejection"*Proc. Natl. Acad. Sci. USA* 91, 11153–11157 (1994).
Freeman et al., "Uncovering of Functional Alternative CTLA–4 Counter–Receptor in B7–Deficient Mice" *Science* 262, 907–909 (1993).
Fuleihan et al., "Cyclosporin A Inhibits CD40 Ligand Expression in T Lymphocytes" *J. Clin. Invest.* 93, 1315–1320 (1994).

(List continued on next page.)

Primary Examiner—George C. Elliott
Assistant Examiner—Andrew Wang

(57) ABSTRACT

Nucleic acid molecule which blocks synthesis and/or expression of an mRNA encoding B7-1, B7-2, B7-3 and/or CD40.

26 Claims, 6 Drawing Sheets

OTHER PUBLICATIONS

Gao et al., "Cytoplasmic Expression of a Reporter Gene by Co–Delivery of T7 RNA Polymerase and T7 Promoter Sequence With Cationic Liposomes" *Nucl. Acid Res.* 21(12) 2867–2872 (1993).

Guerrier–Takada et al., "The RNA Moiety Ribonuclease P is the Catalytic Subunit of the Enzyme" *Cell* 35, 849–857 (1983).

Hampel et al., "RNA Catalytic Properties of the Minumum (=)s TRSV Sequence" *Am. Chem. Soc.* 28, 4929–4933 (1989).

Hampel et al., "'Hairpin' Catalytic RNA Model: Evidence for Helices and Sequence Requirement for Substrate RNA" *Nucl. Acid. Res.* 18(2) 299–304 (1989).

Harding et al., "CD28–Mediated Signalling Co–Stimulates Murine T Cells and Prevents Induction of Anergy in T–Cell Clones" *Nature* 356, 607–609 (1992).

Haseloff et al., "Simple RNA Enzymes with New and Highly Specific Endoribonuclease Activities" *Nature* 334, 585–591 (1988).

Hathcock et al., "Comparitive Analysis of B7–1 and B7–2 Costimulatory Ligands: Expression and Function" *J. of Exper. Medicine* 180, 631–640 (1994).

Hathcock et al., "Identification of an Alternative CTLA–4 Ligand Costimulatory for T Cell Activation" *Science* 262, 905–907 (1993).

Hertel et al., "Numbering System for the Hammerhead" *Nucl. Acids Res.* 20(12) 252 (1992).

Jaeger et al., "Improved Predictions of Secondary Structures for RNA" *Proc. Natl. Acad Sci. USA* 86, 7706–7710 (1989).

Janeway et al., "Signals and Signs for Lymphocyte Responses" *Cell* 76, 275–285 (1994).

Jeffries et al., "A Catalytic 13–mer Ribozyme," *Nucleic Acids Research* 17:1371–1377 (1989).

Jenkins et al., "Molecular Events in the Induction of Non-responsive State in Interleukin 2–Producing Helper T–Lymphocyte Clones" *Proc. Natl Acad. Sci USA* 84, 5409–5413 (1987).

Kashani–Sabet et al., "Reversal of the Malignant Phenotype by an Anti–ras Ribozyme" *Antisense Res. and Dev.* 2, 3–15 (1992).

Kemeny et al., "Can Persistent IgE Responses be Suppressed?" *Clin Exp. Immunol.* 82, 423–426 (1990).

Kim et al., "Three Dimensional Model of the Active Site of the Self–Splicing rRNA Precursor of Tetrahymena" *Proc. Natl. Acad. Sci* 84, 8788–8792 (1987).

Koulova et al., "The CD28 Ligand B7/BB1 Provides Costimulatory Signal for Alloactivation of CD4$^+$ T Cells" *J. Exp. Med.* 173, 759–762 (1991).

Kuchroo et al., "B7–1 and B7–2 Costimulatory Molecules Activate Differentially the Th1/Th2 Developmental Pathways: Application to Autoimmune Disease Therapy" *Cell* 80, 707–718(1995).

Lenschow et al., "Expression and Functional Significance of an additional Ligand for CTLA–4" *Proc. Natl. Acad. Sci* 90, 11054–11058 (1993).

Lenschow et al., "Long–Term Survival of Xenogenic Pacreatic Islet Grafts Induced by CTLA4lg" *Science* 257, 789–792 (1992).

L'Hullier et al., "Cytoplasmic Delivery of Ribozymes Lead to Efficient Reduction in α–Lactalbumin mRNA Levels in C127I Mouse Cells" *EMBO J.* 11(12) 4411–4418 (1992).

Lieber et al., "Stable High–Level Gene Expression in Mammalian Cell By T7 Phage RNA Polymerase" *Methods in Enzymol.* 217, 47–66 (1993).

Linsley et al., "Binding of the B Cell Activation Antigen B7 to CD28 Costimulates T Cell Proliferation and Interleukin 2 mRNA Accumulation" *J. Exp. Med.* 173, 721–730 (1991).

Linsley et al., "Immunosuppression In Vivo by a Soluble Form of The CTLA–4 T Cell Activation Molecule" *Science* 257, 792–795 (1992).

Lisziewicz et al., "Inhibition of Human Immunodeficiency Virus Type 1 Replication By Regulated Expression of a Polymeric Tat Activation Response RNA Decoy as a Strategy for Gene Therapy in AIDS" *Proc. Natl. Acad. Sci USA* 90, 8000–8004 (1993).

Marshall et al., "The Molecular Basis for T Cell Help in Humoral Immunity: CD40 and Its Ligand, gp39" *J of Clin. Immunol.* 13(3) 165–174 (1993).

Milligan et al., " Synthesis of Small RNAs Using T7 RNA Polymerase" *Methods in Enzymol.* 180, 51–62 (1989).

Nowak, " Xenotransplants Set to Resume" *Science* 266, 1148–1151 (1994).

Ohkawa et al., "Activities of HIV–RNA Targeted Ribozymes Transcribed Form a 'Shot–Gun' Type Ribozyme–Trimming Plasmid" *Oxford Univ. Press* 15–16 (1992).

Ojwang et al., "Inhibition of Human Immunodeficiency Virus Type 1 Expression by a Hairpin Ribozyme" *Proc. Natl Acad. Sci.* 89, 10802–10806 (1992).

Perreault et al., "Mixed Deoxyribo– and Ribo–Oligonucleotide with Catalytic Activity" *Nature* 344, 565–567 (1990).

Perrotta et al., "Cleavage of Oligoribonucleotides by Ribozyme Derived From The Hepatitis δ Virus RNA Sequence" *Am. Chem. Soc.* 31, 16–21 (1992).

Pieken et al., "Kinetic Characterization of Ribonuclease–Resistant 2'–Modified Hammerhead Ribozymes" *Science* 253, 314–317 (1991).

Pretolani et al., "Cytokines–Eosinophil Interactions in Experimental Allergy" *Annals NY Acad of Sci.* 725, 247–258 (1994).

Rossi et al., "RNA Enzymes (Ribozymes) as Antiviral Therapeutic Agents" *Tibtech* 8, 179–183 (1990).

Sarver et al., "Ribozymes as a Potential Anti–HIV–1 Therapeutic Agents" *Science* 247, 1222–1225 (1990).

Saville et al., "A Site–Specific Self–Cleavage Reaction Performed by a Novel RNA in Neurospora Mitochondria" *Cell* 61,685–696 (1990).

Saville et al., "RNA–Mediated Litigation of Self–Cleavage Products of a Neurospora Mitochondrial Plasmid Transcript" *Proc. Natl. Acad. Sci. USA* 88, 8826–8830 (1991).

Scanlon et al., "Ribozyme–Mediated Cleavage of C–fos mRNA Reduces Gene Expression of DNA Synthesis Enzymes and Metallothionein" *Proc. Natl. Acad.* 88, 10591–10595 (1991).

Scaringe et al., "Chemical Synthesis of Biologically Active Oligoribonucleotides Using β–Cyano ethyl Protected Ribonucleoside Phospharamidites" *Nucl. Acid Res.* 18(18) 5433–5441 (1990).

Stein et al., "Antisense Oligonucleotide as Therapeutic Agents—Is the Bullet Really Magic?" *Science* 261, 1004–1012 (1993).

Taira et al., "Construction of a Novel RNA–Transcription–Trimming Plasmid Which Can Be Used Both In Vitro In Place of Run–Off and (G)–Free Transcriptions and In Vivo as Multi–Sequences Transcription Vectors" *Nucl. Acids Res.* 19(19) 5125–5130 (1991).

Torrence et al., "Targeting RNA for Degradation with a (2'–5') Oligoadenylateantisense Chimera" *Proc. Natl. Acad. Sci USA* 90, 1300–1304 (1993).

Turka et al., "T–Cell Activation by the CD28 Ligand B7 is Required for Cardiac Allograft Rejection In Vivo" *Proc. Natl. Acad. Sci.* 89, 11102–11105 (1992).

Uhlenbeck, "A Small Catalytic Oligoribonucleotide" *Nature* 328, 596–900 (1987).

Usman et al., " Exploiting the Chemical Synthesis of RNA" *TIBS* 17, 334–339 (1992).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia Coli* Formylmethionine tRNA" *Am. Chem. Soc.* 109(25) 7845–7854 (1987).

Van Gool et al., "Synergy Between Cyclosporin A and a Monoclonal Antibody to B7 in Blocking Alloantigen–Induced T–Cell Activation" *Blood* 83(1) 176–183 (1994).

Van Laar et al., "Towards T Cell Vaccination in Rheumatoid Arthritis" *Chem Immunol.* 58, 206–235 (1994).

Ventura et al., "Activation of HIV–Specific Ribozyme Activity by Self–Cleavage" *Nucl. Acid Res.* 21(14) 3249–3255 (1993).

Weerasinghe et al., "Resistance to Human Immunodeficiency Virus Type 1 (HIV–1) Infection in Human CD4$^+$ Lymphocyte–Derived Cell Lines Conferred by Using Retroviral Vectors Expressing an HIV–1 RNA–Specific Ribozyme" *J. Virol.* 65(10) 5531–5534 (1991).

Wekerle et al., "Animal Models" *Annals of Neurol.* 36, s47–s53 (1994).

Yu et al., "A Hairpin Ribozyme Inhibits Expression of Diverse Strains of Human Immunodeficiency Virus Type 1" *Proc. Natl. Acad. Sci. USA* 90, 6340–6344 (1993).

Zabner et al., "Adenovirus–Mediated Gene Transfer Transiently Corrects the Chloride Transport Defect in Nasal Epithelia with Cystic Fibrosis" *Cell* 75, 207–216 (1993).

Zhou et al., "Synthesis of Functional mRNA in Mammalian Cells By Bacteriophage T3 RNA Polymerase" *Mol. Cell. Biol.* 10(9) 4529–4537 (1990).

Branch TIBS 23:45–50, Feb. 1998.*

Flanagan et al. Nature Biotechnology 17:48–52, Jan. 1999.*

* cited by examiner

HAMMERHEAD RIBOZYME SUBSTRATE MOTIFS

HEPATITIS DELTA VIRUS RIBOZYME

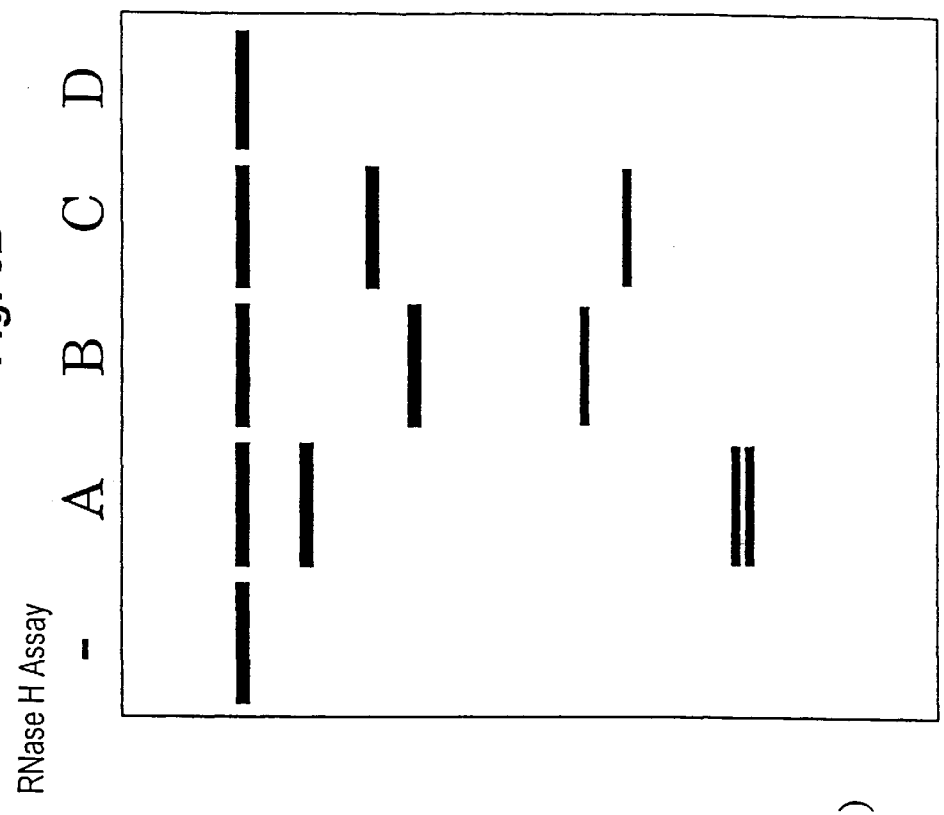
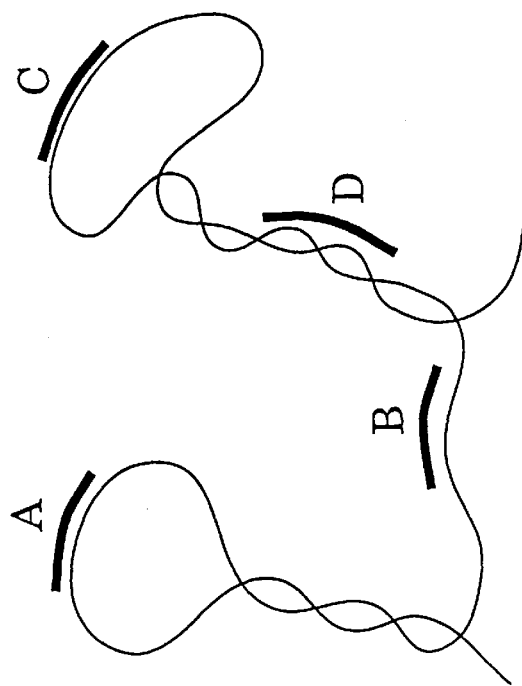
Fig. 6A
Fig. 6B
RNase H Assay
- Body-labeled transcript (not purified)
- DNA oligo (10 nM, 100 nM and 1000 nM)
- RNAse H (0.08 -1.0 u/µl)
- 37°C, 10 min

SEQUENCE LISTING (1) GENERAL INFORMATION:

(iii) NUMBER OF SEQUENCES:        2751

(2) INFORMATION FOR SEQ ID NO:1:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1:

AAACCCUCUG UAAAG                                                    15

(2) INFORMATION FOR SEQ ID NO:2:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2:

CCUCUGUAAA GUAAC                                                    15

(2) INFORMATION FOR SEQ ID NO:3:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:3:

GUAAAGUAAC AGAAG                                                    15

(2) INFORMATION FOR SEQ ID NO:4:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:4:

CAGAAGUUAG AAGGG                                                    15

(2) INFORMATION FOR SEQ ID NO:5:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:5:

AGAAGUUAGA AGGGG                                                    15

(2) INFORMATION FOR SEQ ID NO:6:

(i) SEQUENCE CHARACTERISTICS:
        (A) LENGTH:        15 base pairs
        (B) TYPE:          nucleic acid
        (C) STRANDEDNESS:  single (D) TOPOLOGY:      linear (xi) SEQUENCE DESCRIPTION: SEQ ID NO:6:

GAAAUGUCGC CUCUC                                                              15

(2) INFORMATION FOR SEQ ID NO:7:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:7:

GUCGCCUCUC UGAAG                                                              15

(2) INFORMATION FOR SEQ ID NO:8:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:8:

CGCCUCUCUG AAGAU                                                              15

(2) INFORMATION FOR SEQ ID NO:9:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:9:

UGAAGAUUAC CCAAA                                                              15

(2) INFORMATION FOR SEQ ID NO:10:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:10:

GAAGAUUACC CAAAG                                                              15

(2) INFORMATION FOR SEQ ID NO:11:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:11:

AAGUGAUUUG UCAUU                                                              15

(2) INFORMATION FOR SEQ ID NO:12:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:12:

AGUGAUUUGU CAUUG                                                    15

(2) INFORMATION FOR SEQ ID NO:13:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:13:

GAUUUGUCAU UGCUU                                                    15

(2) INFORMATION FOR SEQ ID NO:14:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:14:

UUGUCAUUGC UUUAU                                                    15

(2) INFORMATION FOR SEQ ID NO:15:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:15:

CAUUGCUUUA UAGAC                                                    15

(2) INFORMATION FOR SEQ ID NO:16:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:16:

AUUGCUUUAU AGACU                                                    15

(2) INFORMATION FOR SEQ ID NO:17:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:17:

UUGCUUUAUA GACUG                                                    15

(2) INFORMATION FOR SEQ ID NO:18:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear

```
        (xi) SEQUENCE DESCRIPTION: SEQ ID NO:18:

GCUUUAUAGA CUGUA                                                      15

(2) INFORMATION FOR SEQ ID NO:19:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:19:

AGACUGUAAG AAGAG                                                      15

(2) INFORMATION FOR SEQ ID NO:20:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:20:

AGAACAUCUC AGAAG                                                      15

(2) INFORMATION FOR SEQ ID NO:21:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:21:

AACAUCUCAG AAGUG                                                      15

(2) INFORMATION FOR SEQ ID NO:22:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:22:

GUGGAGUCUU ACCCU                                                      15

(2) INFORMATION FOR SEQ ID NO:23:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:23:

GGAGUCUUAC CCUGA                                                      15

(2) INFORMATION FOR SEQ ID NO:24:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:24:
```

GAGUCUUACC CUGAA                                                                    15

(2) INFORMATION FOR SEQ ID NO:25:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:25:

CUGAAAUCAA AGGAU                                                                    15

(2) INFORMATION FOR SEQ ID NO:26:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:26:

AAAGGAUUUA AAGAA                                                                    15

(2) INFORMATION FOR SEQ ID NO:27:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:27:

AAGGAUUUAA AGAAA                                                                    15

(2) INFORMATION FOR SEQ ID NO:28:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:28:

AGGAUUUAAA GAAAA                                                                    15

(2) INFORMATION FOR SEQ ID NO:29:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:29:

GUGGAAUUUU UCUUC                                                                    15

(2) INFORMATION FOR SEQ ID NO:30:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:30:

```
UGGAAUUUUU CUUCA                                                15
```

(2) INFORMATION FOR SEQ ID NO:31:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:31:

```
GGAAUUUUUC UUCAG                                                15
```

(2) INFORMATION FOR SEQ ID NO:32:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:32:

```
GAAUUUUUCU UCAGC                                                15
```

(2) INFORMATION FOR SEQ ID NO:33:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:33:

```
AAUUUUUCUU CAGCA                                                15
```

(2) INFORMATION FOR SEQ ID NO:34:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:34:

```
UUUUUCUUCA GCAAG                                                15
```

(2) INFORMATION FOR SEQ ID NO:35:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:35:

```
UUUUCUUCAG CAAGC                                                15
```

(2) INFORMATION FOR SEQ ID NO:36:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:36:

```
UGAAACUAAA UCCAC                                                15
```

(2) INFORMATION FOR SEQ ID NO:37:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:37:

ACUAAAUCCA CAACC                                                    15

(2) INFORMATION FOR SEQ ID NO:38:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:38:

ACAACCUUUG GAGAC                                                    15

(2) INFORMATION FOR SEQ ID NO:39:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:39:

CAACCUUUGG AGACC                                                    15

(2) INFORMATION FOR SEQ ID NO:40:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:40:

ACACCCUCCA AUCUC                                                    15

(2) INFORMATION FOR SEQ ID NO:41:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:41:

CUCCAAUCUC UGUGU                                                    15

(2) INFORMATION FOR SEQ ID NO:42:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:42:

CCAAUCUCUG UGUGU                                                    15

(2) INFORMATION FOR SEQ ID NO:43:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:43:

UGUGUGUUUU GUAAA                    15

(2) INFORMATION FOR SEQ ID NO:44:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:44:

GUGUGUUUUG UAAAC                    15

(2) INFORMATION FOR SEQ ID NO:45:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:45:

UGUGUUUUGU AAACA                    15

(2) INFORMATION FOR SEQ ID NO:46:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:46:

GUUUUGUAAA CAUCA                    15

(2) INFORMATION FOR SEQ ID NO:47:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:47:

UAAACAUCAC UGGAG                    15

(2) INFORMATION FOR SEQ ID NO:48:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:48:

GGAGGGUCUU CUACG                    15

(2) INFORMATION FOR SEQ ID NO:49:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:49:

AGGGUCUUCU ACGUG                                                        15

(2) INFORMATION FOR SEQ ID NO:50:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:50:

GGGUCUUCUA CGUGA                                                        15

(2) INFORMATION FOR SEQ ID NO:51:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:51:

GUCUUCUACG UGAGC                                                        15

(2) INFORMATION FOR SEQ ID NO:52:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:52:

GAGCAAUUGG AUUGU                                                        15

(2) INFORMATION FOR SEQ ID NO:53:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:53:

AUUGGAUUGU CAUCA                                                        15

(2) INFORMATION FOR SEQ ID NO:54:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:54:

GGAUUGUCAU CAGCC                                                        15

(2) INFORMATION FOR SEQ ID NO:55:

(i) SEQUENCE CHARACTERISTICS:
    (A) LENGTH:        15 base pairs
    (B) TYPE:          nucleic acid
    (C) STRANDEDNESS:  single
    (D) TOPOLOGY:      linear (xi) SEQUENCE DESCRIPTION: SEQ ID NO:55:

UUGUCAUCAG CCCUG                                                              15

(2) INFORMATION FOR SEQ ID NO:56:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:56:

UGCCUGUUUU GCACC                                                              15

(2) INFORMATION FOR SEQ ID NO:57:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:57:

GCCUGUUUUG CACCU                                                              15

(2) INFORMATION FOR SEQ ID NO:58:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:58:

CCUGUUUUGC ACCUG                                                              15

(2) INFORMATION FOR SEQ ID NO:59:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:59:

CCCUGGUCUU ACUUG                                                              15

(2) INFORMATION FOR SEQ ID NO:60:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:60:

CUGGUCUUAC UUGGG                                                              15

(2) INFORMATION FOR SEQ ID NO:61:

(i) SEQUENCE CHARACTERISTICS:
    (A) LENGTH:        15 base pairs
    (B) TYPE:          nucleic acid
    (C) STRANDEDNESS:  single
    (D) TOPOLOGY:      linear (xi) SEQUENCE DESCRIPTION: SEQ ID NO:61:

UGGUCUUACU UGGGU                                                15

(2) INFORMATION FOR SEQ ID NO:62:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:62:

UCUUACUUGG GUCCA                                                15

(2) INFORMATION FOR SEQ ID NO:63:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:63:

CUUGGGUCCA AAUUG                                                15

(2) INFORMATION FOR SEQ ID NO:64:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:64:

UCCAAAUUGU UGGCU                                                15

(2) INFORMATION FOR SEQ ID NO:65:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:65:

AAAUUGUUGG CUUUC                                                15

(2) INFORMATION FOR SEQ ID NO:66:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:66:

GUUGGCUUUC ACUUU                                                15

(2) INFORMATION FOR SEQ ID NO:67:

(i) SEQUENCE CHARACTERISTICS:

```
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:67:

UUGGCUUUCA CUUUU                                                   15

(2) INFORMATION FOR SEQ ID NO:68:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:68:

UGGCUUUCAC UUUUG                                                   15

(2) INFORMATION FOR SEQ ID NO:69:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:69:

UUUCACUUUU GACCC                                                   15

(2) INFORMATION FOR SEQ ID NO:70:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:70:

UUCACUUUUG ACCCU                                                   15

(2) INFORMATION FOR SEQ ID NO:71:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:71:

UCACUUUUGA CCCUA                                                   15

(2) INFORMATION FOR SEQ ID NO:72:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:72:

UGACCCUAAG CAUCU                                                   15

(2) INFORMATION FOR SEQ ID NO:73:

(i) SEQUENCE CHARACTERISTICS:
            (A) LENGTH:          15 base pairs
```

(B) TYPE:           nucleic acid
            (C) STRANDEDNESS:   single
            (D) TOPOLOGY:       linear (xi) SEQUENCE DESCRIPTION: SEQ ID NO:73:

UAAGCAUCUG AAGCC                                                            15

(2) INFORMATION FOR SEQ ID NO:74:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:74:

GGAACAUCAC CAUCC                                                            15

(2) INFORMATION FOR SEQ ID NO:75:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:75:

UCACCAUCCA AGUGU                                                            15

(2) INFORMATION FOR SEQ ID NO:76:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:76:

CAAGUGUCCA UACCU                                                            15

(2) INFORMATION FOR SEQ ID NO:77:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:77:

UGUCCAUACC UCAAU                                                            15

(2) INFORMATION FOR SEQ ID NO:78:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:78:

CAUACCUCAA UUUCU                                                            15

(2) INFORMATION FOR SEQ ID NO:79:

(i) SEQUENCE CHARACTERISTICS:
            (A) LENGTH:         15 base pairs
            (B) TYPE:           nucleic acid

```
            (C) STRANDEDNESS:    single
            (D) TOPOLOGY:        linear (xi) SEQUENCE DESCRIPTION: SEQ ID NO:79:

CCUCAAUUUC UUUCA                                                      15

(2) INFORMATION FOR SEQ ID NO:80:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:80:

CUCAAUUUCU UUCAG                                                      15

(2) INFORMATION FOR SEQ ID NO:81:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:81:

UCAAUUUCUU UCAGC                                                      15

(2) INFORMATION FOR SEQ ID NO:82:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:82:

AAUUUCUUUC AGCUC                                                      15

(2) INFORMATION FOR SEQ ID NO:83:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:83:

AUUUCUUUCA GCUCU                                                      15

(2) INFORMATION FOR SEQ ID NO:84:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:84:

UUUCUUUCAG CUCUU                                                      15

(2) INFORMATION FOR SEQ ID NO:85:

(i) SEQUENCE CHARACTERISTICS:
            (A) LENGTH:          15 base pairs
            (B) TYPE:            nucleic acid
            (C) STRANDEDNESS:    single
```

```
            (D) TOPOLOGY:       linear (xi) SEQUENCE DESCRIPTION: SEQ ID NO:85:

UUCAGCUCUU GGUGC                                                    15

(2) INFORMATION FOR SEQ ID NO:86:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:86:

CAGCUCUUGG UGCUG                                                    15

(2) INFORMATION FOR SEQ ID NO:87:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:87:

GGCUGGUCUU UCUCA                                                    15

(2) INFORMATION FOR SEQ ID NO:88:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:88:

CUGGUCUUUC UCACU                                                    15

(2) INFORMATION FOR SEQ ID NO:89:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:89:

UGGUCUUUCU CACUU                                                    15

(2) INFORMATION FOR SEQ ID NO:90:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:90:

GGUCUUUCUC ACUUC                                                    15

(2) INFORMATION FOR SEQ ID NO:91:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear
```

(xi) SEQUENCE DESCRIPTION: SEQ ID NO:91:

UCUUUCUCAC UUCUG                                                        15

(2) INFORMATION FOR SEQ ID NO:92:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:92:

UCUCACUUCU GUUCA                                                        15

(2) INFORMATION FOR SEQ ID NO:93:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:93:

CUCACUUCUG UUCAG                                                        15

(2) INFORMATION FOR SEQ ID NO:94:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:94:

CUUCUGUUCA GGUGU                                                        15

(2) INFORMATION FOR SEQ ID NO:95:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:95:

UUCUGUUCAG GUGUU                                                        15

(2) INFORMATION FOR SEQ ID NO:96:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:96:

CAGGUGUUAU CCACG                                                        15

(2) INFORMATION FOR SEQ ID NO:97:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear

```
        (xi) SEQUENCE DESCRIPTION: SEQ ID NO:97:

AGGUGUUAUC CACGU                                                          15

(2) INFORMATION FOR SEQ ID NO:98:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:98:

GUGUUAUCCA CGUGA                                                          15

(2) INFORMATION FOR SEQ ID NO:99:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:99:

ACGCUGUCCU GUGGU                                                          15

(2) INFORMATION FOR SEQ ID NO:100:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:100:

CUGUGGUCAC AAUGU                                                          15

(2) INFORMATION FOR SEQ ID NO:101:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:101:

ACAAUGUUUC UGUUG                                                          15

(2) INFORMATION FOR SEQ ID NO:102:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:102:

CAAUGUUUCU GUUGA                                                          15

(2) INFORMATION FOR SEQ ID NO:103:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:103:
```

AAUGUUUCUG UUGAA 15

(2) INFORMATION FOR SEQ ID NO:104:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:104:

UUUCUGUUGA AGAGC 15

(2) INFORMATION FOR SEQ ID NO:105:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:105:

ACAAACUCGC AUCUA 15

(2) INFORMATION FOR SEQ ID NO:106:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:106:

CUCGCAUCUA CUGGC 15

(2) INFORMATION FOR SEQ ID NO:107:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:107:

CGCAUCUACU GGCAA 15

(2) INFORMATION FOR SEQ ID NO:108:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:108:

GCUGACUAUG AUGUC 15

(2) INFORMATION FOR SEQ ID NO:109:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:109:

```
AUGAUGUCUG GGGAC                                                             15

(2) INFORMATION FOR SEQ ID NO:110:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:110:

CAUGAAUAUA UGGCC                                                             15

(2) INFORMATION FOR SEQ ID NO:111:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:111:

UGAAUAUAUG GCCCG                                                             15

(2) INFORMATION FOR SEQ ID NO:112:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:112:

CCCGAGUACA AGAAC                                                             15

(2) INFORMATION FOR SEQ ID NO:113:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:113:

GGACCAUCUU UGAUA                                                             15

(2) INFORMATION FOR SEQ ID NO:114:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:114:

ACCAUCUUUG AUAUC                                                             15

(2) INFORMATION FOR SEQ ID NO:115:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:115:

CCAUCUUUGA UAUCA                                                             15
```

(2) INFORMATION FOR SEQ ID NO:116:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:116:

CUUUGAUAUC ACUAA                                             15

(2) INFORMATION FOR SEQ ID NO:117:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:117:

UUGAUAUCAC UAAUA                                             15

(2) INFORMATION FOR SEQ ID NO:118:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:118:

UAUCACUAAU AACCU                                             15

(2) INFORMATION FOR SEQ ID NO:119:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:119:

CACUAAUAAC CUCUC                                             15

(2) INFORMATION FOR SEQ ID NO:120:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:120:

AUAACCUCUC CAUUG                                             15

(2) INFORMATION FOR SEQ ID NO:121:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:121:

AACCUCUCCA UUGUG                                             15

(2) INFORMATION FOR SEQ ID NO:122:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:122:

UCUCCAUUGU GAUCC                                                          15

(2) INFORMATION FOR SEQ ID NO:123:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:123:

UUGUGAUCCU GGCUC                                                          15

(2) INFORMATION FOR SEQ ID NO:124:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:124:

CCUGGCUCUG CGCCC                                                          15

(2) INFORMATION FOR SEQ ID NO:125:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:125:

CGCCCAUCUG ACGAG                                                          15

(2) INFORMATION FOR SEQ ID NO:126:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:126:

GGCACAUACG AGUGU                                                          15

(2) INFORMATION FOR SEQ ID NO:127:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:127:

AGUGUGUUGU UCUGA                                                          15

(2) INFORMATION FOR SEQ ID NO:128:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:128:

GUGUUGUUCU GAAGU                                           15

(2) INFORMATION FOR SEQ ID NO:129:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:129:

UGUUGUUCUG AAGUA                                           15

(2) INFORMATION FOR SEQ ID NO:130:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:130:

CUGAAGUAUG AAAAA                                           15

(2) INFORMATION FOR SEQ ID NO:131:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:131:

AGACGCUUUC AAGCG                                           15

(2) INFORMATION FOR SEQ ID NO:132:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:132:

GACGCUUUCA AGCGG                                           15

(2) INFORMATION FOR SEQ ID NO:133:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:133:

ACGCUUUCAA GCGGG                                           15

(2) INFORMATION FOR SEQ ID NO:134:

```
            (i) SEQUENCE CHARACTERISTICS:
                  (A) LENGTH:        15 base pairs
                  (B) TYPE:          nucleic acid
                  (C) STRANDEDNESS:  single
                  (D) TOPOLOGY:      linear (xi) SEQUENCE DESCRIPTION: SEQ ID NO:134:

GUGACGUUAU CAGUC                                                          15

(2) INFORMATION FOR SEQ ID NO:135:

(i) SEQUENCE CHARACTERISTICS:
                  (A) LENGTH:        15 base pairs
                  (B) TYPE:          nucleic acid
                  (C) STRANDEDNESS:  single
                  (D) TOPOLOGY:      linear (xi) SEQUENCE DESCRIPTION: SEQ ID NO:135:

UGACGUUAUC AGUCA                                                          15

(2) INFORMATION FOR SEQ ID NO:136:

(i) SEQUENCE CHARACTERISTICS:
                  (A) LENGTH:        15 base pairs
                  (B) TYPE:          nucleic acid
                  (C) STRANDEDNESS:  single
                  (D) TOPOLOGY:      linear (xi) SEQUENCE DESCRIPTION: SEQ ID NO:136:

ACGUUAUCAG UCAAA                                                          15

(2) INFORMATION FOR SEQ ID NO:137:

(i) SEQUENCE CHARACTERISTICS:
                  (A) LENGTH:        15 base pairs
                  (B) TYPE:          nucleic acid
                  (C) STRANDEDNESS:  single
                  (D) TOPOLOGY:      linear (xi) SEQUENCE DESCRIPTION: SEQ ID NO:137:

UAUCAGUCAA AGCUG                                                          15

(2) INFORMATION FOR SEQ ID NO:138:

(i) SEQUENCE CHARACTERISTICS:
                  (A) LENGTH:        15 base pairs
                  (B) TYPE:          nucleic acid
                  (C) STRANDEDNESS:  single
                  (D) TOPOLOGY:      linear (xi) SEQUENCE DESCRIPTION: SEQ ID NO:138:

GCUGACUUCC CUACA                                                          15

(2) INFORMATION FOR SEQ ID NO:139:

(i) SEQUENCE CHARACTERISTICS:
                  (A) LENGTH:        15 base pairs
                  (B) TYPE:          nucleic acid
                  (C) STRANDEDNESS:  single
                  (D) TOPOLOGY:      linear (xi) SEQUENCE DESCRIPTION: SEQ ID NO:139:

CUGACUUCCC UACAC                                                          15

(2) INFORMATION FOR SEQ ID NO:140:
```

```
    (i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:140:

CUUCCCUACA CCUAG                                                     15

(2) INFORMATION FOR SEQ ID NO:141:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:141:

UACACCUAGU AUAUC                                                     15

(2) INFORMATION FOR SEQ ID NO:142:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:142:

ACCUAGUAUA UCUGA                                                     15

(2) INFORMATION FOR SEQ ID NO:143:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:143:

CUAGUAUAUC UGACU                                                     15

(2) INFORMATION FOR SEQ ID NO:144:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:144:

AGUAUAUCUG ACUUU                                                     15

(2) INFORMATION FOR SEQ ID NO:145:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:145:

UCUGACUUUG AAAUU                                                     15

(2) INFORMATION FOR SEQ ID NO:146:

(i) SEQUENCE CHARACTERISTICS:
```

```
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:146:

CUGACUUUGA AAUUC                                                    15

(2) INFORMATION FOR SEQ ID NO:147:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:147:

UUGAAAUUCC AACUU                                                    15

(2) INFORMATION FOR SEQ ID NO:148:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:148:

UGAAAUUCCA ACUUC                                                    15

(2) INFORMATION FOR SEQ ID NO:149:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:149:

UCCAACUUCU AAUAU                                                    15

(2) INFORMATION FOR SEQ ID NO:150:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:150:

CCAACUUCUA AUAUU                                                    15

(2) INFORMATION FOR SEQ ID NO:151:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:151:

AACUUCUAAU AUUAG                                                    15

(2) INFORMATION FOR SEQ ID NO:152:

(i) SEQUENCE CHARACTERISTICS:
          (A) LENGTH:          15 base pairs
```

```
            (B) TYPE:           nucleic acid
            (C) STRANDEDNESS:   single
            (D) TOPOLOGY:       linear (xi) SEQUENCE DESCRIPTION: SEQ ID NO:152:

UUCUAAUAUU AGAAG                                                15

(2) INFORMATION FOR SEQ ID NO:153:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:153:

CUAAUAUUAG AAGGA                                                15

(2) INFORMATION FOR SEQ ID NO:154:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:154:

UAAUAUUAGA AGGAU                                                15

(2) INFORMATION FOR SEQ ID NO:155:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:155:

GAAGGAUAAU UUGCU                                                15

(2) INFORMATION FOR SEQ ID NO:156:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:156:

GGAUAAUUUG CUCAA                                                15

(2) INFORMATION FOR SEQ ID NO:157:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:157:

GAUAAUUUGC UCAAC                                                15

(2) INFORMATION FOR SEQ ID NO:158:

(i) SEQUENCE CHARACTERISTICS:
            (A) LENGTH:         15 base pairs
            (B) TYPE:           nucleic acid
```

```
          (C) STRANDEDNESS:    single
          (D) TOPOLOGY:        linear (xi) SEQUENCE DESCRIPTION: SEQ ID NO:158:

AUUUGCUCAA CCUCU                                                    15

(2) INFORMATION FOR SEQ ID NO:159:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:159:

UCAACCUCUG GAGGU                                                    15

(2) INFORMATION FOR SEQ ID NO:160:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:160:

UGGAGGUUUU CCAGA                                                    15

(2) INFORMATION FOR SEQ ID NO:161:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:161:

GGAGGUUUUC CAGAG                                                    15

(2) INFORMATION FOR SEQ ID NO:162:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:162:

GAGGUUUUCC AGAGC                                                    15

(2) INFORMATION FOR SEQ ID NO:163:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:163:

AGGUUUUCCA GAGCC                                                    15

(2) INFORMATION FOR SEQ ID NO:164:

(i) SEQUENCE CHARACTERISTICS:
          (A) LENGTH:          15 base pairs
          (B) TYPE:            nucleic acid
          (C) STRANDEDNESS:    single
```

```
          (D) TOPOLOGY:        linear (xi) SEQUENCE DESCRIPTION: SEQ ID NO:164:

AGAGCCUCAC CUCUC                                                    15

(2) INFORMATION FOR SEQ ID NO:165:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:165:

CUCACCUCUC CUGGU                                                    15

(2) INFORMATION FOR SEQ ID NO:166:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:166:

CACCUCUCCU GGUUG                                                    15

(2) INFORMATION FOR SEQ ID NO:167:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:167:

UCCUGGUUGG AAAAU                                                    15

(2) INFORMATION FOR SEQ ID NO:168:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:168:

GAAGAAUUAA AUGCC                                                    15

(2) INFORMATION FOR SEQ ID NO:169:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:169:

AAGAAUUAAA UGCCA                                                    15

(2) INFORMATION FOR SEQ ID NO:170:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear
```

(xi) SEQUENCE DESCRIPTION: SEQ ID NO:170:

AUGCCAUCAA CACAA                                                        15

(2) INFORMATION FOR SEQ ID NO:171:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:171:

CAACAGUUUC CCAAG                                                        15

(2) INFORMATION FOR SEQ ID NO:172:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:172:

AACAGUUUCC CAAGA                                                        15

(2) INFORMATION FOR SEQ ID NO:173:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:173:

ACAGUUUCCC AAGAU                                                        15

(2) INFORMATION FOR SEQ ID NO:174:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:174:

CCAAGAUCCU GAAAC                                                        15

(2) INFORMATION FOR SEQ ID NO:175:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:175:

CUGAGCUCUA UGCUG                                                        15

(2) INFORMATION FOR SEQ ID NO:176:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear -continued (xi) SEQUENCE DESCRIPTION: SEQ ID NO:176:

GAGCUCUAUG CUGUU                                                    15

(2) INFORMATION FOR SEQ ID NO:177:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:177:

AUGCUGUUAG CAGCA                                                    15

(2) INFORMATION FOR SEQ ID NO:178:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:178:

UGCUGUUAGC AGCAA                                                    15

(2) INFORMATION FOR SEQ ID NO:179:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:179:

ACUGGAUUUC AAUAU                                                    15

(2) INFORMATION FOR SEQ ID NO:180:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:180:

CUGGAUUUCA AUAUG                                                    15

(2) INFORMATION FOR SEQ ID NO:181:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:181:

UGGAUUUCAA UAUGA                                                    15

(2) INFORMATION FOR SEQ ID NO:182:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:182:

UUUCAAUAUG ACAAC                                                        15

(2) INFORMATION FOR SEQ ID NO:183:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:183:

CACAGCUUCA UGUGU                                                        15

(2) INFORMATION FOR SEQ ID NO:184:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:184:

ACAGCUUCAU GUGUC                                                        15

(2) INFORMATION FOR SEQ ID NO:185:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:185:

CAUGUGUCUC AUCAA                                                        15

(2) INFORMATION FOR SEQ ID NO:186:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:186:

UGUGUCUCAU CAAGU                                                        15

(2) INFORMATION FOR SEQ ID NO:187:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:187:

GUCUCAUCAA GUAUG                                                        15

(2) INFORMATION FOR SEQ ID NO:188:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:188:

```
AUCAAGUAUG GACAU                                              15
```

(2) INFORMATION FOR SEQ ID NO:189:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:189:

```
UGGACAUUUA AGAGU                                              15
```

(2) INFORMATION FOR SEQ ID NO:190:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:190:

```
GGACAUUUAA GAGUG                                              15
```

(2) INFORMATION FOR SEQ ID NO:191:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:191:

```
GACAUUUAAG AGUGA                                              15
```

(2) INFORMATION FOR SEQ ID NO:192:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:192:

```
AGUGAAUCAG ACCUU                                              15
```

(2) INFORMATION FOR SEQ ID NO:193:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:193:

```
CAGACCUUCA ACUGG                                              15
```

(2) INFORMATION FOR SEQ ID NO:194:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:194:

```
AGACCUUCAA CUGGA                                              15
```

(2) INFORMATION FOR SEQ ID NO:195:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:195:

CUGGAAUACA ACCAA                                              15

(2) INFORMATION FOR SEQ ID NO:196:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:196:

AGAGCAUUUU CCUGA                                              15

(2) INFORMATION FOR SEQ ID NO:197:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:197:

GAGCAUUUUC CUGAU                                              15

(2) INFORMATION FOR SEQ ID NO:198:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:198:

AGCAUUUUCC UGAUA                                              15

(2) INFORMATION FOR SEQ ID NO:199:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:199:

GCAUUUUCCU GAUAA                                              15

(2) INFORMATION FOR SEQ ID NO:200:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:200:

UCCUGAUAAC CUGCU                                              15

(2) INFORMATION FOR SEQ ID NO:201:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:201:

ACCUGCUCCC AUCCU 15

(2) INFORMATION FOR SEQ ID NO:202:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:202:

CUCCCAUCCU GGGCC 15

(2) INFORMATION FOR SEQ ID NO:203:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:203:

GGGCCAUUAC CUUAA 15

(2) INFORMATION FOR SEQ ID NO:204:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:204:

GGCCAUUACC UUAAU 15

(2) INFORMATION FOR SEQ ID NO:205:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:205:

AUUACCUUAA UCUCA 15

(2) INFORMATION FOR SEQ ID NO:206:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:206:

UUACCUUAAU CUCAG 15

(2) INFORMATION FOR SEQ ID NO:207:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:207:

CCUUAAUCUC AGUAA                                                        15

(2) INFORMATION FOR SEQ ID NO:208:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:208:

UUAAUCUCAG UAAAU                                                        15

(2) INFORMATION FOR SEQ ID NO:209:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:209:

UCUCAGUAAA UGGAA                                                        15

(2) INFORMATION FOR SEQ ID NO:210:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:210:

AUGGAAUUUU UGUGA                                                        15

(2) INFORMATION FOR SEQ ID NO:211:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:211:

UGGAAUUUUU GUGAU                                                        15

(2) INFORMATION FOR SEQ ID NO:212:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:212:

GGAAUUUUUG UGAUA                                                        15

(2) INFORMATION FOR SEQ ID NO:213:

```
        (i) SEQUENCE CHARACTERISTICS:
             (A) LENGTH:        15 base pairs
             (B) TYPE:          nucleic acid
             (C) STRANDEDNESS:  single
             (D) TOPOLOGY:      linear (xi) SEQUENCE DESCRIPTION: SEQ ID NO:213:

GAAUUUUUGU GAUAU                                                     15

(2) INFORMATION FOR SEQ ID NO:214:

(i) SEQUENCE CHARACTERISTICS:
             (A) LENGTH:        15 base pairs
             (B) TYPE:          nucleic acid
             (C) STRANDEDNESS:  single
             (D) TOPOLOGY:      linear (xi) SEQUENCE DESCRIPTION: SEQ ID NO:214:

UUGUGAUAUG CUGCC                                                     15

(2) INFORMATION FOR SEQ ID NO:215:

(i) SEQUENCE CHARACTERISTICS:
             (A) LENGTH:        15 base pairs
             (B) TYPE:          nucleic acid
             (C) STRANDEDNESS:  single
             (D) TOPOLOGY:      linear (xi) SEQUENCE DESCRIPTION: SEQ ID NO:215:

CUGACCUACU GCUUU                                                     15

(2) INFORMATION FOR SEQ ID NO:216:

(i) SEQUENCE CHARACTERISTICS:
             (A) LENGTH:        15 base pairs
             (B) TYPE:          nucleic acid
             (C) STRANDEDNESS:  single
             (D) TOPOLOGY:      linear (xi) SEQUENCE DESCRIPTION: SEQ ID NO:216:

UACUGCUUUG CCCCA                                                     15

(2) INFORMATION FOR SEQ ID NO:217:

(i) SEQUENCE CHARACTERISTICS:
             (A) LENGTH:        15 base pairs
             (B) TYPE:          nucleic acid
             (C) STRANDEDNESS:  single
             (D) TOPOLOGY:      linear (xi) SEQUENCE DESCRIPTION: SEQ ID NO:217:

ACUGCUUUGC CCCAA                                                     15

(2) INFORMATION FOR SEQ ID NO:218:

(i) SEQUENCE CHARACTERISTICS:
             (A) LENGTH:        15 base pairs
             (B) TYPE:          nucleic acid
             (C) STRANDEDNESS:  single
             (D) TOPOLOGY:      linear (xi) SEQUENCE DESCRIPTION: SEQ ID NO:218:

GAGAGAUUGA GAAGG                                                     15

(2) INFORMATION FOR SEQ ID NO:219:
```

(i) SEQUENCE CHARACTERISTICS:
    (A) LENGTH:         15 base pairs
    (B) TYPE:           nucleic acid
    (C) STRANDEDNESS:   single
    (D) TOPOLOGY:       linear (xi) SEQUENCE DESCRIPTION: SEQ ID NO:219:

AAAGUGUACG CCCUG                                                    15

(2) INFORMATION FOR SEQ ID NO:220:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:220:

GCCCUGUAUA ACAGU                                                    15

(2) INFORMATION FOR SEQ ID NO:221:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:221:

CCUGUAUAAC AGUGU                                                    15

(2) INFORMATION FOR SEQ ID NO:222:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:222:

ACAGUGUCCG CAGAA                                                    15

(2) INFORMATION FOR SEQ ID NO:223:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:223:

AAAAGAUCUG AAGGU                                                    15

(2) INFORMATION FOR SEQ ID NO:224:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:224:

UGAAGGUAGC CUCCG                                                    15

(2) INFORMATION FOR SEQ ID NO:225:

(i) SEQUENCE CHARACTERISTICS:

```
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:225:

GUAGCCUCCG UCAUC                                                   15

(2) INFORMATION FOR SEQ ID NO:226:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:226:

CCUCCGUCAU CUCUU                                                   15

(2) INFORMATION FOR SEQ ID NO:227:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:227:

CCGUCAUCUC UUCUG                                                   15

(2) INFORMATION FOR SEQ ID NO:228:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:228:

GUCAUCUCUU CUGGG                                                   15

(2) INFORMATION FOR SEQ ID NO:229:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:229:

CAUCUCUUCU GGGAU                                                   15

(2) INFORMATION FOR SEQ ID NO:230:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:230:

AUCUCUUCUG GGAUA                                                   15

(2) INFORMATION FOR SEQ ID NO:231:

(i) SEQUENCE CHARACTERISTICS:
        (A) LENGTH:         15 base pairs
```

```
            (B) TYPE:           nucleic acid
            (C) STRANDEDNESS:   single
            (D) TOPOLOGY:       linear (xi) SEQUENCE DESCRIPTION: SEQ ID NO:231:

CUGGGAUACA UGGAU                                                          15

(2) INFORMATION FOR SEQ ID NO:232:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:232:

CAUGGAUCGU GGGGA                                                          15

(2) INFORMATION FOR SEQ ID NO:233:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:233:

UGGGGAUCAU GAGGC                                                          15

(2) INFORMATION FOR SEQ ID NO:234:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:234:

GAGGCAUUCU UCCCU                                                          15

(2) INFORMATION FOR SEQ ID NO:235:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:235:

AGGCAUUCUU CCCUU                                                          15

(2) INFORMATION FOR SEQ ID NO:236:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:236:

GCAUUCUUCC CUUAA                                                          15

(2) INFORMATION FOR SEQ ID NO:237:

(i) SEQUENCE CHARACTERISTICS:
            (A) LENGTH:         15 base pairs
            (B) TYPE:           nucleic acid
```

```
        (C) STRANDEDNESS:    single
        (D) TOPOLOGY:        linear (xi) SEQUENCE DESCRIPTION: SEQ ID NO:237:

CAUUCUUCCC UUAAC                                                    15

(2) INFORMATION FOR SEQ ID NO:238:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:238:

CUUCCCUUAA CAAAU                                                    15

(2) INFORMATION FOR SEQ ID NO:239:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:239:

UUCCCUUAAC AAAUU                                                    15

(2) INFORMATION FOR SEQ ID NO:240:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:240:

AACAAAUUUA AGCUG                                                    15

(2) INFORMATION FOR SEQ ID NO:241:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:241:

ACAAAUUUAA GCUGU                                                    15

(2) INFORMATION FOR SEQ ID NO:242:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:242:

CAAAUUUAAG CUGUU                                                    15

(2) INFORMATION FOR SEQ ID NO:243:

(i) SEQUENCE CHARACTERISTICS:
        (A) LENGTH:          15 base pairs
        (B) TYPE:            nucleic acid
        (C) STRANDEDNESS:    single
```

```
          (D) TOPOLOGY:       linear (xi) SEQUENCE DESCRIPTION: SEQ ID NO:243:

AAGCUGUUUU ACCCA                                                    15

(2) INFORMATION FOR SEQ ID NO:244:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:244:

AGCUGUUUUA CCCAC                                                    15

(2) INFORMATION FOR SEQ ID NO:245:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:245:

GCUGUUUUAC CCACU                                                    15

(2) INFORMATION FOR SEQ ID NO:246:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:246:

CUGUUUUACC CACUA                                                    15

(2) INFORMATION FOR SEQ ID NO:247:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:247:

ACCCACUACC UCACC                                                    15

(2) INFORMATION FOR SEQ ID NO:248:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:248:

ACUACCUCAC CUUCU                                                    15

(2) INFORMATION FOR SEQ ID NO:249:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear
```

(xi) SEQUENCE DESCRIPTION: SEQ ID NO:249:

CUCACCUUCU UAAAA                                                              15

(2) INFORMATION FOR SEQ ID NO:250:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:250:

UCACCUUCUU AAAAA                                                              15

(2) INFORMATION FOR SEQ ID NO:251:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:251:

ACCUUCUUAA AAACC                                                              15

(2) INFORMATION FOR SEQ ID NO:252:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:252:

CCUUCUUAAA AACCU                                                              15

(2) INFORMATION FOR SEQ ID NO:253:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:253:

AAAACCUCUU UCAGA                                                              15

(2) INFORMATION FOR SEQ ID NO:254:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:254:

AACCUCUUUC AGAUU                                                              15

(2) INFORMATION FOR SEQ ID NO:255:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear -continued (xi) SEQUENCE DESCRIPTION: SEQ ID NO:255:

ACCUCUUUCA GAUUA                                              15

(2) INFORMATION FOR SEQ ID NO:256:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:256:

CCUCUUUCAG AUUAA                                              15

(2) INFORMATION FOR SEQ ID NO:257:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:257:

UUCAGAUUAA GCUGA                                              15

(2) INFORMATION FOR SEQ ID NO:258:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:258:

UCAGAUUAAG CUGAA                                              15

(2) INFORMATION FOR SEQ ID NO:259:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:259:

GAACAGUUAC AAGAU                                              15

(2) INFORMATION FOR SEQ ID NO:260:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:260:

AACAGUUACA AGAUG                                              15

(2) INFORMATION FOR SEQ ID NO:261:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:261:

CUGGCAUCCC UCUCC                                                    15

(2) INFORMATION FOR SEQ ID NO:262:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:262:

CAUCCCUCUC CUUUC                                                    15

(2) INFORMATION FOR SEQ ID NO:263:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:263:

UCCCUCUCCU UUCUC                                                    15

(2) INFORMATION FOR SEQ ID NO:264:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:264:

CUCUCCUUUC UCCCC                                                    15

(2) INFORMATION FOR SEQ ID NO:265:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:265:

UCUCCUUUCU CCCCA                                                    15

(2) INFORMATION FOR SEQ ID NO:266:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:266:

CUCCUUUCUC CCCAU                                                    15

(2) INFORMATION FOR SEQ ID NO:267:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:267:

```
CCUUUCUCCC CAUAU                                                         15

(2) INFORMATION FOR SEQ ID NO:268:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:268:

UCCCCAUAUG CAAUU                                                         15

(2) INFORMATION FOR SEQ ID NO:269:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:269:

AUGCAAUUUG CUUAA                                                         15

(2) INFORMATION FOR SEQ ID NO:270:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:270:

UGCAAUUUGC UUAAU                                                         15

(2) INFORMATION FOR SEQ ID NO:271:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:271:

AUUUGCUUAA UGUAA                                                         15

(2) INFORMATION FOR SEQ ID NO:272:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:272:

UUUGCUUAAU GUAAC                                                         15

(2) INFORMATION FOR SEQ ID NO:273:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:273:

UUAAUGUAAC CUCUU                                                         15
```

(2) INFORMATION FOR SEQ ID NO:274:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:274:

GUAACCUCUU CUUUU                                             15

(2) INFORMATION FOR SEQ ID NO:275:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:275:

AACCUCUUCU UUUGC                                             15

(2) INFORMATION FOR SEQ ID NO:276:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:276:

ACCUCUUCUU UUGCC                                             15

(2) INFORMATION FOR SEQ ID NO:277:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:277:

CUCUUCUUUU GCCAU                                             15

(2) INFORMATION FOR SEQ ID NO:278:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:278:

UCUUCUUUUG CCAUG                                             15

(2) INFORMATION FOR SEQ ID NO:279:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:279:

CUUCUUUUGC CAUGU                                             15

(2) INFORMATION FOR SEQ ID NO:280:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:280:

GCCAUGUUUC CAUUC                                                        15

(2) INFORMATION FOR SEQ ID NO:281:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:281:

CCAUGUUUCC AUUCU                                                        15

(2) INFORMATION FOR SEQ ID NO:282:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:282:

CAUGUUUCCA UUCUG                                                        15

(2) INFORMATION FOR SEQ ID NO:283:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:283:

UUUCCAUUCU GCCAU                                                        15

(2) INFORMATION FOR SEQ ID NO:284:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:284:

UUCCAUUCUG CCAUC                                                        15

(2) INFORMATION FOR SEQ ID NO:285:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:285:

CUGCCAUCUU GAAUU                                                        15

(2) INFORMATION FOR SEQ ID NO:286:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:286:

GCCAUCUUGA AUUGU                                          15

(2) INFORMATION FOR SEQ ID NO:287:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:287:

CUUGAAUUGU CUUGU                                          15

(2) INFORMATION FOR SEQ ID NO:288:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:288:

GAAUUGUCUU GUCAG                                          15

(2) INFORMATION FOR SEQ ID NO:289:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:289:

AUUGUCUUGU CAGCC                                          15

(2) INFORMATION FOR SEQ ID NO:290:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:290:

GUCUUGUCAG CCAAU                                          15

(2) INFORMATION FOR SEQ ID NO:291:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:291:

AGCCAAUUCA UUAUC                                          15

(2) INFORMATION FOR SEQ ID NO:292:

```
        (i) SEQUENCE CHARACTERISTICS:
              (A) LENGTH:        15 base pairs
              (B) TYPE:          nucleic acid
              (C) STRANDEDNESS:  single
              (D) TOPOLOGY:      linear (xi) SEQUENCE DESCRIPTION: SEQ ID NO:292:

GCCAAUUCAU UAUCU                                                        15

(2) INFORMATION FOR SEQ ID NO:293:

(i) SEQUENCE CHARACTERISTICS:
              (A) LENGTH:        15 base pairs
              (B) TYPE:          nucleic acid
              (C) STRANDEDNESS:  single
              (D) TOPOLOGY:      linear (xi) SEQUENCE DESCRIPTION: SEQ ID NO:293:

AAUUCAUUAU CUAUU                                                        15

(2) INFORMATION FOR SEQ ID NO:294:

(i) SEQUENCE CHARACTERISTICS:
              (A) LENGTH:        15 base pairs
              (B) TYPE:          nucleic acid
              (C) STRANDEDNESS:  single
              (D) TOPOLOGY:      linear (xi) SEQUENCE DESCRIPTION: SEQ ID NO:294:

AUUCAUUAUC UAUUA                                                        15

(2) INFORMATION FOR SEQ ID NO:295:

(i) SEQUENCE CHARACTERISTICS:
              (A) LENGTH:        15 base pairs
              (B) TYPE:          nucleic acid
              (C) STRANDEDNESS:  single
              (D) TOPOLOGY:      linear (xi) SEQUENCE DESCRIPTION: SEQ ID NO:295:

UCAUUAUCUA UUAAA                                                        15

(2) INFORMATION FOR SEQ ID NO:296:

(i) SEQUENCE CHARACTERISTICS:
              (A) LENGTH:        15 base pairs
              (B) TYPE:          nucleic acid
              (C) STRANDEDNESS:  single
              (D) TOPOLOGY:      linear (xi) SEQUENCE DESCRIPTION: SEQ ID NO:296:

AUUAUCUAUU AAACA                                                        15

(2) INFORMATION FOR SEQ ID NO:297:

(i) SEQUENCE CHARACTERISTICS:
              (A) LENGTH:        15 base pairs
              (B) TYPE:          nucleic acid
              (C) STRANDEDNESS:  single
              (D) TOPOLOGY:      linear (xi) SEQUENCE DESCRIPTION: SEQ ID NO:297:

UAUCUAUUAA ACACU                                                        15

(2) INFORMATION FOR SEQ ID NO:298:
```

```
       (i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:298:

AUCUAUUAAA CACUA                                                           15

(2) INFORMATION FOR SEQ ID NO:299:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:299:

AAACACUAAU UUGAG                                                           15

(2) INFORMATION FOR SEQ ID NO:300:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:300:

CUUUACACUG AUGAGGCCGA AAGGCCGAAA GGGUUU                                    36

(2) INFORMATION FOR SEQ ID NO:301:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:301:

GUUACUUCUG AUGAGGCCGA AAGGCCGAAA CAGAGG                                    36

(2) INFORMATION FOR SEQ ID NO:302:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:302:

CUUCUGUCUG AUGAGGCCGA AAGGCCGAAA CUUUAC                                    36

(2) INFORMATION FOR SEQ ID NO:303:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:303:

CCCUUCUCUG AUGAGGCCGA AAGGCCGAAA CUUCUG                                    36

(2) INFORMATION FOR SEQ ID NO:304:

(i) SEQUENCE CHARACTERISTICS:
```

```
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:304:

CCCCUUCCUG AUGAGGCCGA AAGGCCGAAA ACUUCU                              36

(2) INFORMATION FOR SEQ ID NO:305:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:305:

GAGAGGCCUG AUGAGGCCGA AAGGCCGAAA CAUUUC                              36

(2) INFORMATION FOR SEQ ID NO:306:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:306:

CUUCAGACUG AUGAGGCCGA AAGGCCGAAA GGCGAC                              36

(2) INFORMATION FOR SEQ ID NO:307:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:307:

AUCUUCACUG AUGAGGCCGA AAGGCCGAAA GAGGCG                              36

(2) INFORMATION FOR SEQ ID NO:308:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:308:

UUUGGGUCUG AUGAGGCCGA AAGGCCGAAA UCUUCA                              36

(2) INFORMATION FOR SEQ ID NO:309:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:309:

CUUUGGGCUG AUGAGGCCGA AAGGCCGAAA AUCUUC                              36

(2) INFORMATION FOR SEQ ID NO:310:

(i) SEQUENCE CHARACTERISTICS:
            (A) LENGTH:         36 base pairs
```

```
            (B) TYPE:            nucleic acid
            (C) STRANDEDNESS:    single
            (D) TOPOLOGY:        linear (xi) SEQUENCE DESCRIPTION: SEQ ID NO:310:

AAUGACACUG AUGAGGCCGA AAGGCCGAAA UCACUU                                36

(2) INFORMATION FOR SEQ ID NO:311:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:311:

CAAUGACCUG AUGAGGCCGA AAGGCCGAAA AUCACU                                36

(2) INFORMATION FOR SEQ ID NO:312:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:312:

AAGCAAUCUG AUGAGGCCGA AAGGCCGAAA CAAAUC                                36

(2) INFORMATION FOR SEQ ID NO:313:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:313:

AUAAAGCCUG AUGAGGCCGA AAGGCCGAAA UGACAA                                36

(2) INFORMATION FOR SEQ ID NO:314:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:314:

GUCUAUACUG AUGAGGCCGA AAGGCCGAAA GCAAUG                                36

(2) INFORMATION FOR SEQ ID NO:315:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:315:

AGUCUAUCUG AUGAGGCCGA AAGGCCGAAA AGCAAU                                36

(2) INFORMATION FOR SEQ ID NO:316:

(i) SEQUENCE CHARACTERISTICS:
            (A) LENGTH:          36 base pairs
            (B) TYPE:            nucleic acid
```

```
            (C) STRANDEDNESS:     single
            (D) TOPOLOGY:         linear (xi) SEQUENCE DESCRIPTION: SEQ ID NO:316:

CAGUCUACUG AUGAGGCCGA AAGGCCGAAA AAGCAA                                    36

(2) INFORMATION FOR SEQ ID NO:317:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:317:

UACAGUCCUG AUGAGGCCGA AAGGCCGAAA UAAAGC                                    36

(2) INFORMATION FOR SEQ ID NO:318:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:318:

CUCUUCUCUG AUGAGGCCGA AAGGCCGAAA CAGUCU                                    36

(2) INFORMATION FOR SEQ ID NO:319:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:319:

CUUCUGACUG AUGAGGCCGA AAGGCCGAAA UGUUCU                                    36

(2) INFORMATION FOR SEQ ID NO:320:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:320:

CACUUCUCUG AUGAGGCCGA AAGGCCGAAA GAUGUU                                    36

(2) INFORMATION FOR SEQ ID NO:321:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:321:

AGGGUAACUG AUGAGGCCGA AAGGCCGAAA CUCCAC                                    36

(2) INFORMATION FOR SEQ ID NO:322:

(i) SEQUENCE CHARACTERISTICS:
            (A) LENGTH:           36 base pairs
            (B) TYPE:             nucleic acid
            (C) STRANDEDNESS:     single
```

(D) TOPOLOGY:         linear (xi) SEQUENCE DESCRIPTION: SEQ ID NO:322:

UCAGGGUCUG AUGAGGCCGA AAGGCCGAAA GACUCC                                36

(2) INFORMATION FOR SEQ ID NO:323:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:323:

UUCAGGGCUG AUGAGGCCGA AAGGCCGAAA AGACUC                                36

(2) INFORMATION FOR SEQ ID NO:324:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:324:

AUCCUUUCUG AUGAGGCCGA AAGGCCGAAA UUUCAG                                36

(2) INFORMATION FOR SEQ ID NO:325:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:325:

UUCUUUACUG AUGAGGCCGA AAGGCCGAAA UCCUUU                                36

(2) INFORMATION FOR SEQ ID NO:326:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:326:

UUUCUUUCUG AUGAGGCCGA AAGGCCGAAA AUCCUU                                36

(2) INFORMATION FOR SEQ ID NO:327:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:327:

UUUUCUUCUG AUGAGGCCGA AAGGCCGAAA AAUCCU                                36

(2) INFORMATION FOR SEQ ID NO:328:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:328:

GAAGAAACUG AUGAGGCCGA AAGGCCGAAA UUCCAC                                    36

(2) INFORMATION FOR SEQ ID NO:329:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:329:

UGAAGAACUG AUGAGGCCGA AAGGCCGAAA AUUCCA                                    36

(2) INFORMATION FOR SEQ ID NO:330:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:330:

CUGAAGACUG AUGAGGCCGA AAGGCCGAAA AAUUCC                                    36

(2) INFORMATION FOR SEQ ID NO:331:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:331:

GCUGAAGCUG AUGAGGCCGA AAGGCCGAAA AAAUUC                                    36

(2) INFORMATION FOR SEQ ID NO:332:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:332:

UGCUGAACUG AUGAGGCCGA AAGGCCGAAA AAAAUU                                    36

(2) INFORMATION FOR SEQ ID NO:333:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:333:

CUUGCUGCUG AUGAGGCCGA AAGGCCGAAA GAAAAA                                    36

(2) INFORMATION FOR SEQ ID NO:334:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:334:

GCUUGCUCUG AUGAGGCCGA AAGGCCGAAA AGAAAA                    36

(2) INFORMATION FOR SEQ ID NO:335:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:335:

GUGGAUUCUG AUGAGGCCGA AAGGCCGAAA GUUUCA                    36

(2) INFORMATION FOR SEQ ID NO:336:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:336:

GGUUGUGCUG AUGAGGCCGA AAGGCCGAAA UUUAGU                    36

(2) INFORMATION FOR SEQ ID NO:337:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:337:

GUCUCCACUG AUGAGGCCGA AAGGCCGAAA GGUUGU                    36

(2) INFORMATION FOR SEQ ID NO:338:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:338:

GGUCUCCCUG AUGAGGCCGA AAGGCCGAAA AGGUUG                    36

(2) INFORMATION FOR SEQ ID NO:339:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:339:

GAGAUUGCUG AUGAGGCCGA AAGGCCGAAA GGGUGU                    36

(2) INFORMATION FOR SEQ ID NO:340:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:340:

ACACAGACUG AUGAGGCCGA AAGGCCGAAA UUGGAG                                    36

(2) INFORMATION FOR SEQ ID NO:341:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:341:

ACACACACUG AUGAGGCCGA AAGGCCGAAA GAUUGG                                    36

(2) INFORMATION FOR SEQ ID NO:342:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:342:

UUUACAACUG AUGAGGCCGA AAGGCCGAAA CACACA                                    36

(2) INFORMATION FOR SEQ ID NO:343:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:343:

GUUUACACUG AUGAGGCCGA AAGGCCGAAA ACACAC                                    36

(2) INFORMATION FOR SEQ ID NO:344:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:344:

UGUUUACCUG AUGAGGCCGA AAGGCCGAAA AACACA                                    36

(2) INFORMATION FOR SEQ ID NO:345:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:345:

UGAUGUUCUG AUGAGGCCGA AAGGCCGAAA CAAAAC                                    36

(2) INFORMATION FOR SEQ ID NO:346:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:346:

```
CUCCAGUCUG AUGAGGCCGA AAGGCCGAAA UGUUUA                                   36

(2) INFORMATION FOR SEQ ID NO:347:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:347:

CGUAGAACUG AUGAGGCCGA AAGGCCGAAA CCCUCC                                   36

(2) INFORMATION FOR SEQ ID NO:348:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:348:

CACGUAGCUG AUGAGGCCGA AAGGCCGAAA GACCCU                                   36

(2) INFORMATION FOR SEQ ID NO:349:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:349:

UCACGUACUG AUGAGGCCGA AAGGCCGAAA AGACCC                                   36

(2) INFORMATION FOR SEQ ID NO:350:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:350:

GCUCACGCUG AUGAGGCCGA AAGGCCGAAA GAAGAC                                   36

(2) INFORMATION FOR SEQ ID NO:351:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:351:

ACAAUCCCUG AUGAGGCCGA AAGGCCGAAA UUGCUC                                   36

(2) INFORMATION FOR SEQ ID NO:352:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:352:

UGAUGACCUG AUGAGGCCGA AAGGCCGAAA UCCAAU                                   36
```

(2) INFORMATION FOR SEQ ID NO:353:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:353:

GGCUGAUCUG AUGAGGCCGA AAGGCCGAAA CAAUCC                      36

(2) INFORMATION FOR SEQ ID NO:354:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:354:

CAGGGCUCUG AUGAGGCCGA AAGGCCGAAA UGACAA                      36

(2) INFORMATION FOR SEQ ID NO:355:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:355:

GGUGCAACUG AUGAGGCCGA AAGGCCGAAA CAGGCA                      36

(2) INFORMATION FOR SEQ ID NO:356:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:356:

AGGUGCACUG AUGAGGCCGA AAGGCCGAAA ACAGGC                      36

(2) INFORMATION FOR SEQ ID NO:357:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:357:

CAGGUGCCUG AUGAGGCCGA AAGGCCGAAA AACAGG                      36

(2) INFORMATION FOR SEQ ID NO:358:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:358:

CAAGUAACUG AUGAGGCCGA AAGGCCGAAA CCAGGG                      36

(2) INFORMATION FOR SEQ ID NO:359:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:359:

CCCAAGUCUG AUGAGGCCGA AAGGCCGAAA GACCAG                                     36

(2) INFORMATION FOR SEQ ID NO:360:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:360:

ACCCAAGCUG AUGAGGCCGA AAGGCCGAAA AGACCA                                     36

(2) INFORMATION FOR SEQ ID NO:361:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:361:

UGGACCCCUG AUGAGGCCGA AAGGCCGAAA GUAAGA                                     36

(2) INFORMATION FOR SEQ ID NO:362:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:362:

CAAUUUGCUG AUGAGGCCGA AAGGCCGAAA CCCAAG                                     36

(2) INFORMATION FOR SEQ ID NO:363:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:363:

AGCCAACCUG AUGAGGCCGA AAGGCCGAAA UUUGGA                                     36

(2) INFORMATION FOR SEQ ID NO:364:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:364:

GAAAGCCCUG AUGAGGCCGA AAGGCCGAAA CAAUUU                                     36

(2) INFORMATION FOR SEQ ID NO:365:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:365:

AAAGUGACUG AUGAGGCCGA AAGGCCGAAA GCCAAC                                      36

(2) INFORMATION FOR SEQ ID NO:366:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:366:

AAAAGUGCUG AUGAGGCCGA AAGGCCGAAA AGCCAA                                      36

(2) INFORMATION FOR SEQ ID NO:367:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:367:

CAAAAGUCUG AUGAGGCCGA AAGGCCGAAA AAGCCA                                      36

(2) INFORMATION FOR SEQ ID NO:368:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:368:

GGGUCAACUG AUGAGGCCGA AAGGCCGAAA GUGAAA                                      36

(2) INFORMATION FOR SEQ ID NO:369:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:369:

AGGGUCACUG AUGAGGCCGA AAGGCCGAAA AGUGAA                                      36

(2) INFORMATION FOR SEQ ID NO:370:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:370:

UAGGGUCCUG AUGAGGCCGA AAGGCCGAAA AAGUGA                                      36

(2) INFORMATION FOR SEQ ID NO:371:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:371:

AGAUGCUCUG AUGAGGCCGA AAGGCCGAAA GGGUCA                           36

(2) INFORMATION FOR SEQ ID NO:372:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:372:

GGCUUCACUG AUGAGGCCGA AAGGCCGAAA UGCUUA                           36

(2) INFORMATION FOR SEQ ID NO:373:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:373:

GGAUGGUCUG AUGAGGCCGA AAGGCCGAAA UGUUCC                           36

(2) INFORMATION FOR SEQ ID NO:374:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:374:

ACACUUGCUG AUGAGGCCGA AAGGCCGAAA UGGUGA                           36

(2) INFORMATION FOR SEQ ID NO:375:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:375:

AGGUAUGCUG AUGAGGCCGA AAGGCCGAAA CACUUG                           36

(2) INFORMATION FOR SEQ ID NO:376:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:376:

AUUGAGGCUG AUGAGGCCGA AAGGCCGAAA UGGACA                           36

(2) INFORMATION FOR SEQ ID NO:377:

```
        (i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:377:

AGAAAUUCUG AUGAGGCCGA AAGGCCGAAA GGUAUG                              36

(2) INFORMATION FOR SEQ ID NO:378:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:378:

UGAAAGACUG AUGAGGCCGA AAGGCCGAAA UUGAGG                              36

(2) INFORMATION FOR SEQ ID NO:379:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:379:

CUGAAAGCUG AUGAGGCCGA AAGGCCGAAA AUUGAG                              36

(2) INFORMATION FOR SEQ ID NO:380:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:380:

GCUGAAACUG AUGAGGCCGA AAGGCCGAAA AAUUGA                              36

(2) INFORMATION FOR SEQ ID NO:381:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:381:

GAGCUGACUG AUGAGGCCGA AAGGCCGAAA GAAAUU                              36

(2) INFORMATION FOR SEQ ID NO:382:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:382:

AGAGCUGCUG AUGAGGCCGA AAGGCCGAAA AGAAAU                              36

(2) INFORMATION FOR SEQ ID NO:383:

(i) SEQUENCE CHARACTERISTICS:
```

```
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO:383:

AAGAGCUCUG AUGAGGCCGA AAGGCCGAAA AAGAAA                              36

(2) INFORMATION FOR SEQ ID NO:384:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO:384:

GCACCAACUG AUGAGGCCGA AAGGCCGAAA GCUGAA                              36

(2) INFORMATION FOR SEQ ID NO:385:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO:385:

CAGCACCCUG AUGAGGCCGA AAGGCCGAAA GAGCUG                              36

(2) INFORMATION FOR SEQ ID NO:386:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO:386:

UGAGAAACUG AUGAGGCCGA AAGGCCGAAA CCAGCC                              36

(2) INFORMATION FOR SEQ ID NO:387:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO:387:

AGUGAGACUG AUGAGGCCGA AAGGCCGAAA GACCAG                              36

(2) INFORMATION FOR SEQ ID NO:388:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO:388:

AAGUGAGCUG AUGAGGCCGA AAGGCCGAAA AGACCA                              36

(2) INFORMATION FOR SEQ ID NO:389:

(i) SEQUENCE CHARACTERISTICS:
        (A) LENGTH:           36 base pairs
```

(B) TYPE:           nucleic acid
        (C) STRANDEDNESS:   single
        (D) TOPOLOGY:       linear (xi) SEQUENCE DESCRIPTION: SEQ ID NO:389:

GAAGUGACUG AUGAGGCCGA AAGGCCGAAA AAGACC                         36

(2) INFORMATION FOR SEQ ID NO:390:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:390:

CAGAAGUCUG AUGAGGCCGA AAGGCCGAAA GAAAGA                         36

(2) INFORMATION FOR SEQ ID NO:391:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:391:

UGAACAGCUG AUGAGGCCGA AAGGCCGAAA GUGAGA                         36

(2) INFORMATION FOR SEQ ID NO:392:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:392:

CUGAACACUG AUGAGGCCGA AAGGCCGAAA AGUGAG                         36

(2) INFORMATION FOR SEQ ID NO:393:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:393:

ACACCUGCUG AUGAGGCCGA AAGGCCGAAA CAGAAG                         36

(2) INFORMATION FOR SEQ ID NO:394:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:394:

AACACCUCUG AUGAGGCCGA AAGGCCGAAA ACAGAA                         36

(2) INFORMATION FOR SEQ ID NO:395:

(i) SEQUENCE CHARACTERISTICS:
        (A) LENGTH:         36 base pairs
        (B) TYPE:           nucleic acid

```
              (C) STRANDEDNESS:   single
              (D) TOPOLOGY:       linear (xi) SEQUENCE DESCRIPTION: SEQ ID NO:395:

CGUGGAUCUG AUGAGGCCGA AAGGCCGAAA CACCUG                              36

(2) INFORMATION FOR SEQ ID NO:396:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:396:

ACGUGGACUG AUGAGGCCGA AAGGCCGAAA ACACCU                              36

(2) INFORMATION FOR SEQ ID NO:397:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:397:

UCACGUGCUG AUGAGGCCGA AAGGCCGAAA UAACAC                              36

(2) INFORMATION FOR SEQ ID NO:398:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:398:

ACCACAGCUG AUGAGGCCGA AAGGCCGAAA CAGCGU                              36

(2) INFORMATION FOR SEQ ID NO:399:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:399:

ACAUUGUCUG AUGAGGCCGA AAGGCCGAAA CCACAG                              36

(2) INFORMATION FOR SEQ ID NO:400:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:400:

CAACAGACUG AUGAGGCCGA AAGGCCGAAA CAUUGU                              36

(2) INFORMATION FOR SEQ ID NO:401:

(i) SEQUENCE CHARACTERISTICS:
              (A) LENGTH:         36 base pairs
              (B) TYPE:           nucleic acid
              (C) STRANDEDNESS:   single
```

(D) TOPOLOGY: linear (xi) SEQUENCE DESCRIPTION: SEQ ID NO:401:

UCAACAGCUG AUGAGGCCGA AAGGCCGAAA ACAUUG                    36

(2) INFORMATION FOR SEQ ID NO:402:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:402:

UUCAACACUG AUGAGGCCGA AAGGCCGAAA AACAUU                    36

(2) INFORMATION FOR SEQ ID NO:403:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:403:

GCUCUUCCUG AUGAGGCCGA AAGGCCGAAA CAGAAA                    36

(2) INFORMATION FOR SEQ ID NO:404:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:404:

UAGAUGCCUG AUGAGGCCGA AAGGCCGAAA GUUUGU                    36

(2) INFORMATION FOR SEQ ID NO:405:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:405:

GCCAGUACUG AUGAGGCCGA AAGGCCGAAA UGCGAG                    36

(2) INFORMATION FOR SEQ ID NO:406:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:406:

UUGCCAGCUG AUGAGGCCGA AAGGCCGAAA GAUGCG                    36

(2) INFORMATION FOR SEQ ID NO:407:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:407:

GACAUCACUG AUGAGGCCGA AAGGCCGAAA GUCAGC          36

(2) INFORMATION FOR SEQ ID NO:408:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:408:

GUCCCCACUG AUGAGGCCGA AAGGCCGAAA CAUCAU          36

(2) INFORMATION FOR SEQ ID NO:409:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:409:

GGCCAUACUG AUGAGGCCGA AAGGCCGAAA UUCAUG          36

(2) INFORMATION FOR SEQ ID NO:410:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:410:

CGGGCCACUG AUGAGGCCGA AAGGCCGAAA UAUUCA          36

(2) INFORMATION FOR SEQ ID NO:411:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:411:

GUUCUUGCUG AUGAGGCCGA AAGGCCGAAA CUCGGG          36

(2) INFORMATION FOR SEQ ID NO:412:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:412:

UAUCAAACUG AUGAGGCCGA AAGGCCGAAA UGGUCC          36

(2) INFORMATION FOR SEQ ID NO:413:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:413:

GAUAUCACUG AUGAGGCCGA AAGGCCGAAA GAUGGU                                          36

(2) INFORMATION FOR SEQ ID NO:414:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:414:

UGAUAUCCUG AUGAGGCCGA AAGGCCGAAA AGAUGG                                          36

(2) INFORMATION FOR SEQ ID NO:415:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:415:

UUAGUGACUG AUGAGGCCGA AAGGCCGAAA UCAAAG                                          36

(2) INFORMATION FOR SEQ ID NO:416:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:416:

UAUUAGUCUG AUGAGGCCGA AAGGCCGAAA UAUCAA                                          36

(2) INFORMATION FOR SEQ ID NO:417:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:417:

AGGUUAUCUG AUGAGGCCGA AAGGCCGAAA GUGAUA                                          36

(2) INFORMATION FOR SEQ ID NO:418:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:418:

GAGAGGUCUG AUGAGGCCGA AAGGCCGAAA UUAGUG                                          36

(2) INFORMATION FOR SEQ ID NO:419:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:419:

CAAUGGACUG AUGAGGCCGA AAGGCCGAAA GGUUAU                                              36

(2) INFORMATION FOR SEQ ID NO:420:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:420:

CACAAUGCUG AUGAGGCCGA AAGGCCGAAA GAGGUU                                              36

(2) INFORMATION FOR SEQ ID NO:421:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:421:

GGAUCACCUG AUGAGGCCGA AAGGCCGAAA UGGAGA                                              36

(2) INFORMATION FOR SEQ ID NO:422:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:422:

GAGCCAGCUG AUGAGGCCGA AAGGCCGAAA UCACAA                                              36

(2) INFORMATION FOR SEQ ID NO:423:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:423:

GGGCGCACUG AUGAGGCCGA AAGGCCGAAA GCCAGG                                              36

(2) INFORMATION FOR SEQ ID NO:424:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:424:

CUCGUCACUG AUGAGGCCGA AAGGCCGAAA UGGGCG                                              36

(2) INFORMATION FOR SEQ ID NO:425:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:425:

```
ACACUCGCUG AUGAGGCCGA AAGGCCGAAA UGUGCC                                        36

(2) INFORMATION FOR SEQ ID NO:426:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:426:

UCAGAACCUG AUGAGGCCGA AAGGCCGAAA CACACU                                        36

(2) INFORMATION FOR SEQ ID NO:427:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:427:

ACUUCAGCUG AUGAGGCCGA AAGGCCGAAA CAACAC                                        36

(2) INFORMATION FOR SEQ ID NO:428:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:428:

UACUUCACUG AUGAGGCCGA AAGGCCGAAA ACAACA                                        36

(2) INFORMATION FOR SEQ ID NO:429:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:429:

UUUUUCACUG AUGAGGCCGA AAGGCCGAAA CUUCAG                                        36

(2) INFORMATION FOR SEQ ID NO:430:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:430:

CGCUUGACUG AUGAGGCCGA AAGGCCGAAA GCGUCU                                        36

(2) INFORMATION FOR SEQ ID NO:431:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:431:

CCGCUUGCUG AUGAGGCCGA AAGGCCGAAA AGCGUC                                        36
```

(2) INFORMATION FOR SEQ ID NO:432:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:432:

CCCGCUUCUG AUGAGGCCGA AAGGCCGAAA AAGCGU                      36

(2) INFORMATION FOR SEQ ID NO:433:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:433:

GACUGAUCUG AUGAGGCCGA AAGGCCGAAA CGUCAC                      36

(2) INFORMATION FOR SEQ ID NO:434:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:434:

UGACUGACUG AUGAGGCCGA AAGGCCGAAA ACGUCA                      36

(2) INFORMATION FOR SEQ ID NO:435:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:435:

UUUGACUCUG AUGAGGCCGA AAGGCCGAAA UAACGU                      36

(2) INFORMATION FOR SEQ ID NO:436:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:436:

CAGCUUUCUG AUGAGGCCGA AAGGCCGAAA CUGAUA                      36

(2) INFORMATION FOR SEQ ID NO:437:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:437:

UGUAGGGCUG AUGAGGCCGA AAGGCCGAAA GUCAGC                      36

(2) INFORMATION FOR SEQ ID NO:438:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:438:

GUGUAGGCUG AUGAGGCCGA AAGGCCGAAA AGUCAG                              36

(2) INFORMATION FOR SEQ ID NO:439:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:439:

CUAGGUGCUG AUGAGGCCGA AAGGCCGAAA GGGAAG                              36

(2) INFORMATION FOR SEQ ID NO:440:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:440:

GAUAUACCUG AUGAGGCCGA AAGGCCGAAA GGUGUA                              36

(2) INFORMATION FOR SEQ ID NO:441:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:441:

UCAGAUACUG AUGAGGCCGA AAGGCCGAAA CUAGGU                              36

(2) INFORMATION FOR SEQ ID NO:442:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:442:

AGUCAGACUG AUGAGGCCGA AAGGCCGAAA UACUAG                              36

(2) INFORMATION FOR SEQ ID NO:443:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:443:

AAAGUCACUG AUGAGGCCGA AAGGCCGAAA UAUACU                              36

(2) INFORMATION FOR SEQ ID NO:444:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:444:

AAUUUCACUG AUGAGGCCGA AAGGCCGAAA GUCAGA                                      36

(2) INFORMATION FOR SEQ ID NO:445:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:445:

GAAUUUCCUG AUGAGGCCGA AAGGCCGAAA AGUCAG                                      36

(2) INFORMATION FOR SEQ ID NO:446:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:446:

AAGUUGGCUG AUGAGGCCGA AAGGCCGAAA UUUCAA                                      36

(2) INFORMATION FOR SEQ ID NO:447:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:447:

GAAGUUGCUG AUGAGGCCGA AAGGCCGAAA AUUUCA                                      36

(2) INFORMATION FOR SEQ ID NO:448:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:448:

AUAUUAGCUG AUGAGGCCGA AAGGCCGAAA GUUGGA                                      36

(2) INFORMATION FOR SEQ ID NO:449:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:449:

AAUAUUACUG AUGAGGCCGA AAGGCCGAAA AGUUGG                                      36

(2) INFORMATION FOR SEQ ID NO:450:

```
       (i) SEQUENCE CHARACTERISTICS:
             (A) LENGTH:          36 base pairs
             (B) TYPE:            nucleic acid
             (C) STRANDEDNESS:    single
             (D) TOPOLOGY:        linear (xi) SEQUENCE DESCRIPTION: SEQ ID NO:450:

CUAAUAUCUG AUGAGGCCGA AAGGCCGAAA GAAGUU                              36

(2) INFORMATION FOR SEQ ID NO:451:

(i) SEQUENCE CHARACTERISTICS:
             (A) LENGTH:          36 base pairs
             (B) TYPE:            nucleic acid
             (C) STRANDEDNESS:    single
             (D) TOPOLOGY:        linear (xi) SEQUENCE DESCRIPTION: SEQ ID NO:451:

CUUCUAACUG AUGAGGCCGA AAGGCCGAAA UUAGAA                              36

(2) INFORMATION FOR SEQ ID NO:452:

(i) SEQUENCE CHARACTERISTICS:
             (A) LENGTH:          36 base pairs
             (B) TYPE:            nucleic acid
             (C) STRANDEDNESS:    single
             (D) TOPOLOGY:        linear (xi) SEQUENCE DESCRIPTION: SEQ ID NO:452:

UCCUUCUCUG AUGAGGCCGA AAGGCCGAAA UAUUAG                              36

(2) INFORMATION FOR SEQ ID NO:453:

(i) SEQUENCE CHARACTERISTICS:
             (A) LENGTH:          36 base pairs
             (B) TYPE:            nucleic acid
             (C) STRANDEDNESS:    single
             (D) TOPOLOGY:        linear (xi) SEQUENCE DESCRIPTION: SEQ ID NO:453:

AUCCUUCCUG AUGAGGCCGA AAGGCCGAAA AUAUUA                              36

(2) INFORMATION FOR SEQ ID NO:454:

(i) SEQUENCE CHARACTERISTICS:
             (A) LENGTH:          36 base pairs
             (B) TYPE:            nucleic acid
             (C) STRANDEDNESS:    single
             (D) TOPOLOGY:        linear (xi) SEQUENCE DESCRIPTION: SEQ ID NO:454:

AGCAAAUCUG AUGAGGCCGA AAGGCCGAAA UCCUUC                              36

(2) INFORMATION FOR SEQ ID NO:455:

(i) SEQUENCE CHARACTERISTICS:
             (A) LENGTH:          36 base pairs
             (B) TYPE:            nucleic acid
             (C) STRANDEDNESS:    single
             (D) TOPOLOGY:        linear (xi) SEQUENCE DESCRIPTION: SEQ ID NO:455:

UUGAGCACUG AUGAGGCCGA AAGGCCGAAA UUAUCC                              36

(2) INFORMATION FOR SEQ ID NO:456:
```

```
    (i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:456:

GUUGAGCCUG AUGAGGCCGA AAGGCCGAAA AUUAUC                           36

(2) INFORMATION FOR SEQ ID NO:457:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:457:

AGAGGUUCUG AUGAGGCCGA AAGGCCGAAA GCAAAU                           36

(2) INFORMATION FOR SEQ ID NO:458:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:458:

ACCUCCACUG AUGAGGCCGA AAGGCCGAAA GGUUGA                           36

(2) INFORMATION FOR SEQ ID NO:459:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:459:

UCUGGAACUG AUGAGGCCGA AAGGCCGAAA CCUCCA                           36

(2) INFORMATION FOR SEQ ID NO:460:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:460:

CUCUGGACUG AUGAGGCCGA AAGGCCGAAA ACCUCC                           36

(2) INFORMATION FOR SEQ ID NO:461:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:461:

GCUCUGGCUG AUGAGGCCGA AAGGCCGAAA AACCUC                           36

(2) INFORMATION FOR SEQ ID NO:462:

(i) SEQUENCE CHARACTERISTICS:
```

```
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:462:

GGCUCUGCUG AUGAGGCCGA AAGGCCGAAA AAACCU                              36

(2) INFORMATION FOR SEQ ID NO:463:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:463:

GAGAGGUCUG AUGAGGCCGA AAGGCCGAAA GGCUCU                              36

(2) INFORMATION FOR SEQ ID NO:464:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:464:

ACCAGGACUG AUGAGGCCGA AAGGCCGAAA GGUGAG                              36

(2) INFORMATION FOR SEQ ID NO:465:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:465:

CAACCAGCUG AUGAGGCCGA AAGGCCGAAA GAGGUG                              36

(2) INFORMATION FOR SEQ ID NO:466:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:466:

AUUUUCCCUG AUGAGGCCGA AAGGCCGAAA CCAGGA                              36

(2) INFORMATION FOR SEQ ID NO:467:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:467:

GGCAUUUCUG AUGAGGCCGA AAGGCCGAAA UUCUUC                              36

(2) INFORMATION FOR SEQ ID NO:468:

(i) SEQUENCE CHARACTERISTICS:
          (A) LENGTH:         36 base pairs
```

```
          (B) TYPE:           nucleic acid
          (C) STRANDEDNESS:   single
          (D) TOPOLOGY:       linear (xi) SEQUENCE DESCRIPTION: SEQ ID NO:468:

UGGCAUUCUG AUGAGGCCGA AAGGCCGAAA AUUCUU                              36

(2) INFORMATION FOR SEQ ID NO:469:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:469:

UUGUGUUCUG AUGAGGCCGA AAGGCCGAAA UGGCAU                              36

(2) INFORMATION FOR SEQ ID NO:470:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:470:

CUUGGGACUG AUGAGGCCGA AAGGCCGAAA CUGUUG                              36

(2) INFORMATION FOR SEQ ID NO:471:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:471:

UCUUGGGCUG AUGAGGCCGA AAGGCCGAAA ACUGUU                              36

(2) INFORMATION FOR SEQ ID NO:472:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:472:

AUCUUGGCUG AUGAGGCCGA AAGGCCGAAA AACUGU                              36

(2) INFORMATION FOR SEQ ID NO:473:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:473:

GUUUCAGCUG AUGAGGCCGA AAGGCCGAAA UCUUGG                              36

(2) INFORMATION FOR SEQ ID NO:474:

(i) SEQUENCE CHARACTERISTICS:
          (A) LENGTH:         36 base pairs
          (B) TYPE:           nucleic acid
```

```
            (C) STRANDEDNESS:    single
            (D) TOPOLOGY:        linear (xi) SEQUENCE DESCRIPTION: SEQ ID NO:474:

CAGCAUACUG AUGAGGCCGA AAGGCCGAAA GCUCAG                                36

(2) INFORMATION FOR SEQ ID NO:475:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:475:

AACAGCACUG AUGAGGCCGA AAGGCCGAAA GAGCUC                                36

(2) INFORMATION FOR SEQ ID NO:476:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:476:

UGCUGCUCUG AUGAGGCCGA AAGGCCGAAA CAGCAU                                36

(2) INFORMATION FOR SEQ ID NO:477:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:477:

UUGCUGCCUG AUGAGGCCGA AAGGCCGAAA ACAGCA                                36

(2) INFORMATION FOR SEQ ID NO:478:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:478:

AUAUUGACUG AUGAGGCCGA AAGGCCGAAA UCCAGU                                36

(2) INFORMATION FOR SEQ ID NO:479:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:479:

CAUAUUGCUG AUGAGGCCGA AAGGCCGAAA AUCCAG                                36

(2) INFORMATION FOR SEQ ID NO:480:

(i) SEQUENCE CHARACTERISTICS:
            (A) LENGTH:          36 base pairs
            (B) TYPE:            nucleic acid
            (C) STRANDEDNESS:    single
```

(D) TOPOLOGY:       linear (xi) SEQUENCE DESCRIPTION: SEQ ID NO:480:

UCAUAUUCUG AUGAGGCCGA AAGGCCGAAA AAUCCA                          36

(2) INFORMATION FOR SEQ ID NO:481:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:481:

GUUGUCACUG AUGAGGCCGA AAGGCCGAAA UUGAAA                          36

(2) INFORMATION FOR SEQ ID NO:482:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:482:

ACACAUGCUG AUGAGGCCGA AAGGCCGAAA GCUGUG                          36

(2) INFORMATION FOR SEQ ID NO:483:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:483:

GACACAUCUG AUGAGGCCGA AAGGCCGAAA AGCUGU                          36

(2) INFORMATION FOR SEQ ID NO:484:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:484:

UUGAUGACUG AUGAGGCCGA AAGGCCGAAA CACAUG                          36

(2) INFORMATION FOR SEQ ID NO:485:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:485:

ACUUGAUCUG AUGAGGCCGA AAGGCCGAAA GACACA                          36

(2) INFORMATION FOR SEQ ID NO:486:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:486:

CAUACUUCUG AUGAGGCCGA AAGGCCGAAA UGAGAC                                    36

(2) INFORMATION FOR SEQ ID NO:487:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:487:

AUGUCCACUG AUGAGGCCGA AAGGCCGAAA CUUGAU                                    36

(2) INFORMATION FOR SEQ ID NO:488:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:488:

ACUCUUACUG AUGAGGCCGA AAGGCCGAAA UGUCCA                                    36

(2) INFORMATION FOR SEQ ID NO:489:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:489:

CACUCUUCUG AUGAGGCCGA AAGGCCGAAA AUGUCC                                    36

(2) INFORMATION FOR SEQ ID NO:490:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:490:

UCACUCUCUG AUGAGGCCGA AAGGCCGAAA AAUGUC                                    36

(2) INFORMATION FOR SEQ ID NO:491:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:491:

AAGGUCUCUG AUGAGGCCGA AAGGCCGAAA UUCACU                                    36

(2) INFORMATION FOR SEQ ID NO:492:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:492:

CCAGUUGCUG AUGAGGCCGA AAGGCCGAAA GGUCUG          36

(2) INFORMATION FOR SEQ ID NO:493:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:493:

UCCAGUUCUG AUGAGGCCGA AAGGCCGAAA AGGUCU          36

(2) INFORMATION FOR SEQ ID NO:494:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:494:

UUGGUUGCUG AUGAGGCCGA AAGGCCGAAA UUCCAG          36

(2) INFORMATION FOR SEQ ID NO:495:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:495:

UCAGGAACUG AUGAGGCCGA AAGGCCGAAA UGCUCU          36

(2) INFORMATION FOR SEQ ID NO:496:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:496:

AUCAGGACUG AUGAGGCCGA AAGGCCGAAA AUGCUC          36

(2) INFORMATION FOR SEQ ID NO:497:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:497:

UAUCAGGCUG AUGAGGCCGA AAGGCCGAAA AAUGCU          36

(2) INFORMATION FOR SEQ ID NO:498:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:498:

UUAUCAGCUG AUGAGGCCGA AAGGCCGAAA AAAUGC 36

(2) INFORMATION FOR SEQ ID NO:499:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:499:

AGCAGGUCUG AUGAGGCCGA AAGGCCGAAA UCAGGA 36

(2) INFORMATION FOR SEQ ID NO:500:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:500:

AGGAUGGCUG AUGAGGCCGA AAGGCCGAAA GCAGGU 36

(2) INFORMATION FOR SEQ ID NO:501:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:501:

GGCCCAGCUG AUGAGGCCGA AAGGCCGAAA UGGGAG 36

(2) INFORMATION FOR SEQ ID NO:502:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:502:

UUAAGGUCUG AUGAGGCCGA AAGGCCGAAA UGGCCC 36

(2) INFORMATION FOR SEQ ID NO:503:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:503:

AUUAAGGCUG AUGAGGCCGA AAGGCCGAAA AUGGCC 36

(2) INFORMATION FOR SEQ ID NO:504:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:504:

```
UGAGAUUCUG AUGAGGCCGA AAGGCCGAAA GGUAAU                                     36

(2) INFORMATION FOR SEQ ID NO:505:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:505:

CUGAGAUCUG AUGAGGCCGA AAGGCCGAAA AGGUAA                                     36

(2) INFORMATION FOR SEQ ID NO:506:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:506:

UUACUGACUG AUGAGGCCGA AAGGCCGAAA UUAAGG                                     36

(2) INFORMATION FOR SEQ ID NO:507:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:507:

AUUUACUCUG AUGAGGCCGA AAGGCCGAAA GAUUAA                                     36

(2) INFORMATION FOR SEQ ID NO:508:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:508:

UUCCAUUCUG AUGAGGCCGA AAGGCCGAAA CUGAGA                                     36

(2) INFORMATION FOR SEQ ID NO:509:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:509:

UCACAAACUG AUGAGGCCGA AAGGCCGAAA UUCCAU                                     36

(2) INFORMATION FOR SEQ ID NO:510:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:510:

AUCACAACUG AUGAGGCCGA AAGGCCGAAA AUUCCA                                     36
```

(2) INFORMATION FOR SEQ ID NO:511:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:511:

UAUCACACUG AUGAGGCCGA AAGGCCGAAA AAUUCC                             36

(2) INFORMATION FOR SEQ ID NO:512:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:512:

AUAUCACCUG AUGAGGCCGA AAGGCCGAAA AAAUUC                             36

(2) INFORMATION FOR SEQ ID NO:513:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:513:

GGCAGCACUG AUGAGGCCGA AAGGCCGAAA UCACAA                             36

(2) INFORMATION FOR SEQ ID NO:514:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:514:

AAAGCAGCUG AUGAGGCCGA AAGGCCGAAA GGUCAG                             36

(2) INFORMATION FOR SEQ ID NO:515:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:515:

UGGGGCACUG AUGAGGCCGA AAGGCCGAAA GCAGUA                             36

(2) INFORMATION FOR SEQ ID NO:516:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:516:

UUGGGGCCUG AUGAGGCCGA AAGGCCGAAA AGCAGU                             36

(2) INFORMATION FOR SEQ ID NO:517:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:517:

CCUUCUCCUG AUGAGGCCGA AAGGCCGAAA UCUCUC          36

(2) INFORMATION FOR SEQ ID NO:518:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:518:

CAGGGCGCUG AUGAGGCCGA AAGGCCGAAA CACUUU          36

(2) INFORMATION FOR SEQ ID NO:519:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:519:

ACUGUUACUG AUGAGGCCGA AAGGCCGAAA CAGGGC          36

(2) INFORMATION FOR SEQ ID NO:520:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:520:

ACACUGUCUG AUGAGGCCGA AAGGCCGAAA UACAGG          36

(2) INFORMATION FOR SEQ ID NO:521:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:521:

UUCUGCGCUG AUGAGGCCGA AAGGCCGAAA CACUGU          36

(2) INFORMATION FOR SEQ ID NO:522:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:522:

ACCUUCACUG AUGAGGCCGA AAGGCCGAAA UCUUUU          36

(2) INFORMATION FOR SEQ ID NO:523:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:523:

CGGAGGCCUG AUGAGGCCGA AAGGCCGAAA CCUUCA                     36

(2) INFORMATION FOR SEQ ID NO:524:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:524:

GAUGACGCUG AUGAGGCCGA AAGGCCGAAA GGCUAC                     36

(2) INFORMATION FOR SEQ ID NO:525:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:525:

AAGAGAUCUG AUGAGGCCGA AAGGCCGAAA CGGAGG                     36

(2) INFORMATION FOR SEQ ID NO:526:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:526:

CAGAAGACUG AUGAGGCCGA AAGGCCGAAA UGACGG                     36

(2) INFORMATION FOR SEQ ID NO:527:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:527:

CCCAGAACUG AUGAGGCCGA AAGGCCGAAA GAUGAC                     36

(2) INFORMATION FOR SEQ ID NO:528:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:528:

AUCCCAGCUG AUGAGGCCGA AAGGCCGAAA GAGAUG                     36

(2) INFORMATION FOR SEQ ID NO:529:

```
        (i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:529:

UAUCCCACUG AUGAGGCCGA AAGGCCGAAA AGAGAU                         36

(2) INFORMATION FOR SEQ ID NO:530:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:530:

AUCCAUGCUG AUGAGGCCGA AAGGCCGAAA UCCCAG                         36

(2) INFORMATION FOR SEQ ID NO:531:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:531:

UCCCCACCUG AUGAGGCCGA AAGGCCGAAA UCCAUG                         36

(2) INFORMATION FOR SEQ ID NO:532:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:532:

GCCUCAUCUG AUGAGGCCGA AAGGCCGAAA UCCCCA                         36

(2) INFORMATION FOR SEQ ID NO:533:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:533:

AGGGAAGCUG AUGAGGCCGA AAGGCCGAAA UGCCUC                         36

(2) INFORMATION FOR SEQ ID NO:534:

(i) SEQUENCE CHARACTERISTICS:
              (A) LENGTH:         36 base pairs
              (B) TYPE:           nucleic acid
              (C) STRANDEDNESS:   single
              (D) TOPOLOGY:       linear (xi) SEQUENCE DESCRIPTION: SEQ ID NO:534:

AAGGGAACUG AUGAGGCCGA AAGGCCGAAA AUGCCU                         36

(2) INFORMATION FOR SEQ ID NO:535:
```

```
    (i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:535:

UUAAGGGCUG AUGAGGCCGA AAGGCCGAAA GAAUGC                          36

(2) INFORMATION FOR SEQ ID NO:536:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:536:

GUUAAGGCUG AUGAGGCCGA AAGGCCGAAA AGAAUG                          36

(2) INFORMATION FOR SEQ ID NO:537:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:537:

AUUUGUUCUG AUGAGGCCGA AAGGCCGAAA GGGAAG                          36

(2) INFORMATION FOR SEQ ID NO:538:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:538:

AAUUUGUCUG AUGAGGCCGA AAGGCCGAAA AGGGAA                          36

(2) INFORMATION FOR SEQ ID NO:539:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:539:

CAGCUUACUG AUGAGGCCGA AAGGCCGAAA UUUGUU                          36

(2) INFORMATION FOR SEQ ID NO:540:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:540:

ACAGCUUCUG AUGAGGCCGA AAGGCCGAAA AUUUGU                          36

(2) INFORMATION FOR SEQ ID NO:541:

(i) SEQUENCE CHARACTERISTICS:
```

```
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:541:

AACAGCUCUG AUGAGGCCGA AAGGCCGAAA AAUUUG                        36

(2) INFORMATION FOR SEQ ID NO:542:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:542:

UGGGUAACUG AUGAGGCCGA AAGGCCGAAA CAGCUU                        36

(2) INFORMATION FOR SEQ ID NO:543:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:543:

GUGGGUACUG AUGAGGCCGA AAGGCCGAAA ACAGCU                        36

(2) INFORMATION FOR SEQ ID NO:544:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:544:

AGUGGGUCUG AUGAGGCCGA AAGGCCGAAA AACAGC                        36

(2) INFORMATION FOR SEQ ID NO:545:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:545:

UAGUGGGCUG AUGAGGCCGA AAGGCCGAAA AAACAG                        36

(2) INFORMATION FOR SEQ ID NO:546:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:546:

GGUGAGGCUG AUGAGGCCGA AAGGCCGAAA GUGGGU                        36

(2) INFORMATION FOR SEQ ID NO:547:

(i) SEQUENCE CHARACTERISTICS:
        (A) LENGTH:         36 base pairs
```

```
            (B) TYPE:            nucleic acid
            (C) STRANDEDNESS:    single
            (D) TOPOLOGY:        linear (xi) SEQUENCE DESCRIPTION: SEQ ID NO:547:

AGAAGGUCUG AUGAGGCCGA AAGGCCGAAA GGUAGU                                  36

(2) INFORMATION FOR SEQ ID NO:548:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:548:

UUUUAAGCUG AUGAGGCCGA AAGGCCGAAA GGUGAG                                  36

(2) INFORMATION FOR SEQ ID NO:549:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:549:

UUUUUAACUG AUGAGGCCGA AAGGCCGAAA AGGUGA                                  36

(2) INFORMATION FOR SEQ ID NO:550:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:550:

GGUUUUUCUG AUGAGGCCGA AAGGCCGAAA GAAGGU                                  36

(2) INFORMATION FOR SEQ ID NO:551:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:551:

AGGUUUUCUG AUGAGGCCGA AAGGCCGAAA AGAAGG                                  36

(2) INFORMATION FOR SEQ ID NO:552:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:552:

UCUGAAACUG AUGAGGCCGA AAGGCCGAAA GGUUUU                                  36

(2) INFORMATION FOR SEQ ID NO:553:

(i) SEQUENCE CHARACTERISTICS:
            (A) LENGTH:          36 base pairs
            (B) TYPE:            nucleic acid
```

```
            (C) STRANDEDNESS:    single
            (D) TOPOLOGY:        linear (xi) SEQUENCE DESCRIPTION: SEQ ID NO:553:

AAUCUGACUG AUGAGGCCGA AAGGCCGAAA GAGGUU                                36

(2) INFORMATION FOR SEQ ID NO:554:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:554:

UAAUCUGCUG AUGAGGCCGA AAGGCCGAAA AGAGGU                                36

(2) INFORMATION FOR SEQ ID NO:555:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:555:

UUAAUCUCUG AUGAGGCCGA AAGGCCGAAA AAGAGG                                36

(2) INFORMATION FOR SEQ ID NO:556:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:556:

UCAGCUUCUG AUGAGGCCGA AAGGCCGAAA UCUGAA                                36

(2) INFORMATION FOR SEQ ID NO:557:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:557:

UUCAGCUCUG AUGAGGCCGA AAGGCCGAAA AUCUGA                                36

(2) INFORMATION FOR SEQ ID NO:558:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:558:

AUCUUGUCUG AUGAGGCCGA AAGGCCGAAA CUGUUC                                36

(2) INFORMATION FOR SEQ ID NO:559:

(i) SEQUENCE CHARACTERISTICS:
            (A) LENGTH:          36 base pairs
            (B) TYPE:            nucleic acid
            (C) STRANDEDNESS:    single
```

(D) TOPOLOGY:      linear (xi) SEQUENCE DESCRIPTION: SEQ ID NO:559:

CAUCUUGCUG AUGAGGCCGA AAGGCCGAAA ACUGUU                    36

(2) INFORMATION FOR SEQ ID NO:560:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:560:

GGAGAGGCUG AUGAGGCCGA AAGGCCGAAA UGCCAG                    36

(2) INFORMATION FOR SEQ ID NO:561:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:561:

GAAAGGACUG AUGAGGCCGA AAGGCCGAAA GGGAUG                    36

(2) INFORMATION FOR SEQ ID NO:562:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:562:

GAGAAAGCUG AUGAGGCCGA AAGGCCGAAA GAGGGA                    36

(2) INFORMATION FOR SEQ ID NO:563:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:563:

GGGGAGACUG AUGAGGCCGA AAGGCCGAAA GGAGAG                    36

(2) INFORMATION FOR SEQ ID NO:564:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:564:

UGGGGAGCUG AUGAGGCCGA AAGGCCGAAA AGGAGA                    36

(2) INFORMATION FOR SEQ ID NO:565:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:565:

AUGGGGACUG AUGAGGCCGA AAGGCCGAAA AAGGAG                                    36

(2) INFORMATION FOR SEQ ID NO:566:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:566:

AUAUGGGCUG AUGAGGCCGA AAGGCCGAAA GAAAGG                                    36

(2) INFORMATION FOR SEQ ID NO:567:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:567:

AAUUGCACUG AUGAGGCCGA AAGGCCGAAA UGGGGA                                    36

(2) INFORMATION FOR SEQ ID NO:568:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:568:

UUAAGCACUG AUGAGGCCGA AAGGCCGAAA UUGCAU                                    36

(2) INFORMATION FOR SEQ ID NO:569:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:569:

AUUAAGCCUG AUGAGGCCGA AAGGCCGAAA AUUGCA                                    36

(2) INFORMATION FOR SEQ ID NO:570:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:570:

UUACAUUCUG AUGAGGCCGA AAGGCCGAAA GCAAAU                                    36

(2) INFORMATION FOR SEQ ID NO:571:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:571:

GUUACAUCUG AUGAGGCCGA AAGGCCGAAA AGCAAA                    36

(2) INFORMATION FOR SEQ ID NO:572:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:572:

AAGAGGUCUG AUGAGGCCGA AAGGCCGAAA CAUUAA                    36

(2) INFORMATION FOR SEQ ID NO:573:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:573:

AAAAGAACUG AUGAGGCCGA AAGGCCGAAA GGUUAC                    36

(2) INFORMATION FOR SEQ ID NO:574:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:574:

GCAAAAGCUG AUGAGGCCGA AAGGCCGAAA GAGGUU                    36

(2) INFORMATION FOR SEQ ID NO:575:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:575:

GGCAAAACUG AUGAGGCCGA AAGGCCGAAA AGAGGU                    36

(2) INFORMATION FOR SEQ ID NO:576:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:576:

AUGGCAACUG AUGAGGCCGA AAGGCCGAAA GAAGAG                    36

(2) INFORMATION FOR SEQ ID NO:577:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:577:

CAUGGCACUG AUGAGGCCGA AAGGCCGAAA AGAAGA                                      36

(2) INFORMATION FOR SEQ ID NO:578:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:578:

ACAUGGCCUG AUGAGGCCGA AAGGCCGAAA AAGAAG                                      36

(2) INFORMATION FOR SEQ ID NO:579:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:579:

GAAUGGACUG AUGAGGCCGA AAGGCCGAAA CAUGGC                                      36

(2) INFORMATION FOR SEQ ID NO:580:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:580:

AGAAUGGCUG AUGAGGCCGA AAGGCCGAAA ACAUGG                                      36

(2) INFORMATION FOR SEQ ID NO:581:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:581:

CAGAAUGCUG AUGAGGCCGA AAGGCCGAAA AACAUG                                      36

(2) INFORMATION FOR SEQ ID NO:582:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:582:

AUGGCAGCUG AUGAGGCCGA AAGGCCGAAA UGGAAA                                      36

(2) INFORMATION FOR SEQ ID NO:583:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:583:

GAUGGCACUG AUGAGGCCGA AAGGCCGAAA AUGGAA                                  36

(2) INFORMATION FOR SEQ ID NO:584:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:584:

AAUUCAACUG AUGAGGCCGA AAGGCCGAAA UGGCAG                                  36

(2) INFORMATION FOR SEQ ID NO:585:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:585:

ACAAUUCCUG AUGAGGCCGA AAGGCCGAAA GAUGGC                                  36

(2) INFORMATION FOR SEQ ID NO:586:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:586:

ACAAGACCUG AUGAGGCCGA AAGGCCGAAA UUCAAG                                  36

(2) INFORMATION FOR SEQ ID NO:587:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:587:

CUGACAACUG AUGAGGCCGA AAGGCCGAAA CAAUUC                                  36

(2) INFORMATION FOR SEQ ID NO:588:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:588:

GGCUGACCUG AUGAGGCCGA AAGGCCGAAA GACAAU                                  36

(2) INFORMATION FOR SEQ ID NO:589:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:589:

AUUGGCUCUG AUGAGGCCGA AAGGCCGAAA CAAGAC                                  36

(2) INFORMATION FOR SEQ ID NO:590:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:590:

GAUAAUGCUG AUGAGGCCGA AAGGCCGAAA UUGGCU                      36

(2) INFORMATION FOR SEQ ID NO:591:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:591:

AGAUAAUCUG AUGAGGCCGA AAGGCCGAAA AUUGGC                      36

(2) INFORMATION FOR SEQ ID NO:592:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:592:

AAUAGAUCUG AUGAGGCCGA AAGGCCGAAA UGAAUU                      36

(2) INFORMATION FOR SEQ ID NO:593:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:593:

UAAUAGACUG AUGAGGCCGA AAGGCCGAAA AUGAAU                      36

(2) INFORMATION FOR SEQ ID NO:594:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:594:

UUUAAUACUG AUGAGGCCGA AAGGCCGAAA UAAUGA                      36

(2) INFORMATION FOR SEQ ID NO:595:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:595:

UGUUUAACUG AUGAGGCCGA AAGGCCGAAA GAUAAU                      36

(2) INFORMATION FOR SEQ ID NO:596:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:596:

AGUGUUUCUG AUGAGGCCGA AAGGCCGAAA UAGAUA                         36

(2) INFORMATION FOR SEQ ID NO:597:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:597:

UAGUGUUCUG AUGAGGCCGA AAGGCCGAAA AUAGAU                         36

(2) INFORMATION FOR SEQ ID NO:598:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:598:

CUCAAAUCUG AUGAGGCCGA AAGGCCGAAA GUGUUU                         36

(2) INFORMATION FOR SEQ ID NO:599:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:599:

GAGUUUUAUA CCUCA                                            15

(2) INFORMATION FOR SEQ ID NO:600:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:600:

GUUUUAUACC UCAAU                                            15

(2) INFORMATION FOR SEQ ID NO:601:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:601:

GUUUUAUACC UCAAU                                            15

(2) INFORMATION FOR SEQ ID NO:602:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:602:

UAUACCUCAA UAGAC                                                           15

(2) INFORMATION FOR SEQ ID NO:603:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:603:

CCUCAAUAGA CUCUU                                                           15

(2) INFORMATION FOR SEQ ID NO:604:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:604:

CCUCAAUAGA CUCUU                                                           15

(2) INFORMATION FOR SEQ ID NO:605:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:605:

CCUCAAUAGA CUCUU                                                           15

(2) INFORMATION FOR SEQ ID NO:606:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:606:

AUAGACUCUU ACUAG                                                           15

(2) INFORMATION FOR SEQ ID NO:607:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:607:

AGACUCUUAC UAGUU                                                           15

(2) INFORMATION FOR SEQ ID NO:608:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:608:

GACUCUUACU AGUUU                                                            15

(2) INFORMATION FOR SEQ ID NO:609:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:609:

UCUUACUAGU UUCUC                                                            15

(2) INFORMATION FOR SEQ ID NO:610:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:610:

UCUUACUAGU UUCUC                                                            15

(2) INFORMATION FOR SEQ ID NO:611:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:611:

UCUUACUAGU UUCUC                                                            15

(2) INFORMATION FOR SEQ ID NO:612:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:612:

UCUUACUAGU UUCUC                                                            15

(2) INFORMATION FOR SEQ ID NO:613:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:613:

CUAGUUUCUC UUUUU                                                            15

(2) INFORMATION FOR SEQ ID NO:614:

(i) SEQUENCE CHARACTERISTICS:
    (A) LENGTH:       15 base pairs
    (B) TYPE:         nucleic acid
    (C) STRANDEDNESS:  single
    (D) TOPOLOGY:     linear (xi) SEQUENCE DESCRIPTION: SEQ ID NO:614:

CUAGUUUCUC UUUUU                                        15

(2) INFORMATION FOR SEQ ID NO:615:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:615:

CUAGUUUCUC UUUUU                                        15

(2) INFORMATION FOR SEQ ID NO:616:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:616:

UCUCUUUUUC AGGUU                                        15

(2) INFORMATION FOR SEQ ID NO:617:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:617:

CUCUUUUUCA GGUUG                                        15

(2) INFORMATION FOR SEQ ID NO:618:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:618:

CUCUUUUUCA GGUUG                                        15

(2) INFORMATION FOR SEQ ID NO:619:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:619:

UCUUUUUCAG GUUGU                                        15

(2) INFORMATION FOR SEQ ID NO:620:

(i) SEQUENCE CHARACTERISTICS:

```
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO:620:

UGAAACUCAA CCUUC                                                             15

(2) INFORMATION FOR SEQ ID NO:621:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO:621:

UGAAACUCAA CCUUC                                                             15

(2) INFORMATION FOR SEQ ID NO:622:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO:622:

UCAACCUUCA AAGAC                                                             15

(2) INFORMATION FOR SEQ ID NO:623:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO:623:

UCAACCUUCA AAGAC                                                             15

(2) INFORMATION FOR SEQ ID NO:624:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO:624:

UCAACCUUCA AAGAC                                                             15

(2) INFORMATION FOR SEQ ID NO:625:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO:625:

CAACCUUCAA AGACA                                                             15

(2) INFORMATION FOR SEQ ID NO:626:

(i) SEQUENCE CHARACTERISTICS:
            (A) LENGTH:           15 base pairs
```

```
            (B) TYPE:          nucleic acid
            (C) STRANDEDNESS:  single
            (D) TOPOLOGY:      linear (xi) SEQUENCE DESCRIPTION: SEQ ID NO:626:

AGACACUCUG UUCCA                                                    15

(2) INFORMATION FOR SEQ ID NO:627:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:627:

ACUCUGUUCC AUUUC                                                    15

(2) INFORMATION FOR SEQ ID NO:628:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:628:

CUCUGUUCCA UUUCU                                                    15

(2) INFORMATION FOR SEQ ID NO:629:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:629:

UUCCAUUUCU GUGGA                                                    15

(2) INFORMATION FOR SEQ ID NO:630:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:630:

GUGGACUAAU AGGAU                                                    15

(2) INFORMATION FOR SEQ ID NO:631:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:631:

GUGGACUAAU AGGAU                                                    15

(2) INFORMATION FOR SEQ ID NO:632:

(i) SEQUENCE CHARACTERISTICS:
            (A) LENGTH:        15 base pairs
            (B) TYPE:          nucleic acid
```

```
            (C) STRANDEDNESS:    single
            (D) TOPOLOGY:        linear (xi) SEQUENCE DESCRIPTION: SEQ ID NO:632:

GUGGACUAAU AGGAU                                                         15

(2) INFORMATION FOR SEQ ID NO:633:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:633:

GACUAAUAGG AUCAU                                                         15

(2) INFORMATION FOR SEQ ID NO:634:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:634:

GACUAAUAGG AUCAU                                                         15

(2) INFORMATION FOR SEQ ID NO:635:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:635:

AUAGGAUCAU CUUUA                                                         15

(2) INFORMATION FOR SEQ ID NO:636:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:636:

GGAUCAUCUU UAGCA                                                         15

(2) INFORMATION FOR SEQ ID NO:637:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:637:

GGAUCAUCUU UAGCA                                                         15

(2) INFORMATION FOR SEQ ID NO:638:

(i) SEQUENCE CHARACTERISTICS:
            (A) LENGTH:          15 base pairs
            (B) TYPE:            nucleic acid
            (C) STRANDEDNESS:    single
```

(D) TOPOLOGY:        linear (xi) SEQUENCE DESCRIPTION: SEQ ID NO:638:

AUCAUCUUUA GCAUC                                                15

(2) INFORMATION FOR SEQ ID NO:639:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:639:

UCAUCUUUAG CAUCU                                                15

(2) INFORMATION FOR SEQ ID NO:640:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:640:

UCAUCUUUAG CAUCU                                                15

(2) INFORMATION FOR SEQ ID NO:641:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:641:

CAUCUUUAGC AUCUG                                                15

(2) INFORMATION FOR SEQ ID NO:642:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:642:

CAUCUUUAGC AUCUG                                                15

(2) INFORMATION FOR SEQ ID NO:643:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:643:

AUGCCAUCCA GGCUU                                                15

(2) INFORMATION FOR SEQ ID NO:644:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:644:

GCUUCUUUUU CUACA                                                                15

(2) INFORMATION FOR SEQ ID NO:645:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:645:

GCUUCUUUUU CUACA                                                                15

(2) INFORMATION FOR SEQ ID NO:646:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:646:

CUUCUUUUUC UACAU                                                                15

(2) INFORMATION FOR SEQ ID NO:647:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:647:

CUUCUUUUUC UACAU                                                                15

(2) INFORMATION FOR SEQ ID NO:648:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:648:

CUUCUUUUUC UACAU                                                                15

(2) INFORMATION FOR SEQ ID NO:649:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:649:

CUUCUUUUUC UACAU                                                                15

(2) INFORMATION FOR SEQ ID NO:650:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:650:

UUCUUUUUCU ACAUC                                                15

(2) INFORMATION FOR SEQ ID NO:651:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:651:

UUCUUUUUCU ACAUC                                                15

(2) INFORMATION FOR SEQ ID NO:652:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:652:

UUCUUUUUCU ACAUC                                                15

(2) INFORMATION FOR SEQ ID NO:653:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:653:

UUUUUCUACA UCUCU                                                15

(2) INFORMATION FOR SEQ ID NO:654:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:654:

UACAUCUCUG UUUCU                                                15

(2) INFORMATION FOR SEQ ID NO:655:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:655:

UCUCGAUUUU UGUGA                                                15

(2) INFORMATION FOR SEQ ID NO:656:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:656:

UCUCGAUUUU UGUGA                                                    15

(2) INFORMATION FOR SEQ ID NO:657:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:657:

UCUCGAUUUU UGUGA                                                    15

(2) INFORMATION FOR SEQ ID NO:658:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:658:

CUCGAUUUUU GUGAG                                                    15

(2) INFORMATION FOR SEQ ID NO:659:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:659:

UCGAUUUUUG UGAGC                                                    15

(2) INFORMATION FOR SEQ ID NO:660:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:660:

UCGAUUUUUG UGAGC                                                    15

(2) INFORMATION FOR SEQ ID NO:661:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:661:

UCGAUUUUUG UGAGC                                                    15

(2) INFORMATION FOR SEQ ID NO:662:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:662:

```
CGAUUUUUGU GAGCC                                                                15
```

(2) INFORMATION FOR SEQ ID NO:663:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:663:

```
CGAUUUUUGU GAGCC                                                                15
```

(2) INFORMATION FOR SEQ ID NO:664:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:664:

```
GCUCCAUUGG CUCUA                                                                15
```

(2) INFORMATION FOR SEQ ID NO:665:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:665:

```
AUUGGCUCUA GAUUC                                                                15
```

(2) INFORMATION FOR SEQ ID NO:666:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:666:

```
UCUAGAUUCC UGGCU                                                                15
```

(2) INFORMATION FOR SEQ ID NO:667:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:667:

```
CCUGGCUUUC CCCAU                                                                15
```

(2) INFORMATION FOR SEQ ID NO:668:

(i) SEQUENCE CHARACTERISTICS:
        (A) LENGTH:      15 base pairs
        (B) TYPE:        nucleic acid
        (C) STRANDEDNESS: single
        (D) TOPOLOGY:    linear (xi) SEQUENCE DESCRIPTION: SEQ ID NO:668:

```
CUGGCUUUCC CCAUC                                                                15
```

(2) INFORMATION FOR SEQ ID NO:669:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:669:

CUGGCUUUCC CCAUC                                          15

(2) INFORMATION FOR SEQ ID NO:670:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:670:

CUGGCUUUCC CCAUC                                          15

(2) INFORMATION FOR SEQ ID NO:671:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:671:

UGGCUUUCCC CAUCA                                          15

(2) INFORMATION FOR SEQ ID NO:672:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:672:

UGGCUUUCCC CAUCA                                          15

(2) INFORMATION FOR SEQ ID NO:673:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:673:

UGGCUUUCCC CAUCA                                          15

(2) INFORMATION FOR SEQ ID NO:674:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:674:

UGGCUUUCCC CAUCA                                          15

```
(2) INFORMATION FOR SEQ ID NO:675:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:675:

UCCCCAUCAU GUUCU                                                15

(2) INFORMATION FOR SEQ ID NO:676:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:676:

UCCCCAUCAU GUUCU                                                15

(2) INFORMATION FOR SEQ ID NO:677:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:677:

UCAUGUUCUC CAAAG                                                15

(2) INFORMATION FOR SEQ ID NO:678:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:678:

AUGUUCUCCA AAGCA                                                15

(2) INFORMATION FOR SEQ ID NO:679:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:679:

AUGUUCUCCA AAGCA                                                15

(2) INFORMATION FOR SEQ ID NO:680:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:680:

AUGUUCUCCA AAGCA                                                15
```

(2) INFORMATION FOR SEQ ID NO:681:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:681:

AAAGCAUCUG AAGCU                                                 15

(2) INFORMATION FOR SEQ ID NO:682:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:682:

AAAGCAUCUG AAGCU                                                 15

(2) INFORMATION FOR SEQ ID NO:683:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:683:

AAAGCAUCUG AAGCU                                                 15

(2) INFORMATION FOR SEQ ID NO:684:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:684:

UGAAGCUAUG GCUUG                                                 15

(2) INFORMATION FOR SEQ ID NO:685:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:685:

CAAUUGUCAG UUGAU                                               15

(2) INFORMATION FOR SEQ ID NO:686:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:686:

CACCACUCCU CAAGU                                               15

(2) INFORMATION FOR SEQ ID NO:687:

```
    (i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:687:

CUCAAGUUUC CAUGU                                                          15

(2) INFORMATION FOR SEQ ID NO:688:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:688:

CUCAAGUUUC CAUGU                                                          15

(2) INFORMATION FOR SEQ ID NO:689:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:689:

UCAAGUUUCC AUGUC                                                          15

(2) INFORMATION FOR SEQ ID NO:690:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:690:

CAAGUUUCCA UGUCC                                                          15

(2) INFORMATION FOR SEQ ID NO:691:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:691:

CAAGUUUCCA UGUCC                                                          15

(2) INFORMATION FOR SEQ ID NO:692:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:692:

GGCUCAUUCU UCUCU                                                          15

(2) INFORMATION FOR SEQ ID NO:693:
```

```
        (i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:693:

GGCUCAUUCU UCUCU                                                          15

(2) INFORMATION FOR SEQ ID NO:694:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:694:

GCUCAUUCUU CUCUU                                                          15

(2) INFORMATION FOR SEQ ID NO:695:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:695:

GCUCAUUCUU CUCUU                                                          15

(2) INFORMATION FOR SEQ ID NO:696:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:696:

UCAUUCUUCU CUUUG                                                          15

(2) INFORMATION FOR SEQ ID NO:697:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:697:

CAUUCUUCUC UUUGU                                                          15

(2) INFORMATION FOR SEQ ID NO:698:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:698:

CAUUCUUCUC UUUGU                                                          15

(2) INFORMATION FOR SEQ ID NO:699:

(i) SEQUENCE CHARACTERISTICS:
```

```
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:699:

UUCUUCUCUU UGUGC                                                    15

(2) INFORMATION FOR SEQ ID NO:700:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:700:

UUCUUCUCUU UGUGC                                                    15

(2) INFORMATION FOR SEQ ID NO:701:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:701:

CUUCUCUUUG UGCUG                                                    15

(2) INFORMATION FOR SEQ ID NO:702:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:702:

CUUCUCUUUG UGCUG                                                    15

(2) INFORMATION FOR SEQ ID NO:703:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:703:

UUCUCUUUGU GCUGC                                                    15

(2) INFORMATION FOR SEQ ID NO:704:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:704:

GCUGAUUCGU CUUUC                                                    15

(2) INFORMATION FOR SEQ ID NO:705:

(i) SEQUENCE CHARACTERISTICS:
            (A) LENGTH:          15 base pairs
```

(B) TYPE:           nucleic acid
            (C) STRANDEDNESS:   single
            (D) TOPOLOGY:       linear (xi) SEQUENCE DESCRIPTION: SEQ ID NO:705:

UUCGUCUUUC ACAAG                                                        15

(2) INFORMATION FOR SEQ ID NO:706:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:706:

UUCGUCUUUC ACAAG                                                        15

(2) INFORMATION FOR SEQ ID NO:707:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:707:

UCGUCUUUCA CAAGU                                                        15

(2) INFORMATION FOR SEQ ID NO:708:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:708:

CGUCUUUCAC AAGUG                                                        15

(2) INFORMATION FOR SEQ ID NO:709:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:709:

CGUCUUUCAC AAGUG                                                        15

(2) INFORMATION FOR SEQ ID NO:710:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:710:

CAAGUGUCUU CAGAU                                                        15

(2) INFORMATION FOR SEQ ID NO:711:

(i) SEQUENCE CHARACTERISTICS:
            (A) LENGTH:         15 base pairs
            (B) TYPE:           nucleic acid

```
            (C) STRANDEDNESS:    single
            (D) TOPOLOGY:        linear (xi) SEQUENCE DESCRIPTION: SEQ ID NO:711:

GUGUCUUCAG AUGUU                                                         15

(2) INFORMATION FOR SEQ ID NO:712:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:712:

UCCAAGUCAG UGAAA                                                         15

(2) INFORMATION FOR SEQ ID NO:713:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:713:

GCUGCCUUGC CGUUA                                                         15

(2) INFORMATION FOR SEQ ID NO:714:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:714:

UUGCCGUUAC AACUC                                                         15

(2) INFORMATION FOR SEQ ID NO:715:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:715:

UUGCCGUUAC AACUC                                                         15

(2) INFORMATION FOR SEQ ID NO:716:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:716:

UACAACUCUC CUCAU                                                         15

(2) INFORMATION FOR SEQ ID NO:717:

(i) SEQUENCE CHARACTERISTICS:
            (A) LENGTH:          15 base pairs
            (B) TYPE:            nucleic acid
            (C) STRANDEDNESS:    single
```

```
            (D) TOPOLOGY:       linear (xi) SEQUENCE DESCRIPTION: SEQ ID NO:717:

CUCUCCUCAU GAAGA                                                    15

(2) INFORMATION FOR SEQ ID NO:718:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:718:

GAUGAGUCUG AAGAC                                                    15

(2) INFORMATION FOR SEQ ID NO:719:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:719:

ACCGAAUCUA CUGGC                                                    15

(2) INFORMATION FOR SEQ ID NO:720:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:720:

CGAAUCUACU GGCAA                                                    15

(2) INFORMATION FOR SEQ ID NO:721:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:721:

GUGCUGUCUG UCAUU                                                    15

(2) INFORMATION FOR SEQ ID NO:722:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:722:

GUGCUGUCUG UCAUU                                                    15

(2) INFORMATION FOR SEQ ID NO:723:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear
```

(xi) SEQUENCE DESCRIPTION: SEQ ID NO:723:

UGUCUGUCAU UGCUG                                                  15

(2) INFORMATION FOR SEQ ID NO:724:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:724:

GGAAACUAAA AGUGU                                                  15

(2) INFORMATION FOR SEQ ID NO:725:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:725:

GGAAACUAAA AGUGU                                                  15

(2) INFORMATION FOR SEQ ID NO:726:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:726:

CCCGAGUAUA AGAAC                                                  15

(2) INFORMATION FOR SEQ ID NO:727:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:727:

CGGACUUUAU AUGAC                                                  15

(2) INFORMATION FOR SEQ ID NO:728:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:728:

GGACUUUAUA UGACA                                                  15

(2) INFORMATION FOR SEQ ID NO:729:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:729:

ACUUUAUAUG ACAAC                                                15

(2) INFORMATION FOR SEQ ID NO:730:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:730:

ACUACCUACU CUCUU                                                15

(2) INFORMATION FOR SEQ ID NO:731:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:731:

ACUACCUACU CUCUU                                                15

(2) INFORMATION FOR SEQ ID NO:732:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:732:

ACCUACUCUC UUAUC                                                15

(2) INFORMATION FOR SEQ ID NO:733:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:733:

ACCUACUCUC UUAUC                                                15

(2) INFORMATION FOR SEQ ID NO:734:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:734:

ACUCUCUUAU CAUCC                                                15

(2) INFORMATION FOR SEQ ID NO:735:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:735:

CUCUCUUAUC AUCCU                                                               15

(2) INFORMATION FOR SEQ ID NO:736:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:736:

CUCUCUUAUC AUCCU                                                               15

(2) INFORMATION FOR SEQ ID NO:737:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:737:

CUCUCUUAUC AUCCU                                                               15

(2) INFORMATION FOR SEQ ID NO:738:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:738:

UUAUCAUCCU GGGCC                                                               15

(2) INFORMATION FOR SEQ ID NO:739:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:739:

UUAUCAUCCU GGGCC                                                               15

(2) INFORMATION FOR SEQ ID NO:740:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:740:

UGGUCCUUUC AGACC                                                               15

(2) INFORMATION FOR SEQ ID NO:741:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:741:

```
GUCCUUUCAG ACCGG                                                   15

(2) INFORMATION FOR SEQ ID NO:742:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:742:

GUCCUUUCAG ACCGG                                                   15

(2) INFORMATION FOR SEQ ID NO:743:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:743:

GGCACAUACA GCUGU                                                   15

(2) INFORMATION FOR SEQ ID NO:744:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:744:

GCUGUGUCGU UCAAA                                                   15

(2) INFORMATION FOR SEQ ID NO:745:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:745:

GUGUCGUUCA AAAGA                                                   15

(2) INFORMATION FOR SEQ ID NO:746:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:746:

GUGUCGUUCA AAAGA                                                   15

(2) INFORMATION FOR SEQ ID NO:747:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:747:

UGUCGUUCAA AAGAA                                                   15
```

(2) INFORMATION FOR SEQ ID NO:748:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:748:

AUGAAGUUAA ACACU                                    15

(2) INFORMATION FOR SEQ ID NO:749:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:749:

AAACACUUGG CUUUA                                    15

(2) INFORMATION FOR SEQ ID NO:750:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:750:

AAACACUUGG CUUUA                                    15

(2) INFORMATION FOR SEQ ID NO:751:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:751:

UUGGCUUUAG UAAAG                                    15

(2) INFORMATION FOR SEQ ID NO:752:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:752:

UGGCUUUAGU AAAGU                                    15

(2) INFORMATION FOR SEQ ID NO:753:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:753:

CUUUAGUAAA GUUGU                                    15

(2) INFORMATION FOR SEQ ID NO:754:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:754:

GUAAAGUUGU CCAUC                                                    15

(2) INFORMATION FOR SEQ ID NO:755:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:755:

AAGUUGUCCA UCAAA                                                    15

(2) INFORMATION FOR SEQ ID NO:756:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:756:

UGUCCAUCAA AGCUG                                                    15

(2) INFORMATION FOR SEQ ID NO:757:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:757:

GCUGACUUCU CUACC                                                    15

(2) INFORMATION FOR SEQ ID NO:758:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:758:

GCUGACUUCU CUACC                                                    15

(2) INFORMATION FOR SEQ ID NO:759:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:759:

GCUGACUUCU CUACC                                                    15

(2) INFORMATION FOR SEQ ID NO:760:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:760:

CUGACUUCUC UACCC                                                          15

(2) INFORMATION FOR SEQ ID NO:761:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:761:

CUGACUUCUC UACCC                                                          15

(2) INFORMATION FOR SEQ ID NO:762:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:762:

GACUUCUCUA CCCCC                                                          15

(2) INFORMATION FOR SEQ ID NO:763:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:763:

GACUUCUCUA CCCCC                                                          15

(2) INFORMATION FOR SEQ ID NO:764:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:764:

CUUCUCUACC CCCAA                                                         15

(2) INFORMATION FOR SEQ ID NO:765:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:765:

CCAACAUAAC UGAGU                                                         15

(2) INFORMATION FOR SEQ ID NO:766:

(i) SEQUENCE CHARACTERISTICS:
    (A) LENGTH:        15 base pairs
    (B) TYPE:          nucleic acid
    (C) STRANDEDNESS:  single
    (D) TOPOLOGY:      linear (xi) SEQUENCE DESCRIPTION: SEQ ID NO:766:

CCAACAUAAC UGAGU                                              15

(2) INFORMATION FOR SEQ ID NO:767:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:767:

AACCCAUCUG CAGAC                                              15

(2) INFORMATION FOR SEQ ID NO:768:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:768:

AACCCAUCUG CAGAC                                              15

(2) INFORMATION FOR SEQ ID NO:769:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:769:

AGACACUAAA AGGAU                                              15

(2) INFORMATION FOR SEQ ID NO:770:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:770:

AGACACUAAA AGGAU                                              15

(2) INFORMATION FOR SEQ ID NO:771:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:771:

AGACACUAAA AGGAU                                              15

(2) INFORMATION FOR SEQ ID NO:772:

```
    (i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:772:

AAAGGAUUAC CUGCU                                                       15

(2) INFORMATION FOR SEQ ID NO:773:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:773:

AAAGGAUUAC CUGCU                                                       15

(2) INFORMATION FOR SEQ ID NO:774:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:774:

AAAGGAUUAC CUGCU                                                       15

(2) INFORMATION FOR SEQ ID NO:775:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:775:

ACCUGCUUUG CUUCC                                                       15

(2) INFORMATION FOR SEQ ID NO:776:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:776:

ACCUGCUUUG CUUCC                                                       15

(2) INFORMATION FOR SEQ ID NO:777:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:777:

CGGGGGUUUC CCAAA                                                       15

(2) INFORMATION FOR SEQ ID NO:778:

(i) SEQUENCE CHARACTERISTICS:
```

```
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:778:

CGGGGGUUUC CCAAA                                                    15

(2) INFORMATION FOR SEQ ID NO:779:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:779:

CGGGGGUUUC CCAAA                                                    15

(2) INFORMATION FOR SEQ ID NO:780:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:780:

GGGGGUUUCC CAAAG                                                    15

(2) INFORMATION FOR SEQ ID NO:781:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:781:

GGGGGUUUCC CAAAG                                                    15

(2) INFORMATION FOR SEQ ID NO:782:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:782:

GGGGGUUUCC CAAAG                                                    15

(2) INFORMATION FOR SEQ ID NO:783:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:783:

GGGGUUUCCC AAAGC                                                    15

(2) INFORMATION FOR SEQ ID NO:784:

(i) SEQUENCE CHARACTERISTICS:
            (A) LENGTH:         15 base pairs
```

```
        (B) TYPE:           nucleic acid
        (C) STRANDEDNESS:   single
        (D) TOPOLOGY:       linear (xi) SEQUENCE DESCRIPTION: SEQ ID NO:784:

AAAGCCUCGC UUCUC                                                      15

(2) INFORMATION FOR SEQ ID NO:785:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:785:

AAAGCCUCGC UUCUC                                                      15

(2) INFORMATION FOR SEQ ID NO:786:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:786:

CUCGCUUCUC UUGGU                                                      15

(2) INFORMATION FOR SEQ ID NO:787:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:787:

CUCGCUUCUC UUGGU                                                      15

(2) INFORMATION FOR SEQ ID NO:788:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:788:

CGCUUCUCUU GGUUG                                                      15

(2) INFORMATION FOR SEQ ID NO:789:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:789:

UCUUGGUUGG AAAAU                                                      15

(2) INFORMATION FOR SEQ ID NO:790:

(i) SEQUENCE CHARACTERISTICS:
        (A) LENGTH:         15 base pairs
        (B) TYPE:           nucleic acid
```

```
        (C) STRANDEDNESS:    single
        (D) TOPOLOGY:        linear (xi) SEQUENCE DESCRIPTION: SEQ ID NO:790:

GAGAAUUACC UGGCA                                                        15

(2) INFORMATION FOR SEQ ID NO:791:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:791:

GAGAAUUACC UGGCA                                                        15

(2) INFORMATION FOR SEQ ID NO:792:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:792:

GAGAAUUACC UGGCA                                                        15

(2) INFORMATION FOR SEQ ID NO:793:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:793:

CUGGCAUCAA UACGA                                                        15

(2) INFORMATION FOR SEQ ID NO:794:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:794:

CUGGCAUCAA UACGA                                                        15

(2) INFORMATION FOR SEQ ID NO:795:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:795:

CAUCAAUACG ACAAU                                                        15

(2) INFORMATION FOR SEQ ID NO:796:

(i) SEQUENCE CHARACTERISTICS:
        (A) LENGTH:          15 base pairs
        (B) TYPE:            nucleic acid
        (C) STRANDEDNESS:    single
```

(D) TOPOLOGY:      linear (xi) SEQUENCE DESCRIPTION: SEQ ID NO:796:

CAUCAAUACG ACAAU                                                              15

(2) INFORMATION FOR SEQ ID NO:797:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:797:

CGACAAUUUC CCAGG                                                              15

(2) INFORMATION FOR SEQ ID NO:798:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:798:

GACAAUUUCC CAGGA                                                              15

(2) INFORMATION FOR SEQ ID NO:799:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:799:

ACAAUUUCCC AGGAU                                                              15

(2) INFORMATION FOR SEQ ID NO:800:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:800:

CCAGGAUCCU GAAUC                                                              15

(2) INFORMATION FOR SEQ ID NO:801:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:801:

CCUGAAUCUG AAUUG                                                              15

(2) INFORMATION FOR SEQ ID NO:802:

(i) SEQUENCE CHARACTERISTICS:
          (A) LENGTH:        15 base pairs
          (B) TYPE:          nucleic acid
          (C) STRANDEDNESS:  single
          (D) TOPOLOGY:      linear (xi) SEQUENCE DESCRIPTION: SEQ ID NO:802:

CCUGAAUCUG AAUUG                                                15

(2) INFORMATION FOR SEQ ID NO:803:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:803:

GAAUUGUACA CCAUU                                                15

(2) INFORMATION FOR SEQ ID NO:804:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:804:

GCCAACUAGA UUUCA                                                15

(2) INFORMATION FOR SEQ ID NO:805:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:805:

GCCAACUAGA UUUCA                                                15

(2) INFORMATION FOR SEQ ID NO:806:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:806:

GCCAACUAGA UUUCA                                                15

(2) INFORMATION FOR SEQ ID NO:807:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:807:

ACUAGAUUUC AAUAC                                                15

(2) INFORMATION FOR SEQ ID NO:808:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:808:

ACUAGAUUUC AAUAC                                                      15

(2) INFORMATION FOR SEQ ID NO:809:

(i) SEQUENCE CHARACTERISTICS:
       (A) LENGTH:         15 base pairs
       (B) TYPE:           nucleic acid
       (C) STRANDEDNESS:   single
       (D) TOPOLOGY:       linear (xi) SEQUENCE DESCRIPTION: SEQ ID NO:809:

CUAGAUUUCA AUACG                                                      15

(2) INFORMATION FOR SEQ ID NO:810:

(i) SEQUENCE CHARACTERISTICS:
       (A) LENGTH:         15 base pairs
       (B) TYPE:           nucleic acid
       (C) STRANDEDNESS:   single
       (D) TOPOLOGY:       linear (xi) SEQUENCE DESCRIPTION: SEQ ID NO:810:

UAGAUUUCAA UACGA                                                      15

(2) INFORMATION FOR SEQ ID NO:811:

(i) SEQUENCE CHARACTERISTICS:
       (A) LENGTH:         15 base pairs
       (B) TYPE:           nucleic acid
       (C) STRANDEDNESS:   single
       (D) TOPOLOGY:       linear (xi) SEQUENCE DESCRIPTION: SEQ ID NO:811:

UACGACUCGC AACCA                                                      15

(2) INFORMATION FOR SEQ ID NO:812:

(i) SEQUENCE CHARACTERISTICS:
       (A) LENGTH:         15 base pairs
       (B) TYPE:           nucleic acid
       (C) STRANDEDNESS:   single
       (D) TOPOLOGY:       linear (xi) SEQUENCE DESCRIPTION: SEQ ID NO:812:

ACACCAUUAA GUGUC                                                      15

(2) INFORMATION FOR SEQ ID NO:813:

(i) SEQUENCE CHARACTERISTICS:
       (A) LENGTH:         15 base pairs
       (B) TYPE:           nucleic acid
       (C) STRANDEDNESS:   single
       (D) TOPOLOGY:       linear (xi) SEQUENCE DESCRIPTION: SEQ ID NO:813:

ACACCAUUAA GUGUC                                                      15

(2) INFORMATION FOR SEQ ID NO:814:

(i) SEQUENCE CHARACTERISTICS:
       (A) LENGTH:         15 base pairs
       (B) TYPE:           nucleic acid
       (C) STRANDEDNESS:   single
       (D) TOPOLOGY:       linear (xi) SEQUENCE DESCRIPTION: SEQ ID NO:814:

UAAGUGUCUC AUUAA     15

(2) INFORMATION FOR SEQ ID NO:815:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:815:

UAAGUGUCUC AUUAA     15

(2) INFORMATION FOR SEQ ID NO:816:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:816:

AGUGUCUCAU UAAAU     15

(2) INFORMATION FOR SEQ ID NO:817:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:817:

GUCUCAUUAA AUAUG     15

(2) INFORMATION FOR SEQ ID NO:818:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:818:

AUUAAAUAUG GAGAU     15

(2) INFORMATION FOR SEQ ID NO:819:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:819:

AUUAAAUAUG GAGAU     15

(2) INFORMATION FOR SEQ ID NO:820:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:820:

```
GAGGACUUCA CCUGG                                                     15

(2) INFORMATION FOR SEQ ID NO:821:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:821:

AGGACUUCAC CUGGG                                                     15

(2) INFORMATION FOR SEQ ID NO:822:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:822:

UGCUCUUUGG GGCAG                                                     15

(2) INFORMATION FOR SEQ ID NO:823:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:823:

CAGUCGUCGU CAUCG                                                     15

(2) INFORMATION FOR SEQ ID NO:824:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:824:

UCGUCGUCAU CGUUG                                                     15

(2) INFORMATION FOR SEQ ID NO:825:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:825:

UCAUCGUUGU CAUCA                                                     15

(2) INFORMATION FOR SEQ ID NO:826:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:826:

UCGUUGUCAU CAUCA                                                     15
```

(2) INFORMATION FOR SEQ ID NO:827:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:827:

UUGUCAUCAU CAAAU                                                        15

(2) INFORMATION FOR SEQ ID NO:828:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:828:

AAAUGCUUCU GUAAG                                                        15

(2) INFORMATION FOR SEQ ID NO:829:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:829:

AAAUGCUUCU GUAAG                                                        15

(2) INFORMATION FOR SEQ ID NO:830:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:830:

AAAUGCUUCU GUAAG                                                        15

(2) INFORMATION FOR SEQ ID NO:831:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:831:

AAAUGCUUCU GUAAG                                                        15

(2) INFORMATION FOR SEQ ID NO:832:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:832:

AAUGCUUCUG UAAGC                                                        15

(2) INFORMATION FOR SEQ ID NO:833:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:833:

AAGCUGUUUC AGAAG                                                                15

(2) INFORMATION FOR SEQ ID NO:834:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:834:

AAGCUGUUUC AGAAG                                                                15

(2) INFORMATION FOR SEQ ID NO:835:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:835:

AGCUGUUUCA GAAGA                                                                 15

(2) INFORMATION FOR SEQ ID NO:836:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:836:

ACAGCCUUAC CUUCG                                                                15

(2) INFORMATION FOR SEQ ID NO:837:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:837:

ACAGCCUUAC CUUCG                                                                15

(2) INFORMATION FOR SEQ ID NO:838:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:838:

ACAGCCUUAC CUUCG                                                                15

(2) INFORMATION FOR SEQ ID NO:839:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:839:

CAGCCUUACC UUCGG                                                       15

(2) INFORMATION FOR SEQ ID NO:840:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:840:

CUUACCUUCG GGCCU                                                       15

(2) INFORMATION FOR SEQ ID NO:841:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:841:

UUACCUUCGG GCCUG                                                       15

(2) INFORMATION FOR SEQ ID NO:842:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:842:

UUACCUUCGG GCCUG                                                       15

(2) INFORMATION FOR SEQ ID NO:843:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:843:

GAAGCAUUAG CUGAA                                                       15

(2) INFORMATION FOR SEQ ID NO:844:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:844:

GAAGCAUUAG CUGAA                                                       15

(2) INFORMATION FOR SEQ ID NO:845:

(i) SEQUENCE CHARACTERISTICS:
    (A) LENGTH:        15 base pairs
    (B) TYPE:          nucleic acid
    (C) STRANDEDNESS:  single
    (D) TOPOLOGY:      linear (xi) SEQUENCE DESCRIPTION: SEQ ID NO:845:

AAGCAUUAGC UGAAC                                                    15

(2) INFORMATION FOR SEQ ID NO:846:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:846:

AGACCGUCUU CCUUU                                                    15

(2) INFORMATION FOR SEQ ID NO:847:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:847:

ACCGUCUUCC UUUAG                                                    15

(2) INFORMATION FOR SEQ ID NO:848:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:848:

CCGUCUUCCU UUAGU                                                    15

(2) INFORMATION FOR SEQ ID NO:849:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:849:

CUUCCUUUAG UUCUU                                                    15

(2) INFORMATION FOR SEQ ID NO:850:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:850:

UUCUUCUCUG UCCAU                                                    15

(2) INFORMATION FOR SEQ ID NO:851:

```
    (i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:851:

UCUCUGUCCA UGUGG                                                15

(2) INFORMATION FOR SEQ ID NO:852:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:852:

UCUCUGUCCA UGUGG                                                15

(2) INFORMATION FOR SEQ ID NO:853:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:853:

GUGGGAUACA UGGUA                                                15

(2) INFORMATION FOR SEQ ID NO:854:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:854:

ACAUGGUAUU AUGUG                                                15

(2) INFORMATION FOR SEQ ID NO:855:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:855:

AUGGUAUUAU GUGGC                                                15

(2) INFORMATION FOR SEQ ID NO:856:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:856:

UGUGGCUCAU GAGGU                                                15

(2) INFORMATION FOR SEQ ID NO:857:

(i) SEQUENCE CHARACTERISTICS:
```

```
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:857:

UGUGGCUCAU GAGGU                                                    15

(2) INFORMATION FOR SEQ ID NO:858:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:858:

GUACAAUCUU UCUUU                                                    15

(2) INFORMATION FOR SEQ ID NO:859:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:859:

ACAAUCUUUC UUUCA                                                    15

(2) INFORMATION FOR SEQ ID NO:860:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:860:

ACAAUCUUUC UUUCA                                                    15

(2) INFORMATION FOR SEQ ID NO:861:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:861:

CAAUCUUUCU UUCAG                                                    15

(2) INFORMATION FOR SEQ ID NO:862:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:862:

AAUCUUUCUU UCAGC                                                    15

(2) INFORMATION FOR SEQ ID NO:863:

(i) SEQUENCE CHARACTERISTICS:
          (A) LENGTH:         15 base pairs
```

```
            (B) TYPE:           nucleic acid
            (C) STRANDEDNESS:   single
            (D) TOPOLOGY:       linear (xi) SEQUENCE DESCRIPTION: SEQ ID NO:863:

AAUCUUUCUU UCAGC                                                          15

(2) INFORMATION FOR SEQ ID NO:864:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:864:

AAUCUUUCUU UCAGC                                                          15

(2) INFORMATION FOR SEQ ID NO:865:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:865:

UCUUUCUUUC AGCAC                                                          15

(2) INFORMATION FOR SEQ ID NO:866:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:866:

CUUUCUUUCA GCACC                                                          15

(2) INFORMATION FOR SEQ ID NO:867:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:867:

CUGAUCUUUC GGACA                                                          15

(2) INFORMATION FOR SEQ ID NO:868:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:868:

ACAAGAUAGA GUUAA                                                          15

(2) INFORMATION FOR SEQ ID NO:869:

(i) SEQUENCE CHARACTERISTICS:
            (A) LENGTH:         15 base pairs
            (B) TYPE:           nucleic acid
```

```
        (C) STRANDEDNESS:    single
        (D) TOPOLOGY:        linear (xi) SEQUENCE DESCRIPTION: SEQ ID NO:869:

UGAGGAUUUC UUUCC                                                              15

(2) INFORMATION FOR SEQ ID NO:870:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:870:

AGGAUUUCUU UCCAU                                                              15

(2) INFORMATION FOR SEQ ID NO:871:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:871:

GAUUUCUUUC CAUCA                                                              15

(2) INFORMATION FOR SEQ ID NO:872:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:872:

UUUCUUUCCA UCAGG                                                              15

(2) INFORMATION FOR SEQ ID NO:873:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:873:

UUUCCAUCAG GAAGC                                                              15

(2) INFORMATION FOR SEQ ID NO:874:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:874:

UUUCCAUCAG GAAGC                                                              15

(2) INFORMATION FOR SEQ ID NO:875:

(i) SEQUENCE CHARACTERISTICS:
        (A) LENGTH:          15 base pairs
        (B) TYPE:            nucleic acid
        (C) STRANDEDNESS:    single
```

```
        (D) TOPOLOGY:       linear (xi) SEQUENCE DESCRIPTION: SEQ ID NO:875:

GGCAAGUUUG CUGGG                                                    15

(2) INFORMATION FOR SEQ ID NO:876:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:876:

CUUUGAUUGC UUGAU                                                    15

(2) INFORMATION FOR SEQ ID NO:877:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:877:

GUGGUAUAAG AAAAA                                                    15

(2) INFORMATION FOR SEQ ID NO:878:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:878:

GUGGUAUAAG AAAAA                                                    15

(2) INFORMATION FOR SEQ ID NO:879:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:879:

GCCUAGUCUU ACUGC                                                    15

(2) INFORMATION FOR SEQ ID NO:880:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:880:

CUAGUCUUAC UGCAA                                                    15

(2) INFORMATION FOR SEQ ID NO:881:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear
```

(xi) SEQUENCE DESCRIPTION: SEQ ID NO:881:

UGCAACUUGA UAUGU                                                    15

(2) INFORMATION FOR SEQ ID NO:882:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:882:

ACUUGAUAUG UCAUG                                                    15

(2) INFORMATION FOR SEQ ID NO:883:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:883:

ACUUGAUAUG UCAUG                                                    15

(2) INFORMATION FOR SEQ ID NO:884:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:884:

GUUUGGUUGG UGUCU                                                    15

(2) INFORMATION FOR SEQ ID NO:885:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:885:

UGCCCUUUUC UGAAG                                                    15

(2) INFORMATION FOR SEQ ID NO:886:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:886:

GCCCUUUUCU GAAGA                                                    15

(2) INFORMATION FOR SEQ ID NO:887:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:887:

CCCUUUUCUG AAGAG                                                15

(2) INFORMATION FOR SEQ ID NO:888:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:888:

CCCUUUUCUG AAGAG                                                15

(2) INFORMATION FOR SEQ ID NO:889:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:889:

CUAUGGUUGG GAUGU                                                15

(2) INFORMATION FOR SEQ ID NO:890:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:890:

GGGAUGUAAA AACGG                                                15

(2) INFORMATION FOR SEQ ID NO:891:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:891:

GGGAUGUAAA AACGG                                                15

(2) INFORMATION FOR SEQ ID NO:892:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:892:

AUAAUAUAAA UAUUA                                                15

(2) INFORMATION FOR SEQ ID NO:893:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:893:

UAUAAAUAUU AAAUA 15

(2) INFORMATION FOR SEQ ID NO:894:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:894:

UAAAUAUUAA AUAAA 15

(2) INFORMATION FOR SEQ ID NO:895:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:895:

AAAUAUUAAA UAAAA 15

(2) INFORMATION FOR SEQ ID NO:896:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:896:

AAAUAUUAAA UAAAA 15

(2) INFORMATION FOR SEQ ID NO:897:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:897:

AGAGUAUUGA GCAAA 15

(2) INFORMATION FOR SEQ ID NO:898:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:898:

UGAGGUACUG AUGAGGCCGA AAGGCCGAAA AAACUC 36

(2) INFORMATION FOR SEQ ID NO:899:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:899:

AUUGAGGCUG AUGAGGCCGA AAGGCCGAAA UAAAAC                                    36

(2) INFORMATION FOR SEQ ID NO:900:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:900:

AUUGAGGCUG AUGAGGCCGA AAGGCCGAAA UAAAAC                                    36

(2) INFORMATION FOR SEQ ID NO:901:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:901:

GUCUAUUCUG AUGAGGCCGA AAGGCCGAAA GGUAUA                                    36

(2) INFORMATION FOR SEQ ID NO:902:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:902:

AAGAGUCCUG AUGAGGCCGA AAGGCCGAAA UUGAGG                                    36

(2) INFORMATION FOR SEQ ID NO:903:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:903:

AAGAGUCCUG AUGAGGCCGA AAGGCCGAAA UUGAGG                                    36

(2) INFORMATION FOR SEQ ID NO:904:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:904:

AAGAGUCCUG AUGAGGCCGA AAGGCCGAAA UUGAGG                                    36

(2) INFORMATION FOR SEQ ID NO:905:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:905:

CUAGUAACUG AUGAGGCCGA AAGGCCGAAA GUCUAU                                    36

(2) INFORMATION FOR SEQ ID NO:906:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:906:

AACUAGUCUG AUGAGGCCGA AAGGCCGAAA GAGUCU                          36

(2) INFORMATION FOR SEQ ID NO:907:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:907:

AAACUAGCUG AUGAGGCCGA AAGGCCGAAA AGAGUC                          36

(2) INFORMATION FOR SEQ ID NO:908:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:908:

GAGAAACCUG AUGAGGCCGA AAGGCCGAAA GUAAGA                          36

(2) INFORMATION FOR SEQ ID NO:909:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:909:

GAGAAACCUG AUGAGGCCGA AAGGCCGAAA GUAAGA                          36

(2) INFORMATION FOR SEQ ID NO:910:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:910:

GAGAAACCUG AUGAGGCCGA AAGGCCGAAA GUAAGA                          36

(2) INFORMATION FOR SEQ ID NO:911:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:911:

GAGAAACCUG AUGAGGCCGA AAGGCCGAAA GUAAGA                          36

(2) INFORMATION FOR SEQ ID NO:912:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:912:

AAAAAGACUG AUGAGGCCGA AAGGCCGAAA AACUAG                              36

(2) INFORMATION FOR SEQ ID NO:913:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:913:

AAAAAGACUG AUGAGGCCGA AAGGCCGAAA AACUAG                              36

(2) INFORMATION FOR SEQ ID NO:914:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:914:

AAAAAGACUG AUGAGGCCGA AAGGCCGAAA AACUAG                              36

(2) INFORMATION FOR SEQ ID NO:915:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:915:

AACCUGACUG AUGAGGCCGA AAGGCCGAAA AAGAGA                              36

(2) INFORMATION FOR SEQ ID NO:916:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:916:

CAACCUGCUG AUGAGGCCGA AAGGCCGAAA AAAGAG                              36

(2) INFORMATION FOR SEQ ID NO:917:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:917:

CAACCUGCUG AUGAGGCCGA AAGGCCGAAA AAAGAG                              36

```
(2) INFORMATION FOR SEQ ID NO:918:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:918:

ACAACCUCUG AUGAGGCCGA AAGGCCGAAA AAAAGA                                    36

(2) INFORMATION FOR SEQ ID NO:919:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:919:

GAAGGUUCUG AUGAGGCCGA AAGGCCGAAA GUUUCA                                    36

(2) INFORMATION FOR SEQ ID NO:920:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:920:

GAAGGUUCUG AUGAGGCCGA AAGGCCGAAA GUUUCA                                    36

(2) INFORMATION FOR SEQ ID NO:921:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:921:

GUCUUUGCUG AUGAGGCCGA AAGGCCGAAA GGUUGA                                    36

(2) INFORMATION FOR SEQ ID NO:922:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:922:

GUCUUUGCUG AUGAGGCCGA AAGGCCGAAA GGUUGA                                    36

(2) INFORMATION FOR SEQ ID NO:923:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:923:

GUCUUUGCUG AUGAGGCCGA AAGGCCGAAA GGUUGA                                    36

(2) INFORMATION FOR SEQ ID NO:924:
```

```
   (i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:924:

UGUCUUUCUG AUGAGGCCGA AAGGCCGAAA AGGUUG                               36

(2) INFORMATION FOR SEQ ID NO:925:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:925:

UGGAACACUG AUGAGGCCGA AAGGCCGAAA GUGUCU                               36

(2) INFORMATION FOR SEQ ID NO:926:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:926:

GAAAUGGCUG AUGAGGCCGA AAGGCCGAAA CAGAGU                               36

(2) INFORMATION FOR SEQ ID NO:927:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:927:

AGAAAUGCUG AUGAGGCCGA AAGGCCGAAA ACAGAG                               36

(2) INFORMATION FOR SEQ ID NO:928:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:928:

UCCACAGCUG AUGAGGCCGA AAGGCCGAAA AUGGAA                               36

(2) INFORMATION FOR SEQ ID NO:929:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:929:

AUCCUAUCUG AUGAGGCCGA AAGGCCGAAA GUCCAC                               36

(2) INFORMATION FOR SEQ ID NO:930:
```

```
    (i) SEQUENCE CHARACTERISTICS:
         (A) LENGTH:         36 base pairs
         (B) TYPE:           nucleic acid
         (C) STRANDEDNESS:   single
         (D) TOPOLOGY:       linear (xi) SEQUENCE DESCRIPTION: SEQ ID NO:930:

AUCCUAUCUG AUGAGGCCGA AAGGCCGAAA GUCCAC                              36

(2) INFORMATION FOR SEQ ID NO:931:

(i) SEQUENCE CHARACTERISTICS:
         (A) LENGTH:         36 base pairs
         (B) TYPE:           nucleic acid
         (C) STRANDEDNESS:   single
         (D) TOPOLOGY:       linear (xi) SEQUENCE DESCRIPTION: SEQ ID NO:931:

AUCCUAUCUG AUGAGGCCGA AAGGCCGAAA GUCCAC                              36

(2) INFORMATION FOR SEQ ID NO:932:

(i) SEQUENCE CHARACTERISTICS:
         (A) LENGTH:         36 base pairs
         (B) TYPE:           nucleic acid
         (C) STRANDEDNESS:   single
         (D) TOPOLOGY:       linear (xi) SEQUENCE DESCRIPTION: SEQ ID NO:932:

AUGAUCCCUG AUGAGGCCGA AAGGCCGAAA UUAGUC                              36

(2) INFORMATION FOR SEQ ID NO:933:

(i) SEQUENCE CHARACTERISTICS:
         (A) LENGTH:         36 base pairs
         (B) TYPE:           nucleic acid
         (C) STRANDEDNESS:   single
         (D) TOPOLOGY:       linear (xi) SEQUENCE DESCRIPTION: SEQ ID NO:933:

AUGAUCCCUG AUGAGGCCGA AAGGCCGAAA UUAGUC                              36

(2) INFORMATION FOR SEQ ID NO:934:

(i) SEQUENCE CHARACTERISTICS:
         (A) LENGTH:         36 base pairs
         (B) TYPE:           nucleic acid
         (C) STRANDEDNESS:   single
         (D) TOPOLOGY:       linear (xi) SEQUENCE DESCRIPTION: SEQ ID NO:934:

UAAAGAUCUG AUGAGGCCGA AAGGCCGAAA UCCUAU                              36

(2) INFORMATION FOR SEQ ID NO:935:

(i) SEQUENCE CHARACTERISTICS:
         (A) LENGTH:         36 base pairs
         (B) TYPE:           nucleic acid
         (C) STRANDEDNESS:   single
         (D) TOPOLOGY:       linear (xi) SEQUENCE DESCRIPTION: SEQ ID NO:935:

UGCUAAACUG AUGAGGCCGA AAGGCCGAAA UGAUCC                              36

(2) INFORMATION FOR SEQ ID NO:936:

(i) SEQUENCE CHARACTERISTICS:
```

(A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:936:

UGCUAAACUG AUGAGGCCGA AAGGCCGAAA UGAUCC                          36

(2) INFORMATION FOR SEQ ID NO:937:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:937:

GAUGCUACUG AUGAGGCCGA AAGGCCGAAA GAUGAU                          36

(2) INFORMATION FOR SEQ ID NO:938:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:938:

AGAUGCUCUG AUGAGGCCGA AAGGCCGAAA AGAUGA                          36

(2) INFORMATION FOR SEQ ID NO:939:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:939:

AGAUGCUCUG AUGAGGCCGA AAGGCCGAAA AGAUGA                          36

(2) INFORMATION FOR SEQ ID NO:940:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:940:

CAGAUGCCUG AUGAGGCCGA AAGGCCGAAA AAGAUG                          36

(2) INFORMATION FOR SEQ ID NO:941:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:941:

CAGAUGCCUG AUGAGGCCGA AAGGCCGAAA AAGAUG                          36

(2) INFORMATION FOR SEQ ID NO:942:

(i) SEQUENCE CHARACTERISTICS:
            (A) LENGTH:         36 base pairs

```
          (B) TYPE:           nucleic acid
          (C) STRANDEDNESS:   single
          (D) TOPOLOGY:       linear (xi) SEQUENCE DESCRIPTION: SEQ ID NO:942:

AAGCCUGCUG AUGAGGCCGA AAGGCCGAAA UGGCAU                              36

(2) INFORMATION FOR SEQ ID NO:943:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:943:

UGUAGAACUG AUGAGGCCGA AAGGCCGAAA AGAAGC                              36

(2) INFORMATION FOR SEQ ID NO:944:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:944:

UGUAGAACUG AUGAGGCCGA AAGGCCGAAA AGAAGC                              36

(2) INFORMATION FOR SEQ ID NO:945:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:945:

AUGUAGACUG AUGAGGCCGA AAGGCCGAAA AAGAAG                              36

(2) INFORMATION FOR SEQ ID NO:946:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:946:

AUGUAGACUG AUGAGGCCGA AAGGCCGAAA AAGAAG                              36

(2) INFORMATION FOR SEQ ID NO:947:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:947:

AUGUAGACUG AUGAGGCCGA AAGGCCGAAA AAGAAG                              36

(2) INFORMATION FOR SEQ ID NO:948:

(i) SEQUENCE CHARACTERISTICS:
          (A) LENGTH:         36 base pairs
          (B) TYPE:           nucleic acid
```

```
            (C) STRANDEDNESS:    single
            (D) TOPOLOGY:        linear (xi) SEQUENCE DESCRIPTION: SEQ ID NO:948:

AUGUAGACUG AUGAGGCCGA AAGGCCGAAA AAGAAG                              36

(2) INFORMATION FOR SEQ ID NO:949:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:949:

GAUGUAGCUG AUGAGGCCGA AAGGCCGAAA AAAGAA                              36

(2) INFORMATION FOR SEQ ID NO:950:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:950:

GAUGUAGCUG AUGAGGCCGA AAGGCCGAAA AAAGAA                              36

(2) INFORMATION FOR SEQ ID NO:951:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:951:

GAUGUAGCUG AUGAGGCCGA AAGGCCGAAA AAAGAA                              36

(2) INFORMATION FOR SEQ ID NO:952:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:952:

AGAGAUGCUG AUGAGGCCGA AAGGCCGAAA GAAAAA                              36

(2) INFORMATION FOR SEQ ID NO:953:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:953:

AGAAACACUG AUGAGGCCGA AAGGCCGAAA GAUGUA                              36

(2) INFORMATION FOR SEQ ID NO:954:

(i) SEQUENCE CHARACTERISTICS:
            (A) LENGTH:          36 base pairs
            (B) TYPE:            nucleic acid
            (C) STRANDEDNESS:    single
```

(D) TOPOLOGY:      linear (xi) SEQUENCE DESCRIPTION: SEQ ID NO:954:

UCACAAACUG AUGAGGCCGA AAGGCCGAAA UCGAGA                              36

(2) INFORMATION FOR SEQ ID NO:955:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:955:

UCACAAACUG AUGAGGCCGA AAGGCCGAAA UCGAGA                              36

(2) INFORMATION FOR SEQ ID NO:956:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:956:

UCACAAACUG AUGAGGCCGA AAGGCCGAAA UCGAGA                              36

(2) INFORMATION FOR SEQ ID NO:957:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:957:

CUCACAACUG AUGAGGCCGA AAGGCCGAAA AUCGAG                              36

(2) INFORMATION FOR SEQ ID NO:958:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:958:

GCUCACACUG AUGAGGCCGA AAGGCCGAAA AAUCGA                              36

(2) INFORMATION FOR SEQ ID NO:959:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:959:

GCUCACACUG AUGAGGCCGA AAGGCCGAAA AAUCGA                              36

(2) INFORMATION FOR SEQ ID NO:960:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:960:

GCUCACACUG AUGAGGCCGA AAGGCCGAAA AAUCGA                                      36

(2) INFORMATION FOR SEQ ID NO:961:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:961:

GGCUCACCUG AUGAGGCCGA AAGGCCGAAA AAAUCG                                      36

(2) INFORMATION FOR SEQ ID NO:962:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:962:

GGCUCACCUG AUGAGGCCGA AAGGCCGAAA AAAUCG                                      36

(2) INFORMATION FOR SEQ ID NO:963:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:963:

UAGAGCCCUG AUGAGGCCGA AAGGCCGAAA UGGAGC                                      36

(2) INFORMATION FOR SEQ ID NO:964:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:964:

GAAUCUACUG AUGAGGCCGA AAGGCCGAAA GCCAAU                                      36

(2) INFORMATION FOR SEQ ID NO:965:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:965:

AGCCAGGCUG AUGAGGCCGA AAGGCCGAAA UCUAGA                                      36

(2) INFORMATION FOR SEQ ID NO:966:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear -continued (xi) SEQUENCE DESCRIPTION: SEQ ID NO:966:

AUGGGGACUG AUGAGGCCGA AAGGCCGAAA GCCAGG                                    36

(2) INFORMATION FOR SEQ ID NO:967:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:967:

GAUGGGGCUG AUGAGGCCGA AAGGCCGAAA AGCCAG                                    36

(2) INFORMATION FOR SEQ ID NO:968:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:968:

GAUGGGGCUG AUGAGGCCGA AAGGCCGAAA AGCCAG                                    36

(2) INFORMATION FOR SEQ ID NO:969:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:969:

GAUGGGGCUG AUGAGGCCGA AAGGCCGAAA AGCCAG                                    36

(2) INFORMATION FOR SEQ ID NO:970:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:970:

UGAUGGGCUG AUGAGGCCGA AAGGCCGAAA AAGCCA                                    36

(2) INFORMATION FOR SEQ ID NO:971:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:971:

UGAUGGGCUG AUGAGGCCGA AAGGCCGAAA AAGCCA                                    36

(2) INFORMATION FOR SEQ ID NO:972:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:972:

UGAUGGGCUG AUGAGGCCGA AAGGCCGAAA AAGCCA 36

(2) INFORMATION FOR SEQ ID NO:973:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:973:

UGAUGGGCUG AUGAGGCCGA AAGGCCGAAA AAGCCA 36

(2) INFORMATION FOR SEQ ID NO:974:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:974:

AGAACAUCUG AUGAGGCCGA AAGGCCGAAA UGGGGA 36

(2) INFORMATION FOR SEQ ID NO:975:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:975:

AGAACAUCUG AUGAGGCCGA AAGGCCGAAA UGGGGA 36

(2) INFORMATION FOR SEQ ID NO:976:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:976:

CUUUGGACUG AUGAGGCCGA AAGGCCGAAA ACAUGA 36

(2) INFORMATION FOR SEQ ID NO:977:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:977:

UGCUUUGCUG AUGAGGCCGA AAGGCCGAAA GAACAU 36

(2) INFORMATION FOR SEQ ID NO:978:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:978:

UGCUUUGCUG AUGAGGCCGA AAGGCCGAAA GAACAU                                           36

(2) INFORMATION FOR SEQ ID NO:979:

(i) SEQUENCE CHARACTERISTICS:
          (A) LENGTH:        36 base pairs
          (B) TYPE:          nucleic acid
          (C) STRANDEDNESS:  single
          (D) TOPOLOGY:      linear (xi) SEQUENCE DESCRIPTION: SEQ ID NO:979:

UGCUUUGCUG AUGAGGCCGA AAGGCCGAAA GAACAU                                           36

(2) INFORMATION FOR SEQ ID NO:980:

(i) SEQUENCE CHARACTERISTICS:
          (A) LENGTH:        36 base pairs
          (B) TYPE:          nucleic acid
          (C) STRANDEDNESS:  single
          (D) TOPOLOGY:      linear (xi) SEQUENCE DESCRIPTION: SEQ ID NO:980:

AGCUUCACUG AUGAGGCCGA AAGGCCGAAA UGCUUU                                           36

(2) INFORMATION FOR SEQ ID NO:981:

(i) SEQUENCE CHARACTERISTICS:
          (A) LENGTH:        36 base pairs
          (B) TYPE:          nucleic acid
          (C) STRANDEDNESS:  single
          (D) TOPOLOGY:      linear (xi) SEQUENCE DESCRIPTION: SEQ ID NO:981:

AGCUUCACUG AUGAGGCCGA AAGGCCGAAA UGCUUU                                           36

(2) INFORMATION FOR SEQ ID NO:982:

(i) SEQUENCE CHARACTERISTICS:
          (A) LENGTH:        36 base pairs
          (B) TYPE:          nucleic acid
          (C) STRANDEDNESS:  single
          (D) TOPOLOGY:      linear (xi) SEQUENCE DESCRIPTION: SEQ ID NO:982:

AGCUUCACUG AUGAGGCCGA AAGGCCGAAA UGCUUU                                           36

(2) INFORMATION FOR SEQ ID NO:983:

(i) SEQUENCE CHARACTERISTICS:
          (A) LENGTH:        36 base pairs
          (B) TYPE:          nucleic acid
          (C) STRANDEDNESS:  single
          (D) TOPOLOGY:      linear (xi) SEQUENCE DESCRIPTION: SEQ ID NO:983:

CAAGCCACUG AUGAGGCCGA AAGGCCGAAA GCUUCA                                           36

(2) INFORMATION FOR SEQ ID NO:984:

(i) SEQUENCE CHARACTERISTICS:
          (A) LENGTH:        36 base pairs
          (B) TYPE:          nucleic acid
          (C) STRANDEDNESS:  single
          (D) TOPOLOGY:      linear (xi) SEQUENCE DESCRIPTION: SEQ ID NO:984:

AUCAACUCUG AUGAGGCCGA AAGGCCGAAA CAAUUG                                           36

(2) INFORMATION FOR SEQ ID NO:985:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:985:

ACUUGAGCUG AUGAGGCCGA AAGGCCGAAA GUGGUG					36

(2) INFORMATION FOR SEQ ID NO:986:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:986:

ACAUGGACUG AUGAGGCCGA AAGGCCGAAA CUUGAG					36

(2) INFORMATION FOR SEQ ID NO:987:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:987:

ACAUGGACUG AUGAGGCCGA AAGGCCGAAA CUUGAG					36

(2) INFORMATION FOR SEQ ID NO:988:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:988:

GACAUGGCUG AUGAGGCCGA AAGGCCGAAA ACUUGA					36

(2) INFORMATION FOR SEQ ID NO:989:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:989:

GGACAUGCUG AUGAGGCCGA AAGGCCGAAA AACUUG					36

(2) INFORMATION FOR SEQ ID NO:990:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:990:

GGACAUGCUG AUGAGGCCGA AAGGCCGAAA AACUUG					36

(2) INFORMATION FOR SEQ ID NO:991:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:991:

AGAGAAGCUG AUGAGGCCGA AAGGCCGAAA UGAGCC                            36

(2) INFORMATION FOR SEQ ID NO:992:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:992:

AGAGAAGCUG AUGAGGCCGA AAGGCCGAAA UGAGCC                            36

(2) INFORMATION FOR SEQ ID NO:993:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:993:

AAGAGAACUG AUGAGGCCGA AAGGCCGAAA AUGAGC                            36

(2) INFORMATION FOR SEQ ID NO:994:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:994:

AAGAGAACUG AUGAGGCCGA AAGGCCGAAA AUGAGC                            36

(2) INFORMATION FOR SEQ ID NO:995:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:995:

CAAAGAGCUG AUGAGGCCGA AAGGCCGAAA GAAUGA                            36

(2) INFORMATION FOR SEQ ID NO:996:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:996:

ACAAAGACUG AUGAGGCCGA AAGGCCGAAA AGAAUG                            36

(2) INFORMATION FOR SEQ ID NO:997:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:997:

ACAAAGACUG AUGAGGCCGA AAGGCCGAAA AGAAUG                                     36

(2) INFORMATION FOR SEQ ID NO:998:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:998:

GCACAAACUG AUGAGGCCGA AAGGCCGAAA GAAGAA                                     36

(2) INFORMATION FOR SEQ ID NO:999:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:999:

GCACAAACUG AUGAGGCCGA AAGGCCGAAA GAAGAA                                     36

(2) INFORMATION FOR SEQ ID NO:1000:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1000:

CAGCACACUG AUGAGGCCGA AAGGCCGAAA GAGAAG                                     36

(2) INFORMATION FOR SEQ ID NO:1001:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1001:

CAGCACACUG AUGAGGCCGA AAGGCCGAAA GAGAAG                                     36

(2) INFORMATION FOR SEQ ID NO:1002:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1002:

GCAGCACCUG AUGAGGCCGA AAGGCCGAAA AGAGAA                                     36

(2) INFORMATION FOR SEQ ID NO:1003:

```
    (i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1003:

GAAAGACCUG AUGAGGCCGA AAGGCCGAAA AUCAGC                              36

(2) INFORMATION FOR SEQ ID NO:1004:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1004:

CUUGUGACUG AUGAGGCCGA AAGGCCGAAA GACGAA                              36

(2) INFORMATION FOR SEQ ID NO:1005:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1005:

CUUGUGACUG AUGAGGCCGA AAGGCCGAAA GACGAA                              36

(2) INFORMATION FOR SEQ ID NO:1006:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1006:

ACUUGUGCUG AUGAGGCCGA AAGGCCGAAA AGACGA                              36

(2) INFORMATION FOR SEQ ID NO:1007:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1007:

CACUUGUCUG AUGAGGCCGA AAGGCCGAAA AAGACG                              36

(2) INFORMATION FOR SEQ ID NO:1008:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1008:

CACUUGUCUG AUGAGGCCGA AAGGCCGAAA AAGACG                              36

(2) INFORMATION FOR SEQ ID NO:1009:
```

(i) SEQUENCE CHARACTERISTICS:
    (A) LENGTH:        36 base pairs
    (B) TYPE:          nucleic acid
    (C) STRANDEDNESS:  single
    (D) TOPOLOGY:      linear (xi) SEQUENCE DESCRIPTION: SEQ ID NO:1009:

AUCUGAACUG AUGAGGCCGA AAGGCCGAAA CACUUG                         36

(2) INFORMATION FOR SEQ ID NO:1010:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1010:

AACAUCUCUG AUGAGGCCGA AAGGCCGAAA AGACAC                         36

(2) INFORMATION FOR SEQ ID NO:1011:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1011:

UUUCACUCUG AUGAGGCCGA AAGGCCGAAA CUUGGA                         36

(2) INFORMATION FOR SEQ ID NO:1012:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1012:

UAACGGCCUG AUGAGGCCGA AAGGCCGAAA GGCAGC                         36

(2) INFORMATION FOR SEQ ID NO:1013:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1013:

GAGUUGUCUG AUGAGGCCGA AAGGCCGAAA CGGCAA                         36

(2) INFORMATION FOR SEQ ID NO:1014:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1014:

GAGUUGUCUG AUGAGGCCGA AAGGCCGAAA CGGCAA                         36

(2) INFORMATION FOR SEQ ID NO:1015:

(i) SEQUENCE CHARACTERISTICS:

```
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1015:

AUGAGGACUG AUGAGGCCGA AAGGCCGAAA GUUGUA                            36

(2) INFORMATION FOR SEQ ID NO:1016:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1016:

UCUUCAUCUG AUGAGGCCGA AAGGCCGAAA GGAGAG                            36

(2) INFORMATION FOR SEQ ID NO:1017:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1017:

GUCUUCACUG AUGAGGCCGA AAGGCCGAAA CUCAUC                            36

(2) INFORMATION FOR SEQ ID NO:1018:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1018:

GCCAGUACUG AUGAGGCCGA AAGGCCGAAA UUCGGU                            36

(2) INFORMATION FOR SEQ ID NO:1019:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1019:

UUGCCAGCUG AUGAGGCCGA AAGGCCGAAA GAUUCG                            36

(2) INFORMATION FOR SEQ ID NO:1020:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1020:

AAUGACACUG AUGAGGCCGA AAGGCCGAAA CAGCAC                            36

(2) INFORMATION FOR SEQ ID NO:1021:

(i) SEQUENCE CHARACTERISTICS:
          (A) LENGTH:          36 base pairs
```

```
            (B) TYPE:           nucleic acid
            (C) STRANDEDNESS:   single
            (D) TOPOLOGY:       linear (xi) SEQUENCE DESCRIPTION: SEQ ID NO:1021:

AAUGACACUG AUGAGGCCGA AAGGCCGAAA CAGCAC                              36

(2) INFORMATION FOR SEQ ID NO:1022:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1022:

CAGCAAUCUG AUGAGGCCGA AAGGCCGAAA CAGACA                              36

(2) INFORMATION FOR SEQ ID NO:1023:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1023:

ACACUUUCUG AUGAGGCCGA AAGGCCGAAA GUUUCC                              36

(2) INFORMATION FOR SEQ ID NO:1024:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1024:

ACACUUUCUG AUGAGGCCGA AAGGCCGAAA GUUUCC                              36

(2) INFORMATION FOR SEQ ID NO:1025:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1025:

GUUCUUACUG AUGAGGCCGA AAGGCCGAAA CUCGGG                              36

(2) INFORMATION FOR SEQ ID NO:1026:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1026:

GUCAUAUCUG AUGAGGCCGA AAGGCCGAAA AGUCCG                              36

(2) INFORMATION FOR SEQ ID NO:1027:

(i) SEQUENCE CHARACTERISTICS:
            (A) LENGTH:         36 base pairs
            (B) TYPE:           nucleic acid
```

```
            (C) STRANDEDNESS:     single
            (D) TOPOLOGY:         linear (xi) SEQUENCE DESCRIPTION: SEQ ID NO:1027:

UGUCAUACUG AUGAGGCCGA AAGGCCGAAA AAGUCC                                  36

(2) INFORMATION FOR SEQ ID NO:1028:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1028:

GUUGUCACUG AUGAGGCCGA AAGGCCGAAA UAAAGU                                  36

(2) INFORMATION FOR SEQ ID NO:1029:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1029:

AAGAGAGCUG AUGAGGCCGA AAGGCCGAAA GGUAGU                                  36

(2) INFORMATION FOR SEQ ID NO:1030:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1030:

AAGAGAGCUG AUGAGGCCGA AAGGCCGAAA GGUAGU                                  36

(2) INFORMATION FOR SEQ ID NO:1031:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1031:

GAUAAGACUG AUGAGGCCGA AAGGCCGAAA GUAGGU                                  36

(2) INFORMATION FOR SEQ ID NO:1032:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1032:

GAUAAGACUG AUGAGGCCGA AAGGCCGAAA GUAGGU                                  36

(2) INFORMATION FOR SEQ ID NO:1033:

(i) SEQUENCE CHARACTERISTICS:
            (A) LENGTH:           36 base pairs
            (B) TYPE:             nucleic acid
            (C) STRANDEDNESS:     single
```

(D) TOPOLOGY:         linear (xi) SEQUENCE DESCRIPTION: SEQ ID NO:1033:

GGAUGAUCUG AUGAGGCCGA AAGGCCGAAA GAGAGU                    36

(2) INFORMATION FOR SEQ ID NO:1034:

(i) SEQUENCE CHARACTERISTICS:
       (A) LENGTH:           36 base pairs
       (B) TYPE:             nucleic acid
       (C) STRANDEDNESS:     single
       (D) TOPOLOGY:         linear (xi) SEQUENCE DESCRIPTION: SEQ ID NO:1034:

AGGAUGACUG AUGAGGCCGA AAGGCCGAAA AGAGAG                    36

(2) INFORMATION FOR SEQ ID NO:1035:

(i) SEQUENCE CHARACTERISTICS:
       (A) LENGTH:           36 base pairs
       (B) TYPE:             nucleic acid
       (C) STRANDEDNESS:     single
       (D) TOPOLOGY:         linear (xi) SEQUENCE DESCRIPTION: SEQ ID NO:1035:

AGGAUGACUG AUGAGGCCGA AAGGCCGAAA AGAGAG                    36

(2) INFORMATION FOR SEQ ID NO:1036:

(i) SEQUENCE CHARACTERISTICS:
       (A) LENGTH:           36 base pairs
       (B) TYPE:             nucleic acid
       (C) STRANDEDNESS:     single
       (D) TOPOLOGY:         linear (xi) SEQUENCE DESCRIPTION: SEQ ID NO:1036:

AGGAUGACUG AUGAGGCCGA AAGGCCGAAA AGAGAG                    36

(2) INFORMATION FOR SEQ ID NO:1037:

(i) SEQUENCE CHARACTERISTICS:
       (A) LENGTH:           36 base pairs
       (B) TYPE:             nucleic acid
       (C) STRANDEDNESS:     single
       (D) TOPOLOGY:         linear (xi) SEQUENCE DESCRIPTION: SEQ ID NO:1037:

GGCCCAGCUG AUGAGGCCGA AAGGCCGAAA UGAUAA                    36

(2) INFORMATION FOR SEQ ID NO:1038:

(i) SEQUENCE CHARACTERISTICS:
       (A) LENGTH:           36 base pairs
       (B) TYPE:             nucleic acid
       (C) STRANDEDNESS:     single
       (D) TOPOLOGY:         linear (xi) SEQUENCE DESCRIPTION: SEQ ID NO:1038:

GGCCCAGCUG AUGAGGCCGA AAGGCCGAAA UGAUAA                    36

(2) INFORMATION FOR SEQ ID NO:1039:

(i) SEQUENCE CHARACTERISTICS:
       (A) LENGTH:           36 base pairs
       (B) TYPE:             nucleic acid
       (C) STRANDEDNESS:     single
       (D) TOPOLOGY:         linear (xi) SEQUENCE DESCRIPTION: SEQ ID NO:1039:

GGUCUGACUG AUGAGGCCGA AAGGCCGAAA GGACCA                36

(2) INFORMATION FOR SEQ ID NO:1040:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1040:

CCGGUCUCUG AUGAGGCCGA AAGGCCGAAA AAGGAC                36

(2) INFORMATION FOR SEQ ID NO:1041:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1041:

CCGGUCUCUG AUGAGGCCGA AAGGCCGAAA AAGGAC                36

(2) INFORMATION FOR SEQ ID NO:1042:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1042:

ACAGCUGCUG AUGAGGCCGA AAGGCCGAAA UGUGCC                36

(2) INFORMATION FOR SEQ ID NO:1043:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1043:

UUUGAACCUG AUGAGGCCGA AAGGCCGAAA CACAGC                36

(2) INFORMATION FOR SEQ ID NO:1044:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1044:

UCUUUUGCUG AUGAGGCCGA AAGGCCGAAA CGACAC                36

(2) INFORMATION FOR SEQ ID NO:1045:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1045:

UCUUUUGCUG AUGAGGCCGA AAGGCCGAAA CGACAC          36

(2) INFORMATION FOR SEQ ID NO:1046:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1046:

UUCUUUUCUG AUGAGGCCGA AAGGCCGAAA ACGACA          36

(2) INFORMATION FOR SEQ ID NO:1047:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1047:

AGUGUUUCUG AUGAGGCCGA AAGGCCGAAA CUUCAU          36

(2) INFORMATION FOR SEQ ID NO:1048:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1048:

UAAAGCCCUG AUGAGGCCGA AAGGCCGAAA GUGUUU          36

(2) INFORMATION FOR SEQ ID NO:1049:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1049:

UAAAGCCCUG AUGAGGCCGA AAGGCCGAAA GUGUUU          36

(2) INFORMATION FOR SEQ ID NO:1050:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1050:

CUUUACUCUG AUGAGGCCGA AAGGCCGAAA AGCCAA          36

(2) INFORMATION FOR SEQ ID NO:1051:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1051:

ACUUUACCUG AUGAGGCCGA AAGGCCGAAA AAGCCA                                    36

(2) INFORMATION FOR SEQ ID NO:1052:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1052:

ACAACUUCUG AUGAGGCCGA AAGGCCGAAA CUAAAG                                    36

(2) INFORMATION FOR SEQ ID NO:1053:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1053:

GAUGGACCUG AUGAGGCCGA AAGGCCGAAA CUUUAC                                    36

(2) INFORMATION FOR SEQ ID NO:1054:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1054:

UUUGAUGCUG AUGAGGCCGA AAGGCCGAAA CAACUU                                    36

(2) INFORMATION FOR SEQ ID NO:1055:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1055:

CAGCUUUCUG AUGAGGCCGA AAGGCCGAAA UGGACA                                    36

(2) INFORMATION FOR SEQ ID NO:1056:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1056:

GGUAGAGCUG AUGAGGCCGA AAGGCCGAAA GUCAGC                                    36

(2) INFORMATION FOR SEQ ID NO:1057:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1057:

```
GGUAGAGCUG AUGAGGCCGA AAGGCCGAAA GUCAGC                                      36

(2) INFORMATION FOR SEQ ID NO:1058:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1058:

GGUAGAGCUG AUGAGGCCGA AAGGCCGAAA GUCAGC                                      36

(2) INFORMATION FOR SEQ ID NO:1059:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1059:

GGGUAGACUG AUGAGGCCGA AAGGCCGAAA AGUCAG                                      36

(2) INFORMATION FOR SEQ ID NO:1060:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1060:

GGGUAGACUG AUGAGGCCGA AAGGCCGAAA AGUCAG                                      36

(2) INFORMATION FOR SEQ ID NO:1061:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1061:

GGGGGUACUG AUGAGGCCGA AAGGCCGAAA GAAGUC                                      36

(2) INFORMATION FOR SEQ ID NO:1062:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1062:

GGGGGUACUG AUGAGGCCGA AAGGCCGAAA GAAGUC                                      36

(2) INFORMATION FOR SEQ ID NO:1063:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1063:

UUGGGGGCUG AUGAGGCCGA AAGGCCGAAA GAGAAG                                      36
```

(2) INFORMATION FOR SEQ ID NO:1064:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1064:

ACUCAGUCUG AUGAGGCCGA AAGGCCGAAA UGUUGG                          36

(2) INFORMATION FOR SEQ ID NO:1065:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1065:

ACUCAGUCUG AUGAGGCCGA AAGGCCGAAA UGUUGG                          36

(2) INFORMATION FOR SEQ ID NO:1066:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1066:

GUCUGCACUG AUGAGGCCGA AAGGCCGAAA UGGGUU                          36

(2) INFORMATION FOR SEQ ID NO:1067:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1067:

GUCUGCACUG AUGAGGCCGA AAGGCCGAAA UGGGUU                          36

(2) INFORMATION FOR SEQ ID NO:1068:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1068:

AUCCUUUCUG AUGAGGCCGA AAGGCCGAAA GUGUCU                          36

(2) INFORMATION FOR SEQ ID NO:1069:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1069:

AUCCUUUCUG AUGAGGCCGA AAGGCCGAAA GUGUCU                          36

(2) INFORMATION FOR SEQ ID NO:1070:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1070:

AUCCUUUCUG AUGAGGCCGA AAGGCCGAAA GUGUCU                      36

(2) INFORMATION FOR SEQ ID NO:1071:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1071:

AGCAGGUCUG AUGAGGCCGA AAGGCCGAAA UCCUUU                      36

(2) INFORMATION FOR SEQ ID NO:1072:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1072:

AGCAGGUCUG AUGAGGCCGA AAGGCCGAAA UCCUUU                      36

(2) INFORMATION FOR SEQ ID NO:1073:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1073:

AGCAGGUCUG AUGAGGCCGA AAGGCCGAAA UCCUUU                      36

(2) INFORMATION FOR SEQ ID NO:1074:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1074:

GGAAGCACUG AUGAGGCCGA AAGGCCGAAA GCAGGU                      36

(2) INFORMATION FOR SEQ ID NO:1075:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1075:

GGAAGCACUG AUGAGGCCGA AAGGCCGAAA GCAGGU                      36

```
(2) INFORMATION FOR SEQ ID NO:1076:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1076:

UUUGGGACUG AUGAGGCCGA AAGGCCGAAA CCCCCG                             36

(2) INFORMATION FOR SEQ ID NO:1077:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1077:

UUUGGGACUG AUGAGGCCGA AAGGCCGAAA CCCCCG                             36

(2) INFORMATION FOR SEQ ID NO:1078:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1078:

UUUGGGACUG AUGAGGCCGA AAGGCCGAAA CCCCCG                             36

(2) INFORMATION FOR SEQ ID NO:1079:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1079:

CUUUGGGCUG AUGAGGCCGA AAGGCCGAAA ACCCCC                             36

(2) INFORMATION FOR SEQ ID NO:1080:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1080:

CUUUGGGCUG AUGAGGCCGA AAGGCCGAAA ACCCCC                             36

(2) INFORMATION FOR SEQ ID NO:1081:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1081:

CUUUGGGCUG AUGAGGCCGA AAGGCCGAAA ACCCCC                             36

(2) INFORMATION FOR SEQ ID NO:1082:
```

```
    (i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1082:

GCUUUGGCUG AUGAGGCCGA AAGGCCGAAA AACCCC                          36

(2) INFORMATION FOR SEQ ID NO:1083:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1083:

GAGAAGCCUG AUGAGGCCGA AAGGCCGAAA GGCUUU                          36

(2) INFORMATION FOR SEQ ID NO:1084:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1084:

GAGAAGCCUG AUGAGGCCGA AAGGCCGAAA GGCUUU                          36

(2) INFORMATION FOR SEQ ID NO:1085:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1085:

ACCAAGACUG AUGAGGCCGA AAGGCCGAAA AGCGAG                          36

(2) INFORMATION FOR SEQ ID NO:1086:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1086:

ACCAAGACUG AUGAGGCCGA AAGGCCGAAA AGCGAG                          36

(2) INFORMATION FOR SEQ ID NO:1087:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1087:

CAACCAACUG AUGAGGCCGA AAGGCCGAAA GAAGCG                          36

(2) INFORMATION FOR SEQ ID NO:1088:
```

(i) SEQUENCE CHARACTERISTICS:
    (A) LENGTH:        36 base pairs
    (B) TYPE:          nucleic acid
    (C) STRANDEDNESS:  single
    (D) TOPOLOGY:      linear (xi) SEQUENCE DESCRIPTION: SEQ ID NO:1088:

AUUUUCCCUG AUGAGGCCGA AAGGCCGAAA CCAAGA                    36

(2) INFORMATION FOR SEQ ID NO:1089:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1089:

UGCCAGGCUG AUGAGGCCGA AAGGCCGAAA AUUCUC                    36

(2) INFORMATION FOR SEQ ID NO:1090:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1090:

UGCCAGGCUG AUGAGGCCGA AAGGCCGAAA AUUCUC                    36

(2) INFORMATION FOR SEQ ID NO:1091:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1091:

UGCCAGGCUG AUGAGGCCGA AAGGCCGAAA AUUCUC                    36

(2) INFORMATION FOR SEQ ID NO:1092:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1092:

UCGUAUUCUG AUGAGGCCGA AAGGCCGAAA UGCCAG                    36

(2) INFORMATION FOR SEQ ID NO:1093:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1093:

UCGUAUUCUG AUGAGGCCGA AAGGCCGAAA UGCCAG                    36

(2) INFORMATION FOR SEQ ID NO:1094:

(i) SEQUENCE CHARACTERISTICS:

(A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1094:

AUUGUCGCUG AUGAGGCCGA AAGGCCGAAA UUGAUG                                      36

(2) INFORMATION FOR SEQ ID NO:1095:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1095:

AUUGUCGCUG AUGAGGCCGA AAGGCCGAAA UUGAUG                                      36

(2) INFORMATION FOR SEQ ID NO:1096:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1096:

CCUGGGACUG AUGAGGCCGA AAGGCCGAAA UUGUCG                                      36

(2) INFORMATION FOR SEQ ID NO:1097:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1097:

UCCUGGGCUG AUGAGGCCGA AAGGCCGAAA AUUGUC                                      36

(2) INFORMATION FOR SEQ ID NO:1098:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1098:

AUCCUGGCUG AUGAGGCCGA AAGGCCGAAA AAUUGU                                      36

(2) INFORMATION FOR SEQ ID NO:1099:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1099:

GAUUCAGCUG AUGAGGCCGA AAGGCCGAAA UCCUGG                                      36

(2) INFORMATION FOR SEQ ID NO:1100:

(i) SEQUENCE CHARACTERISTICS:
        (A) LENGTH:         36 base pairs

```
        (B) TYPE:           nucleic acid
        (C) STRANDEDNESS:   single
        (D) TOPOLOGY:       linear (xi) SEQUENCE DESCRIPTION: SEQ ID NO:1100:

CAAUUCACUG AUGAGGCCGA AAGGCCGAAA UUCAGG                                36

(2) INFORMATION FOR SEQ ID NO:1101:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1101:

CAAUUCACUG AUGAGGCCGA AAGGCCGAAA UUCAGG                                36

(2) INFORMATION FOR SEQ ID NO:1102:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1102:

AAUGGUGCUG AUGAGGCCGA AAGGCCGAAA CAAUUC                                36

(2) INFORMATION FOR SEQ ID NO:1103:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1103:

UGAAAUCCUG AUGAGGCCGA AAGGCCGAAA GUUGGC                                36

(2) INFORMATION FOR SEQ ID NO:1104:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1104:

UGAAAUCCUG AUGAGGCCGA AAGGCCGAAA GUUGGC                                36

(2) INFORMATION FOR SEQ ID NO:1105:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1105:

UGAAAUCCUG AUGAGGCCGA AAGGCCGAAA GUUGGC                                36

(2) INFORMATION FOR SEQ ID NO:1106:

(i) SEQUENCE CHARACTERISTICS:
        (A) LENGTH:         36 base pairs
        (B) TYPE:           nucleic acid
```

```
            (C) STRANDEDNESS:    single
            (D) TOPOLOGY:        linear (xi) SEQUENCE DESCRIPTION: SEQ ID NO:1106:

GUAUUGACUG AUGAGGCCGA AAGGCCGAAA UCUAGU                                    36

(2) INFORMATION FOR SEQ ID NO:1107:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1107:

GUAUUGACUG AUGAGGCCGA AAGGCCGAAA UCUAGU                                    36

(2) INFORMATION FOR SEQ ID NO:1108:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1108:

CGUAUUGCUG AUGAGGCCGA AAGGCCGAAA AUCUAG                                    36

(2) INFORMATION FOR SEQ ID NO:1109:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1109:

UCGUAUUCUG AUGAGGCCGA AAGGCCGAAA AAUCUA                                    36

(2) INFORMATION FOR SEQ ID NO:1110:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1110:

UGGUUGCCUG AUGAGGCCGA AAGGCCGAAA GUCGUA                                    36

(2) INFORMATION FOR SEQ ID NO:1111:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1111:

GACACUUCUG AUGAGGCCGA AAGGCCGAAA UGGUGU                                    36

(2) INFORMATION FOR SEQ ID NO:1112:

(i) SEQUENCE CHARACTERISTICS:
            (A) LENGTH:          36 base pairs
            (B) TYPE:            nucleic acid
            (C) STRANDEDNESS:    single
```

(D) TOPOLOGY:        linear (xi) SEQUENCE DESCRIPTION: SEQ ID NO:1112:

GACACUUCUG AUGAGGCCGA AAGGCCGAAA UGGUGU                                36

(2) INFORMATION FOR SEQ ID NO:1113:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1113:

UUAAUGACUG AUGAGGCCGA AAGGCCGAAA CACUUA                                36

(2) INFORMATION FOR SEQ ID NO:1114:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1114:

UUAAUGACUG AUGAGGCCGA AAGGCCGAAA CACUUA                                36

(2) INFORMATION FOR SEQ ID NO:1115:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1115:

AUUUAAUCUG AUGAGGCCGA AAGGCCGAAA GACACU                                36

(2) INFORMATION FOR SEQ ID NO:1116:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1116:

CAUAUUUCUG AUGAGGCCGA AAGGCCGAAA UGAGAC                                36

(2) INFORMATION FOR SEQ ID NO:1117:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1117:

AUCUCCACUG AUGAGGCCGA AAGGCCGAAA UUUAAU                                36

(2) INFORMATION FOR SEQ ID NO:1118:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1118:

AUCUCCACUG AUGAGGCCGA AAGGCCGAAA UUUAAU                    36

(2) INFORMATION FOR SEQ ID NO:1119:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1119:

CCAGGUGCUG AUGAGGCCGA AAGGCCGAAA GUCCUC                    36

(2) INFORMATION FOR SEQ ID NO:1120:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1120:

CCCAGGUCUG AUGAGGCCGA AAGGCCGAAA AGUCCU                    36

(2) INFORMATION FOR SEQ ID NO:1121:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1121:

CUGCCCCUG AUGAGGCCGA AAGGCCGAAA AGAGCA                     36

(2) INFORMATION FOR SEQ ID NO:1122:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1122:

CGAUGACCUG AUGAGGCCGA AAGGCCGAAA CGACUG                    36

(2) INFORMATION FOR SEQ ID NO:1123:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1123:

CAACGAUCUG AUGAGGCCGA AAGGCCGAAA CGACGA                    36

(2) INFORMATION FOR SEQ ID NO:1124:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1124:

UGAUGACCUG AUGAGGCCGA AAGGCCGAAA CGAUGA                            36

(2) INFORMATION FOR SEQ ID NO:1125:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1125:

UGAUGAUCUG AUGAGGCCGA AAGGCCGAAA CAACGA                            36

(2) INFORMATION FOR SEQ ID NO:1126:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1126:

AUUUGAUCUG AUGAGGCCGA AAGGCCGAAA UGACAA                            36

(2) INFORMATION FOR SEQ ID NO:1127:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1127:

CUUACAGCUG AUGAGGCCGA AAGGCCGAAA GCAUUU                            36

(2) INFORMATION FOR SEQ ID NO:1128:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1128:

CUUACAGCUG AUGAGGCCGA AAGGCCGAAA GCAUUU                            36

(2) INFORMATION FOR SEQ ID NO:1129:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1129:

CUUACAGCUG AUGAGGCCGA AAGGCCGAAA GCAUUU                            36

(2) INFORMATION FOR SEQ ID NO:1130:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1130:

CUUACAGCUG AUGAGGCCGA AAGGCCGAAA GCAUUU					36

(2) INFORMATION FOR SEQ ID NO:1131:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1131:

GCUUACACUG AUGAGGCCGA AAGGCCGAAA AGCAUU					36

(2) INFORMATION FOR SEQ ID NO:1132:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1132:

CUUCUGACUG AUGAGGCCGA AAGGCCGAAA CAGCUU					36

(2) INFORMATION FOR SEQ ID NO:1133:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1133:

CUUCUGACUG AUGAGGCCGA AAGGCCGAAA CAGCUU					36

(2) INFORMATION FOR SEQ ID NO:1134:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1134:

UCUUCUGCUG AUGAGGCCGA AAGGCCGAAA ACAGCU					36

(2) INFORMATION FOR SEQ ID NO:1135:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1135:

CGAAGGUCUG AUGAGGCCGA AAGGCCGAAA GGCUGU					36

(2) INFORMATION FOR SEQ ID NO:1136:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1136:

CGAAGGUCUG AUGAGGCCGA AAGGCCGAAA GGCUGU                                  36

(2) INFORMATION FOR SEQ ID NO:1137:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1137:

CGAAGGUCUG AUGAGGCCGA AAGGCCGAAA GGCUGU                                  36

(2) INFORMATION FOR SEQ ID NO:1138:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1138:

CCGAAGGCUG AUGAGGCCGA AAGGCCGAAA AGGCUG                                  36

(2) INFORMATION FOR SEQ ID NO:1139:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1139:

AGGCCCGCUG AUGAGGCCGA AAGGCCGAAA GGUAAG                                  36

(2) INFORMATION FOR SEQ ID NO:1140:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1140:

CAGGCCCCUG AUGAGGCCGA AAGGCCGAAA AGGUAA                                  36

(2) INFORMATION FOR SEQ ID NO:1141:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1141:

CAGGCCCCUG AUGAGGCCGA AAGGCCGAAA AGGUAA                                  36

(2) INFORMATION FOR SEQ ID NO:1142:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1142:

UUCAGCUCUG AUGAGGCCGA AAGGCCGAAA UGCUUC                                  36

(2) INFORMATION FOR SEQ ID NO:1143:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1143:

UUCAGCUCUG AUGAGGCCGA AAGGCCGAAA UGCUUC                    36

(2) INFORMATION FOR SEQ ID NO:1144:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1144:

GUUCAGCCUG AUGAGGCCGA AAGGCCGAAA AUGCUU                    36

(2) INFORMATION FOR SEQ ID NO:1145:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1145:

AAAGGAACUG AUGAGGCCGA AAGGCCGAAA CGGUCU                    36

(2) INFORMATION FOR SEQ ID NO:1146:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1146:

CUAAAGGCUG AUGAGGCCGA AAGGCCGAAA GACGGU                    36

(2) INFORMATION FOR SEQ ID NO:1147:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1147:

ACUAAAGCUG AUGAGGCCGA AAGGCCGAAA AGACGG                    36

(2) INFORMATION FOR SEQ ID NO:1148:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1148:

AAGAACUCUG AUGAGGCCGA AAGGCCGAAA AGGAAG                    36

(2) INFORMATION FOR SEQ ID NO:1149:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1149:

AUGGACACUG AUGAGGCCGA AAGGCCGAAA GAAGAA                      36

(2) INFORMATION FOR SEQ ID NO:1150:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1150:

CCACAUGCUG AUGAGGCCGA AAGGCCGAAA CAGAGA                      36

(2) INFORMATION FOR SEQ ID NO:1151:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1151:

CCACAUGCUG AUGAGGCCGA AAGGCCGAAA CAGAGA                      36

(2) INFORMATION FOR SEQ ID NO:1152:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1152:

UACCAUGCUG AUGAGGCCGA AAGGCCGAAA UCCCAC                      36

(2) INFORMATION FOR SEQ ID NO:1153:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1153:

CACAUAACUG AUGAGGCCGA AAGGCCGAAA CCAUGU                      36

(2) INFORMATION FOR SEQ ID NO:1154:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1154:

GCCACAUCUG AUGAGGCCGA AAGGCCGAAA UACCAU                      36

```
(2) INFORMATION FOR SEQ ID NO:1155:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1155:

ACCUCAUCUG AUGAGGCCGA AAGGCCGAAA GCCACA                                36

(2) INFORMATION FOR SEQ ID NO:1156:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1156:

ACCUCAUCUG AUGAGGCCGA AAGGCCGAAA GCCACA                                36

(2) INFORMATION FOR SEQ ID NO:1157:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1157:

AAAGAAACUG AUGAGGCCGA AAGGCCGAAA UUGUAC                                36

(2) INFORMATION FOR SEQ ID NO:1158:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1158:

UGAAAGACUG AUGAGGCCGA AAGGCCGAAA GAUUGU                                36

(2) INFORMATION FOR SEQ ID NO:1159:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1159:

UGAAAGACUG AUGAGGCCGA AAGGCCGAAA GAUUGU                                36

(2) INFORMATION FOR SEQ ID NO:1160:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1160:

CUGAAAGCUG AUGAGGCCGA AAGGCCGAAA AGAUUG                                36

(2) INFORMATION FOR SEQ ID NO:1161:
```

```
    (i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1161:

GCUGAAACUG AUGAGGCCGA AAGGCCGAAA AAGAUU                              36

(2) INFORMATION FOR SEQ ID NO:1162:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1162:

GCUGAAACUG AUGAGGCCGA AAGGCCGAAA AAGAUU                              36

(2) INFORMATION FOR SEQ ID NO:1163:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1163:

GCUGAAACUG AUGAGGCCGA AAGGCCGAAA AAGAUU                              36

(2) INFORMATION FOR SEQ ID NO:1164:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1164:

GUGCUGACUG AUGAGGCCGA AAGGCCGAAA GAAAGA                              36

(2) INFORMATION FOR SEQ ID NO:1165:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1165:

GGUGCUGCUG AUGAGGCCGA AAGGCCGAAA AGAAAG                              36

(2) INFORMATION FOR SEQ ID NO:1166:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1166:

UGUCCGACUG AUGAGGCCGA AAGGCCGAAA GAUCAG                              36

(2) INFORMATION FOR SEQ ID NO:1167:
```

(i) SEQUENCE CHARACTERISTICS:
    (A) LENGTH:        36 base pairs
    (B) TYPE:          nucleic acid
    (C) STRANDEDNESS:  single
    (D) TOPOLOGY:      linear (xi) SEQUENCE DESCRIPTION: SEQ ID NO:1167:

UUAACUCCUG AUGAGGCCGA AAGGCCGAAA UCUUGU                    36

(2) INFORMATION FOR SEQ ID NO:1168:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1168:

GGAAAGACUG AUGAGGCCGA AAGGCCGAAA UCCUCA                    36

(2) INFORMATION FOR SEQ ID NO:1169:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1169:

AUGGAAACUG AUGAGGCCGA AAGGCCGAAA AAUCCU                    36

(2) INFORMATION FOR SEQ ID NO:1170:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1170:

UGAUGGACUG AUGAGGCCGA AAGGCCGAAA GAAAUC                    36

(2) INFORMATION FOR SEQ ID NO:1171:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1171:

CCUGAUGCUG AUGAGGCCGA AAGGCCGAAA AAGAAA                    36

(2) INFORMATION FOR SEQ ID NO:1172:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1172:

GCUUCCUCUG AUGAGGCCGA AAGGCCGAAA UGGAAA                    36

(2) INFORMATION FOR SEQ ID NO:1173:

(i) SEQUENCE CHARACTERISTICS:

```
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1173:

GCUUCCUCUG AUGAGGCCGA AAGGCCGAAA UGGAAA                              36

(2) INFORMATION FOR SEQ ID NO:1174:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1174:

CCCAGCACUG AUGAGGCCGA AAGGCCGAAA CUUGCC                              36

(2) INFORMATION FOR SEQ ID NO:1175:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1175:

AUCAAGCCUG AUGAGGCCGA AAGGCCGAAA UCAAAG                              36

(2) INFORMATION FOR SEQ ID NO:1176:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1176:

UUUUUCUCUG AUGAGGCCGA AAGGCCGAAA UACCAC                              36

(2) INFORMATION FOR SEQ ID NO:1177:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1177:

UUUUUCUCUG AUGAGGCCGA AAGGCCGAAA UACCAC                              36

(2) INFORMATION FOR SEQ ID NO:1178:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1178:

GCAGUAACUG AUGAGGCCGA AAGGCCGAAA CUAGGC                              36

(2) INFORMATION FOR SEQ ID NO:1179:

(i) SEQUENCE CHARACTERISTICS:
            (A) LENGTH:          36 base pairs
```

```
            (B) TYPE:           nucleic acid
            (C) STRANDEDNESS:   single
            (D) TOPOLOGY:       linear (xi) SEQUENCE DESCRIPTION: SEQ ID NO:1179:

UUGCAGUCUG AUGAGGCCGA AAGGCCGAAA GACUAG                              36

(2) INFORMATION FOR SEQ ID NO:1180:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1180:

ACAUAUCCUG AUGAGGCCGA AAGGCCGAAA GUUGCA                              36

(2) INFORMATION FOR SEQ ID NO:1181:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1181:

CAUGACACUG AUGAGGCCGA AAGGCCGAAA UCAAGU                              36

(2) INFORMATION FOR SEQ ID NO:1182:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1182:

CAUGACACUG AUGAGGCCGA AAGGCCGAAA UCAAGU                              36

(2) INFORMATION FOR SEQ ID NO:1183:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1183:

AGACACCCUG AUGAGGCCGA AAGGCCGAAA CCAAAC                              36

(2) INFORMATION FOR SEQ ID NO:1184:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO:1184:

CUUCAGACUG AUGAGGCCGA AAGGCCGAAA AGGGCA                              36

(2) INFORMATION FOR SEQ ID NO:1185:

(i) SEQUENCE CHARACTERISTICS:
            (A) LENGTH:         36 base pairs
            (B) TYPE:           nucleic acid
```

```
            (C) STRANDEDNESS:    single
            (D) TOPOLOGY:        linear (xi) SEQUENCE DESCRIPTION: SEQ ID NO:1185:

UCUUCAGCUG AUGAGGCCGA AAGGCCGAAA AAGGGC                              36

(2) INFORMATION FOR SEQ ID NO:1186:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1186:

CUCUUCACUG AUGAGGCCGA AAGGCCGAAA AAAGGG                              36

(2) INFORMATION FOR SEQ ID NO:1187:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1187:

CUCUUCACUG AUGAGGCCGA AAGGCCGAAA AAAGGG                              36

(2) INFORMATION FOR SEQ ID NO:1188:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1188:

ACAUCCCCUG AUGAGGCCGA AAGGCCGAAA CCAUAG                              36

(2) INFORMATION FOR SEQ ID NO:1189:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1189:

CCGUUUUCUG AUGAGGCCGA AAGGCCGAAA CAUCCC                              36

(2) INFORMATION FOR SEQ ID NO:1190:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1190:

CCGUUUUCUG AUGAGGCCGA AAGGCCGAAA CAUCCC                              36

(2) INFORMATION FOR SEQ ID NO:1191:

(i) SEQUENCE CHARACTERISTICS:
            (A) LENGTH:          36 base pairs
            (B) TYPE:            nucleic acid
            (C) STRANDEDNESS:    single
```

(D) TOPOLOGY:      linear (xi) SEQUENCE DESCRIPTION: SEQ ID NO:1191:

UAAUAUUCUG AUGAGGCCGA AAGGCCGAAA UAUUAU                    36

(2) INFORMATION FOR SEQ ID NO:1192:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1192:

UAUUUAACUG AUGAGGCCGA AAGGCCGAAA UUUAUA                    36

(2) INFORMATION FOR SEQ ID NO:1193:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1193:

UUUAUUCUG AUGAGGCCGA AAGGCCGAAA UAUUUA                     36

(2) INFORMATION FOR SEQ ID NO:1194:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1194:

UUUUAUUCUG AUGAGGCCGA AAGGCCGAAA AUAUUU                    36

(2) INFORMATION FOR SEQ ID NO:1195:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1195:

UUUUAUUCUG AUGAGGCCGA AAGGCCGAAA AUAUUU                    36

(2) INFORMATION FOR SEQ ID NO:1196:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1196:

UUUGCUCCUG AUGAGGCCGA AAGGCCGAAA UACUCU                    36

(2) INFORMATION FOR SEQ ID NO:1197:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1197:

GAAAGCUUUG CUUCU                                                        15

(2) INFORMATION FOR SEQ ID NO:1198:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1198:

AAAGCUUUGC UUCUC                                                        15

(2) INFORMATION FOR SEQ ID NO:1199:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1199:

CUUUGCUUCU CUGCU                                                        15

(2) INFORMATION FOR SEQ ID NO:1200:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1200:

UUUGCUUCUC UGCUG                                                        15

(2) INFORMATION FOR SEQ ID NO:1201:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1201:

UGCUUCUCUG CUGCU                                                        15

(2) INFORMATION FOR SEQ ID NO:1202:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1202:

CUGCUGUAAC AGGGA                                                        15

(2) INFORMATION FOR SEQ ID NO:1203:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1203:

AGGGACUAGC ACAGA 15

(2) INFORMATION FOR SEQ ID NO:1204:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1204:

GUGGGGUCAU UUCCA 15

(2) INFORMATION FOR SEQ ID NO:1205:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1205:

GGGUCAUUUC CAGAU 15

(2) INFORMATION FOR SEQ ID NO:1206:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1206:

GGUCAUUUCC AGAUA 15

(2) INFORMATION FOR SEQ ID NO:1207:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1207:

GUCAUUUCCA GAUAU 15

(2) INFORMATION FOR SEQ ID NO:1208:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1208:

UCCAGAUAUU AGGUC 15

(2) INFORMATION FOR SEQ ID NO:1209:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1209:

CAGAUAUUAG GUCAC                                               15

(2) INFORMATION FOR SEQ ID NO:1210:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1210:

AGAUAUUAGG UCACA                                               15

(2) INFORMATION FOR SEQ ID NO:1211:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1211:

AUUAGGUCAC AGCAG                                               15

(2) INFORMATION FOR SEQ ID NO:1212:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1212:

AAUGGAUCCC CAGUG                                               15

(2) INFORMATION FOR SEQ ID NO:1213:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1213:

GUGCACUAUG GGACU                                               15

(2) INFORMATION FOR SEQ ID NO:1214:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1214:

ACUGAGUAAC AUUCU                                               15

(2) INFORMATION FOR SEQ ID NO:1215:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1215:

```
GUAACAUUCU CUUUG                                                           15

(2) INFORMATION FOR SEQ ID NO:1216:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1216:

UAACAUUCUC UUUGU                                                           15

(2) INFORMATION FOR SEQ ID NO:1217:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1217:

ACAUUCUCUU UGUGA                                                           15

(2) INFORMATION FOR SEQ ID NO:1218:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1218:

AUUCUCUUUG UGAUG                                                           15

(2) INFORMATION FOR SEQ ID NO:1219:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1219:

UUCUCUUUGU GAUGG                                                           15

(2) INFORMATION FOR SEQ ID NO:1220:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1220:

AUGGCCUUCC UGCUC                                                           15

(2) INFORMATION FOR SEQ ID NO:1221:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1221:

UGGCCUUCCU GCUCU                                                           15
```

(2) INFORMATION FOR SEQ ID NO:1222:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1222:

UCCUGCUCUC UGGUG                                                    15

(2) INFORMATION FOR SEQ ID NO:1223:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1223:

CUGCUCUCUG GUGCU                                                    15

(2) INFORMATION FOR SEQ ID NO:1224:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1224:

UGCUGCUCCU CUGAA                                                    15

(2) INFORMATION FOR SEQ ID NO:1225:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1225:

UGCUCCUCUG AAGAU                                                    15

(2) INFORMATION FOR SEQ ID NO:1226:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1226:

UGAAGAUUCA AGCUU                                                    15

(2) INFORMATION FOR SEQ ID NO:1227:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1227:

GAAGAUUCAA GCUUA                                                    15

(2) INFORMATION FOR SEQ ID NO:1228:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1228:

UCAAGCUUAU UUCAA                                                        15

(2) INFORMATION FOR SEQ ID NO:1229:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1229:

CAAGCUUAUU UCAAU                                                        15

(2) INFORMATION FOR SEQ ID NO:1230:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1230:

AGCUUAUUUC AAUGA                                                        15

(2) INFORMATION FOR SEQ ID NO:1231:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1231:

GCUUAUUUCA AUGAG                                                        15

(2) INFORMATION FOR SEQ ID NO:1232:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1232:

CUUAUUUCAA UGAGA                                                        15

(2) INFORMATION FOR SEQ ID NO:1233:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1233:

UGCCAAUUUG CAAAC                                                        15

(2) INFORMATION FOR SEQ ID NO:1234:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1234:

GCCAAUUUGC AAACU                                                            15

(2) INFORMATION FOR SEQ ID NO:1235:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1235:

GCAAACUCUC AAAAC                                                            15

(2) INFORMATION FOR SEQ ID NO:1236:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1236:

AAACUCUCAA AACCA                                                            15

(2) INFORMATION FOR SEQ ID NO:1237:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1237:

GUGAGCUAGU AGUAU                                                            15

(2) INFORMATION FOR SEQ ID NO:1238:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1238:

AGCUAGUAGU AUUUU                                                            15

(2) INFORMATION FOR SEQ ID NO:1239:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1239:

UAGUAGUAUU UUGGC                                                            15

(2) INFORMATION FOR SEQ ID NO:1240:

```
        (i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1240:

GUAGUAUUUU GGCAG                                                        15

(2) INFORMATION FOR SEQ ID NO:1241:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1241:

UAGUAUUUUG GCAGG                                                        15

(2) INFORMATION FOR SEQ ID NO:1242:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1242:

AGUAUUUUGG CAGGA                                                        15

(2) INFORMATION FOR SEQ ID NO:1243:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1243:

GAAAACUUGG UUCUG                                                        15

(2) INFORMATION FOR SEQ ID NO:1244:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1244:

ACUUGGUUCU GAAUG                                                        15

(2) INFORMATION FOR SEQ ID NO:1245:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1245:

CUUGGUUCUG AAUGA                                                        15

(2) INFORMATION FOR SEQ ID NO:1246:
```

```
    (i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1246:

AUGAGGUAUA CUUAG                                                       15

(2) INFORMATION FOR SEQ ID NO:1247:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1247:

GAGGUAUACU UAGGC                                                       15

(2) INFORMATION FOR SEQ ID NO:1248:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1248:

GUAUACUUAG GCAAA                                                       15

(2) INFORMATION FOR SEQ ID NO:1249:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1249:

UAUACUUAGG CAAAG                                                       15

(2) INFORMATION FOR SEQ ID NO:1250:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1250:

GAGAAAUUUG ACAGU                                                       15

(2) INFORMATION FOR SEQ ID NO:1251:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1251:

AGAAAUUUGA CAGUG                                                       15

(2) INFORMATION FOR SEQ ID NO:1252:

(i) SEQUENCE CHARACTERISTICS:
```

```
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1252:

ACAGUGUUCA UUCCA                                                15

(2) INFORMATION FOR SEQ ID NO:1253:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1253:

CAGUGUUCAU UCCAA                                                15

(2) INFORMATION FOR SEQ ID NO:1254:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1254:

UGUUCAUUCC AAGUA                                                15

(2) INFORMATION FOR SEQ ID NO:1255:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1255:

GUUCAUUCCA AGUAU                                                15

(2) INFORMATION FOR SEQ ID NO:1256:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1256:

UCCAAGUAUA UGGGC                                                15

(2) INFORMATION FOR SEQ ID NO:1257:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1257:

CAAGUAUAUG GGCCG                                                15

(2) INFORMATION FOR SEQ ID NO:1258:

(i) SEQUENCE CHARACTERISTICS:
          (A) LENGTH:         15 base pairs
```

```
            (B) TYPE:           nucleic acid
            (C) STRANDEDNESS:   single
            (D) TOPOLOGY:       linear (xi) SEQUENCE DESCRIPTION: SEQ ID NO:1258:

CACAAGUUUU GAUUC                                                     15

(2) INFORMATION FOR SEQ ID NO:1259:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1259:

ACAAGUUUUG AUUCG                                                     15

(2) INFORMATION FOR SEQ ID NO:1260:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1260:

CAAGUUUUGA UUCGG                                                     15

(2) INFORMATION FOR SEQ ID NO:1261:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1261:

UUUUGAUUCG GACAG                                                     15

(2) INFORMATION FOR SEQ ID NO:1262:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1262:

UUUGAUUCGG ACAGU                                                     15

(2) INFORMATION FOR SEQ ID NO:1263:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1263:

GGACAGUUGG ACCCU                                                     15

(2) INFORMATION FOR SEQ ID NO:1264:

(i) SEQUENCE CHARACTERISTICS:
            (A) LENGTH:         15 base pairs
            (B) TYPE:           nucleic acid
```

(C) STRANDEDNESS:    single
            (D) TOPOLOGY:        linear (xi) SEQUENCE DESCRIPTION: SEQ ID NO:1264:

UGAGACUUCA CAAUC                                                    15

(2) INFORMATION FOR SEQ ID NO:1265:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1265:

GAGACUUCAC AAUCU                                                    15

(2) INFORMATION FOR SEQ ID NO:1266:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1266:

UCACAAUCUU CAGAU                                                    15

(2) INFORMATION FOR SEQ ID NO:1267:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1267:

ACAAUCUUCA GAUCA                                                    15

(2) INFORMATION FOR SEQ ID NO:1268:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1268:

CAAUCUUCAG AUCAA                                                    15

(2) INFORMATION FOR SEQ ID NO:1269:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1269:

UUCAGAUCAA GGACA                                                    15

(2) INFORMATION FOR SEQ ID NO:1270:

(i) SEQUENCE CHARACTERISTICS:
            (A) LENGTH:          15 base pairs
            (B) TYPE:            nucleic acid
            (C) STRANDEDNESS:    single

```
        (D) TOPOLOGY:         linear (xi) SEQUENCE DESCRIPTION: SEQ ID NO:1270:

AAGGGCUUGU AUCAA                                                          15

(2) INFORMATION FOR SEQ ID NO:1271:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:1271:

GGCUUGUAUC AAUGU                                                          15

(2) INFORMATION FOR SEQ ID NO:1272:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:1272:

CUUGUAUCAA UGUAU                                                          15

(2) INFORMATION FOR SEQ ID NO:1273:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:1273:

UCAAUGUAUC AUCCA                                                          15

(2) INFORMATION FOR SEQ ID NO:1274:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:1274:

AAUGUAUCAU CCAUC                                                          15

(2) INFORMATION FOR SEQ ID NO:1275:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:1275:

GUAUCAUCCA UCACA                                                          15

(2) INFORMATION FOR SEQ ID NO:1276:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear
```

(xi) SEQUENCE DESCRIPTION: SEQ ID NO:1276:

CAUCCAUCAC AAAAA                                                    15

(2) INFORMATION FOR SEQ ID NO:1277:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1277:

GAAUGAUUCG CAUCC                                                    15

(2) INFORMATION FOR SEQ ID NO:1278:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1278:

AAUGAUUCGC AUCCA                                                    15

(2) INFORMATION FOR SEQ ID NO:1279:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1279:

UUCGCAUCCA CCAGA                                                    15

(2) INFORMATION FOR SEQ ID NO:1280:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1280:

GAUGAAUUCU GAACU                                                    15

(2) INFORMATION FOR SEQ ID NO:1281:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1281:

AUGAAUUCUG AACUG                                                    15

(2) INFORMATION FOR SEQ ID NO:1282:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1282:

GAACUGUCAG UGCUU                                                    15

(2) INFORMATION FOR SEQ ID NO:1283:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1283:

CAGUGCUUGC UAACU                                                    15

(2) INFORMATION FOR SEQ ID NO:1284:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1284:

GCUUGCUAAC UUCAG                                                    15

(2) INFORMATION FOR SEQ ID NO:1285:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1285:

GCUAACUUCA GUCAA                                                    15

(2) INFORMATION FOR SEQ ID NO:1286:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1286:

CUAACUUCAG UCAAC                                                    15

(2) INFORMATION FOR SEQ ID NO:1287:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1287:

CUUCAGUCAA CCUGA                                                    15

(2) INFORMATION FOR SEQ ID NO:1288:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1288:

CUGAAAUAGU ACCAA                                                15

(2) INFORMATION FOR SEQ ID NO:1289:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1289:

AAAUAGUACC AAUUU                                                15

(2) INFORMATION FOR SEQ ID NO:1290:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1290:

UACCAAUUUC UAAUA                                                15

(2) INFORMATION FOR SEQ ID NO:1291:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1291:

ACCAAUUUCU AAUAU                                                15

(2) INFORMATION FOR SEQ ID NO:1292:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1292:

CCAAUUUCUA AUAUA                                                15

(2) INFORMATION FOR SEQ ID NO:1293:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1293:

AAUUUCUAAU AUAAC                                                15

(2) INFORMATION FOR SEQ ID NO:1294:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1294:

```
UUCUAAUAUA ACAGA                                                            15

(2) INFORMATION FOR SEQ ID NO:1295:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1295:

CUAAUAUAAC AGAAA                                                            15

(2) INFORMATION FOR SEQ ID NO:1296:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1296:

AAUGUGUACA UAAAU                                                            15

(2) INFORMATION FOR SEQ ID NO:1297:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1297:

UGUACAUAAA UUUGA                                                            15

(2) INFORMATION FOR SEQ ID NO:1298:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1298:

CAUAAAUUUG ACCUG                                                            15

(2) INFORMATION FOR SEQ ID NO:1299:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1299:

AUAAAUUUGA CCUGC                                                            15

(2) INFORMATION FOR SEQ ID NO:1300:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1300:

ACCUGCUCAU CUAUA                                                            15
```

(2) INFORMATION FOR SEQ ID NO:1301:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO:1301:

UGCUCAUCUA UACAC    15

(2) INFORMATION FOR SEQ ID NO:1302:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO:1302:

CUCAUCUAUA CACGG    15

(2) INFORMATION FOR SEQ ID NO:1303:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO:1303:

CAUCUAUACA CGGUU    15

(2) INFORMATION FOR SEQ ID NO:1304:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO:1304:

ACACGGUUAC CCAGA    15

(2) INFORMATION FOR SEQ ID NO:1305:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO:1305:

CACGGUUACC CAGAA    15

(2) INFORMATION FOR SEQ ID NO:1306:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO:1306:

AGAACCUAAG AAGAU    15

(2) INFORMATION FOR SEQ ID NO:1307:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1307:

UGAGUGUUUU GCUAA                                           15

(2) INFORMATION FOR SEQ ID NO:1308:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1308:

GAGUGUUUUG CUAAG                                           15

(2) INFORMATION FOR SEQ ID NO:1309:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1309:

AGUGUUUUGC UAAGA                                           15

(2) INFORMATION FOR SEQ ID NO:1310:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1310:

UUUUGCUAAG AACCA                                           15

(2) INFORMATION FOR SEQ ID NO:1311:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1311:

CAAGAAUUCA ACUAU                                           15

(2) INFORMATION FOR SEQ ID NO:1312:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1312:

AAGAAUUCAA CUAUC                                           15

(2) INFORMATION FOR SEQ ID NO:1313:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1313:

UUCAACUAUC GAGUA                                             15

(2) INFORMATION FOR SEQ ID NO:1314:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1314:

CAACUAUCGA GUAUG                                             15

(2) INFORMATION FOR SEQ ID NO:1315:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1315:

AUCGAGUAUG AUGGU                                             15

(2) INFORMATION FOR SEQ ID NO:1316:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1316:

UGAUGGUAUU AUGCA                                             15

(2) INFORMATION FOR SEQ ID NO:1317:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1317:

AUGGUAUUAU GCAGA                                             15

(2) INFORMATION FOR SEQ ID NO:1318:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1318:

UGGUAUUAUG CAGAA                                             15

(2) INFORMATION FOR SEQ ID NO:1319:

```
        (i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1319:

CAGAAAUCUC AAGAU                                                    15

(2) INFORMATION FOR SEQ ID NO:1320:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1320:

GAAAUCUCAA GAUAA                                                    15

(2) INFORMATION FOR SEQ ID NO:1321:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1321:

UCAAGAUAAU GUCAC                                                    15

(2) INFORMATION FOR SEQ ID NO:1322:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1322:

AUAAUGUCAC AGAAC                                                    15

(2) INFORMATION FOR SEQ ID NO:1323:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1323:

GAACUGUACG ACGUU                                                    15

(2) INFORMATION FOR SEQ ID NO:1324:

(i) SEQUENCE CHARACTERISTICS:
              (A) LENGTH:         15 base pairs
              (B) TYPE:           nucleic acid
              (C) STRANDEDNESS:   single
              (D) TOPOLOGY:       linear (xi) SEQUENCE DESCRIPTION: SEQ ID NO:1324:

ACGACGUUUC CAUCA                                                    15

(2) INFORMATION FOR SEQ ID NO:1325:
```

```
    (i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1325:

CGACGUUUCC AUCAG                                                   15

(2) INFORMATION FOR SEQ ID NO:1326:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1326:

GACGUUUCCA UCAGC                                                   15

(2) INFORMATION FOR SEQ ID NO:1327:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1327:

UUUCCAUCAG CUUGU                                                   15

(2) INFORMATION FOR SEQ ID NO:1328:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1328:

AUCAGCUUGU CUGUU                                                   15

(2) INFORMATION FOR SEQ ID NO:1329:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1329:

AGCUUGUCUG UUUCA                                                   15

(2) INFORMATION FOR SEQ ID NO:1330:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1330:

UGUCUGUUUC AUUCC                                                   15

(2) INFORMATION FOR SEQ ID NO:1331:

(i) SEQUENCE CHARACTERISTICS:
```

```
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1331:

GUCUGUUUCA UUCCC                                                        15

(2) INFORMATION FOR SEQ ID NO:1332:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1332:

UCUGUUUCAU UCCCU                                                        15

(2) INFORMATION FOR SEQ ID NO:1333:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1333:

GUUUCAUUCC CUGAU                                                        15

(2) INFORMATION FOR SEQ ID NO:1334:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1334:

UUUCAUUCCC UGAUG                                                        15

(2) INFORMATION FOR SEQ ID NO:1335:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1335:

CUGAUGUUAC GAGCA                                                        15

(2) INFORMATION FOR SEQ ID NO:1336:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1336:

UGAUGUUACG AGCAA                                                        15

(2) INFORMATION FOR SEQ ID NO:1337:

(i) SEQUENCE CHARACTERISTICS:
            (A) LENGTH:         15 base pairs
```

```
            (B) TYPE:          nucleic acid
            (C) STRANDEDNESS:  single
            (D) TOPOLOGY:      linear (xi) SEQUENCE DESCRIPTION: SEQ ID NO:1337:

GAGCAAUAUG ACCAU                                                15

(2) INFORMATION FOR SEQ ID NO:1338:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1338:

UGACCAUCUU CUGUA                                                15

(2) INFORMATION FOR SEQ ID NO:1339:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1339:

ACCAUCUUCU GUAUU                                                15

(2) INFORMATION FOR SEQ ID NO:1340:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1340:

CCAUCUUCUG UAUUC                                                15

(2) INFORMATION FOR SEQ ID NO:1341:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1341:

CUUCUGUAUU CUGGA                                                15

(2) INFORMATION FOR SEQ ID NO:1342:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1342:

UCUGUAUUCU GGAAA                                                15

(2) INFORMATION FOR SEQ ID NO:1343:

(i) SEQUENCE CHARACTERISTICS:
            (A) LENGTH:        15 base pairs
            (B) TYPE:          nucleic acid
```

```
        (C) STRANDEDNESS:    single
        (D) TOPOLOGY:        linear (xi) SEQUENCE DESCRIPTION: SEQ ID NO:1343:

CUGUAUUCUG GAAAC                                                        15

(2) INFORMATION FOR SEQ ID NO:1344:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1344:

CGCGGCUUUU AUCUU                                                        15

(2) INFORMATION FOR SEQ ID NO:1345:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1345:

GCGGCUUUUA UCUUC                                                        15

(2) INFORMATION FOR SEQ ID NO:1346:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1346:

CGGCUUUUAU CUUCA                                                        15

(2) INFORMATION FOR SEQ ID NO:1347:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1347:

GGCUUUUAUC UUCAC                                                        15

(2) INFORMATION FOR SEQ ID NO:1348:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1348:

CUUUUAUCUU CACCU                                                        15

(2) INFORMATION FOR SEQ ID NO:1349:

(i) SEQUENCE CHARACTERISTICS:
        (A) LENGTH:          15 base pairs
        (B) TYPE:            nucleic acid
        (C) STRANDEDNESS:    single
```

(D) TOPOLOGY:      linear (xi) SEQUENCE DESCRIPTION: SEQ ID NO:1349:

UUUAUCUUCA CCUUU                                                        15

(2) INFORMATION FOR SEQ ID NO:1350:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1350:

UUAUCUUCAC CUUUC                                                        15

(2) INFORMATION FOR SEQ ID NO:1351:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1351:

UUCACCUUUC UCUAU                                                        15

(2) INFORMATION FOR SEQ ID NO:1352:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1352:

UCACCUUUCU CUAUA                                                        15

(2) INFORMATION FOR SEQ ID NO:1353:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1353:

CACCUUUCUC UAUAG                                                        15

(2) INFORMATION FOR SEQ ID NO:1354:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1354:

CCUUUCUCUA UAGAG                                                        15

(2) INFORMATION FOR SEQ ID NO:1355:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1355:

UUUCUCUAUA GAGCU                                                    15

(2) INFORMATION FOR SEQ ID NO:1356:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1356:

UCUCUAUAGA GCUUG                                                    15

(2) INFORMATION FOR SEQ ID NO:1357:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1357:

UAGAGCUUGA GGACC                                                    15

(2) INFORMATION FOR SEQ ID NO:1358:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1358:

GGACCCUCAG CCUCC                                                    15

(2) INFORMATION FOR SEQ ID NO:1359:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1359:

UCAGCCUCCC CCAGA                                                    15

(2) INFORMATION FOR SEQ ID NO:1360:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1360:

ACCACAUUCC UUGGA                                                    15

(2) INFORMATION FOR SEQ ID NO:1361:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1361:

CCACAUUCCU UGGAU                                                    15

(2) INFORMATION FOR SEQ ID NO:1362:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1362:

CAUUCCUUGG AUUAC                                                    15

(2) INFORMATION FOR SEQ ID NO:1363:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1363:

CUUGGAUUAC AGCUG                                                    15

(2) INFORMATION FOR SEQ ID NO:1364:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1364:

UUGGAUUACA GCUGU                                                    15

(2) INFORMATION FOR SEQ ID NO:1365:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1365:

CAGCUGUACU UCCAA                                                    15

(2) INFORMATION FOR SEQ ID NO:1366:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1366:

CUGUACUUCC AACAG                                                    15

(2) INFORMATION FOR SEQ ID NO:1367:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1367:

UGUACUUCCA ACAGU                    15

(2) INFORMATION FOR SEQ ID NO:1368:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1368:

CAACAGUUAU UAUAU                    15

(2) INFORMATION FOR SEQ ID NO:1369:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1369:

AACAGUUAUU AUAUG                    15

(2) INFORMATION FOR SEQ ID NO:1370:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1370:

CAGUUAUUAU AUGUG                    15

(2) INFORMATION FOR SEQ ID NO:1371:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1371:

AGUUAUUAUA UGUGU                    15

(2) INFORMATION FOR SEQ ID NO:1372:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1372:

UUAUUAUAUG UGUGA                    15

(2) INFORMATION FOR SEQ ID NO:1373:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1373:

```
UGAUGGUUUU CUGUC                                                     15

(2) INFORMATION FOR SEQ ID NO:1374:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1374:

GAUGGUUUUC UGUCU                                                     15

(2) INFORMATION FOR SEQ ID NO:1375:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1375:

AUGGUUUUCU GUCUA                                                     15

(2) INFORMATION FOR SEQ ID NO:1376:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1376:

UGGUUUUCUG UCUAA                                                     15

(2) INFORMATION FOR SEQ ID NO:1377:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1377:

UUUCUGUCUA AUUCU                                                     15

(2) INFORMATION FOR SEQ ID NO:1378:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1378:

UCUGUCUAAU UCUAU                                                     15

(2) INFORMATION FOR SEQ ID NO:1379:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1379:

GUCUAAUUCU AUGGA                                                     15
```

(2) INFORMATION FOR SEQ ID NO:1380:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1380:

UCUAAUUCUA UGGAA                                               15

(2) INFORMATION FOR SEQ ID NO:1381:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1381:

UAAUUCUAUG GAAAU                                               15

(2) INFORMATION FOR SEQ ID NO:1382:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1382:

GCGGCCUCGC AACUC                                               15

(2) INFORMATION FOR SEQ ID NO:1383:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1383:

CGCAACUCUU AUAAA                                               15

(2) INFORMATION FOR SEQ ID NO:1384:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1384:

CAACUCUUAU AAAUG                                               15

(2) INFORMATION FOR SEQ ID NO:1385:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1385:

AACUCUUAUA AAUGU                                               15

(2) INFORMATION FOR SEQ ID NO:1386:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1386:

CUCUUAUAAA UGUGG                                    15

(2) INFORMATION FOR SEQ ID NO:1387:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1387:

AAAAAAUCCA UAUAC                                    15

(2) INFORMATION FOR SEQ ID NO:1388:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1388:

AAUCCAUAUA CCUGA                                    15

(2) INFORMATION FOR SEQ ID NO:1389:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1389:

UCCAUAUACC UGAAA                                    15

(2) INFORMATION FOR SEQ ID NO:1390:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1390:

GAAAGAUCUG AUGAA                                    15

(2) INFORMATION FOR SEQ ID NO:1391:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1391:

AGCGUGUUUU UAAAA                                    15

(2) INFORMATION FOR SEQ ID NO:1392:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1392:

GCGUGUUUUU AAAAG                                                          15

(2) INFORMATION FOR SEQ ID NO:1393:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1393:

CGUGUUUUUA AAAGU                                                          15

(2) INFORMATION FOR SEQ ID NO:1394:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1394:

GUGUUUUUAA AAGUU                                                          15

(2) INFORMATION FOR SEQ ID NO:1395:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1395:

UGUUUUUAAA AGUUC                                                          15

(2) INFORMATION FOR SEQ ID NO:1396:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1396:

UAAAAGUUCG AAGAC                                                          15

(2) INFORMATION FOR SEQ ID NO:1397:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1397:

AAAAGUUCGA AGACA                                                          15

(2) INFORMATION FOR SEQ ID NO:1398:

(i) SEQUENCE CHARACTERISTICS:
    (A) LENGTH:        15 base pairs
    (B) TYPE:          nucleic acid
    (C) STRANDEDNESS:  single
    (D) TOPOLOGY:      linear (xi) SEQUENCE DESCRIPTION: SEQ ID NO:1398:

AAGACAUCUU CAUGC                                                 15

(2) INFORMATION FOR SEQ ID NO:1399:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1399:

GACAUCUUCA UGCGA                                                 15

(2) INFORMATION FOR SEQ ID NO:1400:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1400:

ACAUCUUCAU GCGAC                                                 15

(2) INFORMATION FOR SEQ ID NO:1401:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1401:

AAGUGAUACA UGUUU                                                 15

(2) INFORMATION FOR SEQ ID NO:1402:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1402:

UACAUGUUUU UAAUU                                                 15

(2) INFORMATION FOR SEQ ID NO:1403:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1403:

ACAUGUUUUU AAUUA                                                 15

(2) INFORMATION FOR SEQ ID NO:1404:

```
    (i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1404:

CAUGUUUUUA AUUAA                                                    15

(2) INFORMATION FOR SEQ ID NO:1405:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1405:

AUGUUUUUAA UUAAA                                                    15

(2) INFORMATION FOR SEQ ID NO:1406:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1406:

UGUUUUUAAU UAAAG                                                    15

(2) INFORMATION FOR SEQ ID NO:1407:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1407:

UUUUAAUUAA AGAGU                                                    15

(2) INFORMATION FOR SEQ ID NO:1408:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1408:

UUUAAUUAAA GAGUA                                                    15

(2) INFORMATION FOR SEQ ID NO:1409:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1409:

AGAAGCACUG AUGAGGCCGA AAGGCCGAAA GCUUUC                              36

(2) INFORMATION FOR SEQ ID NO:1410:

(i) SEQUENCE CHARACTERISTICS:
```

```
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1410:

GAGAAGCCUG AUGAGGCCGA AAGGCCGAAA AGCUUU                               36

(2) INFORMATION FOR SEQ ID NO:1411:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1411:

AGCAGAGCUG AUGAGGCCGA AAGGCCGAAA GCAAAG                               36

(2) INFORMATION FOR SEQ ID NO:1412:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1412:

CAGCAGACUG AUGAGGCCGA AAGGCCGAAA AGCAAA                               36

(2) INFORMATION FOR SEQ ID NO:1413:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1413:

AGCAGCACUG AUGAGGCCGA AAGGCCGAAA GAAGCA                               36

(2) INFORMATION FOR SEQ ID NO:1414:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1414:

UCCCUGUCUG AUGAGGCCGA AAGGCCGAAA CAGCAG                               36

(2) INFORMATION FOR SEQ ID NO:1415:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1415:

UCUGUGCCUG AUGAGGCCGA AAGGCCGAAA GUCCCU                               36

(2) INFORMATION FOR SEQ ID NO:1416:

(i) SEQUENCE CHARACTERISTICS:
        (A) LENGTH:         36 base pairs
```

```
        (B) TYPE:           nucleic acid
        (C) STRANDEDNESS:   single
        (D) TOPOLOGY:       linear (xi) SEQUENCE DESCRIPTION: SEQ ID NO:1416:

UGGAAAUCUG AUGAGGCCGA AAGGCCGAAA CCCCAC                              36

(2) INFORMATION FOR SEQ ID NO:1417:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1417:

AUCUGGACUG AUGAGGCCGA AAGGCCGAAA UGACCC                              36

(2) INFORMATION FOR SEQ ID NO:1418:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1418:

UAUCUGGCUG AUGAGGCCGA AAGGCCGAAA AUGACC                              36

(2) INFORMATION FOR SEQ ID NO:1419:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1419:

AUAUCUGCUG AUGAGGCCGA AAGGCCGAAA AAUGAC                              36

(2) INFORMATION FOR SEQ ID NO:1420:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1420:

GACCUAACUG AUGAGGCCGA AAGGCCGAAA UCUGGA                              36

(2) INFORMATION FOR SEQ ID NO:1421:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1421:

GUGACCUCUG AUGAGGCCGA AAGGCCGAAA UAUCUG                              36

(2) INFORMATION FOR SEQ ID NO:1422:

(i) SEQUENCE CHARACTERISTICS:
        (A) LENGTH:         36 base pairs
        (B) TYPE:           nucleic acid
```

```
            (C) STRANDEDNESS:    single
            (D) TOPOLOGY:        linear (xi) SEQUENCE DESCRIPTION: SEQ ID NO:1422:

UGUGACCCUG AUGAGGCCGA AAGGCCGAAA AUAUCU                                36

(2) INFORMATION FOR SEQ ID NO:1423:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1423:

CUGCUGUCUG AUGAGGCCGA AAGGCCGAAA CCUAAU                                36

(2) INFORMATION FOR SEQ ID NO:1424:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1424:

CACUGGGCUG AUGAGGCCGA AAGGCCGAAA UCCAUU                                36

(2) INFORMATION FOR SEQ ID NO:1425:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1425:

AGUCCCACUG AUGAGGCCGA AAGGCCGAAA GUGCAC                                36

(2) INFORMATION FOR SEQ ID NO:1426:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1426:

AGAAUGUCUG AUGAGGCCGA AAGGCCGAAA CUCAGU                                36

(2) INFORMATION FOR SEQ ID NO:1427:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1427:

CAAAGAGCUG AUGAGGCCGA AAGGCCGAAA UGUUAC                                36

(2) INFORMATION FOR SEQ ID NO:1428:

(i) SEQUENCE CHARACTERISTICS:
            (A) LENGTH:          36 base pairs
            (B) TYPE:            nucleic acid
            (C) STRANDEDNESS:    single
```

(D) TOPOLOGY:      linear (xi) SEQUENCE DESCRIPTION: SEQ ID NO:1428:

ACAAAGACUG AUGAGGCCGA AAGGCCGAAA AUGUUA                         36

(2) INFORMATION FOR SEQ ID NO:1429:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1429:

UCACAAACUG AUGAGGCCGA AAGGCCGAAA GAAUGU                         36

(2) INFORMATION FOR SEQ ID NO:1430:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1430:

CAUCACACUG AUGAGGCCGA AAGGCCGAAA GAGAAU                         36

(2) INFORMATION FOR SEQ ID NO:1431:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1431:

CCAUCACCUG AUGAGGCCGA AAGGCCGAAA AGAGAA                         36

(2) INFORMATION FOR SEQ ID NO:1432:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1432:

GAGCAGGCUG AUGAGGCCGA AAGGCCGAAA GGCCAU                         36

(2) INFORMATION FOR SEQ ID NO:1433:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1433:

AGAGCAGCUG AUGAGGCCGA AAGGCCGAAA AGGCCA                         36

(2) INFORMATION FOR SEQ ID NO:1434:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1434:

CACCAGACUG AUGAGGCCGA AAGGCCGAAA GCAGGA                          36

(2) INFORMATION FOR SEQ ID NO:1435:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1435:

AGCACCACUG AUGAGGCCGA AAGGCCGAAA GAGCAG                          36

(2) INFORMATION FOR SEQ ID NO:1436:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1436:

UUCAGAGCUG AUGAGGCCGA AAGGCCGAAA GCAGCA                          36

(2) INFORMATION FOR SEQ ID NO:1437:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1437:

AUCUUCACUG AUGAGGCCGA AAGGCCGAAA GGAGCA                          36

(2) INFORMATION FOR SEQ ID NO:1438:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1438:

AAGCUUGCUG AUGAGGCCGA AAGGCCGAAA UCUUCA                          36

(2) INFORMATION FOR SEQ ID NO:1439:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1439:

UAAGCUUCUG AUGAGGCCGA AAGGCCGAAA AUCUUC                          36

(2) INFORMATION FOR SEQ ID NO:1440:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1440:

UUGAAAUCUG AUGAGGCCGA AAGGCCGAAA GCUUGA         36

(2) INFORMATION FOR SEQ ID NO:1441:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1441:

AUUGAAACUG AUGAGGCCGA AAGGCCGAAA AGCUUG         36

(2) INFORMATION FOR SEQ ID NO:1442:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1442:

UCAUUGACUG AUGAGGCCGA AAGGCCGAAA UAAGCU         36

(2) INFORMATION FOR SEQ ID NO:1443:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1443:

CUCAUUGCUG AUGAGGCCGA AAGGCCGAAA AUAAGC         36

(2) INFORMATION FOR SEQ ID NO:1444:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1444:

UCUCAUUCUG AUGAGGCCGA AAGGCCGAAA AAUAAG         36

(2) INFORMATION FOR SEQ ID NO:1445:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1445:

GUUUGCACUG AUGAGGCCGA AAGGCCGAAA UUGGCA         36

(2) INFORMATION FOR SEQ ID NO:1446:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1446:

AGUUUGCCUG AUGAGGCCGA AAGGCCGAAA AUUGGC    36

(2) INFORMATION FOR SEQ ID NO:1447:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1447:

GUUUUGACUG AUGAGGCCGA AAGGCCGAAA GUUUGC    36

(2) INFORMATION FOR SEQ ID NO:1448:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1448:

UGGUUUUCUG AUGAGGCCGA AAGGCCGAAA GAGUUU    36

(2) INFORMATION FOR SEQ ID NO:1449:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1449:

AUACUACCUG AUGAGGCCGA AAGGCCGAAA GCUCAC    36

(2) INFORMATION FOR SEQ ID NO:1450:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1450:

AAAAUACCUG AUGAGGCCGA AAGGCCGAAA CUAGCU    36

(2) INFORMATION FOR SEQ ID NO:1451:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1451:

GCCAAAACUG AUGAGGCCGA AAGGCCGAAA CUACUA    36

(2) INFORMATION FOR SEQ ID NO:1452:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1452:

CUGCCAACUG AUGAGGCCGA AAGGCCGAAA UACUAC                36

(2) INFORMATION FOR SEQ ID NO:1453:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:1453:

CCUGCCACUG AUGAGGCCGA AAGGCCGAAA AUACUA                36

(2) INFORMATION FOR SEQ ID NO:1454:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:1454:

UCCUGCCCUG AUGAGGCCGA AAGGCCGAAA AAUACU                36

(2) INFORMATION FOR SEQ ID NO:1455:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:1455:

CAGAACCCUG AUGAGGCCGA AAGGCCGAAA GUUUUC                36

(2) INFORMATION FOR SEQ ID NO:1456:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:1456:

CAUUCAGCUG AUGAGGCCGA AAGGCCGAAA CCAAGU                36

(2) INFORMATION FOR SEQ ID NO:1457:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:1457:

UCAUUCACUG AUGAGGCCGA AAGGCCGAAA ACCAAG                36

(2) INFORMATION FOR SEQ ID NO:1458:

(i) SEQUENCE CHARACTERISTICS:
        (A) LENGTH:      36 base pairs
        (B) TYPE:        nucleic acid
        (C) STRANDEDNESS: single
        (D) TOPOLOGY:    linear (xi) SEQUENCE DESCRIPTION: SEQ ID NO:1458:

CUAAGUACUG AUGAGGCCGA AAGGCCGAAA CCUCAU                36

(2) INFORMATION FOR SEQ ID NO:1459:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1459:

GCCUAAGCUG AUGAGGCCGA AAGGCCGAAA UACCUC                              36

(2) INFORMATION FOR SEQ ID NO:1460:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1460:

UUUGCCUCUG AUGAGGCCGA AAGGCCGAAA GUAUAC                              36

(2) INFORMATION FOR SEQ ID NO:1461:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1461:

CUUUGCCCUG AUGAGGCCGA AAGGCCGAAA AGUAUA                              36

(2) INFORMATION FOR SEQ ID NO:1462:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1462:

ACUGUCACUG AUGAGGCCGA AAGGCCGAAA UUUCUC                              36

(2) INFORMATION FOR SEQ ID NO:1463:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1463:

CACUGUCCUG AUGAGGCCGA AAGGCCGAAA AUUUCU                              36

(2) INFORMATION FOR SEQ ID NO:1464:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1464:

UGGAAUGCUG AUGAGGCCGA AAGGCCGAAA CACUGU                              36

(2) INFORMATION FOR SEQ ID NO:1465:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1465:

UUGGAAUCUG AUGAGGCCGA AAGGCCGAAA ACACUG                          36

(2) INFORMATION FOR SEQ ID NO:1466:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1466:

UACUUGGCUG AUGAGGCCGA AAGGCCGAAA UGAACA                          36

(2) INFORMATION FOR SEQ ID NO:1467:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1467:

AUACUUGCUG AUGAGGCCGA AAGGCCGAAA AUGAAC                          36

(2) INFORMATION FOR SEQ ID NO:1468:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1468:

GCCCAUACUG AUGAGGCCGA AAGGCCGAAA CUUGGA                          36

(2) INFORMATION FOR SEQ ID NO:1469:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1469:

CGGCCCACUG AUGAGGCCGA AAGGCCGAAA UACUUG                          36

(2) INFORMATION FOR SEQ ID NO:1470:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1470:

GAAUCAACUG AUGAGGCCGA AAGGCCGAAA CUUGUG                          36

(2) INFORMATION FOR SEQ ID NO:1471:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1471:

CGAAUCACUG AUGAGGCCGA AAGGCCGAAA ACUUGU                    36

(2) INFORMATION FOR SEQ ID NO:1472:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1472:

CCGAAUCCUG AUGAGGCCGA AAGGCCGAAA AACUUG                    36

(2) INFORMATION FOR SEQ ID NO:1473:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1473:

CUGUCCGCUG AUGAGGCCGA AAGGCCGAAA UCAAAA                    36

(2) INFORMATION FOR SEQ ID NO:1474:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1474:

ACUGUCCCUG AUGAGGCCGA AAGGCCGAAA AUCAAA                    36

(2) INFORMATION FOR SEQ ID NO:1475:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1475:

AGGGUCCCUG AUGAGGCCGA AAGGCCGAAA CUGUCC                    36

(2) INFORMATION FOR SEQ ID NO:1476:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1476:

GAUUGUGCUG AUGAGGCCGA AAGGCCGAAA GUCUCA                    36

(2) INFORMATION FOR SEQ ID NO:1477:

(i) SEQUENCE CHARACTERISTICS:
    (A) LENGTH:         36 base pairs
    (B) TYPE:           nucleic acid
    (C) STRANDEDNESS:   single
    (D) TOPOLOGY:       linear (xi) SEQUENCE DESCRIPTION: SEQ ID NO:1477:

AGAUUGUCUG AUGAGGCCGA AAGGCCGAAA AGUCUC                                36

(2) INFORMATION FOR SEQ ID NO:1478:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1478:

AUCUGAACUG AUGAGGCCGA AAGGCCGAAA UUGUGA                                36

(2) INFORMATION FOR SEQ ID NO:1479:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1479:

UGAUCUGCUG AUGAGGCCGA AAGGCCGAAA GAUUGU                                36

(2) INFORMATION FOR SEQ ID NO:1480:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1480:

UUGAUCUCUG AUGAGGCCGA AAGGCCGAAA AGAUUG                                36

(2) INFORMATION FOR SEQ ID NO:1481:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1481:

UGUCCUUCUG AUGAGGCCGA AAGGCCGAAA UCUGAA                                36

(2) INFORMATION FOR SEQ ID NO:1482:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1482:

UUGAUACCUG AUGAGGCCGA AAGGCCGAAA GCCCUU                                36

(2) INFORMATION FOR SEQ ID NO:1483:

```
    (i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1483:

ACAUUGACUG AUGAGGCCGA AAGGCCGAAA CAAGCC                            36

(2) INFORMATION FOR SEQ ID NO:1484:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1484:

AUACAUUCUG AUGAGGCCGA AAGGCCGAAA UACAAG                            36

(2) INFORMATION FOR SEQ ID NO:1485:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1485:

UGGAUGACUG AUGAGGCCGA AAGGCCGAAA CAUUGA                            36

(2) INFORMATION FOR SEQ ID NO:1486:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1486:

GAUGGAUCUG AUGAGGCCGA AAGGCCGAAA UACAUU                            36

(2) INFORMATION FOR SEQ ID NO:1487:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1487:

UGUGAUGCUG AUGAGGCCGA AAGGCCGAAA UGAUAC                            36

(2) INFORMATION FOR SEQ ID NO:1488:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1488:

UUUUUGUCUG AUGAGGCCGA AAGGCCGAAA UGGAUG                            36

(2) INFORMATION FOR SEQ ID NO:1489:

(i) SEQUENCE CHARACTERISTICS:
```

```
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1489:

GGAUGCGCUG AUGAGGCCGA AAGGCCGAAA UCAUUC                          36

(2) INFORMATION FOR SEQ ID NO:1490:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1490:

UGGAUGCCUG AUGAGGCCGA AAGGCCGAAA AUCAUU                          36

(2) INFORMATION FOR SEQ ID NO:1491:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1491:

UCUGGUGCUG AUGAGGCCGA AAGGCCGAAA UGCGAA                          36

(2) INFORMATION FOR SEQ ID NO:1492:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1492:

AGUUCAGCUG AUGAGGCCGA AAGGCCGAAA UUCAUC                          36

(2) INFORMATION FOR SEQ ID NO:1493:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1493:

CAGUUCACUG AUGAGGCCGA AAGGCCGAAA AUUCAU                          36

(2) INFORMATION FOR SEQ ID NO:1494:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1494:

AAGCACUCUG AUGAGGCCGA AAGGCCGAAA CAGUUC                          36

(2) INFORMATION FOR SEQ ID NO:1495:

(i) SEQUENCE CHARACTERISTICS:
        (A) LENGTH:         36 base pairs
```

```
        (B) TYPE:           nucleic acid
        (C) STRANDEDNESS:   single
        (D) TOPOLOGY:       linear (xi) SEQUENCE DESCRIPTION: SEQ ID NO:1495:

AGUUAGCCUG AUGAGGCCGA AAGGCCGAAA GCACUG                     36

(2) INFORMATION FOR SEQ ID NO:1496:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1496:

CUGAAGUCUG AUGAGGCCGA AAGGCCGAAA GCAAGC                     36

(2) INFORMATION FOR SEQ ID NO:1497:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1497:

UUGACUGCUG AUGAGGCCGA AAGGCCGAAA GUUAGC                     36

(2) INFORMATION FOR SEQ ID NO:1498:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1498:

GUUGACUCUG AUGAGGCCGA AAGGCCGAAA AGUUAG                     36

(2) INFORMATION FOR SEQ ID NO:1499:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1499:

UCAGGUUCUG AUGAGGCCGA AAGGCCGAAA CUGAAG                     36

(2) INFORMATION FOR SEQ ID NO:1500:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1500:

UUGGUACCUG AUGAGGCCGA AAGGCCGAAA UUUCAG                     36

(2) INFORMATION FOR SEQ ID NO:1501:

(i) SEQUENCE CHARACTERISTICS:
        (A) LENGTH:         36 base pairs
        (B) TYPE:           nucleic acid
```

```
         (C) STRANDEDNESS:    single
         (D) TOPOLOGY:        linear (xi) SEQUENCE DESCRIPTION: SEQ ID NO:1501:

AAAUUGGCUG AUGAGGCCGA AAGGCCGAAA CUAUUU                        36

(2) INFORMATION FOR SEQ ID NO:1502:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:1502:

UAUUAGACUG AUGAGGCCGA AAGGCCGAAA UUGGUA                        36

(2) INFORMATION FOR SEQ ID NO:1503:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:1503:

AUAUUAGCUG AUGAGGCCGA AAGGCCGAAA AUUGGU                        36

(2) INFORMATION FOR SEQ ID NO:1504:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:1504:

UAUAUUACUG AUGAGGCCGA AAGGCCGAAA AAUUGG                        36

(2) INFORMATION FOR SEQ ID NO:1505:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:1505:

GUUAUAUCUG AUGAGGCCGA AAGGCCGAAA GAAAUU                        36

(2) INFORMATION FOR SEQ ID NO:1506:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO:1506:

UCUGUUACUG AUGAGGCCGA AAGGCCGAAA UUAGAA                        36

(2) INFORMATION FOR SEQ ID NO:1507:

(i) SEQUENCE CHARACTERISTICS:
         (A) LENGTH:          36 base pairs
         (B) TYPE:            nucleic acid
         (C) STRANDEDNESS:    single
```

(D) TOPOLOGY:      linear (xi) SEQUENCE DESCRIPTION: SEQ ID NO:1507:

UUUCUGUCUG AUGAGGCCGA AAGGCCGAAA UAUUAG                                    36

(2) INFORMATION FOR SEQ ID NO:1508:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:1508:

AUUUAUGCUG AUGAGGCCGA AAGGCCGAAA CACAUU                                    36

(2) INFORMATION FOR SEQ ID NO:1509:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:1509:

UCAAAUUCUG AUGAGGCCGA AAGGCCGAAA UGUACA                                    36

(2) INFORMATION FOR SEQ ID NO:1510:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:1510:

CAGGUCACUG AUGAGGCCGA AAGGCCGAAA UUUAUG                                    36

(2) INFORMATION FOR SEQ ID NO:1511:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:1511:

GCAGGUCCUG AUGAGGCCGA AAGGCCGAAA AUUUAU                                    36

(2) INFORMATION FOR SEQ ID NO:1512:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:1512:

UAUAGAUCUG AUGAGGCCGA AAGGCCGAAA GCAGGU                                    36

(2) INFORMATION FOR SEQ ID NO:1513:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:1513:

GUGUAUACUG AUGAGGCCGA AAGGCCGAAA UGAGCA                                    36

(2) INFORMATION FOR SEQ ID NO:1514:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1514:

CCGUGUACUG AUGAGGCCGA AAGGCCGAAA GAUGAG                                    36

(2) INFORMATION FOR SEQ ID NO:1515:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1515:

AACCGUGCUG AUGAGGCCGA AAGGCCGAAA UAGAUG                                    36

(2) INFORMATION FOR SEQ ID NO:1516:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1516:

UCUGGGUCUG AUGAGGCCGA AAGGCCGAAA CCGUGU                                    36

(2) INFORMATION FOR SEQ ID NO:1517:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1517:

UUCUGGGCUG AUGAGGCCGA AAGGCCGAAA ACCGUG                                    36

(2) INFORMATION FOR SEQ ID NO:1518:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1518:

AUCUUCUCUG AUGAGGCCGA AAGGCCGAAA GGUUCU                                    36

(2) INFORMATION FOR SEQ ID NO:1519:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1519:

UUAGCAACUG AUGAGGCCGA AAGGCCGAAA CACUCA                                     36

(2) INFORMATION FOR SEQ ID NO:1520:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1520:

CUUAGCACUG AUGAGGCCGA AAGGCCGAAA ACACUC                                     36

(2) INFORMATION FOR SEQ ID NO:1521:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1521:

UCUUAGCCUG AUGAGGCCGA AAGGCCGAAA AACACU                                     36

(2) INFORMATION FOR SEQ ID NO:1522:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1522:

UGGUUCUCUG AUGAGGCCGA AAGGCCGAAA GCAAAA                                     36

(2) INFORMATION FOR SEQ ID NO:1523:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1523:

AUAGUUGCUG AUGAGGCCGA AAGGCCGAAA UUCUUG                                     36

(2) INFORMATION FOR SEQ ID NO:1524:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1524:

GAUAGUUCUG AUGAGGCCGA AAGGCCGAAA AUUCUU                                     36

(2) INFORMATION FOR SEQ ID NO:1525:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1525:

UACUCGACUG AUGAGGCCGA AAGGCCGAAA GUUGAA                36

(2) INFORMATION FOR SEQ ID NO:1526:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1526:

CAUACUCCUG AUGAGGCCGA AAGGCCGAAA UAGUUG                36

(2) INFORMATION FOR SEQ ID NO:1527:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1527:

ACCAUCACUG AUGAGGCCGA AAGGCCGAAA CUCGAU                36

(2) INFORMATION FOR SEQ ID NO:1528:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1528:

UGCAUAACUG AUGAGGCCGA AAGGCCGAAA CCAUCA                36

(2) INFORMATION FOR SEQ ID NO:1529:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1529:

UCUGCAUCUG AUGAGGCCGA AAGGCCGAAA UACCAU                36

(2) INFORMATION FOR SEQ ID NO:1530:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1530:

UUCUGCACUG AUGAGGCCGA AAGGCCGAAA AUACCA                36

(2) INFORMATION FOR SEQ ID NO:1531:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1531:

AUCUUGACUG AUGAGGCCGA AAGGCCGAAA UUUCUG 36

(2) INFORMATION FOR SEQ ID NO:1532:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1532:

UUAUCUUCUG AUGAGGCCGA AAGGCCGAAA GAUUUC 36

(2) INFORMATION FOR SEQ ID NO:1533:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1533:

GUGACAUCUG AUGAGGCCGA AAGGCCGAAA UCUUGA 36

(2) INFORMATION FOR SEQ ID NO:1534:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1534:

GUUCUGUCUG AUGAGGCCGA AAGGCCGAAA CAUUAU 36

(2) INFORMATION FOR SEQ ID NO:1535:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1535:

AACGUCGCUG AUGAGGCCGA AAGGCCGAAA CAGUUC 36

(2) INFORMATION FOR SEQ ID NO:1536:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1536:

UGAUGGACUG AUGAGGCCGA AAGGCCGAAA CGUCGU 36

(2) INFORMATION FOR SEQ ID NO:1537:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1537:

CUGAUGGCUG AUGAGGCCGA AAGGCCGAAA ACGUCG 36

(2) INFORMATION FOR SEQ ID NO:1538:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1538:

GCUGAUGCUG AUGAGGCCGA AAGGCCGAAA AACGUC                                  36

(2) INFORMATION FOR SEQ ID NO:1539:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1539:

ACAAGCUCUG AUGAGGCCGA AAGGCCGAAA UGGAAA                                  36

(2) INFORMATION FOR SEQ ID NO:1540:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1540:

AACAGACCUG AUGAGGCCGA AAGGCCGAAA GCUGAU                                  36

(2) INFORMATION FOR SEQ ID NO:1541:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1541:

UGAAACACUG AUGAGGCCGA AAGGCCGAAA CAAGCU                                  36

(2) INFORMATION FOR SEQ ID NO:1542:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1542:

GGAAUGACUG AUGAGGCCGA AAGGCCGAAA CAGACA                                  36

(2) INFORMATION FOR SEQ ID NO:1543:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1543:

GGGAAUGCUG AUGAGGCCGA AAGGCCGAAA ACAGAC                                  36

(2) INFORMATION FOR SEQ ID NO:1544:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1544:

AGGGAAUCUG AUGAGGCCGA AAGGCCGAAA AACAGA                  36

(2) INFORMATION FOR SEQ ID NO:1545:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1545:

AUCAGGGCUG AUGAGGCCGA AAGGCCGAAA UGAAAC                  36

(2) INFORMATION FOR SEQ ID NO:1546:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1546:

CAUCAGGCUG AUGAGGCCGA AAGGCCGAAA AUGAAA                  36

(2) INFORMATION FOR SEQ ID NO:1547:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1547:

UGCUCGUCUG AUGAGGCCGA AAGGCCGAAA CAUCAG                  36

(2) INFORMATION FOR SEQ ID NO:1548:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1548:

UUGCUCGCUG AUGAGGCCGA AAGGCCGAAA ACAUCA                  36

(2) INFORMATION FOR SEQ ID NO:1549:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1549:

AUGGUCACUG AUGAGGCCGA AAGGCCGAAA UUGCUC                  36

(2) INFORMATION FOR SEQ ID NO:1550:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:1550:

UACAGAACUG AUGAGGCCGA AAGGCCGAAA UGGUCA                                    36

(2) INFORMATION FOR SEQ ID NO:1551:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:1551:

AAUACAGCUG AUGAGGCCGA AAGGCCGAAA GAUGGU                                    36

(2) INFORMATION FOR SEQ ID NO:1552:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:1552:

GAAUACACUG AUGAGGCCGA AAGGCCGAAA AGAUGG                                    36

(2) INFORMATION FOR SEQ ID NO:1553:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:1553:

UCCAGAACUG AUGAGGCCGA AAGGCCGAAA CAGAAG                                    36

(2) INFORMATION FOR SEQ ID NO:1554:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:1554:

UUUCCAGCUG AUGAGGCCGA AAGGCCGAAA UACAGA                                    36

(2) INFORMATION FOR SEQ ID NO:1555:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO:1555:

GUUUCCACUG AUGAGGCCGA AAGGCCGAAA AUACAG                                    36

(2) INFORMATION FOR SEQ ID NO:1556:

```
    (i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1556:

AAGAUAACUG AUGAGGCCGA AAGGCCGAAA GCCGCG                                36

(2) INFORMATION FOR SEQ ID NO:1557:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1557:

GAAGAUACUG AUGAGGCCGA AAGGCCGAAA AGCCGC                                36

(2) INFORMATION FOR SEQ ID NO:1558:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1558:

UGAAGAUCUG AUGAGGCCGA AAGGCCGAAA AAGCCG                                36

(2) INFORMATION FOR SEQ ID NO:1559:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1559:

GUGAAGACUG AUGAGGCCGA AAGGCCGAAA AAAGCC                                36

(2) INFORMATION FOR SEQ ID NO:1560:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1560:

AGGUGAACUG AUGAGGCCGA AAGGCCGAAA UAAAAG                                36

(2) INFORMATION FOR SEQ ID NO:1561:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1561:

AAAGGUGCUG AUGAGGCCGA AAGGCCGAAA GAUAAA                                36

(2) INFORMATION FOR SEQ ID NO:1562:
```

```
        (i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:1562:

GAAAGGUCUG AUGAGGCCGA AAGGCCGAAA AGAUAA                                  36

(2) INFORMATION FOR SEQ ID NO:1563:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:1563:

AUAGAGACUG AUGAGGCCGA AAGGCCGAAA GGUGAA                                  36

(2) INFORMATION FOR SEQ ID NO:1564:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:1564:

UAUAGAGCUG AUGAGGCCGA AAGGCCGAAA AGGUGA                                  36

(2) INFORMATION FOR SEQ ID NO:1565:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:1565:

CUAUAGACUG AUGAGGCCGA AAGGCCGAAA AAGGUG                                  36

(2) INFORMATION FOR SEQ ID NO:1566:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:1566:

CUCUAUACUG AUGAGGCCGA AAGGCCGAAA GAAAGG                                  36

(2) INFORMATION FOR SEQ ID NO:1567:

(i) SEQUENCE CHARACTERISTICS:
              (A) LENGTH:          36 base pairs
              (B) TYPE:            nucleic acid
              (C) STRANDEDNESS:    single
              (D) TOPOLOGY:        linear (xi) SEQUENCE DESCRIPTION: SEQ ID NO:1567:

AGCUCUACUG AUGAGGCCGA AAGGCCGAAA GAGAAA                                  36

(2) INFORMATION FOR SEQ ID NO:1568:

(i) SEQUENCE CHARACTERISTICS:
```

```
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1568:

CAAGCUCCUG AUGAGGCCGA AAGGCCGAAA UAGAGA                              36

(2) INFORMATION FOR SEQ ID NO:1569:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1569:

GGUCCUCCUG AUGAGGCCGA AAGGCCGAAA GCUCUA                              36

(2) INFORMATION FOR SEQ ID NO:1570:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1570:

GGAGGCUCUG AUGAGGCCGA AAGGCCGAAA GGGUCC                              36

(2) INFORMATION FOR SEQ ID NO:1571:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1571:

UCUGGGGCUG AUGAGGCCGA AAGGCCGAAA GGCUGA                              36

(2) INFORMATION FOR SEQ ID NO:1572:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1572:

UCCAAGGCUG AUGAGGCCGA AAGGCCGAAA UGUGGU                              36

(2) INFORMATION FOR SEQ ID NO:1573:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1573:

AUCCAAGCUG AUGAGGCCGA AAGGCCGAAA AUGUGG                              36

(2) INFORMATION FOR SEQ ID NO:1574:

(i) SEQUENCE CHARACTERISTICS:
        (A) LENGTH:        36 base pairs
```

```
        (B) TYPE:          nucleic acid
        (C) STRANDEDNESS:  single
        (D) TOPOLOGY:      linear (xi) SEQUENCE DESCRIPTION: SEQ ID NO:1574:

GUAAUCCCUG AUGAGGCCGA AAGGCCGAAA GGAAUG                          36

(2) INFORMATION FOR SEQ ID NO:1575:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1575:

CAGCUGUCUG AUGAGGCCGA AAGGCCGAAA UCCAAG                          36

(2) INFORMATION FOR SEQ ID NO:1576:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1576:

ACAGCUGCUG AUGAGGCCGA AAGGCCGAAA AUCCAA                          36

(2) INFORMATION FOR SEQ ID NO:1577:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1577:

UUGGAAGCUG AUGAGGCCGA AAGGCCGAAA CAGCUG                          36

(2) INFORMATION FOR SEQ ID NO:1578:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1578:

CUGUUGGCUG AUGAGGCCGA AAGGCCGAAA GUACAG                          36

(2) INFORMATION FOR SEQ ID NO:1579:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1579:

ACUGUUGCUG AUGAGGCCGA AAGGCCGAAA AGUACA                          36

(2) INFORMATION FOR SEQ ID NO:1580:

(i) SEQUENCE CHARACTERISTICS:
        (A) LENGTH:        36 base pairs
        (B) TYPE:          nucleic acid
```

```
            (C) STRANDEDNESS:     single
            (D) TOPOLOGY:         linear (xi) SEQUENCE DESCRIPTION: SEQ ID NO:1580:

AUAUAAUCUG AUGAGGCCGA AAGGCCGAAA CUGUUG                              36

(2) INFORMATION FOR SEQ ID NO:1581:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1581:

CAUAUAACUG AUGAGGCCGA AAGGCCGAAA ACUGUU                              36

(2) INFORMATION FOR SEQ ID NO:1582:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1582:

CACAUAUCUG AUGAGGCCGA AAGGCCGAAA UAACUG                              36

(2) INFORMATION FOR SEQ ID NO:1583:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1583:

ACACAUACUG AUGAGGCCGA AAGGCCGAAA AUAACU                              36

(2) INFORMATION FOR SEQ ID NO:1584:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1584:

UCACACACUG AUGAGGCCGA AAGGCCGAAA UAAUAA                              36

(2) INFORMATION FOR SEQ ID NO:1585:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1585:

GACAGAACUG AUGAGGCCGA AAGGCCGAAA CCAUCA                              36

(2) INFORMATION FOR SEQ ID NO:1586:

(i) SEQUENCE CHARACTERISTICS:
            (A) LENGTH:           36 base pairs
            (B) TYPE:             nucleic acid
            (C) STRANDEDNESS:     single
```

(D) TOPOLOGY:     linear (xi) SEQUENCE DESCRIPTION: SEQ ID NO:1586:

AGACAGACUG AUGAGGCCGA AAGGCCGAAA ACCAUC                              36

(2) INFORMATION FOR SEQ ID NO:1587:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1587:

UAGACAGCUG AUGAGGCCGA AAGGCCGAAA AACCAU                              36

(2) INFORMATION FOR SEQ ID NO:1588:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1588:

UUAGACACUG AUGAGGCCGA AAGGCCGAAA AAACCA                              36

(2) INFORMATION FOR SEQ ID NO:1589:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1589:

AGAAUUACUG AUGAGGCCGA AAGGCCGAAA CAGAAA                              36

(2) INFORMATION FOR SEQ ID NO:1590:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1590:

AUAGAAUCUG AUGAGGCCGA AAGGCCGAAA GACAGA                              36

(2) INFORMATION FOR SEQ ID NO:1591:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1591:

UCCAUAGCUG AUGAGGCCGA AAGGCCGAAA UUAGAC                              36

(2) INFORMATION FOR SEQ ID NO:1592:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1592:

UUCCAUACUG AUGAGGCCGA AAGGCCGAAA AUUAGA                36

(2) INFORMATION FOR SEQ ID NO:1593:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1593:

AUUUCCACUG AUGAGGCCGA AAGGCCGAAA GAAUUA                36

(2) INFORMATION FOR SEQ ID NO:1594:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1594:

GAGUUGCCUG AUGAGGCCGA AAGGCCGAAA GGCCGC                36

(2) INFORMATION FOR SEQ ID NO:1595:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1595:

UUUAUAACUG AUGAGGCCGA AAGGCCGAAA GUUGCG                36

(2) INFORMATION FOR SEQ ID NO:1596:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1596:

CAUUUAUCUG AUGAGGCCGA AAGGCCGAAA GAGUUG                36

(2) INFORMATION FOR SEQ ID NO:1597:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1597:

ACAUUUACUG AUGAGGCCGA AAGGCCGAAA AGAGUU                36

(2) INFORMATION FOR SEQ ID NO:1598:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1598:

CCACAUUCUG AUGAGGCCGA AAGGCCGAAA UAAGAG                                      36

(2) INFORMATION FOR SEQ ID NO:1599:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1599:

GUAUAUGCUG AUGAGGCCGA AAGGCCGAAA UUUUUU                                      36

(2) INFORMATION FOR SEQ ID NO:1600:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1600:

UCAGGUACUG AUGAGGCCGA AAGGCCGAAA UGGAUU                                      36

(2) INFORMATION FOR SEQ ID NO:1601:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1601:

UUUCAGGCUG AUGAGGCCGA AAGGCCGAAA UAUGGA                                      36

(2) INFORMATION FOR SEQ ID NO:1602:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1602:

UUCAUCACUG AUGAGGCCGA AAGGCCGAAA UCUUUC                                      36

(2) INFORMATION FOR SEQ ID NO:1603:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1603:

UUUUAAACUG AUGAGGCCGA AAGGCCGAAA CACGCU                                      36

(2) INFORMATION FOR SEQ ID NO:1604:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1604:

CUUUUAACUG AUGAGGCCGA AAGGCCGAAA ACACGC 36

(2) INFORMATION FOR SEQ ID NO:1605:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1605:

ACUUUACUG AUGAGGCCGA AAGGCCGAAA AACACG 36

(2) INFORMATION FOR SEQ ID NO:1606:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1606:

AACUUUUCUG AUGAGGCCGA AAGGCCGAAA AAACAC 36

(2) INFORMATION FOR SEQ ID NO:1607:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1607:

GAACUUUCUG AUGAGGCCGA AAGGCCGAAA AAAACA 36

(2) INFORMATION FOR SEQ ID NO:1608:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1608:

GUCUUCGCUG AUGAGGCCGA AAGGCCGAAA CUUUUA 36

(2) INFORMATION FOR SEQ ID NO:1609:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1609:

UGUCUUCCUG AUGAGGCCGA AAGGCCGAAA ACUUUU 36

(2) INFORMATION FOR SEQ ID NO:1610:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1610:

```
GCAUGAACUG AUGAGGCCGA AAGGCCGAAA UGUCUU                                  36

(2) INFORMATION FOR SEQ ID NO:1611:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1611:

UCGCAUGCUG AUGAGGCCGA AAGGCCGAAA GAUGUC                                  36

(2) INFORMATION FOR SEQ ID NO:1612:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1612:

GUCGCAUCUG AUGAGGCCGA AAGGCCGAAA AGAUGU                                  36

(2) INFORMATION FOR SEQ ID NO:1613:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1613:

AAACAUGCUG AUGAGGCCGA AAGGCCGAAA UCACUU                                  36

(2) INFORMATION FOR SEQ ID NO:1614:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1614:

AAUUAAACUG AUGAGGCCGA AAGGCCGAAA CAUGUA                                  36

(2) INFORMATION FOR SEQ ID NO:1615:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1615:

UAAUUAACUG AUGAGGCCGA AAGGCCGAAA ACAUGU                                  36

(2) INFORMATION FOR SEQ ID NO:1616:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1616:

UUAAUUACUG AUGAGGCCGA AAGGCCGAAA AACAUG                                  36
```

(2) INFORMATION FOR SEQ ID NO:1617:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1617:

UUUAAUUCUG AUGAGGCCGA AAGGCCGAAA AAACAU                            36

(2) INFORMATION FOR SEQ ID NO:1618:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1618:

CUUUAAUCUG AUGAGGCCGA AAGGCCGAAA AAAACA                            36

(2) INFORMATION FOR SEQ ID NO:1619:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1619:

ACUCUUUCUG AUGAGGCCGA AAGGCCGAAA UUAAAA                            36

(2) INFORMATION FOR SEQ ID NO:1620:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1620:

UACUCUUCUG AUGAGGCCGA AAGGCCGAAA AUUAAA                            36

(2) INFORMATION FOR SEQ ID NO:1621:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1621:

ACGGACUUGA ACAAC                                                            15

(2) INFORMATION FOR SEQ ID NO:1622:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1622:

ACGGACUUGA ACAAC                                                            15

(2) INFORMATION FOR SEQ ID NO:1623:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1623:

CUCCUGUAGA CGUGU          15

(2) INFORMATION FOR SEQ ID NO:1624:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1624:

CUCCUGUAGA CGUGU          15

(2) INFORMATION FOR SEQ ID NO:1625:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1625:

GACGUGUUCC AGAAC          15

(2) INFORMATION FOR SEQ ID NO:1626:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1626:

CAGAACUUAC GGAAG          15

(2) INFORMATION FOR SEQ ID NO:1627:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1627:

CAAUCCUUAU CUUUG          15

(2) INFORMATION FOR SEQ ID NO:1628:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1628:

CAAUCCUUAU CUUUG          15

(2) INFORMATION FOR SEQ ID NO:1629:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1629:

CAAUCCUUAU CUUUG                                              15

(2) INFORMATION FOR SEQ ID NO:1630:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1630:

CAAUCCUUAU CUUUG                                              15

(2) INFORMATION FOR SEQ ID NO:1631:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1631:

CAAUCCUUAU CUUUG                                              15

(2) INFORMATION FOR SEQ ID NO:1632:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1632:

AAUCCUUAUC UUUGU                                              15

(2) INFORMATION FOR SEQ ID NO:1633:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1633:

AAUCCUUAUC UUUGU                                              15

(2) INFORMATION FOR SEQ ID NO:1634:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1634:

AAUCCUUAUC UUUGU                                              15

(2) INFORMATION FOR SEQ ID NO:1635:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1635:

AAUCCUUAUC UUUGU                                                        15

(2) INFORMATION FOR SEQ ID NO:1636:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1636:

UCCUUAUCUU UGUGA                                                        15

(2) INFORMATION FOR SEQ ID NO:1637:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1637:

UCCUUAUCUU UGUGA                                                        15

(2) INFORMATION FOR SEQ ID NO:1638:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1638:

UCCUUAUCUU UGUGA                                                        15

(2) INFORMATION FOR SEQ ID NO:1639:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1639:

CUUAUCUUUG UGACA                                                        15

(2) INFORMATION FOR SEQ ID NO:1640:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1640:

UUAUCUUUGU GACAG                                                        15

(2) INFORMATION FOR SEQ ID NO:1641:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1641:

UUAUCUUUGU GACAG                                                        15

(2) INFORMATION FOR SEQ ID NO:1642:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1642:

UGACAGUCUU GCUGA                                                        15

(2) INFORMATION FOR SEQ ID NO:1643:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1643:

ACAGUCUUGC UGAUC                                                        15

(2) INFORMATION FOR SEQ ID NO:1644:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1644:

ACAGUCUUGC UGAUC                                                        15

(2) INFORMATION FOR SEQ ID NO:1645:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1645:

UGCUGAUCUC AGAUG                                                        15

(2) INFORMATION FOR SEQ ID NO:1646:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1646:

UGCUGAUCUC AGAUG                                                        15

(2) INFORMATION FOR SEQ ID NO:1647:

(i) SEQUENCE CHARACTERISTICS:

```
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1647:

UGCUGAUCUC AGAUG                                                    15

(2) INFORMATION FOR SEQ ID NO:1648:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1648:

UGCUGAUCUC AGAUG                                                    15

(2) INFORMATION FOR SEQ ID NO:1649:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1649:

CUGAUCUCAG AUGCU                                                    15

(2) INFORMATION FOR SEQ ID NO:1650:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1650:

CUGAUCUCAG AUGCU                                                    15

(2) INFORMATION FOR SEQ ID NO:1651:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1651:

AUGCUGUUUC CGUGG                                                    15

(2) INFORMATION FOR SEQ ID NO:1652:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1652:

UGCUGUUUCC GUGGA                                                    15

(2) INFORMATION FOR SEQ ID NO:1653:

(i) SEQUENCE CHARACTERISTICS:
        (A) LENGTH:          15 base pairs
```

```
        (B) TYPE:           nucleic acid
        (C) STRANDEDNESS:   single
        (D) TOPOLOGY:       linear (xi) SEQUENCE DESCRIPTION: SEQ ID NO:1653:

GCUGUUUCCG UGGAG                                                        15

(2) INFORMATION FOR SEQ ID NO:1654:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1654:

GCAAGCUUAU UUCAA                                                        15

(2) INFORMATION FOR SEQ ID NO:1655:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1655:

GCAAGCUUAU UUCAA                                                        15

(2) INFORMATION FOR SEQ ID NO:1656:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1656:

GCAAGCUUAU UUCAA                                                        15

(2) INFORMATION FOR SEQ ID NO:1657:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1657:

CAAGCUUAUU UCAAU                                                        15

(2) INFORMATION FOR SEQ ID NO:1658:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1658:

CAAGCUUAUU UCAAU                                                        15

(2) INFORMATION FOR SEQ ID NO:1659:

(i) SEQUENCE CHARACTERISTICS:
        (A) LENGTH:         15 base pairs
        (B) TYPE:           nucleic acid
```

```
        (C) STRANDEDNESS:    single
        (D) TOPOLOGY:        linear (xi) SEQUENCE DESCRIPTION: SEQ ID NO:1659:

AGCUUAUUUC AAUGG                                                        15

(2) INFORMATION FOR SEQ ID NO:1660:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1660:

AGCUUAUUUC AAUGG                                                        15

(2) INFORMATION FOR SEQ ID NO:1661:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1661:

GCUUAUUUCA AUGGG                                                        15

(2) INFORMATION FOR SEQ ID NO:1662:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1662:

GCUUAUUUCA AUGGG                                                        15

(2) INFORMATION FOR SEQ ID NO:1663:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1663:

CUUAUUUCAA UGGGA                                                        15

(2) INFORMATION FOR SEQ ID NO:1664:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1664:

CUUAUUUCAA UGGGA                                                        15

(2) INFORMATION FOR SEQ ID NO:1665:

(i) SEQUENCE CHARACTERISTICS:
        (A) LENGTH:          15 base pairs
        (B) TYPE:            nucleic acid
        (C) STRANDEDNESS:    single
```

(D) TOPOLOGY:      linear (xi) SEQUENCE DESCRIPTION: SEQ ID NO:1665:

ACUGCAUAUC UGCCG                                                    15

(2) INFORMATION FOR SEQ ID NO:1666:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1666:

UGCAUAUCUG CCGUG                                                    15

(2) INFORMATION FOR SEQ ID NO:1667:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1667:

UGCCCAUUUA CAAAG                                                    15

(2) INFORMATION FOR SEQ ID NO:1668:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1668:

UGCCCAUUUA CAAAG                                                    15

(2) INFORMATION FOR SEQ ID NO:1669:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1669:

GCCCAUUUAC AAAGG                                                    15

(2) INFORMATION FOR SEQ ID NO:1670:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1670:

CCCAUUUACA AAGGC                                                    15

(2) INFORMATION FOR SEQ ID NO:1671:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:1671:

CCCAUUUACA AAGGC                                                15

(2) INFORMATION FOR SEQ ID NO:1672:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1672:

AAAACAUAAG CCUGA                                                15

(2) INFORMATION FOR SEQ ID NO:1673:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1673:

AGCUGGUAGU AUUUU                                                15

(2) INFORMATION FOR SEQ ID NO:1674:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1674:

AGCUGGUAGU AUUUU                                                15

(2) INFORMATION FOR SEQ ID NO:1675:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1675:

UGGUAGUAUU UUGGC                                                15

(2) INFORMATION FOR SEQ ID NO:1676:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1676:

UGGUAGUAUU UUGGC                                                15

(2) INFORMATION FOR SEQ ID NO:1677:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1677:

GUAGUAUUUU GGCAG                                                15

(2) INFORMATION FOR SEQ ID NO:1678:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1678:

GUAGUAUUUU GGCAG                                                15

(2) INFORMATION FOR SEQ ID NO:1679:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1679:

UAGUAUUUUG GCAGG                                                15

(2) INFORMATION FOR SEQ ID NO:1680:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1680:

UAGUAUUUUG GCAGG                                                15

(2) INFORMATION FOR SEQ ID NO:1681:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1681:

UAGUAUUUUG GCAGG                                                15

(2) INFORMATION FOR SEQ ID NO:1682:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1682:

AGUAUUUUGG CAGGA                                                15

(2) INFORMATION FOR SEQ ID NO:1683:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1683:

AGUAUUUUGG CAGGA                                                                15

(2) INFORMATION FOR SEQ ID NO:1684:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1684:

CAAAAGUUGG UUCUG                                                                15

(2) INFORMATION FOR SEQ ID NO:1685:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1685:

CAAAAGUUGG UUCUG                                                                15

(2) INFORMATION FOR SEQ ID NO:1686:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1686:

AGUUGGUUCU GUACG                                                                15

(2) INFORMATION FOR SEQ ID NO:1687:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1687:

GUUGGUUCUG UACGA                                                                15

(2) INFORMATION FOR SEQ ID NO:1688:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1688:

GUUCUGUACG AGCAC                                                                15

(2) INFORMATION FOR SEQ ID NO:1689:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1689:

```
GAGCACUAUU UGGGC                                                    15

(2) INFORMATION FOR SEQ ID NO:1690:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1690:

CACUAUUUGG GCACA                                                    15

(2) INFORMATION FOR SEQ ID NO:1691:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1691:

AGAAACUUGA UAGUG                                                    15

(2) INFORMATION FOR SEQ ID NO:1692:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1692:

GCCAAGUACC UGGGC                                                    15

(2) INFORMATION FOR SEQ ID NO:1693:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1693:

GCCAAGUACC UGGGC                                                    15

(2) INFORMATION FOR SEQ ID NO:1694:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1694:

ACGAGCUUUG ACAGG                                                    15

(2) INFORMATION FOR SEQ ID NO:1695:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1695:

CUGGACUCUA CGACU                                                    15
```

(2) INFORMATION FOR SEQ ID NO:1696:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1696:

GGACUCUACG ACUUC                                                    15

(2) INFORMATION FOR SEQ ID NO:1697:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1697:

GGACUCUACG ACUUC                                                    15

(2) INFORMATION FOR SEQ ID NO:1698:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1698:

UACGACUUCA CAAUG                                                    15

(2) INFORMATION FOR SEQ ID NO:1699:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1699:

UACGACUUCA CAAUG                                                    15

(2) INFORMATION FOR SEQ ID NO:1700:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1700:

ACGACUUCAC AAUGU                                                    15

(2) INFORMATION FOR SEQ ID NO:1701:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1701:

ACGACUUCAC AAUGU                                                    15

(2) INFORMATION FOR SEQ ID NO:1702:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1702:

ACAAUGUUCA GAUCA                                                               15

(2) INFORMATION FOR SEQ ID NO:1703:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1703:

ACAAUGUUCA GAUCA                                                               15

(2) INFORMATION FOR SEQ ID NO:1704:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1704:

ACAAUGUUCA GAUCA                                                               15

(2) INFORMATION FOR SEQ ID NO:1705:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1705:

CAAUGUUCAG AUCAA                                                               15

(2) INFORMATION FOR SEQ ID NO:1706:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1706:

CAAUGUUCAG AUCAA                                                               15

(2) INFORMATION FOR SEQ ID NO:1707:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1707:

CAAUGUUCAG AUCAA                                                               15

(2) INFORMATION FOR SEQ ID NO:1708:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1708:

CAAUGUUCAG AUCAA                                                           15

(2) INFORMATION FOR SEQ ID NO:1709:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1709:

CAAUGUUCAG AUCAA                                                           15

(2) INFORMATION FOR SEQ ID NO:1710:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1710:

CAAUGUUCAG AUCAA                                                           15

(2) INFORMATION FOR SEQ ID NO:1711:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1711:

CAAUGUUCAG AUCAA                                                           15

(2) INFORMATION FOR SEQ ID NO:1712:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1712:

UUCAGAUCAA GGACA                                                           15

(2) INFORMATION FOR SEQ ID NO:1713:

(i) SEQUENCE CHARACTERISTICS:
       (A) LENGTH:        15 base pairs
       (B) TYPE:          nucleic acid
       (C) STRANDEDNESS:  single
       (D) TOPOLOGY:      linear (xi) SEQUENCE DESCRIPTION: SEQ ID NO:1713:

UUCAGAUCAA GGACA                                                           15

(2) INFORMATION FOR SEQ ID NO:1714:

-continued

```
    (i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1714:

AUGGGCUCGU AUGAU                                                    15

(2) INFORMATION FOR SEQ ID NO:1715:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1715:

AUGGGCUCGU AUGAU                                                    15

(2) INFORMATION FOR SEQ ID NO:1716:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1716:

AUGGGCUCGU AUGAU                                                    15

(2) INFORMATION FOR SEQ ID NO:1717:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1717:

GGCUCGUAUG AUUGU                                                    15

(2) INFORMATION FOR SEQ ID NO:1718:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1718:

GGCUCGUAUG AUUGU                                                    15

(2) INFORMATION FOR SEQ ID NO:1719:

(i) SEQUENCE CHARACTERISTICS:
         (A) LENGTH:        15 base pairs
         (B) TYPE:          nucleic acid
         (C) STRANDEDNESS:  single
         (D) TOPOLOGY:      linear (xi) SEQUENCE DESCRIPTION: SEQ ID NO:1719:

UGAUUGUUUU AUACA                                                    15

(2) INFORMATION FOR SEQ ID NO:1720:
```

```
    (i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1720:

UGAUUGUUUU AUACA                                               15

(2) INFORMATION FOR SEQ ID NO:1721:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1721:

AUUGUUUUAU ACAAA                                               15

(2) INFORMATION FOR SEQ ID NO:1722:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1722:

AUUGUUUUAU ACAAA                                               15

(2) INFORMATION FOR SEQ ID NO:1723:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1723:

UUGUUUUAUA CAAAA                                               15

(2) INFORMATION FOR SEQ ID NO:1724:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1724:

UUGUUUUAUA CAAAA                                               15

(2) INFORMATION FOR SEQ ID NO:1725:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1725:

UUGUUUUAUA CAAAA                                               15

(2) INFORMATION FOR SEQ ID NO:1726:

(i) SEQUENCE CHARACTERISTICS:
```

```
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1726:

GAUCAAUUAU CCUCC                                                    15

(2) INFORMATION FOR SEQ ID NO:1727:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1727:

AUCAAUUAUC CUCCA                                                    15

(2) INFORMATION FOR SEQ ID NO:1728:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1728:

CAAUUAUCCU CCAAC                                                    15

(2) INFORMATION FOR SEQ ID NO:1729:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1729:

UUAUCCUCCA ACAGA                                                    15

(2) INFORMATION FOR SEQ ID NO:1730:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1730:

UUAUCCUCCA ACAGA                                                    15

(2) INFORMATION FOR SEQ ID NO:1731:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1731:

UUAUCCUCCA ACAGA                                                    15

(2) INFORMATION FOR SEQ ID NO:1732:

(i) SEQUENCE CHARACTERISTICS:
        (A) LENGTH:        15 base pairs
```

```
            (B) TYPE:           nucleic acid
            (C) STRANDEDNESS:   single
            (D) TOPOLOGY:       linear (xi) SEQUENCE DESCRIPTION: SEQ ID NO:1732:

UUAUCCUCCA ACAGA                                                        15

(2) INFORMATION FOR SEQ ID NO:1733:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1733:

GAACUGUCAG UGAUC                                                        15

(2) INFORMATION FOR SEQ ID NO:1734:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1734:

CAGUGAUCGC CAACU                                                        15

(2) INFORMATION FOR SEQ ID NO:1735:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1735:

GCCAACUUCA GUGAA                                                        15

(2) INFORMATION FOR SEQ ID NO:1736:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1736:

CCAACUUCAG UGAAC                                                        15

(2) INFORMATION FOR SEQ ID NO:1737:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:1737:

CCAACUUCAG UGAAC                                                        15

(2) INFORMATION FOR SEQ ID NO:1738:

(i) SEQUENCE CHARACTERISTICS:
            (A) LENGTH:         15 base pairs
            (B) TYPE:           nucleic acid
```

```
              (C) STRANDEDNESS:    single
              (D) TOPOLOGY:        linear (xi) SEQUENCE DESCRIPTION: SEQ ID NO:1738:

CUGAAAUAAA ACUGG                                                    15

(2) INFORMATION FOR SEQ ID NO:1739:

(i) SEQUENCE CHARACTERISTICS:
              (A) LENGTH:          15 base pairs
              (B) TYPE:            nucleic acid
              (C) STRANDEDNESS:    single
              (D) TOPOLOGY:        linear (xi) SEQUENCE DESCRIPTION: SEQ ID NO:1739:

ACUGGCUCAG AAUGU                                                    15

(2) INFORMATION FOR SEQ ID NO:1740:

(i) SEQUENCE CHARACTERISTICS:
              (A) LENGTH:          15 base pairs
              (B) TYPE:            nucleic acid
              (C) STRANDEDNESS:    single
              (D) TOPOLOGY:        linear (xi) SEQUENCE DESCRIPTION: SEQ ID NO:1740:

AGAAUGUAAC AGGAA                                                    15

(2) INFORMATION FOR SEQ ID NO:1741:

(i) SEQUENCE CHARACTERISTICS:
              (A) LENGTH:          15 base pairs
              (B) TYPE:            nucleic acid
              (C) STRANDEDNESS:    single
              (D) TOPOLOGY:        linear (xi) SEQUENCE DESCRIPTION: SEQ ID NO:1741:

GGAAAUUCUG GCAUA                                                    15

(2) INFORMATION FOR SEQ ID NO:1742:

(i) SEQUENCE CHARACTERISTICS:
              (A) LENGTH:          15 base pairs
              (B) TYPE:            nucleic acid
              (C) STRANDEDNESS:    single
              (D) TOPOLOGY:        linear (xi) SEQUENCE DESCRIPTION: SEQ ID NO:1742:

GGAAAUUCUG GCAUA                                                    15

(2) INFORMATION FOR SEQ ID NO:1743:

(i) SEQUENCE CHARACTERISTICS:
              (A) LENGTH:          15 base pairs
              (B) TYPE:            nucleic acid
              (C) STRANDEDNESS:    single
              (D) TOPOLOGY:        linear (xi) SEQUENCE DESCRIPTION: SEQ ID NO:1743:

CUGGCAUAAA UUUGA                                                    15

(2) INFORMATION FOR SEQ ID NO:1744:

(i) SEQUENCE CHARACTERISTICS:
              (A) LENGTH:          15 base pairs
              (B) TYPE:            nucleic acid
              (C) STRANDEDNESS:    single
```

```
        (D) TOPOLOGY:       linear (xi) SEQUENCE DESCRIPTION: SEQ ID NO:1744:

CAUAAAUUUG ACCUG                                                   15

(2) INFORMATION FOR SEQ ID NO:1745:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1745:

AUAAAUUUGA CCUGC                                                   15

(2) INFORMATION FOR SEQ ID NO:1746:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1746:

CACGUCUAAG CAAGG                                                   15

(2) INFORMATION FOR SEQ ID NO:1747:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1747:

GCAAGGUCAC CCGAA                                                   15

(2) INFORMATION FOR SEQ ID NO:1748:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1748:

GAAACCUAAG AAGAU                                                   15

(2) INFORMATION FOR SEQ ID NO:1749:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1749:

AAGAUGUAUU UUCUG                                                   15

(2) INFORMATION FOR SEQ ID NO:1750:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear
```

(xi) SEQUENCE DESCRIPTION: SEQ ID NO:1750:

UGUAUUUUCU GAUAA                                                      15

(2) INFORMATION FOR SEQ ID NO:1751:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1751:

ACUAAUUCAA CUAAU                                                      15

(2) INFORMATION FOR SEQ ID NO:1752:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1752:

UUCAACUAAU GAGUA                                                      15

(2) INFORMATION FOR SEQ ID NO:1753:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1753:

UUCAACUAAU GAGUA                                                      15

(2) INFORMATION FOR SEQ ID NO:1754:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1754:

AAUGAGUAUG GUGAU                                                      15

(2) INFORMATION FOR SEQ ID NO:1755:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO:1755:

UGCAGAUAUC ACAAG                                                      15

(2) INFORMATION FOR SEQ ID NO:1756:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear

```
    (xi) SEQUENCE DESCRIPTION: SEQ ID NO:1756:

CAGAUAUCAC AAGAU                                                          15

(2) INFORMATION FOR SEQ ID NO:1757:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1757:

CAGAUAUCAC AAGAU                                                          15

(2) INFORMATION FOR SEQ ID NO:1758:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1758:

CAGAUAUCAC AAGAU                                                          15

(2) INFORMATION FOR SEQ ID NO:1759:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1759:

CAGAUAUCAC AAGAU                                                          15

(2) INFORMATION FOR SEQ ID NO:1760:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1760:

ACAAGAUAAU GUCAC                                                          15

(2) INFORMATION FOR SEQ ID NO:1761:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1761:

ACAAGAUAAU GUCAC                                                          15

(2) INFORMATION FOR SEQ ID NO:1762:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:1762:
```

AUAAUGUCAC AGAAC                                                   15

(2) INFORMATION FOR SEQ ID NO:1763:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1763:

AUAAUGUCAC AGAAC                                                   15

(2) INFORMATION FOR SEQ ID NO:1764:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1764:

AUAAUGUCAC AGAAC                                                   15

(2) INFORMATION FOR SEQ ID NO:1765:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1765:

GAACUGUUCA GUAUC                                                   15

(2) INFORMATION FOR SEQ ID NO:1766:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1766:

AACUGUUCAG UAUCU                                                   15

(2) INFORMATION FOR SEQ ID NO:1767:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1767:

AACUGUUCAG UAUCU                                                   15

(2) INFORMATION FOR SEQ ID NO:1768:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1768:

```
AGUAUCUCCA ACAGC                                                        15

(2) INFORMATION FOR SEQ ID NO:1769:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1769:

AGUAUCUCCA ACAGC                                                        15

(2) INFORMATION FOR SEQ ID NO:1770:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1770:

AGUAUCUCCA ACAGC                                                        15

(2) INFORMATION FOR SEQ ID NO:1771:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1771:

ACAGCCUCUC UCUUU                                                        15

(2) INFORMATION FOR SEQ ID NO:1772:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1772:

ACAGCCUCUC UCUUU                                                        15

(2) INFORMATION FOR SEQ ID NO:1773:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1773:

AGCCUCUCUC UUUCA                                                        15

(2) INFORMATION FOR SEQ ID NO:1774:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1774:

AGCCUCUCUC UUUCA                                                        15
```

(2) INFORMATION FOR SEQ ID NO:1775:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1775:

UCUCUCUUUC AUUCC                                                      15

(2) INFORMATION FOR SEQ ID NO:1776:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1776:

UCUCUCUUUC AUUCC                                                      15

(2) INFORMATION FOR SEQ ID NO:1777:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1777:

CUCUCUUUCA UUCCC                                                      15

(2) INFORMATION FOR SEQ ID NO:1778:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1778:

UCUCUUUCAU UCCCG                                                      15

(2) INFORMATION FOR SEQ ID NO:1779:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1779:

UCUCUUUCAU UCCCG                                                      15

(2) INFORMATION FOR SEQ ID NO:1780:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:1780:

UCUCUUUCAU UCCCG                                                      15

(2) INFORMATION FOR SEQ ID NO:1781:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1781:

CUUUCAUUCC CGGAU                                                 15

(2) INFORMATION FOR SEQ ID NO:1782:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1782:

CUUUCAUUCC CGGAU                                                 15

(2) INFORMATION FOR SEQ ID NO:1783:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1783:

CUUUCAUUCC CGGAU                                                 15

(2) INFORMATION FOR SEQ ID NO:1784:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1784:

CUUUCAUUCC CGGAU                                                 15

(2) INFORMATION FOR SEQ ID NO:1785:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1785:

CUUUCAUUCC CGGAU                                                 15

(2) INFORMATION FOR SEQ ID NO:1786:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:1786:

UUUCAUUCCC GGAUG                                                 15

(2) INFORMATION FOR SEQ ID NO:1787:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1787:

UUUCAUUCCC GGAUG                                                          15

(2) INFORMATION FOR SEQ ID NO:1788:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1788:

GUGGCAUAUG ACCGU                                                          15

(2) INFORMATION FOR SEQ ID NO:1789:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1789:

GUGGCAUAUG ACCGU                                                          15

(2) INFORMATION FOR SEQ ID NO:1790:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1790:

UGACCGUUGU GUGUG                                                          15

(2) INFORMATION FOR SEQ ID NO:1791:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1791:

UGUGUGUUCU GGAAA                                                          15

(2) INFORMATION FOR SEQ ID NO:1792:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1792:

UGUGUGUUCU GGAAA                                                          15

(2) INFORMATION FOR SEQ ID NO:1793:

```
    (i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1793:

GUGUGUUCUG GAAAC                                                          15

(2) INFORMATION FOR SEQ ID NO:1794:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1794:

GUGUGUUCUG GAAAC                                                          15

(2) INFORMATION FOR SEQ ID NO:1795:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1795:

UGAAGAUUUC CUCCA                                                          15

(2) INFORMATION FOR SEQ ID NO:1796:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1796:

AUUUCCUCCA AACCU                                                          15

(2) INFORMATION FOR SEQ ID NO:1797:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1797:

AACCUCUCAA UUUCA                                                          15

(2) INFORMATION FOR SEQ ID NO:1798:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1798:

UUUCACUCAA GAGUU                                                          15

(2) INFORMATION FOR SEQ ID NO:1799:
```

(i) SEQUENCE CHARACTERISTICS:
           (A) LENGTH:        15 base pairs
           (B) TYPE:          nucleic acid
           (C) STRANDEDNESS:  single
           (D) TOPOLOGY:      linear (xi) SEQUENCE DESCRIPTION: SEQ ID NO:1799:

CAAGAGUUUC CAUCU                                                    15

(2) INFORMATION FOR SEQ ID NO:1800:

(i) SEQUENCE CHARACTERISTICS:
           (A) LENGTH:        15 base pairs
           (B) TYPE:          nucleic acid
           (C) STRANDEDNESS:  single
           (D) TOPOLOGY:      linear (xi) SEQUENCE DESCRIPTION: SEQ ID NO:1800:

CAAGAGUUUC CAUCU                                                    15

(2) INFORMATION FOR SEQ ID NO:1801:

(i) SEQUENCE CHARACTERISTICS:
           (A) LENGTH:        15 base pairs
           (B) TYPE:          nucleic acid
           (C) STRANDEDNESS:  single
           (D) TOPOLOGY:      linear (xi) SEQUENCE DESCRIPTION: SEQ ID NO:1801:

AAGAGUUUCC AUCUC                                                    15

(2) INFORMATION FOR SEQ ID NO:1802:

(i) SEQUENCE CHARACTERISTICS:
           (A) LENGTH:        15 base pairs
           (B) TYPE:          nucleic acid
           (C) STRANDEDNESS:  single
           (D) TOPOLOGY:      linear (xi) SEQUENCE DESCRIPTION: SEQ ID NO:1802:

UUUCCAUCUC CUCAA                                                    15

(2) INFORMATION FOR SEQ ID NO:1803:

(i) SEQUENCE CHARACTERISTICS:
           (A) LENGTH:        15 base pairs
           (B) TYPE:          nucleic acid
           (C) STRANDEDNESS:  single
           (D) TOPOLOGY:      linear (xi) SEQUENCE DESCRIPTION: SEQ ID NO:1803:

UUUCCAUCUC CUCAA                                                    15

(2) INFORMATION FOR SEQ ID NO:1804:

(i) SEQUENCE CHARACTERISTICS:
           (A) LENGTH:        15 base pairs
           (B) TYPE:          nucleic acid
           (C) STRANDEDNESS:  single
           (D) TOPOLOGY:      linear (xi) SEQUENCE DESCRIPTION: SEQ ID NO:1804:

UCCAUCUCCU CAAAC                                                    15

(2) INFORMATION FOR SEQ ID NO:1805:

(i) SEQUENCE CHARACTERISTICS:

(A) LENGTH:          15 base pairs
           (B) TYPE:            nucleic acid
           (C) STRANDEDNESS:    single
           (D) TOPOLOGY:        linear (xi) SEQUENCE DESCRIPTION: SEQ ID NO:1805:

AGGAGAUUAC AGCUU                                                            15

(2) INFORMATION FOR SEQ ID NO:1806:

(i) SEQUENCE CHARACTERISTICS:
           (A) LENGTH:          15 base pairs
           (B) TYPE:            nucleic acid
           (C) STRANDEDNESS:    single
           (D) TOPOLOGY:        linear (xi) SEQUENCE DESCRIPTION: SEQ ID NO:1806:

AGGAGAUUAC AGCUU                                                            15

(2) INFORMATION FOR SEQ ID NO:1807:

(i) SEQUENCE CHARACTERISTICS:
           (A) LENGTH:          15 base pairs
           (B) TYPE:            nucleic acid
           (C) STRANDEDNESS:    single
           (D) TOPOLOGY:        linear (xi) SEQUENCE DESCRIPTION: SEQ ID NO:1807:

GGAGAUUACA GCUUC                                                            15

(2) INFORMATION FOR SEQ ID NO:1808:

(i) SEQUENCE CHARACTERISTICS:
           (A) LENGTH:          15 base pairs
           (B) TYPE:            nucleic acid
           (C) STRANDEDNESS:    single
           (D) TOPOLOGY:        linear (xi) SEQUENCE DESCRIPTION: SEQ ID NO:1808:

CUUCAGUUAC UGUGG                                                            15

(2) INFORMATION FOR SEQ ID NO:1809:

(i) SEQUENCE CHARACTERISTICS:
           (A) LENGTH:          15 base pairs
           (B) TYPE:            nucleic acid
           (C) STRANDEDNESS:    single
           (D) TOPOLOGY:        linear (xi) SEQUENCE DESCRIPTION: SEQ ID NO:1809:

UGGCCCUCCU CCUUG                                                            15

(2) INFORMATION FOR SEQ ID NO:1810:

(i) SEQUENCE CHARACTERISTICS:
           (A) LENGTH:          15 base pairs
           (B) TYPE:            nucleic acid
           (C) STRANDEDNESS:    single
           (D) TOPOLOGY:        linear (xi) SEQUENCE DESCRIPTION: SEQ ID NO:1810:

UGGCCCUCCU CCUUG                                                            15

(2) INFORMATION FOR SEQ ID NO:1811:

(i) SEQUENCE CHARACTERISTICS:
           (A) LENGTH:          15 base pairs

```
          (B) TYPE:           nucleic acid
          (C) STRANDEDNESS:   single
          (D) TOPOLOGY:       linear (xi) SEQUENCE DESCRIPTION: SEQ ID NO:1811:

UGCUGCUCAU CAUUG                                                15

(2) INFORMATION FOR SEQ ID NO:1812:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1812:

GCGGGAUAGU AACGC                                                15

(2) INFORMATION FOR SEQ ID NO:1813:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1813:

AGACUAUCAA CCUGA                                                15

(2) INFORMATION FOR SEQ ID NO:1814:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1814:

AGGAACUUGA ACCCC                                                15

(2) INFORMATION FOR SEQ ID NO:1815:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1815:

AUUGCUUCAG CAAAA                                                15

(2) INFORMATION FOR SEQ ID NO:1816:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:1816:

AAAGAGUUAA AAAUU                                                15

(2) INFORMATION FOR SEQ ID NO:1817:

(i) SEQUENCE CHARACTERISTICS:
          (A) LENGTH:         15 base pairs
          (B) TYPE:           nucleic acid
```

```
            (C) STRANDEDNESS:    single
            (D) TOPOLOGY:        linear (xi) SEQUENCE DESCRIPTION: SEQ ID NO:1817:

AAGAGUUAAA AAUUG                                                      15

(2) INFORMATION FOR SEQ ID NO:1818:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1818:

UAAAAAUUGC UUUGC                                                      15

(2) INFORMATION FOR SEQ ID NO:1819:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1819:

CAGAGUUUCU CAGAA                                                      15

(2) INFORMATION FOR SEQ ID NO:1820:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1820:

AGUUUCUCAG AAUUC                                                      15

(2) INFORMATION FOR SEQ ID NO:1821:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1821:

UCAGAAUUCA AAAAU                                                      15

(2) INFORMATION FOR SEQ ID NO:1822:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:1822:

UCAGAAUUCA AAAAU                                                      15

(2) INFORMATION FOR SEQ ID NO:1823:

(i) SEQUENCE CHARACTERISTICS:
            (A) LENGTH:          15 base pairs
            (B) TYPE:            nucleic acid
            (C) STRANDEDNESS:    single
```

(D) TOPOLOGY:      linear (xi) SEQUENCE DESCRIPTION: SEQ ID NO:1823:

UCAGAAUUCA AAAAU                                                          15

(2) INFORMATION FOR SEQ ID NO:1824:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1824:

AAAAUGUUCU CAGCU                                                          15

(2) INFORMATION FOR SEQ ID NO:1825:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1825:

AAAUGUUCUC AGCUG                                                          15

(2) INFORMATION FOR SEQ ID NO:1826:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1826:

UUGGAAUUCU ACAGU                                                          15

(2) INFORMATION FOR SEQ ID NO:1827:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1827:

UUGGAAUUCU ACAGU                                                          15

(2) INFORMATION FOR SEQ ID NO:1828:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1828:

GAAUCUACA GUUGA                                                           15

(2) INFORMATION FOR SEQ ID NO:1829:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:1829:

GAAUUCUACA GUUGA                                                15

(2) INFORMATION FOR SEQ ID NO:1830:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1830:

GUUGAAUAAU UAAAG                                                15

(2) INFORMATION FOR SEQ ID NO:1831:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1831:

GAAUAAUUAA AGAAC                                                15

(2) INFORMATION FOR SEQ ID NO:1832:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:1832:

AAUAAUUAAA GAACA                                                15

(2) INFORMATION FOR SEQ ID NO:1833:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1833:

GUUGUUCCUG AUGAGGCCGA AAGGCCGAAA GUCCGU                          36

(2) INFORMATION FOR SEQ ID NO:1834:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1834:

GUUGUUCCUG AUGAGGCCGA AAGGCCGAAA GUCCGU                          36

(2) INFORMATION FOR SEQ ID NO:1835:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1835:

ACACGUCCUG AUGAGGCCGA AAGGCCGAAA CAGGAG      36

(2) INFORMATION FOR SEQ ID NO:1836:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1836:

ACACGUCCUG AUGAGGCCGA AAGGCCGAAA CAGGAG      36

(2) INFORMATION FOR SEQ ID NO:1837:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1837:

GUUCUGGCUG AUGAGGCCGA AAGGCCGAAA CACGUC      36

(2) INFORMATION FOR SEQ ID NO:1838:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1838:

CUUCCGUCUG AUGAGGCCGA AAGGCCGAAA GUUCUG      36

(2) INFORMATION FOR SEQ ID NO:1839:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1839:

CAAAGAUCUG AUGAGGCCGA AAGGCCGAAA GGAUUG      36

(2) INFORMATION FOR SEQ ID NO:1840:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1840:

CAAAGAUCUG AUGAGGCCGA AAGGCCGAAA GGAUUG      36

(2) INFORMATION FOR SEQ ID NO:1841:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1841:

CAAAGAUCUG AUGAGGCCGA AAGGCCGAAA GGAUUG                                    36

(2) INFORMATION FOR SEQ ID NO:1842:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1842:

CAAAGAUCUG AUGAGGCCGA AAGGCCGAAA GGAUUG                                    36

(2) INFORMATION FOR SEQ ID NO:1843:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1843:

CAAAGAUCUG AUGAGGCCGA AAGGCCGAAA GGAUUG                                    36

(2) INFORMATION FOR SEQ ID NO:1844:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1844:

ACAAAGACUG AUGAGGCCGA AAGGCCGAAA AGGAUU                                    36

(2) INFORMATION FOR SEQ ID NO:1845:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1845:

ACAAAGACUG AUGAGGCCGA AAGGCCGAAA AGGAUU                                    36

(2) INFORMATION FOR SEQ ID NO:1846:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1846:

ACAAAGACUG AUGAGGCCGA AAGGCCGAAA AGGAUU                                    36

(2) INFORMATION FOR SEQ ID NO:1847:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:1847:

ACAAAGACUG AUGAGGCCGA AAGGCCGAAA AGGAUU    36

(2) INFORMATION FOR SEQ ID NO:1848:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1848:

UCACAAACUG AUGAGGCCGA AAGGCCGAAA UAAGGA    36

(2) INFORMATION FOR SEQ ID NO:1849:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1849:

UCACAAACUG AUGAGGCCGA AAGGCCGAAA UAAGGA    36

(2) INFORMATION FOR SEQ ID NO:1850:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1850:

UCACAAACUG AUGAGGCCGA AAGGCCGAAA UAAGGA    36

(2) INFORMATION FOR SEQ ID NO:1851:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1851:

UGUCACACUG AUGAGGCCGA AAGGCCGAAA GAUAAG    36

(2) INFORMATION FOR SEQ ID NO:1852:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1852:

CUGUCACCUG AUGAGGCCGA AAGGCCGAAA AGAUAA    36

(2) INFORMATION FOR SEQ ID NO:1853:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1853:

CUGUCACCUG AUGAGGCCGA AAGGCCGAAA AGAUAA    36

(2) INFORMATION FOR SEQ ID NO:1854:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1854:

UCAGCAACUG AUGAGGCCGA AAGGCCGAAA CUGUCA                            36

(2) INFORMATION FOR SEQ ID NO:1855:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1855:

GAUCAGCCUG AUGAGGCCGA AAGGCCGAAA GACUGU                            36

(2) INFORMATION FOR SEQ ID NO:1856:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1856:

GAUCAGCCUG AUGAGGCCGA AAGGCCGAAA GACUGU                            36

(2) INFORMATION FOR SEQ ID NO:1857:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1857:

CAUCUGACUG AUGAGGCCGA AAGGCCGAAA UCAGCA                            36

(2) INFORMATION FOR SEQ ID NO:1858:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1858:

CAUCUGACUG AUGAGGCCGA AAGGCCGAAA UCAGCA                            36

(2) INFORMATION FOR SEQ ID NO:1859:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1859:

CAUCUGACUG AUGAGGCCGA AAGGCCGAAA UCAGCA                            36

(2) INFORMATION FOR SEQ ID NO:1860:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1860:

CAUCUGACUG AUGAGGCCGA AAGGCCGAAA UCAGCA                          36

(2) INFORMATION FOR SEQ ID NO:1861:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1861:

AGCAUCUCUG AUGAGGCCGA AAGGCCGAAA GAUCAG                          36

(2) INFORMATION FOR SEQ ID NO:1862:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1862:

AGCAUCUCUG AUGAGGCCGA AAGGCCGAAA GAUCAG                          36

(2) INFORMATION FOR SEQ ID NO:1863:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1863:

CCACGGACUG AUGAGGCCGA AAGGCCGAAA CAGCAU                          36

(2) INFORMATION FOR SEQ ID NO:1864:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1864:

UCCACGGCUG AUGAGGCCGA AAGGCCGAAA ACAGCA                          36

(2) INFORMATION FOR SEQ ID NO:1865:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1865:

CUCCACGCUG AUGAGGCCGA AAGGCCGAAA AACAGC                          36

(2) INFORMATION FOR SEQ ID NO:1866:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1866:

UUGAAAUCUG AUGAGGCCGA AAGGCCGAAA GCUUGC                              36

(2) INFORMATION FOR SEQ ID NO:1867:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1867:

UUGAAAUCUG AUGAGGCCGA AAGGCCGAAA GCUUGC                              36

(2) INFORMATION FOR SEQ ID NO:1868:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1868:

UUGAAAUCUG AUGAGGCCGA AAGGCCGAAA GCUUGC                              36

(2) INFORMATION FOR SEQ ID NO:1869:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1869:

AUUGAAACUG AUGAGGCCGA AAGGCCGAAA AGCUUG                              36

(2) INFORMATION FOR SEQ ID NO:1870:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1870:

AUUGAAACUG AUGAGGCCGA AAGGCCGAAA AGCUUG                              36

(2) INFORMATION FOR SEQ ID NO:1871:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1871:

CCAUUGACUG AUGAGGCCGA AAGGCCGAAA UAAGCU                              36

(2) INFORMATION FOR SEQ ID NO:1872:

```
       (i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:1872:

CCAUUGACUG AUGAGGCCGA AAGGCCGAAA UAAGCU                         36

(2) INFORMATION FOR SEQ ID NO:1873:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:1873:

CCCAUUGCUG AUGAGGCCGA AAGGCCGAAA AUAAGC                         36

(2) INFORMATION FOR SEQ ID NO:1874:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:1874:

CCCAUUGCUG AUGAGGCCGA AAGGCCGAAA AUAAGC                         36

(2) INFORMATION FOR SEQ ID NO:1875:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:1875:

UCCCAUUCUG AUGAGGCCGA AAGGCCGAAA AAUAAG                         36

(2) INFORMATION FOR SEQ ID NO:1876:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:1876:

UCCCAUUCUG AUGAGGCCGA AAGGCCGAAA AAUAAG                         36

(2) INFORMATION FOR SEQ ID NO:1877:

(i) SEQUENCE CHARACTERISTICS:
             (A) LENGTH:        36 base pairs
             (B) TYPE:          nucleic acid
             (C) STRANDEDNESS:  single
             (D) TOPOLOGY:      linear (xi) SEQUENCE DESCRIPTION: SEQ ID NO:1877:

CGGCAGACUG AUGAGGCCGA AAGGCCGAAA UGCAGU                         36

(2) INFORMATION FOR SEQ ID NO:1878:
```

```
    (i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1878:

CACGGCACUG AUGAGGCCGA AAGGCCGAAA UAUGCA                              36

(2) INFORMATION FOR SEQ ID NO:1879:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1879:

CUUUGUACUG AUGAGGCCGA AAGGCCGAAA UGGGCA                              36

(2) INFORMATION FOR SEQ ID NO:1880:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1880:

CUUUGUACUG AUGAGGCCGA AAGGCCGAAA UGGGCA                              36

(2) INFORMATION FOR SEQ ID NO:1881:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1881:

CCUUUGUCUG AUGAGGCCGA AAGGCCGAAA AUGGGC                              36

(2) INFORMATION FOR SEQ ID NO:1882:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1882:

GCCUUUGCUG AUGAGGCCGA AAGGCCGAAA AAUGGG                              36

(2) INFORMATION FOR SEQ ID NO:1883:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1883:

GCCUUUGCUG AUGAGGCCGA AAGGCCGAAA AAUGGG                              36

(2) INFORMATION FOR SEQ ID NO:1884:

(i) SEQUENCE CHARACTERISTICS:
```

```
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1884:

UCAGGCUCUG AUGAGGCCGA AAGGCCGAAA UGUUUU                                   36

(2) INFORMATION FOR SEQ ID NO:1885:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1885:

AAAAUACCUG AUGAGGCCGA AAGGCCGAAA CCAGCU                                   36

(2) INFORMATION FOR SEQ ID NO:1886:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1886:

AAAAUACCUG AUGAGGCCGA AAGGCCGAAA CCAGCU                                   36

(2) INFORMATION FOR SEQ ID NO:1887:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1887:

GCCAAAACUG AUGAGGCCGA AAGGCCGAAA CUACCA                                   36

(2) INFORMATION FOR SEQ ID NO:1888:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1888:

GCCAAAACUG AUGAGGCCGA AAGGCCGAAA CUACCA                                   36

(2) INFORMATION FOR SEQ ID NO:1889:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:1889:

CUGCCAACUG AUGAGGCCGA AAGGCCGAAA UACUAC                                   36

(2) INFORMATION FOR SEQ ID NO:1890:

(i) SEQUENCE CHARACTERISTICS:
          (A) LENGTH:          36 base pairs
```

```
        (B) TYPE:            nucleic acid
        (C) STRANDEDNESS:    single
        (D) TOPOLOGY:        linear (xi) SEQUENCE DESCRIPTION: SEQ ID NO:1890:

CUGCCAACUG AUGAGGCCGA AAGGCCGAAA UACUAC                              36

(2) INFORMATION FOR SEQ ID NO:1891:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:1891:

CCUGCCACUG AUGAGGCCGA AAGGCCGAAA AUACUA                              36

(2) INFORMATION FOR SEQ ID NO:1892:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:1892:

CCUGCCACUG AUGAGGCCGA AAGGCCGAAA AUACUA                              36

(2) INFORMATION FOR SEQ ID NO:1893:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:1893:

CCUGCCACUG AUGAGGCCGA AAGGCCGAAA AUACUA                              36

(2) INFORMATION FOR SEQ ID NO:1894:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:1894:

UCCUGCCCUG AUGAGGCCGA AAGGCCGAAA AAUACU                              36

(2) INFORMATION FOR SEQ ID NO:1895:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:1895:

UCCUGCCCUG AUGAGGCCGA AAGGCCGAAA AAUACU                              36

(2) INFORMATION FOR SEQ ID NO:1896:

(i) SEQUENCE CHARACTERISTICS:
        (A) LENGTH:          36 base pairs
        (B) TYPE:            nucleic acid
```

```
        (C) STRANDEDNESS:   single
        (D) TOPOLOGY:       linear (xi) SEQUENCE DESCRIPTION: SEQ ID NO:1896:

CAGAACCCUG AUGAGGCCGA AAGGCCGAAA CUUUUG                              36

(2) INFORMATION FOR SEQ ID NO:1897:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1897:

CAGAACCCUG AUGAGGCCGA AAGGCCGAAA CUUUUG                              36

(2) INFORMATION FOR SEQ ID NO:1898:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1898:

CGUACAGCUG AUGAGGCCGA AAGGCCGAAA CCAACU                              36

(2) INFORMATION FOR SEQ ID NO:1899:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1899:

UCGUACACUG AUGAGGCCGA AAGGCCGAAA ACCAAC                              36

(2) INFORMATION FOR SEQ ID NO:1900:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1900:

GUGCUCGCUG AUGAGGCCGA AAGGCCGAAA CAGAAC                              36

(2) INFORMATION FOR SEQ ID NO:1901:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1901:

GCCCAAACUG AUGAGGCCGA AAGGCCGAAA GUGCUC                              36

(2) INFORMATION FOR SEQ ID NO:1902:

(i) SEQUENCE CHARACTERISTICS:
        (A) LENGTH:         36 base pairs
        (B) TYPE:           nucleic acid
        (C) STRANDEDNESS:   single
```

```
          (D) TOPOLOGY:       linear (xi) SEQUENCE DESCRIPTION: SEQ ID NO:1902:

UGUGCCCCUG AUGAGGCCGA AAGGCCGAAA AUAGUG                              36

(2) INFORMATION FOR SEQ ID NO:1903:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:1903:

CACUAUCCUG AUGAGGCCGA AAGGCCGAAA GUUUCU                              36

(2) INFORMATION FOR SEQ ID NO:1904:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:1904:

GCCCAGGCUG AUGAGGCCGA AAGGCCGAAA CUUGGC                              36

(2) INFORMATION FOR SEQ ID NO:1905:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:1905:

GCCCAGGCUG AUGAGGCCGA AAGGCCGAAA CUUGGC                              36

(2) INFORMATION FOR SEQ ID NO:1906:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:1906:

CCUGUCACUG AUGAGGCCGA AAGGCCGAAA GCUCGU                              36

(2) INFORMATION FOR SEQ ID NO:1907:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear (xi) SEQUENCE DESCRIPTION: SEQ ID NO:1907:

AGUCGUACUG AUGAGGCCGA AAGGCCGAAA GUCCAG                              36

(2) INFORMATION FOR SEQ ID NO:1908:

(i) SEQUENCE CHARACTERISTICS:
          (A) LENGTH:         36 base pairs
          (B) TYPE:           nucleic acid
          (C) STRANDEDNESS:   single
          (D) TOPOLOGY:       linear
```

(xi) SEQUENCE DESCRIPTION: SEQ ID NO:1908:

GAAGUCGCUG AUGAGGCCGA AAGGCCGAAA GAGUCC                          36

(2) INFORMATION FOR SEQ ID NO:1909:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1909:

GAAGUCGCUG AUGAGGCCGA AAGGCCGAAA GAGUCC                          36

(2) INFORMATION FOR SEQ ID NO:1910:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1910:

CAUUGUGCUG AUGAGGCCGA AAGGCCGAAA GUCGUA                          36

(2) INFORMATION FOR SEQ ID NO:1911:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1911:

CAUUGUGCUG AUGAGGCCGA AAGGCCGAAA GUCGUA                          36

(2) INFORMATION FOR SEQ ID NO:1912:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1912:

ACAUUGUCUG AUGAGGCCGA AAGGCCGAAA AGUCGU                          36

(2) INFORMATION FOR SEQ ID NO:1913:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1913:

ACAUUGUCUG AUGAGGCCGA AAGGCCGAAA AGUCGU                          36

(2) INFORMATION FOR SEQ ID NO:1914:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1914:

UGAUCUGCUG AUGAGGCCGA AAGGCCGAAA CAUUGU          36

(2) INFORMATION FOR SEQ ID NO:1915:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1915:

UGAUCUGCUG AUGAGGCCGA AAGGCCGAAA CAUUGU          36

(2) INFORMATION FOR SEQ ID NO:1916:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1916:

UGAUCUGCUG AUGAGGCCGA AAGGCCGAAA CAUUGU          36

(2) INFORMATION FOR SEQ ID NO:1917:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1917:

UUGAUCUCUG AUGAGGCCGA AAGGCCGAAA ACAUUG          36

(2) INFORMATION FOR SEQ ID NO:1918:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1918:

UUGAUCUCUG AUGAGGCCGA AAGGCCGAAA ACAUUG          36

(2) INFORMATION FOR SEQ ID NO:1919:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1919:

UUGAUCUCUG AUGAGGCCGA AAGGCCGAAA ACAUUG          36

(2) INFORMATION FOR SEQ ID NO:1920:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1920:

UUGAUCUCUG AUGAGGCCGA AAGGCCGAAA ACAUUG                36

(2) INFORMATION FOR SEQ ID NO:1921:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1921:

UUGAUCUCUG AUGAGGCCGA AAGGCCGAAA ACAUUG                36

(2) INFORMATION FOR SEQ ID NO:1922:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1922:

UUGAUCUCUG AUGAGGCCGA AAGGCCGAAA ACAUUG                36

(2) INFORMATION FOR SEQ ID NO:1923:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1923:

UUGAUCUCUG AUGAGGCCGA AAGGCCGAAA ACAUUG                36

(2) INFORMATION FOR SEQ ID NO:1924:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1924:

UGUCCUUCUG AUGAGGCCGA AAGGCCGAAA UCUGAA                36

(2) INFORMATION FOR SEQ ID NO:1925:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1925:

UGUCCUUCUG AUGAGGCCGA AAGGCCGAAA UCUGAA                36

(2) INFORMATION FOR SEQ ID NO:1926:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1926:

AUCAUACCUG AUGAGGCCGA AAGGCCGAAA GCCCAU                                    36

(2) INFORMATION FOR SEQ ID NO:1927:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1927:

AUCAUACCUG AUGAGGCCGA AAGGCCGAAA GCCCAU                                    36

(2) INFORMATION FOR SEQ ID NO:1928:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1928:

AUCAUACCUG AUGAGGCCGA AAGGCCGAAA GCCCAU                                    36

(2) INFORMATION FOR SEQ ID NO:1929:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1929:

ACAAUCACUG AUGAGGCCGA AAGGCCGAAA CGAGCC                                    36

(2) INFORMATION FOR SEQ ID NO:1930:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1930:

ACAAUCACUG AUGAGGCCGA AAGGCCGAAA CGAGCC                                    36

(2) INFORMATION FOR SEQ ID NO:1931:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1931:

UGUAUAACUG AUGAGGCCGA AAGGCCGAAA CAAUCA                                    36

(2) INFORMATION FOR SEQ ID NO:1932:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1932:

UGUAUAACUG AUGAGGCCGA AAGGCCGAAA CAAUCA                                    36

(2) INFORMATION FOR SEQ ID NO:1933:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1933:

UUUGUAUCUG AUGAGGCCGA AAGGCCGAAA AACAAU                                        36

(2) INFORMATION FOR SEQ ID NO:1934:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1934:

UUUGUAUCUG AUGAGGCCGA AAGGCCGAAA AACAAU                                        36

(2) INFORMATION FOR SEQ ID NO:1935:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1935:

UUUUGUACUG AUGAGGCCGA AAGGCCGAAA AAACAA                                      36

(2) INFORMATION FOR SEQ ID NO:1936:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1936:

UUUUGUACUG AUGAGGCCGA AAGGCCGAAA AAACAA                                      36

(2) INFORMATION FOR SEQ ID NO:1937:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1937:

UUUUGUACUG AUGAGGCCGA AAGGCCGAAA AAACAA                                      36

(2) INFORMATION FOR SEQ ID NO:1938:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1938:

GGAGGAUCUG AUGAGGCCGA AAGGCCGAAA UUGAUC                                        36

(2) INFORMATION FOR SEQ ID NO:1939:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1939:

UGGAGGACUG AUGAGGCCGA AAGGCCGAAA AUUGAU          36

(2) INFORMATION FOR SEQ ID NO:1940:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1940:

GUUGGAGCUG AUGAGGCCGA AAGGCCGAAA UAAUUG          36

(2) INFORMATION FOR SEQ ID NO:1941:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1941:

UCUGUUGCUG AUGAGGCCGA AAGGCCGAAA GGAUAA          36

(2) INFORMATION FOR SEQ ID NO:1942:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1942:

UCUGUUGCUG AUGAGGCCGA AAGGCCGAAA GGAUAA          36

(2) INFORMATION FOR SEQ ID NO:1943:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1943:

UCUGUUGCUG AUGAGGCCGA AAGGCCGAAA GGAUAA          36

(2) INFORMATION FOR SEQ ID NO:1944:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1944:

UCUGUUGCUG AUGAGGCCGA AAGGCCGAAA GGAUAA          36

```
(2) INFORMATION FOR SEQ ID NO:1945:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1945:

GAUCACUCUG AUGAGGCCGA AAGGCCGAAA CAGUUC                              36

(2) INFORMATION FOR SEQ ID NO:1946:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1946:

AGUUGGCCUG AUGAGGCCGA AAGGCCGAAA UCACUG                              36

(2) INFORMATION FOR SEQ ID NO:1947:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1947:

UUCACUGCUG AUGAGGCCGA AAGGCCGAAA GUUGGC                              36

(2) INFORMATION FOR SEQ ID NO:1948:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1948:

GUUCACUCUG AUGAGGCCGA AAGGCCGAAA AGUUGG                              36

(2) INFORMATION FOR SEQ ID NO:1949:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1949:

GUUCACUCUG AUGAGGCCGA AAGGCCGAAA AGUUGG                              36

(2) INFORMATION FOR SEQ ID NO:1950:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1950:

CCAGUUUCUG AUGAGGCCGA AAGGCCGAAA UUUCAG                              36

(2) INFORMATION FOR SEQ ID NO:1951:
```

```
    (i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1951:

ACAUUCUCUG AUGAGGCCGA AAGGCCGAAA GCCAGU                              36

(2) INFORMATION FOR SEQ ID NO:1952:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1952:

UUCCUGUCUG AUGAGGCCGA AAGGCCGAAA CAUUCU                              36

(2) INFORMATION FOR SEQ ID NO:1953:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1953:

UAUGCCACUG AUGAGGCCGA AAGGCCGAAA AUUUCC                              36

(2) INFORMATION FOR SEQ ID NO:1954:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1954:

UAUGCCACUG AUGAGGCCGA AAGGCCGAAA AUUUCC                              36

(2) INFORMATION FOR SEQ ID NO:1955:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1955:

UCAAAUUCUG AUGAGGCCGA AAGGCCGAAA UGCCAG                              36

(2) INFORMATION FOR SEQ ID NO:1956:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1956:

CAGGUCACUG AUGAGGCCGA AAGGCCGAAA UUUAUG                              36

(2) INFORMATION FOR SEQ ID NO:1957:
```

(i) SEQUENCE CHARACTERISTICS:
           (A) LENGTH:        36 base pairs
           (B) TYPE:          nucleic acid
           (C) STRANDEDNESS:  single
           (D) TOPOLOGY:      linear (xi) SEQUENCE DESCRIPTION: SEQ ID NO:1957:

GCAGGUCCUG AUGAGGCCGA AAGGCCGAAA AUUUAU                          36

(2) INFORMATION FOR SEQ ID NO:1958:

(i) SEQUENCE CHARACTERISTICS:
           (A) LENGTH:        36 base pairs
           (B) TYPE:          nucleic acid
           (C) STRANDEDNESS:  single
           (D) TOPOLOGY:      linear (xi) SEQUENCE DESCRIPTION: SEQ ID NO:1958:

CCUUGCUCUG AUGAGGCCGA AAGGCCGAAA GACGUG                          36

(2) INFORMATION FOR SEQ ID NO:1959:

(i) SEQUENCE CHARACTERISTICS:
           (A) LENGTH:        36 base pairs
           (B) TYPE:          nucleic acid
           (C) STRANDEDNESS:  single
           (D) TOPOLOGY:      linear (xi) SEQUENCE DESCRIPTION: SEQ ID NO:1959:

UUCGGGUCUG AUGAGGCCGA AAGGCCGAAA CCUUGC                          36

(2) INFORMATION FOR SEQ ID NO:1960:

(i) SEQUENCE CHARACTERISTICS:
           (A) LENGTH:        36 base pairs
           (B) TYPE:          nucleic acid
           (C) STRANDEDNESS:  single
           (D) TOPOLOGY:      linear (xi) SEQUENCE DESCRIPTION: SEQ ID NO:1960:

AUCUUCUCUG AUGAGGCCGA AAGGCCGAAA GGUUUC                          36

(2) INFORMATION FOR SEQ ID NO:1961:

(i) SEQUENCE CHARACTERISTICS:
           (A) LENGTH:        36 base pairs
           (B) TYPE:          nucleic acid
           (C) STRANDEDNESS:  single
           (D) TOPOLOGY:      linear (xi) SEQUENCE DESCRIPTION: SEQ ID NO:1961:

CAGAAAACUG AUGAGGCCGA AAGGCCGAAA CAUCUU                          36

(2) INFORMATION FOR SEQ ID NO:1962:

(i) SEQUENCE CHARACTERISTICS:
           (A) LENGTH:        36 base pairs
           (B) TYPE:          nucleic acid
           (C) STRANDEDNESS:  single
           (D) TOPOLOGY:      linear (xi) SEQUENCE DESCRIPTION: SEQ ID NO:1962:

UUAUCAGCUG AUGAGGCCGA AAGGCCGAAA AAUACA                          36

(2) INFORMATION FOR SEQ ID NO:1963:

(i) SEQUENCE CHARACTERISTICS:

```
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1963:

AUUAGUUCUG AUGAGGCCGA AAGGCCGAAA AUUAGU                                  36

(2) INFORMATION FOR SEQ ID NO:1964:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1964:

UACUCAUCUG AUGAGGCCGA AAGGCCGAAA GUUGAA                                  36

(2) INFORMATION FOR SEQ ID NO:1965:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1965:

UACUCAUCUG AUGAGGCCGA AAGGCCGAAA GUUGAA                                  36

(2) INFORMATION FOR SEQ ID NO:1966:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1966:

AUCACCACUG AUGAGGCCGA AAGGCCGAAA CUCAUU                                  36

(2) INFORMATION FOR SEQ ID NO:1967:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1967:

CUUGUGACUG AUGAGGCCGA AAGGCCGAAA UCUGCA                                  36

(2) INFORMATION FOR SEQ ID NO:1968:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1968:

AUCUUGUCUG AUGAGGCCGA AAGGCCGAAA UAUCUG                                  36

(2) INFORMATION FOR SEQ ID NO:1969:

(i) SEQUENCE CHARACTERISTICS:
        (A) LENGTH:        36 base pairs
```

```
        (B) TYPE:           nucleic acid
        (C) STRANDEDNESS:   single
        (D) TOPOLOGY:       linear (xi) SEQUENCE DESCRIPTION: SEQ ID NO:1969:

AUCUUGUCUG AUGAGGCCGA AAGGCCGAAA UAUCUG                              36

(2) INFORMATION FOR SEQ ID NO:1970:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1970:

AUCUUGUCUG AUGAGGCCGA AAGGCCGAAA UAUCUG                              36

(2) INFORMATION FOR SEQ ID NO:1971:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1971:

AUCUUGUCUG AUGAGGCCGA AAGGCCGAAA UAUCUG                              36

(2) INFORMATION FOR SEQ ID NO:1972:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1972:

GUGACAUCUG AUGAGGCCGA AAGGCCGAAA UCUUGU                              36

(2) INFORMATION FOR SEQ ID NO:1973:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1973:

GUGACAUCUG AUGAGGCCGA AAGGCCGAAA UCUUGU                              36

(2) INFORMATION FOR SEQ ID NO:1974:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:1974:

GUUCUGUCUG AUGAGGCCGA AAGGCCGAAA CAUUAU                              36

(2) INFORMATION FOR SEQ ID NO:1975:

(i) SEQUENCE CHARACTERISTICS:
        (A) LENGTH:         36 base pairs
        (B) TYPE:           nucleic acid
```

```
            (C) STRANDEDNESS:    single
            (D) TOPOLOGY:        linear (xi) SEQUENCE DESCRIPTION: SEQ ID NO:1975:

GUUCUGUCUG AUGAGGCCGA AAGGCCGAAA CAUUAU                              36

(2) INFORMATION FOR SEQ ID NO:1976:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1976:

GUUCUGUCUG AUGAGGCCGA AAGGCCGAAA CAUUAU                              36

(2) INFORMATION FOR SEQ ID NO:1977:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1977:

GAUACUGCUG AUGAGGCCGA AAGGCCGAAA CAGUUC                              36

(2) INFORMATION FOR SEQ ID NO:1978:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1978:

AGAUACUCUG AUGAGGCCGA AAGGCCGAAA ACAGUU                              36

(2) INFORMATION FOR SEQ ID NO:1979:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1979:

AGAUACUCUG AUGAGGCCGA AAGGCCGAAA ACAGUU                              36

(2) INFORMATION FOR SEQ ID NO:1980:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:1980:

GCUGUUGCUG AUGAGGCCGA AAGGCCGAAA GAUACU                              36

(2) INFORMATION FOR SEQ ID NO:1981:

(i) SEQUENCE CHARACTERISTICS:
            (A) LENGTH:          36 base pairs
            (B) TYPE:            nucleic acid
            (C) STRANDEDNESS:    single
```

(D) TOPOLOGY:         linear (xi) SEQUENCE DESCRIPTION: SEQ ID NO:1981:

GCUGUUGCUG AUGAGGCCGA AAGGCCGAAA GAUACU                              36

(2) INFORMATION FOR SEQ ID NO:1982:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1982:

GCUGUUGCUG AUGAGGCCGA AAGGCCGAAA GAUACU                              36

(2) INFORMATION FOR SEQ ID NO:1983:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1983:

AAAGAGACUG AUGAGGCCGA AAGGCCGAAA GGCUGU                              36

(2) INFORMATION FOR SEQ ID NO:1984:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1984:

AAAGAGACUG AUGAGGCCGA AAGGCCGAAA GGCUGU                              36

(2) INFORMATION FOR SEQ ID NO:1985:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1985:

UGAAAGACUG AUGAGGCCGA AAGGCCGAAA GAGGCU                              36

(2) INFORMATION FOR SEQ ID NO:1986:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1986:

UGAAAGACUG AUGAGGCCGA AAGGCCGAAA GAGGCU                              36

(2) INFORMATION FOR SEQ ID NO:1987:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:1987:

GGAAUGACUG AUGAGGCCGA AAGGCCGAAA GAGAGA					36

(2) INFORMATION FOR SEQ ID NO:1988:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1988:

GGAAUGACUG AUGAGGCCGA AAGGCCGAAA GAGAGA					36

(2) INFORMATION FOR SEQ ID NO:1989:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1989:

GGGAAUGCUG AUGAGGCCGA AAGGCCGAAA AGAGAG					36

(2) INFORMATION FOR SEQ ID NO:1990:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1990:

CGGGAAUCUG AUGAGGCCGA AAGGCCGAAA AAGAGA					36

(2) INFORMATION FOR SEQ ID NO:1991:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1991:

CGGGAAUCUG AUGAGGCCGA AAGGCCGAAA AAGAGA					36

(2) INFORMATION FOR SEQ ID NO:1992:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1992:

CGGGAAUCUG AUGAGGCCGA AAGGCCGAAA AAGAGA					36

(2) INFORMATION FOR SEQ ID NO:1993:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:1993:

AUCCGGGCUG AUGAGGCCGA AAGGCCGAAA UGAAAG					36

(2) INFORMATION FOR SEQ ID NO:1994:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1994:

AUCCGGGCUG AUGAGGCCGA AAGGCCGAAA UGAAAG					36

(2) INFORMATION FOR SEQ ID NO:1995:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1995:

AUCCGGGCUG AUGAGGCCGA AAGGCCGAAA UGAAAG					36

(2) INFORMATION FOR SEQ ID NO:1996:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1996:

AUCCGGGCUG AUGAGGCCGA AAGGCCGAAA UGAAAG					36

(2) INFORMATION FOR SEQ ID NO:1997:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1997:

AUCCGGGCUG AUGAGGCCGA AAGGCCGAAA UGAAAG					36

(2) INFORMATION FOR SEQ ID NO:1998:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1998:

CAUCCGGCUG AUGAGGCCGA AAGGCCGAAA AUGAAA					36

(2) INFORMATION FOR SEQ ID NO:1999:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:1999:

```
CAUCCGGCUG AUGAGGCCGA AAGGCCGAAA AUGAAA                                  36
```

(2) INFORMATION FOR SEQ ID NO:2000:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2000:

```
ACGGUCACUG AUGAGGCCGA AAGGCCGAAA UGCCAC                                  36
```

(2) INFORMATION FOR SEQ ID NO:2001:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2001:

```
ACGGUCACUG AUGAGGCCGA AAGGCCGAAA UGCCAC                                  36
```

(2) INFORMATION FOR SEQ ID NO:2002:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2002:

```
CACACACCUG AUGAGGCCGA AAGGCCGAAA CGGUCA                                  36
```

(2) INFORMATION FOR SEQ ID NO:2003:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2003:

```
UUUCCAGCUG AUGAGGCCGA AAGGCCGAAA CACACA                                  36
```

(2) INFORMATION FOR SEQ ID NO:2004:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2004:

```
UUUCCAGCUG AUGAGGCCGA AAGGCCGAAA CACACA                                  36
```

(2) INFORMATION FOR SEQ ID NO:2005:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2005:

```
GUUUCCACUG AUGAGGCCGA AAGGCCGAAA ACACAC                                        36

(2) INFORMATION FOR SEQ ID NO:2006:

(i) SEQUENCE CHARACTERISTICS:
         (A) LENGTH:       36 base pairs
         (B) TYPE:         nucleic acid
         (C) STRANDEDNESS: single
         (D) TOPOLOGY:     linear (xi) SEQUENCE DESCRIPTION: SEQ ID NO:2006:

GUUUCCACUG AUGAGGCCGA AAGGCCGAAA ACACAC                                        36

(2) INFORMATION FOR SEQ ID NO:2007:

(i) SEQUENCE CHARACTERISTICS:
         (A) LENGTH:       36 base pairs
         (B) TYPE:         nucleic acid
         (C) STRANDEDNESS: single
         (D) TOPOLOGY:     linear (xi) SEQUENCE DESCRIPTION: SEQ ID NO:2007:

UGGAGGACUG AUGAGGCCGA AAGGCCGAAA UCUUCA                                        36

(2) INFORMATION FOR SEQ ID NO:2008:

(i) SEQUENCE CHARACTERISTICS:
         (A) LENGTH:       36 base pairs
         (B) TYPE:         nucleic acid
         (C) STRANDEDNESS: single
         (D) TOPOLOGY:     linear (xi) SEQUENCE DESCRIPTION: SEQ ID NO:2008:

AGGUUUGCUG AUGAGGCCGA AAGGCCGAAA GGAAAU                                        36

(2) INFORMATION FOR SEQ ID NO:2009:

(i) SEQUENCE CHARACTERISTICS:
         (A) LENGTH:       36 base pairs
         (B) TYPE:         nucleic acid
         (C) STRANDEDNESS: single
         (D) TOPOLOGY:     linear (xi) SEQUENCE DESCRIPTION: SEQ ID NO:2009:

UGAAAUUCUG AUGAGGCCGA AAGGCCGAAA GAGGUU                                        36

(2) INFORMATION FOR SEQ ID NO:2010:

(i) SEQUENCE CHARACTERISTICS:
         (A) LENGTH:       36 base pairs
         (B) TYPE:         nucleic acid
         (C) STRANDEDNESS: single
         (D) TOPOLOGY:     linear (xi) SEQUENCE DESCRIPTION: SEQ ID NO:2010:

AACUCUUCUG AUGAGGCCGA AAGGCCGAAA GUGAAA                                        36

(2) INFORMATION FOR SEQ ID NO:2011:

(i) SEQUENCE CHARACTERISTICS:
         (A) LENGTH:       36 base pairs
         (B) TYPE:         nucleic acid
         (C) STRANDEDNESS: single
         (D) TOPOLOGY:     linear (xi) SEQUENCE DESCRIPTION: SEQ ID NO:2011:

AGAUGGACUG AUGAGGCCGA AAGGCCGAAA CUCUUG                                        36
```

-continued (2) INFORMATION FOR SEQ ID NO:2012:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2012:

AGAUGGACUG AUGAGGCCGA AAGGCCGAAA CUCUUG                              36

(2) INFORMATION FOR SEQ ID NO:2013:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2013:

GAGAUGGCUG AUGAGGCCGA AAGGCCGAAA ACUCUU                              36

(2) INFORMATION FOR SEQ ID NO:2014:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2014:

UUGAGGACUG AUGAGGCCGA AAGGCCGAAA UGGAAA                              36

(2) INFORMATION FOR SEQ ID NO:2015:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2015:

UUGAGGACUG AUGAGGCCGA AAGGCCGAAA UGGAAA                              36

(2) INFORMATION FOR SEQ ID NO:2016:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2016:

GUUUGAGCUG AUGAGGCCGA AAGGCCGAAA GAUGGA                              36

(2) INFORMATION FOR SEQ ID NO:2017:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2017:

AAGCUGUCUG AUGAGGCCGA AAGGCCGAAA UCUCCU                              36

(2) INFORMATION FOR SEQ ID NO:2018:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2018:

AAGCUGUCUG AUGAGGCCGA AAGGCCGAAA UCUCCU                        36

(2) INFORMATION FOR SEQ ID NO:2019:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2019:

GAAGCUGCUG AUGAGGCCGA AAGGCCGAAA AUCUCC                        36

(2) INFORMATION FOR SEQ ID NO:2020:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2020:

CCACAGUCUG AUGAGGCCGA AAGGCCGAAA CUGAAG                        36

(2) INFORMATION FOR SEQ ID NO:2021:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2021:

CAAGGAGCUG AUGAGGCCGA AAGGCCGAAA GGGCCA                        36

(2) INFORMATION FOR SEQ ID NO:2022:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2022:

CAAGGAGCUG AUGAGGCCGA AAGGCCGAAA GGGCCA                        36

(2) INFORMATION FOR SEQ ID NO:2023:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2023:

CAAUGAUCUG AUGAGGCCGA AAGGCCGAAA GCAGCA                        36

(2) INFORMATION FOR SEQ ID NO:2024:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2024:

GCGUUACCUG AUGAGGCCGA AAGGCCGAAA UCCCGC                                36

(2) INFORMATION FOR SEQ ID NO:2025:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2025:

UCAGGUUCUG AUGAGGCCGA AAGGCCGAAA UAGUCU                                36

(2) INFORMATION FOR SEQ ID NO:2026:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2026:

GGGGUUCCUG AUGAGGCCGA AAGGCCGAAA GUUCCU                                36

(2) INFORMATION FOR SEQ ID NO:2027:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2027:

UUUUGCUCUG AUGAGGCCGA AAGGCCGAAA AGCAAU                                36

(2) INFORMATION FOR SEQ ID NO:2028:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2028:

AAUUUUUCUG AUGAGGCCGA AAGGCCGAAA CUCUUU                                36

(2) INFORMATION FOR SEQ ID NO:2029:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2029:

CAAUUUUCUG AUGAGGCCGA AAGGCCGAAA ACUCUU                                36

(2) INFORMATION FOR SEQ ID NO:2030:

```
    (i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2030:

GCAAAGCCUG AUGAGGCCGA AAGGCCGAAA UUUUUA                               36

(2) INFORMATION FOR SEQ ID NO:2031:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2031:

UUCUGAGCUG AUGAGGCCGA AAGGCCGAAA ACUCUG                               36

(2) INFORMATION FOR SEQ ID NO:2032:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2032:

GAAUUCUCUG AUGAGGCCGA AAGGCCGAAA GAAACU                               36

(2) INFORMATION FOR SEQ ID NO:2033:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2033:

AUUUUUGCUG AUGAGGCCGA AAGGCCGAAA UUCUGA                               36

(2) INFORMATION FOR SEQ ID NO:2034:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2034:

AUUUUUGCUG AUGAGGCCGA AAGGCCGAAA UUCUGA                               36

(2) INFORMATION FOR SEQ ID NO:2035:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2035:

AUUUUUGCUG AUGAGGCCGA AAGGCCGAAA UUCUGA                               36

(2) INFORMATION FOR SEQ ID NO:2036:
```

```
    (i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:2036:

AGCUGAGCUG AUGAGGCCGA AAGGCCGAAA CAUUUU                                36

(2) INFORMATION FOR SEQ ID NO:2037:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:2037:

CAGCUGACUG AUGAGGCCGA AAGGCCGAAA ACAUUU                                36

(2) INFORMATION FOR SEQ ID NO:2038:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:2038:

ACUGUAGCUG AUGAGGCCGA AAGGCCGAAA UUCCAA                                36

(2) INFORMATION FOR SEQ ID NO:2039:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:2039:

ACUGUAGCUG AUGAGGCCGA AAGGCCGAAA UUCCAA                                36

(2) INFORMATION FOR SEQ ID NO:2040:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:2040:

UCAACUGCUG AUGAGGCCGA AAGGCCGAAA GAAUUC                                36

(2) INFORMATION FOR SEQ ID NO:2041:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:2041:

UCAACUGCUG AUGAGGCCGA AAGGCCGAAA GAAUUC                                36

(2) INFORMATION FOR SEQ ID NO:2042:

(i) SEQUENCE CHARACTERISTICS:
```

```
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:2042:

CUUUAAUCUG AUGAGGCCGA AAGGCCGAAA UUCAAC                              36

(2) INFORMATION FOR SEQ ID NO:2043:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:2043:

GUUCUUUCUG AUGAGGCCGA AAGGCCGAAA UUAUUC                              36

(2) INFORMATION FOR SEQ ID NO:2044:

(i) SEQUENCE CHARACTERISTICS:
          (A) LENGTH:          36 base pairs
          (B) TYPE:            nucleic acid
          (C) STRANDEDNESS:    single
          (D) TOPOLOGY:        linear (xi) SEQUENCE DESCRIPTION: SEQ ID NO:2044:

UGUUCUUCUG AUGAGGCCGA AAGGCCGAAA AUUAUU                              36

(2) INFORMATION FOR SEQ ID NO:2045:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:2045:

CCUCGCUCGG GCGCC                                                    15

(2) INFORMATION FOR SEQ ID NO:2046:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:2046:

CAGUGGUCCU GCCGC                                                    15

(2) INFORMATION FOR SEQ ID NO:2047:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO:2047:

GCCUGGUCUC ACCUC                                                    15

(2) INFORMATION FOR SEQ ID NO:2048:

(i) SEQUENCE CHARACTERISTICS:
          (A) LENGTH:          15 base pairs
```

```
            (B) TYPE:          nucleic acid
            (C) STRANDEDNESS:  single
            (D) TOPOLOGY:      linear (xi) SEQUENCE DESCRIPTION: SEQ ID NO:2048:

CUGGUCUCAC CUCGC                                                15

(2) INFORMATION FOR SEQ ID NO:2049:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2049:

CUCACCUCGC CAUGG                                                15

(2) INFORMATION FOR SEQ ID NO:2050:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2050:

CCAUGGUUCG UCUGC                                                15

(2) INFORMATION FOR SEQ ID NO:2051:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2051:

CAUGGUUCGU CUGCC                                                15

(2) INFORMATION FOR SEQ ID NO:2052:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2052:

GGUUCGUCUG CCUCU                                                15

(2) INFORMATION FOR SEQ ID NO:2053:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2053:

UCUGCCUCUG CAGUG                                                15

(2) INFORMATION FOR SEQ ID NO:2054:

(i) SEQUENCE CHARACTERISTICS:
            (A) LENGTH:        15 base pairs
            (B) TYPE:          nucleic acid
```

```
            (C) STRANDEDNESS:    single
            (D) TOPOLOGY:        linear (xi) SEQUENCE DESCRIPTION: SEQ ID NO:2054:

AGUGCGUCCU CUGGG                                                              15

(2) INFORMATION FOR SEQ ID NO:2055:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:2055:

GCGUCCUCUG GGGCU                                                              15

(2) INFORMATION FOR SEQ ID NO:2056:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:2056:

GGCUGCUUGC UGACC                                                              15

(2) INFORMATION FOR SEQ ID NO:2057:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:2057:

CCGCUGUCCA UCCAG                                                              15

(2) INFORMATION FOR SEQ ID NO:2058:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:2058:

UGUCCAUCCA GAACC                                                              15

(2) INFORMATION FOR SEQ ID NO:2059:

(i) SEQUENCE CHARACTERISTICS:
            (A) LENGTH:          15 base pairs
            (B) TYPE:            nucleic acid
            (C) STRANDEDNESS:    single
            (D) TOPOLOGY:        linear (xi) SEQUENCE DESCRIPTION: SEQ ID NO:2059:

AAACAGUACC UAAUA                                                              15

(2) INFORMATION FOR SEQ ID NO:2060:

(i) SEQUENCE CHARACTERISTICS:
            (A) LENGTH:          15 base pairs
            (B) TYPE:            nucleic acid
            (C) STRANDEDNESS:    single
```

(D) TOPOLOGY:       linear (xi) SEQUENCE DESCRIPTION: SEQ ID NO:2060:

AGUACCUAAU AAACA                                                    15

(2) INFORMATION FOR SEQ ID NO:2061:

(i) SEQUENCE CHARACTERISTICS:
           (A) LENGTH:         15 base pairs
           (B) TYPE:           nucleic acid
           (C) STRANDEDNESS:   single
           (D) TOPOLOGY:       linear (xi) SEQUENCE DESCRIPTION: SEQ ID NO:2061:

ACCUAAUAAA CAGUC                                                    15

(2) INFORMATION FOR SEQ ID NO:2062:

(i) SEQUENCE CHARACTERISTICS:
           (A) LENGTH:         15 base pairs
           (B) TYPE:           nucleic acid
           (C) STRANDEDNESS:   single
           (D) TOPOLOGY:       linear (xi) SEQUENCE DESCRIPTION: SEQ ID NO:2062:

AAACAGUCAG UGCUG                                                    15

(2) INFORMATION FOR SEQ ID NO:2063:

(i) SEQUENCE CHARACTERISTICS:
           (A) LENGTH:         15 base pairs
           (B) TYPE:           nucleic acid
           (C) STRANDEDNESS:   single
           (D) TOPOLOGY:       linear (xi) SEQUENCE DESCRIPTION: SEQ ID NO:2063:

GUGCUGUUCU UUGUG                                                    15

(2) INFORMATION FOR SEQ ID NO:2064:

(i) SEQUENCE CHARACTERISTICS:
           (A) LENGTH:         15 base pairs
           (B) TYPE:           nucleic acid
           (C) STRANDEDNESS:   single
           (D) TOPOLOGY:       linear (xi) SEQUENCE DESCRIPTION: SEQ ID NO:2064:

UGCUGUUCUU UGUGC                                                    15

(2) INFORMATION FOR SEQ ID NO:2065:

(i) SEQUENCE CHARACTERISTICS:
           (A) LENGTH:         15 base pairs
           (B) TYPE:           nucleic acid
           (C) STRANDEDNESS:   single
           (D) TOPOLOGY:       linear (xi) SEQUENCE DESCRIPTION: SEQ ID NO:2065:

CUGUUCUUUG UGCCA                                                    15

(2) INFORMATION FOR SEQ ID NO:2066:

(i) SEQUENCE CHARACTERISTICS:
           (A) LENGTH:         15 base pairs
           (B) TYPE:           nucleic acid
           (C) STRANDEDNESS:   single
           (D) TOPOLOGY:       linear (xi) SEQUENCE DESCRIPTION: SEQ ID NO:2066:

UGUUCUUUGU GCCAG                                                    15

(2) INFORMATION FOR SEQ ID NO:2067:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2067:

ACAGAGUUCA CUGAA                                                    15

(2) INFORMATION FOR SEQ ID NO:2068:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2068:

CAGAGUUCAC UGAAA                                                    15

(2) INFORMATION FOR SEQ ID NO:2069:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2069:

AAUGCCUUCC UUGCG                                                    15

(2) INFORMATION FOR SEQ ID NO:2070:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2070:

AUGCCUUCCU UGCGG                                                    15

(2) INFORMATION FOR SEQ ID NO:2071:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2071:

CCUUCCUUGC GGUGA                                                    15

(2) INFORMATION FOR SEQ ID NO:2072:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear

```
        (xi) SEQUENCE DESCRIPTION: SEQ ID NO:2072:

AGCGAAUUCC UAGAC                                                       15

(2) INFORMATION FOR SEQ ID NO:2073:

(i) SEQUENCE CHARACTERISTICS:
         (A) LENGTH:          15 base pairs
         (B) TYPE:            nucleic acid
         (C) STRANDEDNESS:    single
         (D) TOPOLOGY:        linear (xi) SEQUENCE DESCRIPTION: SEQ ID NO:2073:

GCGAAUUCCU AGACA                                                       15

(2) INFORMATION FOR SEQ ID NO:2074:

(i) SEQUENCE CHARACTERISTICS:
         (A) LENGTH:          15 base pairs
         (B) TYPE:            nucleic acid
         (C) STRANDEDNESS:    single
         (D) TOPOLOGY:        linear (xi) SEQUENCE DESCRIPTION: SEQ ID NO:2074:

AAUUCCUAGA CACCU                                                       15

(2) INFORMATION FOR SEQ ID NO:2075:

(i) SEQUENCE CHARACTERISTICS:
         (A) LENGTH:          15 base pairs
         (B) TYPE:            nucleic acid
         (C) STRANDEDNESS:    single
         (D) TOPOLOGY:        linear (xi) SEQUENCE DESCRIPTION: SEQ ID NO:2075:

CACAAAUACU GCGAC                                                       15

(2) INFORMATION FOR SEQ ID NO:2076:

(i) SEQUENCE CHARACTERISTICS:
         (A) LENGTH:          15 base pairs
         (B) TYPE:            nucleic acid
         (C) STRANDEDNESS:    single
         (D) TOPOLOGY:        linear (xi) SEQUENCE DESCRIPTION: SEQ ID NO:2076:

CCAACCUAGG GCUUC                                                       15

(2) INFORMATION FOR SEQ ID NO:2077:

(i) SEQUENCE CHARACTERISTICS:
         (A) LENGTH:          15 base pairs
         (B) TYPE:            nucleic acid
         (C) STRANDEDNESS:    single
         (D) TOPOLOGY:        linear (xi) SEQUENCE DESCRIPTION: SEQ ID NO:2077:

UAGGGCUUCG GGUCC                                                       15

(2) INFORMATION FOR SEQ ID NO:2078:

(i) SEQUENCE CHARACTERISTICS:
         (A) LENGTH:          15 base pairs
         (B) TYPE:            nucleic acid
         (C) STRANDEDNESS:    single
         (D) TOPOLOGY:        linear (xi) SEQUENCE DESCRIPTION: SEQ ID NO:2078:
```

AGGGCUUCGG GUCCA                                                15

(2) INFORMATION FOR SEQ ID NO:2079:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2079:

UUCGGGUCCA GCAGA                                                15

(2) INFORMATION FOR SEQ ID NO:2080:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2080:

GGCACCUCAG AAACA                                                15

(2) INFORMATION FOR SEQ ID NO:2081:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2081:

ACACCAUCUG CACCU                                                15

(2) INFORMATION FOR SEQ ID NO:2082:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2082:

GCACUGUACG AGUGA                                                15

(2) INFORMATION FOR SEQ ID NO:2083:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2083:

GCUGUGUCCU GCACC                                                15

(2) INFORMATION FOR SEQ ID NO:2084:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2084:

CACCGCUCAU GCUCG        15

(2) INFORMATION FOR SEQ ID NO:2085:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2085:

UCAUGCUCGC CCGGC        15

(2) INFORMATION FOR SEQ ID NO:2086:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2086:

CCCGGCUUUG GGGUC        15

(2) INFORMATION FOR SEQ ID NO:2087:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2087:

CCGGCUUUGG GGUCA        15

(2) INFORMATION FOR SEQ ID NO:2088:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2088:

UUGGGGUCAA GCAGA        15

(2) INFORMATION FOR SEQ ID NO:2089:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2089:

AGCAGAUUGC UACAG        15

(2) INFORMATION FOR SEQ ID NO:2090:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2090:

GAUUGCUACA GGGGU        15

(2) INFORMATION FOR SEQ ID NO:2091:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2091:

CAGGGGUUUC UGAUA                                           15

(2) INFORMATION FOR SEQ ID NO:2092:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2092:

AGGGGUUUCU GAUAC                                           15

(2) INFORMATION FOR SEQ ID NO:2093:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2093:

GGGGUUUCUG AUACC                                           15

(2) INFORMATION FOR SEQ ID NO:2094:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2094:

UUCUGAUACC AUCUG                                           15

(2) INFORMATION FOR SEQ ID NO:2095:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2095:

AUACCAUCUG CGAGC                                           15

(2) INFORMATION FOR SEQ ID NO:2096:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2096:

GCCCAGUCGG CUUCU                                           15

```
(2) INFORMATION FOR SEQ ID NO:2097:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2097:

GUCGGCUUCU UCUCC                                                              15

(2) INFORMATION FOR SEQ ID NO:2098:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2098:

UCGGCUUCUU CUCCA                                                              15

(2) INFORMATION FOR SEQ ID NO:2099:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2099:

GGCUUCUUCU CCAAU                                                              15

(2) INFORMATION FOR SEQ ID NO:2100:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2100:

GCUUCUUCUC CAAUG                                                              15

(2) INFORMATION FOR SEQ ID NO:2101:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2101:

UUCUUCUCCA AUGUG                                                              15

(2) INFORMATION FOR SEQ ID NO:2102:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2102:

AAUGUGUCAU CUGCU                                                              15
```

(2) INFORMATION FOR SEQ ID NO:2103:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2103:

GUGUCAUCUG CUUUC         15

(2) INFORMATION FOR SEQ ID NO:2104:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2104:

AUCUGCUUUC GAAAA         15

(2) INFORMATION FOR SEQ ID NO:2105:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2105:

UCUGCUUUCG AAAAA         15

(2) INFORMATION FOR SEQ ID NO:2106:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2106:

CUGCUUUCGA AAAAU         15

(2) INFORMATION FOR SEQ ID NO:2107:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2107:

AAAAUGUCAC CCUUG         15

(2) INFORMATION FOR SEQ ID NO:2108:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2108:

UCACCCUUGG ACAAG         15

(2) INFORMATION FOR SEQ ID NO:2109:

```
    (i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2109:

ACCUGGUUGU GCAAC                                                          15

(2) INFORMATION FOR SEQ ID NO:2110:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2110:

CUGAUGUUGU CUGUG                                                          15

(2) INFORMATION FOR SEQ ID NO:2111:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2111:

AUGUUGUCUG UGGUC                                                          15

(2) INFORMATION FOR SEQ ID NO:2112:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2112:

CUGUGGUCCC CAGGA                                                          15

(2) INFORMATION FOR SEQ ID NO:2113:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2113:

CCAGGAUCGG CUGAG                                                          15

(2) INFORMATION FOR SEQ ID NO:2114:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2114:

UGGUGAUCCC CAUCA                                                          15

(2) INFORMATION FOR SEQ ID NO:2115:
```

(i) SEQUENCE CHARACTERISTICS:
   (A) LENGTH:        15 base pairs
   (B) TYPE:          nucleic acid
   (C) STRANDEDNESS:  single
   (D) TOPOLOGY:      linear (xi) SEQUENCE DESCRIPTION: SEQ ID NO:2115:

UCCCCAUCAU CUUCG                                                15

(2) INFORMATION FOR SEQ ID NO:2116:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:2116:

CCAUCAUCUU CGGGA                                                15

(2) INFORMATION FOR SEQ ID NO:2117:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:2117:

AUCAUCUUCG GGAUC                                                15

(2) INFORMATION FOR SEQ ID NO:2118:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:2118:

UCAUCUUCGG GAUCC                                                15

(2) INFORMATION FOR SEQ ID NO:2119:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:2119:

UCGGGAUCCU GUUUG                                                15

(2) INFORMATION FOR SEQ ID NO:2120:

(i) SEQUENCE CHARACTERISTICS:
      (A) LENGTH:        15 base pairs
      (B) TYPE:          nucleic acid
      (C) STRANDEDNESS:  single
      (D) TOPOLOGY:      linear (xi) SEQUENCE DESCRIPTION: SEQ ID NO:2120:

AUCCUGUUUG CCAUC                                                15

(2) INFORMATION FOR SEQ ID NO:2121:

(i) SEQUENCE CHARACTERISTICS:

(A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2121:

UCCUGUUUGC CAUCC                                                        15

(2) INFORMATION FOR SEQ ID NO:2122:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2122:

UUGCCAUCCU CUUGG                                                        15

(2) INFORMATION FOR SEQ ID NO:2123:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2123:

CCAUCCUCUU GGUGC                                                        15

(2) INFORMATION FOR SEQ ID NO:2124:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2124:

AUCCUCUUGG UGCUG                                                        15

(2) INFORMATION FOR SEQ ID NO:2125:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2125:

UGCUGGUCUU UAUCA                                                        15

(2) INFORMATION FOR SEQ ID NO:2126:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2126:

CUGGUCUUUA UCAAA                                                        15

(2) INFORMATION FOR SEQ ID NO:2127:

(i) SEQUENCE CHARACTERISTICS:
        (A) LENGTH:        15 base pairs

```
        (B) TYPE:           nucleic acid
        (C) STRANDEDNESS:   single
        (D) TOPOLOGY:       linear (xi) SEQUENCE DESCRIPTION: SEQ ID NO:2127:

UGGUCUUUAU CAAAA                                                15

(2) INFORMATION FOR SEQ ID NO:2128:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2128:

GGUCUUUAUC AAAAA                                                15

(2) INFORMATION FOR SEQ ID NO:2129:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2129:

UCUUUAUCAA AAAGG                                                15

(2) INFORMATION FOR SEQ ID NO:2130:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2130:

AACCAAUAAG GCCCC                                                15

(2) INFORMATION FOR SEQ ID NO:2131:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2131:

AGGAGAUCAA UUUUC                                                15

(2) INFORMATION FOR SEQ ID NO:2132:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2132:

GAUCAAUUUU CCCGA                                                15

(2) INFORMATION FOR SEQ ID NO:2133:

(i) SEQUENCE CHARACTERISTICS:
        (A) LENGTH:         15 base pairs
        (B) TYPE:           nucleic acid
```

```
            (C) STRANDEDNESS:   single
            (D) TOPOLOGY:       linear (xi) SEQUENCE DESCRIPTION: SEQ ID NO:2133:

AUCAAUUUUC CCGAC                                                     15

(2) INFORMATION FOR SEQ ID NO:2134:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2134:

UCAAUUUUCC CGACG                                                     15

(2) INFORMATION FOR SEQ ID NO:2135:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2135:

CAAUUUUCCC GACGA                                                     15

(2) INFORMATION FOR SEQ ID NO:2136:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2136:

CGACGAUCUU CCUGG                                                     15

(2) INFORMATION FOR SEQ ID NO:2137:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2137:

ACGAUCUUCC UGGCU                                                     15

(2) INFORMATION FOR SEQ ID NO:2138:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2138:

CGAUCUUCCU GGCUC                                                     15

(2) INFORMATION FOR SEQ ID NO:2139:

(i) SEQUENCE CHARACTERISTICS:
            (A) LENGTH:         15 base pairs
            (B) TYPE:           nucleic acid
            (C) STRANDEDNESS:   single
```

(D) TOPOLOGY:         linear (xi) SEQUENCE DESCRIPTION: SEQ ID NO:2139:

CCUGGCUCCA ACACU                                                            15

(2) INFORMATION FOR SEQ ID NO:2140:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:2140:

UGCUGCUCCA GUGCA                                                            15

(2) INFORMATION FOR SEQ ID NO:2141:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:2141:

GGAGACUUUA CAUGG                                                            15

(2) INFORMATION FOR SEQ ID NO:2142:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:2142:

GAGACUUUAC AUGGA                                                            15

(2) INFORMATION FOR SEQ ID NO:2143:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:2143:

AGACUUUACA UGGAU                                                            15

(2) INFORMATION FOR SEQ ID NO:2144:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:2144:

AACCGGUCAC CCAGG                                                            15

(2) INFORMATION FOR SEQ ID NO:2145:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO:2145:

AGAGAGUCGC AUCUC                                                    15

(2) INFORMATION FOR SEQ ID NO:2146:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2146:

GUCGCAUCUC AGUGC                                                    15

(2) INFORMATION FOR SEQ ID NO:2147:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2147:

CGCAUCUCAG UGCAG                                                    15

(2) INFORMATION FOR SEQ ID NO:2148:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2148:

AGGCAGUUGG CCAGA                                                    15

(2) INFORMATION FOR SEQ ID NO:2149:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2149:

GGGAGCUAUG CCCAG                                                    15

(2) INFORMATION FOR SEQ ID NO:2150:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2150:

GCCCAGUCAG UGCCA                                                    15

(2) INFORMATION FOR SEQ ID NO:2151:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2151:

GGCGCCCCUG AUGAGGCCGA AAGGCCGAAA GCGAGG                36

(2) INFORMATION FOR SEQ ID NO:2152:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2152:

GCGGCAGCUG AUGAGGCCGA AAGGCCGAAA CCACUG                36

(2) INFORMATION FOR SEQ ID NO:2153:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2153:

GAGGUGACUG AUGAGGCCGA AAGGCCGAAA CCAGGC                36

(2) INFORMATION FOR SEQ ID NO:2154:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2154:

GCGAGGUCUG AUGAGGCCGA AAGGCCGAAA GACCAG                36

(2) INFORMATION FOR SEQ ID NO:2155:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2155:

CCAUGGCCUG AUGAGGCCGA AAGGCCGAAA GGUGAG                36

(2) INFORMATION FOR SEQ ID NO:2156:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2156:

GCAGACGCUG AUGAGGCCGA AAGGCCGAAA CCAUGG                36

(2) INFORMATION FOR SEQ ID NO:2157:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2157:

GGCAGACCUG AUGAGGCCGA AAGGCCGAAA ACCAUG                                    36

(2) INFORMATION FOR SEQ ID NO:2158:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2158:

AGAGGCACUG AUGAGGCCGA AAGGCCGAAA CGAACC                                    36

(2) INFORMATION FOR SEQ ID NO:2159:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2159:

CACUGCACUG AUGAGGCCGA AAGGCCGAAA GGCAGA                                    36

(2) INFORMATION FOR SEQ ID NO:2160:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2160:

CCCAGAGCUG AUGAGGCCGA AAGGCCGAAA CGCACU                                    36

(2) INFORMATION FOR SEQ ID NO:2161:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2161:

AGCCCCACUG AUGAGGCCGA AAGGCCGAAA GGACGC                                    36

(2) INFORMATION FOR SEQ ID NO:2162:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2162:

GGUCAGCCUG AUGAGGCCGA AAGGCCGAAA GCAGCC                                    36

(2) INFORMATION FOR SEQ ID NO:2163:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2163:

```
CUGGAUGCUG AUGAGGCCGA AAGGCCGAAA CAGCGG                                          36

(2) INFORMATION FOR SEQ ID NO:2164:

(i) SEQUENCE CHARACTERISTICS:
           (A) LENGTH:       36 base pairs
           (B) TYPE:         nucleic acid
           (C) STRANDEDNESS: single
           (D) TOPOLOGY:     linear (xi) SEQUENCE DESCRIPTION: SEQ ID NO:2164:

GGUUCUGCUG AUGAGGCCGA AAGGCCGAAA UGGACA                                          36

(2) INFORMATION FOR SEQ ID NO:2165:

(i) SEQUENCE CHARACTERISTICS:
           (A) LENGTH:       36 base pairs
           (B) TYPE:         nucleic acid
           (C) STRANDEDNESS: single
           (D) TOPOLOGY:     linear (xi) SEQUENCE DESCRIPTION: SEQ ID NO:2165:

UAUUAGGCUG AUGAGGCCGA AAGGCCGAAA CUGUUU                                          36

(2) INFORMATION FOR SEQ ID NO:2166:

(i) SEQUENCE CHARACTERISTICS:
           (A) LENGTH:       36 base pairs
           (B) TYPE:         nucleic acid
           (C) STRANDEDNESS: single
           (D) TOPOLOGY:     linear (xi) SEQUENCE DESCRIPTION: SEQ ID NO:2166:

UGUUUAUCUG AUGAGGCCGA AAGGCCGAAA GGUACU                                          36

(2) INFORMATION FOR SEQ ID NO:2167:

(i) SEQUENCE CHARACTERISTICS:
           (A) LENGTH:       36 base pairs
           (B) TYPE:         nucleic acid
           (C) STRANDEDNESS: single
           (D) TOPOLOGY:     linear (xi) SEQUENCE DESCRIPTION: SEQ ID NO:2167:

GACUGUUCUG AUGAGGCCGA AAGGCCGAAA UUAGGU                                          36

(2) INFORMATION FOR SEQ ID NO:2168:

(i) SEQUENCE CHARACTERISTICS:
           (A) LENGTH:       36 base pairs
           (B) TYPE:         nucleic acid
           (C) STRANDEDNESS: single
           (D) TOPOLOGY:     linear (xi) SEQUENCE DESCRIPTION: SEQ ID NO:2168:

CAGCACUCUG AUGAGGCCGA AAGGCCGAAA CUGUUU                                          36

(2) INFORMATION FOR SEQ ID NO:2169:

(i) SEQUENCE CHARACTERISTICS:
           (A) LENGTH:       36 base pairs
           (B) TYPE:         nucleic acid
           (C) STRANDEDNESS: single
           (D) TOPOLOGY:     linear (xi) SEQUENCE DESCRIPTION: SEQ ID NO:2169:

CACAAAGCUG AUGAGGCCGA AAGGCCGAAA CAGCAC                                          36
```

(2) INFORMATION FOR SEQ ID NO:2170:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2170:

GCACAAACUG AUGAGGCCGA AAGGCCGAAA ACAGCA                                  36

(2) INFORMATION FOR SEQ ID NO:2171:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2171:

UGGCACACUG AUGAGGCCGA AAGGCCGAAA GAACAG                                  36

(2) INFORMATION FOR SEQ ID NO:2172:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2172:

CUGGCACCUG AUGAGGCCGA AAGGCCGAAA AGAACA                                  36

(2) INFORMATION FOR SEQ ID NO:2173:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2173:

UUCAGUGCUG AUGAGGCCGA AAGGCCGAAA CUCUGU                                  36

(2) INFORMATION FOR SEQ ID NO:2174:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2174:

UUUCAGUCUG AUGAGGCCGA AAGGCCGAAA ACUCUG                                  36

(2) INFORMATION FOR SEQ ID NO:2175:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2175:

CGCAAGGCUG AUGAGGCCGA AAGGCCGAAA GGCAUU                                  36

(2) INFORMATION FOR SEQ ID NO:2176:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2176:

CCGCAAGCUG AUGAGGCCGA AAGGCCGAAA AGGCAU                        36

(2) INFORMATION FOR SEQ ID NO:2177:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2177:

UCACCGCCUG AUGAGGCCGA AAGGCCGAAA GGAAGG                        36

(2) INFORMATION FOR SEQ ID NO:2178:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2178:

GUCUAGGCUG AUGAGGCCGA AAGGCCGAAA UUCGCU                        36

(2) INFORMATION FOR SEQ ID NO:2179:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2179:

UGUCUAGCUG AUGAGGCCGA AAGGCCGAAA AUUCGC                        36

(2) INFORMATION FOR SEQ ID NO:2180:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2180:

AGGUGUCCUG AUGAGGCCGA AAGGCCGAAA GGAAUU                        36

(2) INFORMATION FOR SEQ ID NO:2181:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2181:

GUCGCAGCUG AUGAGGCCGA AAGGCCGAAA UUUGUG                        36

(2) INFORMATION FOR SEQ ID NO:2182:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2182:

GAAGCCCCUG AUGAGGCCGA AAGGCCGAAA GGUUGG                                 36

(2) INFORMATION FOR SEQ ID NO:2183:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2183:

GGACCCGCUG AUGAGGCCGA AAGGCCGAAA GCCCUA                                 36

(2) INFORMATION FOR SEQ ID NO:2184:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2184:

UGGACCCCUG AUGAGGCCGA AAGGCCGAAA AGCCCU                                 36

(2) INFORMATION FOR SEQ ID NO:2185:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2185:

UCUGCUGCUG AUGAGGCCGA AAGGCCGAAA CCCGAA                                 36

(2) INFORMATION FOR SEQ ID NO:2186:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2186:

UGUUUCUCUG AUGAGGCCGA AAGGCCGAAA GGUGCC                                 36

(2) INFORMATION FOR SEQ ID NO:2187:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2187:

AGGUGCACUG AUGAGGCCGA AAGGCCGAAA UGGUGU                                 36

(2) INFORMATION FOR SEQ ID NO:2188:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2188:

UCACUCGCUG AUGAGGCCGA AAGGCCGAAA CAGUGC                     36

(2) INFORMATION FOR SEQ ID NO:2189:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2189:

GGUGCAGCUG AUGAGGCCGA AAGGCCGAAA CACAGC                     36

(2) INFORMATION FOR SEQ ID NO:2190:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2190:

CGAGCAUCUG AUGAGGCCGA AAGGCCGAAA GCGGUG                     36

(2) INFORMATION FOR SEQ ID NO:2191:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2191:

GCCGGGCCUG AUGAGGCCGA AAGGCCGAAA GCAUGA                     36

(2) INFORMATION FOR SEQ ID NO:2192:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2192:

GACCCCACUG AUGAGGCCGA AAGGCCGAAA GCCGGG                     36

(2) INFORMATION FOR SEQ ID NO:2193:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2193:

UGACCCCCUG AUGAGGCCGA AAGGCCGAAA AGCCGG                     36

(2) INFORMATION FOR SEQ ID NO:2194:

(i) SEQUENCE CHARACTERISTICS:
    (A) LENGTH:        36 base pairs
    (B) TYPE:          nucleic acid
    (C) STRANDEDNESS:  single
    (D) TOPOLOGY:     linear (xi) SEQUENCE DESCRIPTION: SEQ ID NO:2194:

UCUGCUUCUG AUGAGGCCGA AAGGCCGAAA CCCCAA                  36

(2) INFORMATION FOR SEQ ID NO:2195:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO:2195:

CUGUAGCCUG AUGAGGCCGA AAGGCCGAAA UCUGCU                  36

(2) INFORMATION FOR SEQ ID NO:2196:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO:2196:

ACCCCUGCUG AUGAGGCCGA AAGGCCGAAA GCAAUC                  36

(2) INFORMATION FOR SEQ ID NO:2197:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO:2197:

UAUCAGACUG AUGAGGCCGA AAGGCCGAAA CCCCUG                  36

(2) INFORMATION FOR SEQ ID NO:2198:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO:2198:

GUAUCAGCUG AUGAGGCCGA AAGGCCGAAA ACCCCU                  36

(2) INFORMATION FOR SEQ ID NO:2199:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO:2199:

GGUAUCACUG AUGAGGCCGA AAGGCCGAAA AACCCC                  36

(2) INFORMATION FOR SEQ ID NO:2200:

(i) SEQUENCE CHARACTERISTICS:

```
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2200:

CAGAUGGCUG AUGAGGCCGA AAGGCCGAAA UCAGAA                                      36

(2) INFORMATION FOR SEQ ID NO:2201:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2201:

GCUCGCACUG AUGAGGCCGA AAGGCCGAAA UGGUAU                                      36

(2) INFORMATION FOR SEQ ID NO:2202:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2202:

AGAAGCCCUG AUGAGGCCGA AAGGCCGAAA CUGGGC                                      36

(2) INFORMATION FOR SEQ ID NO:2203:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2203:

GGAGAAGCUG AUGAGGCCGA AAGGCCGAAA GCCGAC                                      36

(2) INFORMATION FOR SEQ ID NO:2204:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2204:

UGGAGAACUG AUGAGGCCGA AAGGCCGAAA AGCCGA                                      36

(2) INFORMATION FOR SEQ ID NO:2205:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2205:

AUUGGAGCUG AUGAGGCCGA AAGGCCGAAA GAAGCC                                      36

(2) INFORMATION FOR SEQ ID NO:2206:

(i) SEQUENCE CHARACTERISTICS:
        (A) LENGTH:         36 base pairs
```

```
            (B) TYPE:            nucleic acid
            (C) STRANDEDNESS:    single
            (D) TOPOLOGY:        linear (xi) SEQUENCE DESCRIPTION: SEQ ID NO:2206:

CAUUGGACUG AUGAGGCCGA AAGGCCGAAA AGAAGC                              36

(2) INFORMATION FOR SEQ ID NO:2207:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2207:

CACAUUGCUG AUGAGGCCGA AAGGCCGAAA GAAGAA                              36

(2) INFORMATION FOR SEQ ID NO:2208:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2208:

AGCAGAUCUG AUGAGGCCGA AAGGCCGAAA CACAUU                              36

(2) INFORMATION FOR SEQ ID NO:2209:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2209:

GAAAGCACUG AUGAGGCCGA AAGGCCGAAA UGACAC                              36

(2) INFORMATION FOR SEQ ID NO:2210:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2210:

UUUUCGACUG AUGAGGCCGA AAGGCCGAAA GCAGAU                              36

(2) INFORMATION FOR SEQ ID NO:2211:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2211:

UUUUUCGCUG AUGAGGCCGA AAGGCCGAAA AGCAGA                              36

(2) INFORMATION FOR SEQ ID NO:2212:

(i) SEQUENCE CHARACTERISTICS:
            (A) LENGTH:          36 base pairs
            (B) TYPE:            nucleic acid
```

```
            (C) STRANDEDNESS:    single
            (D) TOPOLOGY:        linear (xi) SEQUENCE DESCRIPTION: SEQ ID NO:2212:

AUUUUUCCUG AUGAGGCCGA AAGGCCGAAA AAGCAG                              36

(2) INFORMATION FOR SEQ ID NO:2213:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2213:

CAAGGGUCUG AUGAGGCCGA AAGGCCGAAA CAUUUU                              36

(2) INFORMATION FOR SEQ ID NO:2214:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2214:

CUUGUCCCUG AUGAGGCCGA AAGGCCGAAA GGGUGA                              36

(2) INFORMATION FOR SEQ ID NO:2215:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2215:

GUUGCACCUG AUGAGGCCGA AAGGCCGAAA CCAGGU                              36

(2) INFORMATION FOR SEQ ID NO:2216:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2216:

CACAGACCUG AUGAGGCCGA AAGGCCGAAA CAUCAG                              36

(2) INFORMATION FOR SEQ ID NO:2217:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2217:

GACCACACUG AUGAGGCCGA AAGGCCGAAA CAACAU                              36

(2) INFORMATION FOR SEQ ID NO:2218:

(i) SEQUENCE CHARACTERISTICS:
            (A) LENGTH:          36 base pairs
            (B) TYPE:            nucleic acid
            (C) STRANDEDNESS:    single
```

(D) TOPOLOGY:      linear (xi) SEQUENCE DESCRIPTION: SEQ ID NO:2218:

UCCUGGGCUG AUGAGGCCGA AAGGCCGAAA CCACAG                36

(2) INFORMATION FOR SEQ ID NO:2219:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2219:

CUCAGCCCUG AUGAGGCCGA AAGGCCGAAA UCCUGG                36

(2) INFORMATION FOR SEQ ID NO:2220:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2220:

UGAUGGGCUG AUGAGGCCGA AAGGCCGAAA UCACCA                36

(2) INFORMATION FOR SEQ ID NO:2221:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2221:

CGAAGAUCUG AUGAGGCCGA AAGGCCGAAA UGGGGA                36

(2) INFORMATION FOR SEQ ID NO:2222:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2222:

UCCCGAACUG AUGAGGCCGA AAGGCCGAAA UGAUGG                36

(2) INFORMATION FOR SEQ ID NO:2223:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2223:

GAUCCCGCUG AUGAGGCCGA AAGGCCGAAA GAUGAU                36

(2) INFORMATION FOR SEQ ID NO:2224:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2224:

GGAUCCCCUG AUGAGGCCGA AAGGCCGAAA AGAUGA                    36

(2) INFORMATION FOR SEQ ID NO:2225:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2225:

CAAACAGCUG AUGAGGCCGA AAGGCCGAAA UCCCGA                    36

(2) INFORMATION FOR SEQ ID NO:2226:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2226:

GAUGGCACUG AUGAGGCCGA AAGGCCGAAA CAGGAU                    36

(2) INFORMATION FOR SEQ ID NO:2227:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2227:

GGAUGGCCUG AUGAGGCCGA AAGGCCGAAA ACAGGA                    36

(2) INFORMATION FOR SEQ ID NO:2228:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2228:

CCAAGAGCUG AUGAGGCCGA AAGGCCGAAA UGGCAA                    36

(2) INFORMATION FOR SEQ ID NO:2229:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2229:

GCACCAACUG AUGAGGCCGA AAGGCCGAAA GGAUGG                    36

(2) INFORMATION FOR SEQ ID NO:2230:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2230:

CAGCACCCUG AUGAGGCCGA AAGGCCGAAA GAGGAU                                36

(2) INFORMATION FOR SEQ ID NO:2231:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2231:

UGAUAAACUG AUGAGGCCGA AAGGCCGAAA CCAGCA                                36

(2) INFORMATION FOR SEQ ID NO:2232:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2232:

UUUGAUACUG AUGAGGCCGA AAGGCCGAAA GACCAG                                36

(2) INFORMATION FOR SEQ ID NO:2233:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2233:

UUUUGAUCUG AUGAGGCCGA AAGGCCGAAA AGACCA                                36

(2) INFORMATION FOR SEQ ID NO:2234:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2234:

UUUUUGACUG AUGAGGCCGA AAGGCCGAAA AAGACC                                36

(2) INFORMATION FOR SEQ ID NO:2235:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2235:

CCUUUUUCUG AUGAGGCCGA AAGGCCGAAA UAAAGA                                36

(2) INFORMATION FOR SEQ ID NO:2236:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2236:

GGGGCCUCUG AUGAGGCCGA AAGGCCGAAA UUGGUU                36

(2) INFORMATION FOR SEQ ID NO:2237:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2237:

GAAAAUUCUG AUGAGGCCGA AAGGCCGAAA UCUCCU                36

(2) INFORMATION FOR SEQ ID NO:2238:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2238:

UCGGGAACUG AUGAGGCCGA AAGGCCGAAA UUGAUC                36

(2) INFORMATION FOR SEQ ID NO:2239:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2239:

GUCGGGACUG AUGAGGCCGA AAGGCCGAAA AUUGAU                36

(2) INFORMATION FOR SEQ ID NO:2240:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2240:

CGUCGGGCUG AUGAGGCCGA AAGGCCGAAA AAUUGA                36

(2) INFORMATION FOR SEQ ID NO:2241:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2241:

UCGUCGGCUG AUGAGGCCGA AAGGCCGAAA AAAUUG                36

(2) INFORMATION FOR SEQ ID NO:2242:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2242:

```
CCAGGAACUG AUGAGGCCGA AAGGCCGAAA UCGUCG                                    36

(2) INFORMATION FOR SEQ ID NO:2243:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2243:

AGCCAGGCUG AUGAGGCCGA AAGGCCGAAA GAUCGU                                    36

(2) INFORMATION FOR SEQ ID NO:2244:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2244:

GAGCCAGCUG AUGAGGCCGA AAGGCCGAAA AGAUCG                                    36

(2) INFORMATION FOR SEQ ID NO:2245:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2245:

AGUGUUGCUG AUGAGGCCGA AAGGCCGAAA GCCAGG                                    36

(2) INFORMATION FOR SEQ ID NO:2246:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2246:

UGCACUGCUG AUGAGGCCGA AAGGCCGAAA GCAGCA                                    36

(2) INFORMATION FOR SEQ ID NO:2247:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2247:

CCAUGUACUG AUGAGGCCGA AAGGCCGAAA GUCUCC                                    36

(2) INFORMATION FOR SEQ ID NO:2248:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2248:

UCCAUGUCUG AUGAGGCCGA AAGGCCGAAA AGUCUC                                    36
```

(2) INFORMATION FOR SEQ ID NO:2249:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2249:

AUCCAUGCUG AUGAGGCCGA AAGGCCGAAA AAGUCU                         36

(2) INFORMATION FOR SEQ ID NO:2250:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2250:

CCUGGGUCUG AUGAGGCCGA AAGGCCGAAA CCGGUU                         36

(2) INFORMATION FOR SEQ ID NO:2251:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2251:

GAGAUGCCUG AUGAGGCCGA AAGGCCGAAA CUCUCU                         36

(2) INFORMATION FOR SEQ ID NO:2252:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2252:

GCACUGACUG AUGAGGCCGA AAGGCCGAAA UGCGAC                         36

(2) INFORMATION FOR SEQ ID NO:2253:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2253:

CUGCACUCUG AUGAGGCCGA AAGGCCGAAA GAUGCG                         36

(2) INFORMATION FOR SEQ ID NO:2254:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2254:

UCUGGCCCUG AUGAGGCCGA AAGGCCGAAA CUGCCU                         36

(2) INFORMATION FOR SEQ ID NO:2255:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:2255:

CUGGGCACUG AUGAGGCCGA AAGGCCGAAA GCUCCC                          36

(2) INFORMATION FOR SEQ ID NO:2256:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO:2256:

UGGCACUCUG AUGAGGCCGA AAGGCCGAAA CUGGGC                          36

(2) INFORMATION FOR SEQ ID NO:2257:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:2257:

GGUGUCUUUG CCUCG                                                 15

(2) INFORMATION FOR SEQ ID NO:2258:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:2258:

GGUGUCUUUG CCUCG                                                 15

(2) INFORMATION FOR SEQ ID NO:2259:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:2259:

UUUGCCUCGG CUGUG                                                 15

(2) INFORMATION FOR SEQ ID NO:2260:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:2260:

GCGCGCUAUG GGGCU                                                 15

(2) INFORMATION FOR SEQ ID NO:2261:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2261:

CAGCGGUCCA UCUAG                                                    15

(2) INFORMATION FOR SEQ ID NO:2262:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2262:

CAGCGGUCCA UCUAG                                                    15

(2) INFORMATION FOR SEQ ID NO:2263:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2263:

GGUCCAUCUA GGGCA                                                   15

(2) INFORMATION FOR SEQ ID NO:2264:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2264:

AGUGUGUUAC GUGCA                                                 15

(2) INFORMATION FOR SEQ ID NO:2265:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2265:

AGUGUGUUAC GUGCA                                                 15

(2) INFORMATION FOR SEQ ID NO:2266:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO:2266:

GUGUGUUACG UGCAG                                                 15

(2) INFORMATION FOR SEQ ID NO:2267:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2267:

AAACAGUACC UCCAC                                                    15

(2) INFORMATION FOR SEQ ID NO:2268:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2268:

CUGUGAUUUG UGCCA                                                    15

(2) INFORMATION FOR SEQ ID NO:2269:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2269:

UGUGAUUUGU GCCAG                                                    15

(2) INFORMATION FOR SEQ ID NO:2270:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2270:

CAGCUCUUGA GAAGA                                                    15

(2) INFORMATION FOR SEQ ID NO:2271:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2271:

GGCGAAUUCU CAGCC                                                    15

(2) INFORMATION FOR SEQ ID NO:2272:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2272:

GCGAAUUCUC AGCCC                                                    15

(2) INFORMATION FOR SEQ ID NO:2273:

(i) SEQUENCE CHARACTERISTICS:
  (A) LENGTH:  15 base pairs
  (B) TYPE:  nucleic acid
  (C) STRANDEDNESS: single
  (D) TOPOLOGY: linear (xi) SEQUENCE DESCRIPTION: SEQ ID NO:2273:

GGGAGAUUCG CUGUC  15

(2) INFORMATION FOR SEQ ID NO:2274:

(i) SEQUENCE CHARACTERISTICS:
  (A) LENGTH:  15 base pairs
  (B) TYPE:  nucleic acid
  (C) STRANDEDNESS: single
  (D) TOPOLOGY: linear (xi) SEQUENCE DESCRIPTION: SEQ ID NO:2274:

ACCCAAUCAA GGGCU  15

(2) INFORMATION FOR SEQ ID NO:2275:

(i) SEQUENCE CHARACTERISTICS:
  (A) LENGTH:  15 base pairs
  (B) TYPE:  nucleic acid
  (C) STRANDEDNESS: single
  (D) TOPOLOGY: linear (xi) SEQUENCE DESCRIPTION: SEQ ID NO:2275:

ACCCAAUCAA GGGCU  15

(2) INFORMATION FOR SEQ ID NO:2276:

(i) SEQUENCE CHARACTERISTICS:
  (A) LENGTH:  15 base pairs
  (B) TYPE:  nucleic acid
  (C) STRANDEDNESS: single
  (D) TOPOLOGY: linear (xi) SEQUENCE DESCRIPTION: SEQ ID NO:2276:

AAGGGCUUCG GGUUA  15

(2) INFORMATION FOR SEQ ID NO:2277:

(i) SEQUENCE CHARACTERISTICS:
  (A) LENGTH:  15 base pairs
  (B) TYPE:  nucleic acid
  (C) STRANDEDNESS: single
  (D) TOPOLOGY: linear (xi) SEQUENCE DESCRIPTION: SEQ ID NO:2277:

AAGGGCUUCG GGUUA  15

(2) INFORMATION FOR SEQ ID NO:2278:

(i) SEQUENCE CHARACTERISTICS:
  (A) LENGTH:  15 base pairs
  (B) TYPE:  nucleic acid
  (C) STRANDEDNESS: single
  (D) TOPOLOGY: linear (xi) SEQUENCE DESCRIPTION: SEQ ID NO:2278:

AGGGCUUCGG GUUAA  15

(2) INFORMATION FOR SEQ ID NO:2279:

(i) SEQUENCE CHARACTERISTICS:

```
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:2279:

UUCGGGUUAA GAAGG                                                    15

(2) INFORMATION FOR SEQ ID NO:2280:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:2280:

UUCGGGUUAA GAAGG                                                    15

(2) INFORMATION FOR SEQ ID NO:2281:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:2281:

ACACUGUCUG UACCU                                                    15

(2) INFORMATION FOR SEQ ID NO:2282:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:2282:

CAAGGAUUGC GAGGC                                                    15

(2) INFORMATION FOR SEQ ID NO:2283:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:2283:

CCUGUAUCCC UGGCU                                                    15

(2) INFORMATION FOR SEQ ID NO:2284:

(i) SEQUENCE CHARACTERISTICS:
          (A) LENGTH:         15 base pairs
          (B) TYPE:           nucleic acid
          (C) STRANDEDNESS:   single
          (D) TOPOLOGY:       linear (xi) SEQUENCE DESCRIPTION: SEQ ID NO:2284:

CCUGGCUUUG GAGUU                                                    15

(2) INFORMATION FOR SEQ ID NO:2285:

(i) SEQUENCE CHARACTERISTICS:
          (A) LENGTH:         15 base pairs
```

```
            (B) TYPE:           nucleic acid
            (C) STRANDEDNESS:   single
            (D) TOPOLOGY:       linear (xi) SEQUENCE DESCRIPTION: SEQ ID NO:2285:

CCUGGCUUUG GAGUU                                                     15

(2) INFORMATION FOR SEQ ID NO:2286:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2286:

CUGGCUUUGG AGUUA                                                     15

(2) INFORMATION FOR SEQ ID NO:2287:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2287:

CACUGAUACC GUCUG                                                     15

(2) INFORMATION FOR SEQ ID NO:2288:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2288:

AUACCGUCUG UCAUC                                                     15

(2) INFORMATION FOR SEQ ID NO:2289:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2289:

AUACCGUCUG UCAUC                                                     15

(2) INFORMATION FOR SEQ ID NO:2290:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2290:

CUGUCAUCCC UGCCC                                                     15

(2) INFORMATION FOR SEQ ID NO:2291:

(i) SEQUENCE CHARACTERISTICS:
            (A) LENGTH:         15 base pairs
            (B) TYPE:           nucleic acid
```

```
        (C) STRANDEDNESS:    single
        (D) TOPOLOGY:        linear (xi) SEQUENCE DESCRIPTION: SEQ ID NO:2291:

GCCCAGUCGG CUUCU                                                         15

(2) INFORMATION FOR SEQ ID NO:2292:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:2292:

GCCCAGUCGG CUUCU                                                         15

(2) INFORMATION FOR SEQ ID NO:2293:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:2293:

GUCGGCUUCU UCUCC                                                         15

(2) INFORMATION FOR SEQ ID NO:2294:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:2294:

UCGGCUUCUU CUCCA                                                         15

(2) INFORMATION FOR SEQ ID NO:2295:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:2295:

GGCUUCUUCU CCAAU                                                         15

(2) INFORMATION FOR SEQ ID NO:2296:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO:2296:

GCUUCUUCUC CAAUC                                                         15

(2) INFORMATION FOR SEQ ID NO:2297:

(i) SEQUENCE CHARACTERISTICS:
        (A) LENGTH:          15 base pairs
        (B) TYPE:            nucleic acid
        (C) STRANDEDNESS:    single
```

```
            (D) TOPOLOGY:       linear (xi) SEQUENCE DESCRIPTION: SEQ ID NO:2297:

UUCUUCUCCA AUCAG                                                    15

(2) INFORMATION FOR SEQ ID NO:2298:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2298:

AAUCAGUCAU CACUU                                                    15

(2) INFORMATION FOR SEQ ID NO:2299:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2299:

AAUCAGUCAU CACUU                                                    15

(2) INFORMATION FOR SEQ ID NO:2300:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2300:

CAUCACUUUU CGAAA                                                    15

(2) INFORMATION FOR SEQ ID NO:2301:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2301:

AUCACUUUUC GAAAA                                                    15

(2) INFORMATION FOR SEQ ID NO:2302:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear (xi) SEQUENCE DESCRIPTION: SEQ ID NO:2302:

UCACUUUUCG AAAAG                                                    15

(2) INFORMATION FOR SEQ ID NO:2303:

(i) SEQUENCE CHARACTERISTICS:
            (A) LENGTH:         15 base pairs
            (B) TYPE:           nucleic acid
            (C) STRANDEDNESS:   single
            (D) TOPOLOGY:       linear
```

(xi) SEQUENCE DESCRIPTION: SEQ ID NO:2303:

UCACUUUUCG AAAAG                                                15

(2) INFORMATION FOR SEQ ID NO:2304:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2304:

AAAGUGUUAU CCCUG                                                15

(2) INFORMATION FOR SEQ ID NO:2305:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2305:

CUAAUGUCAU CUGUG                                                15

(2) INFORMATION FOR SEQ ID NO:2306:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2306:

AUGUCAUCUG UGGUU                                                15

(2) INFORMATION FOR SEQ ID NO:2307:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2307:

GUGGUUUAAA GUCCC                                                15

(2) INFORMATION FOR SEQ ID NO:2308:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2308:

GUGGUUUAAA GUCCC                                                15

(2) INFORMATION FOR SEQ ID NO:2309:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2309:

UUAAAGUCCC GGAUG                                                   15

(2) INFORMATION FOR SEQ ID NO:2310:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2310:

UGGGCAUCCU CAUCA                                                   15

(2) INFORMATION FOR SEQ ID NO:2311:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2311:

UCCUCAUCAC CAUUU                                                   15

(2) INFORMATION FOR SEQ ID NO:2312:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2312:

UCACCAUUUU CGGGG                                                   15

(2) INFORMATION FOR SEQ ID NO:2313:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2313:

UCACCAUUUU CGGGG                                                   15

(2) INFORMATION FOR SEQ ID NO:2314:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2314:

ACCAUUUUCG GGGUG                                                   15

(2) INFORMATION FOR SEQ ID NO:2315:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2315:

```
CCAUUUUCGG GGUGU                                                          15

(2) INFORMATION FOR SEQ ID NO:2316:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2316:

CCAUUUUCGG GGUGU                                                          15

(2) INFORMATION FOR SEQ ID NO:2317:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2317:

CCAUUUUCGG GGUGU                                                          15

(2) INFORMATION FOR SEQ ID NO:2318:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2318:

UGUUUCUCUA UAUCA                                                          15

(2) INFORMATION FOR SEQ ID NO:2319:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2319:

UUUCUCUAUA UCAAA                                                          15

(2) INFORMATION FOR SEQ ID NO:2320:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2320:

UCUCUAUAUC AAAAA                                                          15

(2) INFORMATION FOR SEQ ID NO:2321:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2321:
```

```
                                    -continued
UCUAUAUCAA AAAGG                                                          15

(2) INFORMATION FOR SEQ ID NO:2322:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2322:

GGAAGAUUAU CCCGG                                                          15

(2) INFORMATION FOR SEQ ID NO:2323:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2323:

CGCUGCUCCA GUGCA                                                          15

(2) INFORMATION FOR SEQ ID NO:2324:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2324:

AGCCUGUCAC ACAGG                                                          15

(2) INFORMATION FOR SEQ ID NO:2325:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2325:

AGCCUGUCAC ACAGG                                                          15

(2) INFORMATION FOR SEQ ID NO:2326:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2326:

AGAGAGUCGC AUCUC                                                          15

(2) INFORMATION FOR SEQ ID NO:2327:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2327:

GUCGCAUCUC AGUGC                                                          15
```

(2) INFORMATION FOR SEQ ID NO:2328:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2328:

CGCAUCUCAG UGCAG                                        15

(2) INFORMATION FOR SEQ ID NO:2329:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2329:

CCCUGGUCUG AACCC                                        15

(2) INFORMATION FOR SEQ ID NO:2330:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2330:

GGCUGCUUGC UGACC                                        15

(2) INFORMATION FOR SEQ ID NO:2331:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2331:

CUCAACUUGC UUUUU                                        15

(2) INFORMATION FOR SEQ ID NO:2332:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2332:

UUGCUUUUUA AGGAU                                        15

(2) INFORMATION FOR SEQ ID NO:2333:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2333:

UUGCUUUUUA AGGAU                                        15

(2) INFORMATION FOR SEQ ID NO:2334:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2334:

GAAAGCUCGG GCAUC                                                      15

(2) INFORMATION FOR SEQ ID NO:2335:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2335:

CAGUGAUAUC UACCA                                                      15

(2) INFORMATION FOR SEQ ID NO:2336:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2336:

GAUAUCUACC AAGUG                                                      15

(2) INFORMATION FOR SEQ ID NO:2337:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2337:

CCAGAGUUGU CUUGC                                                      15

(2) INFORMATION FOR SEQ ID NO:2338:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2338:

GAGUUGUCUU GCUGC                                                      15

(2) INFORMATION FOR SEQ ID NO:2339:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO:2339:

GUUGUCUUGC UGCGG                                                      15

(2) INFORMATION FOR SEQ ID NO:2340:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2340:

GCGGCGUUCA CUGUA                                            15

(2) INFORMATION FOR SEQ ID NO:2341:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2341:

CGGCGUUCAC UGUAA                                            15

(2) INFORMATION FOR SEQ ID NO:2342:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2342:

CGUGGCUACA GGAGU                                            15

(2) INFORMATION FOR SEQ ID NO:2343:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2343:

CGUGGCUACA GGAGU                                            15

(2) INFORMATION FOR SEQ ID NO:2344:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2344:

CGCAGCUUGU GCUCG                                            15

(2) INFORMATION FOR SEQ ID NO:2345:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2345:

ACCUGGUUGC CAUCA                                            15

(2) INFORMATION FOR SEQ ID NO:2346:

```
    (i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2346:

UGUAAUUAUU UAUAC                                                        15

(2) INFORMATION FOR SEQ ID NO:2347:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2347:

GGCAUCUCAG AAACU                                                        15

(2) INFORMATION FOR SEQ ID NO:2348:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2348:

GGCAUCUCAG AAACU                                                        15

(2) INFORMATION FOR SEQ ID NO:2349:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2349:

AGAAACUCUA GCAGG                                                        15

(2) INFORMATION FOR SEQ ID NO:2350:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2350:

AACAGGUAGU GGAAU                                                        15

(2) INFORMATION FOR SEQ ID NO:2351:

(i) SEQUENCE CHARACTERISTICS:
        (A) LENGTH:       15 base pairs
        (B) TYPE:         nucleic acid
        (C) STRANDEDNESS: single
        (D) TOPOLOGY:     linear (xi) SEQUENCE DESCRIPTION: SEQ ID NO:2351:

AGGAGCUUGC UGCCC                                                        15

(2) INFORMATION FOR SEQ ID NO:2352:
```

```
        (i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2352:

UUUUGAUCCC UGGGA                                                    15

(2) INFORMATION FOR SEQ ID NO:2353:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2353:

GGGACUUCAU GGUAA                                                    15

(2) INFORMATION FOR SEQ ID NO:2354:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2354:

GGGACUUCAU GGUAA                                                    15

(2) INFORMATION FOR SEQ ID NO:2355:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2355:

UUGUCAUUUG ACCUC                                                    15

(2) INFORMATION FOR SEQ ID NO:2356:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2356:

GUAAUGUACC CCGUG                                                    15

(2) INFORMATION FOR SEQ ID NO:2357:

(i) SEQUENCE CHARACTERISTICS:
            (A) LENGTH:        15 base pairs
            (B) TYPE:          nucleic acid
            (C) STRANDEDNESS:  single
            (D) TOPOLOGY:      linear (xi) SEQUENCE DESCRIPTION: SEQ ID NO:2357:

CACAUAUCCU AAAAU                                                    15

(2) INFORMATION FOR SEQ ID NO:2358:

(i) SEQUENCE CHARACTERISTICS:
```

```
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2358:

GUGGUGUAUU GUAGA                                                         15

(2) INFORMATION FOR SEQ ID NO:2359:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2359:

GUAUUGUAGA AAUUA                                                         15

(2) INFORMATION FOR SEQ ID NO:2360:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2360:

AUUAUUUAAU CCGCC                                                         15

(2) INFORMATION FOR SEQ ID NO:2361:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2361:

AUUAUUUAAU CCGCC                                                         15

(2) INFORMATION FOR SEQ ID NO:2362:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO:2362:

CUGGGUUUCU ACCUG                                                         15

(2) INFORMATION FOR SEQ ID NO:2363:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2363:

CGAGGCACUG AUGAGGCCGA AAGGCCGAAA GACACC                                  36

(2) INFORMATION FOR SEQ ID NO:2364:

(i) SEQUENCE CHARACTERISTICS:
        (A) LENGTH:        36 base pairs
```

```
        (B) TYPE:           nucleic acid
        (C) STRANDEDNESS:   single
        (D) TOPOLOGY:       linear (xi) SEQUENCE DESCRIPTION: SEQ ID NO:2364:

CGAGGCACUG AUGAGGCCGA AAGGCCGAAA GACACC                                  36

(2) INFORMATION FOR SEQ ID NO:2365:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2365:

CACAGCCCUG AUGAGGCCGA AAGGCCGAAA GGCAAA                                  36

(2) INFORMATION FOR SEQ ID NO:2366:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2366:

AGCCCCACUG AUGAGGCCGA AAGGCCGAAA GCGCGC                                  36

(2) INFORMATION FOR SEQ ID NO:2367:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2367:

CUAGAUGCUG AUGAGGCCGA AAGGCCGAAA CCGCUG                                  36

(2) INFORMATION FOR SEQ ID NO:2368:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2368:

CUAGAUGCUG AUGAGGCCGA AAGGCCGAAA CCGCUG                                  36

(2) INFORMATION FOR SEQ ID NO:2369:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2369:

UGCCCUACUG AUGAGGCCGA AAGGCCGAAA UGGACC                                  36

(2) INFORMATION FOR SEQ ID NO:2370:

(i) SEQUENCE CHARACTERISTICS:
        (A) LENGTH:         36 base pairs
        (B) TYPE:           nucleic acid
```

```
            (C) STRANDEDNESS:    single
            (D) TOPOLOGY:        linear (xi) SEQUENCE DESCRIPTION: SEQ ID NO:2370:

UGCACGUCUG AUGAGGCCGA AAGGCCGAAA CACACU                              36

(2) INFORMATION FOR SEQ ID NO:2371:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2371:

UGCACGUCUG AUGAGGCCGA AAGGCCGAAA CACACU                              36

(2) INFORMATION FOR SEQ ID NO:2372:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2372:

CUGCACGCUG AUGAGGCCGA AAGGCCGAAA ACACAC                              36

(2) INFORMATION FOR SEQ ID NO:2373:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2373:

GUGGAGGCUG AUGAGGCCGA AAGGCCGAAA CUGUUU                              36

(2) INFORMATION FOR SEQ ID NO:2374:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2374:

UGGCACACUG AUGAGGCCGA AAGGCCGAAA UCACAG                              36

(2) INFORMATION FOR SEQ ID NO:2375:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2375:

CUGGCACCUG AUGAGGCCGA AAGGCCGAAA AUCACA                              36

(2) INFORMATION FOR SEQ ID NO:2376:

(i) SEQUENCE CHARACTERISTICS:
            (A) LENGTH:          36 base pairs
            (B) TYPE:            nucleic acid
            (C) STRANDEDNESS:    single
```

(D) TOPOLOGY: linear (xi) SEQUENCE DESCRIPTION: SEQ ID NO:2376:

UCUUCUCCUG AUGAGGCCGA AAGGCCGAAA GAGCUG                                          36

(2) INFORMATION FOR SEQ ID NO:2377:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2377:

GGCUGAGCUG AUGAGGCCGA AAGGCCGAAA UUCGCC                                          36

(2) INFORMATION FOR SEQ ID NO:2378:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2378:

GGGCUGACUG AUGAGGCCGA AAGGCCGAAA AUUCGC                                          36

(2) INFORMATION FOR SEQ ID NO:2379:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2379:

GACAGCGCUG AUGAGGCCGA AAGGCCGAAA UCUCCC                                          36

(2) INFORMATION FOR SEQ ID NO:2380:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2380:

AGCCCUUCUG AUGAGGCCGA AAGGCCGAAA UUGGGU                                          36

(2) INFORMATION FOR SEQ ID NO:2381:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2381:

AGCCCUUCUG AUGAGGCCGA AAGGCCGAAA UUGGGU                                          36

(2) INFORMATION FOR SEQ ID NO:2382:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2382:

UAACCCGCUG AUGAGGCCGA AAGGCCGAAA GCCCUU                                    36

(2) INFORMATION FOR SEQ ID NO:2383:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2383:

UAACCCGCUG AUGAGGCCGA AAGGCCGAAA GCCCUU                                    36

(2) INFORMATION FOR SEQ ID NO:2384:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2384:

UUAACCCCUG AUGAGGCCGA AAGGCCGAAA AGCCCU                                    36

(2) INFORMATION FOR SEQ ID NO:2385:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2385:

CCUUCUUCUG AUGAGGCCGA AAGGCCGAAA CCCGAA                                    36

(2) INFORMATION FOR SEQ ID NO:2386:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2386:

CCUUCUUCUG AUGAGGCCGA AAGGCCGAAA CCCGAA                                    36

(2) INFORMATION FOR SEQ ID NO:2387:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2387:

AGGUACACUG AUGAGGCCGA AAGGCCGAAA CAGUGU                                    36

(2) INFORMATION FOR SEQ ID NO:2388:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2388:

GCCUCGCCUG AUGAGGCCGA AAGGCCGAAA UCCUUG                              36

(2) INFORMATION FOR SEQ ID NO:2389:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2389:

AGCCAGGCUG AUGAGGCCGA AAGGCCGAAA UACAGG                              36

(2) INFORMATION FOR SEQ ID NO:2390:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2390:

AACUCCACUG AUGAGGCCGA AAGGCCGAAA GCCAGG                              36

(2) INFORMATION FOR SEQ ID NO:2391:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2391:

AACUCCACUG AUGAGGCCGA AAGGCCGAAA GCCAGG                              36

(2) INFORMATION FOR SEQ ID NO:2392:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2392:

UAACUCCCUG AUGAGGCCGA AAGGCCGAAA AGCCAG                              36

(2) INFORMATION FOR SEQ ID NO:2393:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2393:

CAGACGGCUG AUGAGGCCGA AAGGCCGAAA UCAGUG                              36

(2) INFORMATION FOR SEQ ID NO:2394:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2394:

GAUGACACUG AUGAGGCCGA AAGGCCGAAA CGGUAU                                36

(2) INFORMATION FOR SEQ ID NO:2395:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2395:

GAUGACACUG AUGAGGCCGA AAGGCCGAAA CGGUAU                                36

(2) INFORMATION FOR SEQ ID NO:2396:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2396:

GGGCAGGCUG AUGAGGCCGA AAGGCCGAAA UGACAG                                36

(2) INFORMATION FOR SEQ ID NO:2397:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2397:

AGAAGCCCUG AUGAGGCCGA AAGGCCGAAA CUGGGC                                36

(2) INFORMATION FOR SEQ ID NO:2398:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2398:

AGAAGCCCUG AUGAGGCCGA AAGGCCGAAA CUGGGC                                36

(2) INFORMATION FOR SEQ ID NO:2399:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2399:

GGAGAAGCUG AUGAGGCCGA AAGGCCGAAA GCCGAC                                36

(2) INFORMATION FOR SEQ ID NO:2400:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2400:

UGGAGAACUG AUGAGGCCGA AAGGCCGAAA AGCCGA    36

(2) INFORMATION FOR SEQ ID NO:2401:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2401:

AUUGGAGCUG AUGAGGCCGA AAGGCCGAAA GAAGCC    36

(2) INFORMATION FOR SEQ ID NO:2402:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2402:

GAUUGGACUG AUGAGGCCGA AAGGCCGAAA AGAAGC    36

(2) INFORMATION FOR SEQ ID NO:2403:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2403:

CUGAUUGCUG AUGAGGCCGA AAGGCCGAAA GAAGAA    36

(2) INFORMATION FOR SEQ ID NO:2404:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2404:

AAGUGAUCUG AUGAGGCCGA AAGGCCGAAA CUGAUU    36

(2) INFORMATION FOR SEQ ID NO:2405:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2405:

AAGUGAUCUG AUGAGGCCGA AAGGCCGAAA CUGAUU    36

(2) INFORMATION FOR SEQ ID NO:2406:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2406:

UUUCGAACUG AUGAGGCCGA AAGGCCGAAA GUGAUG    36

(2) INFORMATION FOR SEQ ID NO:2407:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2407:

UUUUCGACUG AUGAGGCCGA AAGGCCGAAA AGUGAU                              36

(2) INFORMATION FOR SEQ ID NO:2408:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2408:

CUUUUCGCUG AUGAGGCCGA AAGGCCGAAA AAGUGA                              36

(2) INFORMATION FOR SEQ ID NO:2409:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2409:

CUUUUCGCUG AUGAGGCCGA AAGGCCGAAA AAGUGA                              36

(2) INFORMATION FOR SEQ ID NO:2410:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2410:

CAGGGAUCUG AUGAGGCCGA AAGGCCGAAA CACUUU                              36

(2) INFORMATION FOR SEQ ID NO:2411:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2411:

CACAGAUCUG AUGAGGCCGA AAGGCCGAAA CAUUAG                              36

(2) INFORMATION FOR SEQ ID NO:2412:

(i) SEQUENCE CHARACTERISTICS:
        (A) LENGTH:       36 base pairs
        (B) TYPE:         nucleic acid
        (C) STRANDEDNESS:  single
        (D) TOPOLOGY:     linear (xi) SEQUENCE DESCRIPTION: SEQ ID NO:2412:

AACCACACUG AUGAGGCCGA AAGGCCGAAA UGACAU                              36

(2) INFORMATION FOR SEQ ID NO:2413:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2413:

GGGACUUCUG AUGAGGCCGA AAGGCCGAAA AACCAC                                  36

(2) INFORMATION FOR SEQ ID NO:2414:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2414:

GGGACUUCUG AUGAGGCCGA AAGGCCGAAA AACCAC                                  36

(2) INFORMATION FOR SEQ ID NO:2415:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2415:

CAUCCGGCUG AUGAGGCCGA AAGGCCGAAA CUUUAA                                  36

(2) INFORMATION FOR SEQ ID NO:2416:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2416:

UGAUGAGCUG AUGAGGCCGA AAGGCCGAAA UGCCCA                                  36

(2) INFORMATION FOR SEQ ID NO:2417:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2417:

AAAUGGUCUG AUGAGGCCGA AAGGCCGAAA UGAGGA                                  36

(2) INFORMATION FOR SEQ ID NO:2418:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2418:

CCCCGAACUG AUGAGGCCGA AAGGCCGAAA UGGUGA                                  36

(2) INFORMATION FOR SEQ ID NO:2419:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2419:

CCCCGAACUG AUGAGGCCGA AAGGCCGAAA UGGUGA                                36

(2) INFORMATION FOR SEQ ID NO:2420:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2420:

CACCCCGCUG AUGAGGCCGA AAGGCCGAAA AAUGGU                                36

(2) INFORMATION FOR SEQ ID NO:2421:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2421:

ACACCCCCUG AUGAGGCCGA AAGGCCGAAA AAAUGG                                36

(2) INFORMATION FOR SEQ ID NO:2422:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2422:

ACACCCCCUG AUGAGGCCGA AAGGCCGAAA AAAUGG                                36

(2) INFORMATION FOR SEQ ID NO:2423:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2423:

ACACCCCCUG AUGAGGCCGA AAGGCCGAAA AAAUGG                                36

(2) INFORMATION FOR SEQ ID NO:2424:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2424:

UGAUAUACUG AUGAGGCCGA AAGGCCGAAA GAAACA                                36

(2) INFORMATION FOR SEQ ID NO:2425:

```
    (i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2425:

UUUGAUACUG AUGAGGCCGA AAGGCCGAAA GAGAAA                          36

(2) INFORMATION FOR SEQ ID NO:2426:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2426:

UUUUUGACUG AUGAGGCCGA AAGGCCGAAA UAGAGA                          36

(2) INFORMATION FOR SEQ ID NO:2427:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2427:

CCUUUUUCUG AUGAGGCCGA AAGGCCGAAA UAUAGA                          36

(2) INFORMATION FOR SEQ ID NO:2428:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2428:

CCGGGAUCUG AUGAGGCCGA AAGGCCGAAA UCUUCC                          36

(2) INFORMATION FOR SEQ ID NO:2429:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2429:

UGCACUGCUG AUGAGGCCGA AAGGCCGAAA GCAGCG                          36

(2) INFORMATION FOR SEQ ID NO:2430:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO:2430:

CCUGUGUCUG AUGAGGCCGA AAGGCCGAAA CAGGCU                          36

(2) INFORMATION FOR SEQ ID NO:2431:
```

```
    (i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2431:

CCUGUGUCUG AUGAGGCCGA AAGGCCGAAA CAGGCU                                36

(2) INFORMATION FOR SEQ ID NO:2432:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2432:

GAGAUGCCUG AUGAGGCCGA AAGGCCGAAA CUCUCU                                36

(2) INFORMATION FOR SEQ ID NO:2433:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2433:

GCACUGACUG AUGAGGCCGA AAGGCCGAAA UGCGAC                                36

(2) INFORMATION FOR SEQ ID NO:2434:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2434:

CUGCACUCUG AUGAGGCCGA AAGGCCGAAA GAUGCG                                36

(2) INFORMATION FOR SEQ ID NO:2435:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2435:

GGGUUCACUG AUGAGGCCGA AAGGCCGAAA CCAGGG                                36

(2) INFORMATION FOR SEQ ID NO:2436:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2436:

GGUCAGCCUG AUGAGGCCGA AAGGCCGAAA GCAGCC                                36

(2) INFORMATION FOR SEQ ID NO:2437:

(i) SEQUENCE CHARACTERISTICS:
```

(A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:2437:

AAAAAGCCUG AUGAGGCCGA AAGGCCGAAA GUUGAG                              36

(2) INFORMATION FOR SEQ ID NO:2438:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:2438:

AUCCUUACUG AUGAGGCCGA AAGGCCGAAA AAGCAA                              36

(2) INFORMATION FOR SEQ ID NO:2439:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:2439:

AUCCUUACUG AUGAGGCCGA AAGGCCGAAA AAGCAA                              36

(2) INFORMATION FOR SEQ ID NO:2440:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:2440:

GAUGCCCCUG AUGAGGCCGA AAGGCCGAAA GCUUUC                              36

(2) INFORMATION FOR SEQ ID NO:2441:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:2441:

UGGUAGACUG AUGAGGCCGA AAGGCCGAAA UCACUG                              36

(2) INFORMATION FOR SEQ ID NO:2442:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO:2442:

CACUUGGCUG AUGAGGCCGA AAGGCCGAAA GAUAUC                              36

(2) INFORMATION FOR SEQ ID NO:2443:

(i) SEQUENCE CHARACTERISTICS:
            (A) LENGTH:           36 base pairs

```
            (B) TYPE:          nucleic acid
            (C) STRANDEDNESS:  single
            (D) TOPOLOGY:      linear (xi) SEQUENCE DESCRIPTION: SEQ ID NO:2443:

GCAAGACCUG AUGAGGCCGA AAGGCCGAAA CUCUGG                                36

(2) INFORMATION FOR SEQ ID NO:2444:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2444:

GCAGCAACUG AUGAGGCCGA AAGGCCGAAA CAACUC                                36

(2) INFORMATION FOR SEQ ID NO:2445:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2445:

CCGCAGCCUG AUGAGGCCGA AAGGCCGAAA GACAAC                                36

(2) INFORMATION FOR SEQ ID NO:2446:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2446:

UACAGUGCUG AUGAGGCCGA AAGGCCGAAA CGCCGC                                36

(2) INFORMATION FOR SEQ ID NO:2447:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2447:

UUACAGUCUG AUGAGGCCGA AAGGCCGAAA ACGCCG                                36

(2) INFORMATION FOR SEQ ID NO:2448:

(i) SEQUENCE CHARACTERISTICS:
            (A) LENGTH:        36 base pairs
            (B) TYPE:          nucleic acid
            (C) STRANDEDNESS:  single
            (D) TOPOLOGY:      linear (xi) SEQUENCE DESCRIPTION: SEQ ID NO:2448:

ACUCCUGCUG AUGAGGCCGA AAGGCCGAAA GCCACG                                36

(2) INFORMATION FOR SEQ ID NO:2449:

(i) SEQUENCE CHARACTERISTICS:
            (A) LENGTH:        36 base pairs
            (B) TYPE:          nucleic acid
```

```
            (C) STRANDEDNESS:    single
            (D) TOPOLOGY:        linear (xi) SEQUENCE DESCRIPTION: SEQ ID NO:2449:

ACUCCUGCUG AUGAGGCCGA AAGGCCGAAA GCCACG                                  36

(2) INFORMATION FOR SEQ ID NO:2450:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2450:

CGAGCACCUG AUGAGGCCGA AAGGCCGAAA GCUGCG                                  36

(2) INFORMATION FOR SEQ ID NO:2451:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2451:

UGAUGGCCUG AUGAGGCCGA AAGGCCGAAA CCAGGU                                  36

(2) INFORMATION FOR SEQ ID NO:2452:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2452:

GUAUAAACUG AUGAGGCCGA AAGGCCGAAA AUUACA                                  36

(2) INFORMATION FOR SEQ ID NO:2453:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2453:

AGUUUCUCUG AUGAGGCCGA AAGGCCGAAA GAUGCC                                  36

(2) INFORMATION FOR SEQ ID NO:2454:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO:2454:

AGUUUCUCUG AUGAGGCCGA AAGGCCGAAA GAUGCC                                  36

(2) INFORMATION FOR SEQ ID NO:2455:

(i) SEQUENCE CHARACTERISTICS:
            (A) LENGTH:          36 base pairs
            (B) TYPE:            nucleic acid
            (C) STRANDEDNESS:    single
```

-continued (D) TOPOLOGY:     linear (xi) SEQUENCE DESCRIPTION: SEQ ID NO:2455:

CCUGCUACUG AUGAGGCCGA AAGGCCGAAA GUUUCU                           36

(2) INFORMATION FOR SEQ ID NO:2456:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:2456:

AUUCCACCUG AUGAGGCCGA AAGGCCGAAA CCUGUU                           36

(2) INFORMATION FOR SEQ ID NO:2457:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:2457:

GGGCAGCCUG AUGAGGCCGA AAGGCCGAAA GCUCCU                           36

(2) INFORMATION FOR SEQ ID NO:2458:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:2458:

UCCCAGGCUG AUGAGGCCGA AAGGCCGAAA UCAAAA                           36

(2) INFORMATION FOR SEQ ID NO:2459:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:2459:

UUACCAUCUG AUGAGGCCGA AAGGCCGAAA AGUCCC                           36

(2) INFORMATION FOR SEQ ID NO:2460:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:2460:

UUACCAUCUG AUGAGGCCGA AAGGCCGAAA AGUCCC                           36

(2) INFORMATION FOR SEQ ID NO:2461:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO:2461:

GAGGUCACUG AUGAGGCCGA AAGGCCGAAA UGACAA                                    36

(2) INFORMATION FOR SEQ ID NO:2462:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2462:

CACGGGGCUG AUGAGGCCGA AAGGCCGAAA CAUUAC                                    36

(2) INFORMATION FOR SEQ ID NO:2463:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2463:

AUUUUAGCUG AUGAGGCCGA AAGGCCGAAA UAUGUG                                    36

(2) INFORMATION FOR SEQ ID NO:2464:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2464:

UCUACAACUG AUGAGGCCGA AAGGCCGAAA CACCAC                                    36

(2) INFORMATION FOR SEQ ID NO:2465:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2465:

UAAUUUCCUG AUGAGGCCGA AAGGCCGAAA CAAUAC                                    36

(2) INFORMATION FOR SEQ ID NO:2466:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2466:

GGCGGAUCUG AUGAGGCCGA AAGGCCGAAA AAUAAU                                    36

(2) INFORMATION FOR SEQ ID NO:2467:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO:2467:

GGCGGAUCUG AUGAGGCCGA AAGGCCGAAA AAUAAU 36

(2) INFORMATION FOR SEQ ID NO:2468:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2468:

CAGGUAGCUG AUGAGGCCGA AAGGCCGAAA ACCCAG 36

(2) INFORMATION FOR SEQ ID NO:2469:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2469:

ACAGGCAGAG AAGAUGACAC CAGAGAAACA CACGUUGUGG UACAUUACCU GGUA 54

(2) INFORMATION FOR SEQ ID NO:2470:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2470:

GCAAAACAAG AAGGGCUGAC CAGAGAAACA CACGUUGUGG UACAUUACCU GGUA 54

(2) INFORMATION FOR SEQ ID NO:2471:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2471:

AGGUGCAAAG AAGGCAGGAC CAGAGAAACA CACGUUGUGG UACAUUACCU GGUA 54

(2) INFORMATION FOR SEQ ID NO:2472:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2472:

GCACCAAGAG AAGAAAGAAC CAGAGAAACA CACGUUGUGG UACAUUACCU GGUA 54

(2) INFORMATION FOR SEQ ID NO:2473:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2473:

AACACCUGAG AAGAAGUGAC CAGAGAAACA CACGUUGUGG UACAUUACCU GGUA         54

(2) INFORMATION FOR SEQ ID NO:2474:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2474:

GACCACAGAG AAGCGUUGAC CAGAGAAACA CACGUUGUGG UACAUUACCU GGUA         54

(2) INFORMATION FOR SEQ ID NO:2475:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2475:

AGCUCUUCAG AAGAAACAAC CAGAGAAACA CACGUUGUGG UACAUUACCU GGUA         54

(2) INFORMATION FOR SEQ ID NO:2476:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2476:

ACAUCAUAAG AAGCACCAAC CAGAGAAACA CACGUUGUGG UACAUUACCU GGUA         54

(2) INFORMATION FOR SEQ ID NO:2477:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2477:

CAAAGAUGAG AAGGUUCUAC CAGAGAAACA CACGUUGUGG UACAUUACCU GGUA         54

(2) INFORMATION FOR SEQ ID NO:2478:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2478:

GUGCCCUCAG AAGAUGGGAC CAGAGAAACA CACGUUGUGG UACAUUACCU GGUA         54

(2) INFORMATION FOR SEQ ID NO:2479:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2479:

```
GUAGGGAAAG AAGCUUUGAC CAGAGAAACA CACGUUGUGG UACAUUACCU GGUA        54

(2) INFORMATION FOR SEQ ID NO:2480:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2480:

AUUUCAAAAG AAGAUAUAAC CAGAGAAACA CACGUUGUGG UACAUUACCU GGUA        54

(2) INFORMATION FOR SEQ ID NO:2481:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2481:

UCUUGGGAAG AAGUUGUGAC CAGAGAAACA CACGUUGUGG UACAUUACCU GGUA        54

(2) INFORMATION FOR SEQ ID NO:2482:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2482:

ACACAUGAAG AAGUGGUUAC CAGAGAAACA CACGUUGUGG UACAUUACCU GGUA        54

(2) INFORMATION FOR SEQ ID NO:2483:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2483:

AGUUGAAGAG AAGAUUCAAC CAGAGAAACA CACGUUGUGG UACAUUACCU GGUA        54

(2) INFORMATION FOR SEQ ID NO:2484:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2484:

AGGAUGGGAG AAGGUUAUAC CAGAGAAACA CACGUUGUGG UACAUUACCU GGUA        54

(2) INFORMATION FOR SEQ ID NO:2485:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2485:

GUAGGUCAAG AAGCAUAUAC CAGAGAAACA CACGUUGUGG UACAUUACCU GGUA        54
```

(2) INFORMATION FOR SEQ ID NO:2486:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2486:

AGCAGUAGAG AAGGCAGCAC CAGAGAAACA CACGUUGUGG UACAUUACCU GGUA       54

(2) INFORMATION FOR SEQ ID NO:2487:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2487:

UGGGGCAAAG AAGUAGGUAC CAGAGAAACA CACGUUGUGG UACAUUACCU GGUA       54

(2) INFORMATION FOR SEQ ID NO:2488:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2488:

GUGGGUAAAG AAGCUUAAAC CAGAGAAACA CACGUUGUGG UACAUUACCU GGUA       54

(2) INFORMATION FOR SEQ ID NO:2489:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2489:

UCAGCUUAAG AAGAAAGAAC CAGAGAAACA CACGUUGUGG UACAUUACCU GGUA       54

(2) INFORMATION FOR SEQ ID NO:2490:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO:2490:

GUCAUCAGCC CUGCCUGU       18

(2) INFORMATION FOR SEQ ID NO:2491:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO:2491:

CAGCCCUGCC UGUUUUGC       18

(2) INFORMATION FOR SEQ ID NO:2492:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2492:

CCUGCCUGUU UUGCACCU                                                      18

(2) INFORMATION FOR SEQ ID NO:2493:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2493:

UCUUUCAGCU CUUGGUGC                                                      18

(2) INFORMATION FOR SEQ ID NO:2494:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2494:

CACUUCUGUU CAGGUGUU                                                      18

(2) INFORMATION FOR SEQ ID NO:2495:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2495:

CAACGCUGUC CUGUGGUC                                                      18

(2) INFORMATION FOR SEQ ID NO:2496:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2496:

UGUUUCUGUU GAAGAGCU                                                      18

(2) INFORMATION FOR SEQ ID NO:2497:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2497:

UGGUGCUGAC UAUGAUGU                                                      18

(2) INFORMATION FOR SEQ ID NO:2498:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2498:

AGAACCGGAC CAUCUUUG                                                      18

(2) INFORMATION FOR SEQ ID NO:2499:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2499:

CCCAUCUGAC GAGGGCAC                                                      18

(2) INFORMATION FOR SEQ ID NO:2500:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2500:

CAAAGCUGAC UUCCCUAC                                                      18

(2) INFORMATION FOR SEQ ID NO:2501:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2501:

UAUAUCUGAC UUUGAAAU                                                      18

(2) INFORMATION FOR SEQ ID NO:2502:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2502:

CACAACAGUU UCCCAAGA                                                      18

(2) INFORMATION FOR SEQ ID NO:2503:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2503:

AACCACAGCU UCAUGUGU                                                      18

(2) INFORMATION FOR SEQ ID NO:2504:

```
      (i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2504:

UGAAUCAGAC CUUCAACU                                                18

(2) INFORMATION FOR SEQ ID NO:2505:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2505:

AUAACCUGCU CCCAUCCU                                                18

(2) INFORMATION FOR SEQ ID NO:2506:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2506:

AUAUGCUGCC UGACCUAC                                                18

(2) INFORMATION FOR SEQ ID NO:2507:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2507:

GCUGCCUGAC CUACUGCU                                                18

(2) INFORMATION FOR SEQ ID NO:2508:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2508:

ACCUACUGCU UUGCCCCA                                                18

(2) INFORMATION FOR SEQ ID NO:2509:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2509:

UUAAGCUGUU UUACCCAC                                                18

(2) INFORMATION FOR SEQ ID NO:2510:
```

```
    (i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2510:

UCUUUCAGAU UAAGCUGA                                                    18

(2) INFORMATION FOR SEQ ID NO:2511:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2511:

AGAAAUGGAG AAGAGUGUAC CAGAGAAACA CACGUUGUGG UACAUUACCU GGUA            54

(2) INFORMATION FOR SEQ ID NO:2512:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2512:

AUCCACCCAG AAGAUGCUAC CAGAGAAACA CACGUUGUGG UACAUUACCU GGUA            54

(2) INFORMATION FOR SEQ ID NO:2513:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2513:

AAUCGAGAAG AAGAGAUGAC CAGAGAAACA CACGUUGUGG UACAUUACCU GGUA            54

(2) INFORMATION FOR SEQ ID NO:2514:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2514:

CCUGCAUCAG AAGACAAUAC CAGAGAAACA CACGUUGUGG UACAUUACCU GGUA            54

(2) INFORMATION FOR SEQ ID NO:2515:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2515:

GACGAAUCAG AAGCACAAAC CAGAGAAACA CACGUUGUGG UACAUUACCU GGUA            54

(2) INFORMATION FOR SEQ ID NO:2516:

(i) SEQUENCE CHARACTERISTICS:
```

```
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2516:

AAAGACGAAG AAGCAGCAAC CAGAGAAACA CACGUUGUGG UACAUUACCU GGUA         54

(2) INFORMATION FOR SEQ ID NO:2517:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2517:

UCAUCAACAG AAGAAGACAC CAGAGAAACA CACGUUGUGG UACAUUACCU GGUA         54

(2) INFORMATION FOR SEQ ID NO:2518:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2518:

CUGACUUGAG AAGUUGUUAC CAGAGAAACA CACGUUGUGG UACAUUACCU GGUA         54

(2) INFORMATION FOR SEQ ID NO:2519:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2519:

AACGGCAAAG AAGCAAUAAC CAGAGAAACA CACGUUGUGG UACAUUACCU GGUA         54

(2) INFORMATION FOR SEQ ID NO:2520:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2520:

CAAUGACAAG AAGCACCAAC CAGAGAAACA CACGUUGUGG UACAUUACCU GGUA         54

(2) INFORMATION FOR SEQ ID NO:2521:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2521:

CAUAUAAAAG AAGGUUCUAC CAGAGAAACA CACGUUGUGG UACAUUACCU GGUA         54

(2) INFORMATION FOR SEQ ID NO:2522:

(i) SEQUENCE CHARACTERISTICS:
            (A) LENGTH:         54 base pairs
```

```
            (B) TYPE:           nucleic acid
            (C) STRANDEDNESS:   single
            (D) TOPOLOGY:       linear (xi) SEQUENCE DESCRIPTION: SEQ ID NO:2522:

GUGCCCCGAG AAGAAAGGAC CAGAGAAACA CACGUUGUGG UACAUUACCU GGUA                54

(2) INFORMATION FOR SEQ ID NO:2523:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2523:

AACGACACAG AAGUAUGUAC CAGAGAAACA CACGUUGUGG UACAUUACCU GGUA                54

(2) INFORMATION FOR SEQ ID NO:2524:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2524:

GUAGAGAAAG AAGCUUUGAC CAGAGAAACA CACGUUGUGG UACAUUACCU GGUA                54

(2) INFORMATION FOR SEQ ID NO:2525:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2525:

GGAAGCAAAG AAGGUAAUAC CAGAGAAACA CACGUUGUGG UACAUUACCU GGUA                54

(2) INFORMATION FOR SEQ ID NO:2526:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2526:

AUGACGACAG AAGUUAUUAC CAGAGAAACA CACGUUGUGG UACAUUACCU GGUA                54

(2) INFORMATION FOR SEQ ID NO:2527:

(i) SEQUENCE CHARACTERISTICS:
            (A) LENGTH:         54 base pairs
            (B) TYPE:           nucleic acid
            (C) STRANDEDNESS:   single
            (D) TOPOLOGY:       linear (xi) SEQUENCE DESCRIPTION: SEQ ID NO:2527:

UCUUCUGAAG AAGCUUCUAC CAGAGAAACA CACGUUGUGG UACAUUACCU GGUA                54

(2) INFORMATION FOR SEQ ID NO:2528:

(i) SEQUENCE CHARACTERISTICS:
            (A) LENGTH:         54 base pairs
            (B) TYPE:           nucleic acid
```

```
            (C) STRANDEDNESS:    single
            (D) TOPOLOGY:        linear (xi) SEQUENCE DESCRIPTION: SEQ ID NO:2528:

GAAGGUAAAG AAGUUGUUAC CAGAGAAACA CACGUUGUGG UACAUUACCU GGUA          54

(2) INFORMATION FOR SEQ ID NO:2529:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2529:

GGAAGACGAG AAGUUCAGAC CAGAGAAACA CACGUUGUGG UACAUUACCU GGUA          54

(2) INFORMATION FOR SEQ ID NO:2530:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2530:

UAAAGGAAAG AAGUCUGUAC CAGAGAAACA CACGUUGUGG UACAUUACCU GGUA          54

(2) INFORMATION FOR SEQ ID NO:2531:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2531:

CCCACAUGAG AAGAGAAGAC CAGAGAAACA CACGUUGUGG UACAUUACCU GGUA          54

(2) INFORMATION FOR SEQ ID NO:2532:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2532:

UCCGAAAGAG AAGCUAGCAC CAGAGAAACA CACGUUGUGG UACAUUACCU GGUA          54

(2) INFORMATION FOR SEQ ID NO:2533:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2533:

CAGAAAAGAG AAGGCCUCAC CAGAGAAACA CACGUUGUGG UACAUUACCU GGUA          54

(2) INFORMATION FOR SEQ ID NO:2534:

(i) SEQUENCE CHARACTERISTICS:
            (A) LENGTH:          18 base pairs
            (B) TYPE:            nucleic acid
            (C) STRANDEDNESS:    single
```

(D) TOPOLOGY:        linear (xi) SEQUENCE DESCRIPTION: SEQ ID NO:2534:

ACACUCUGUU CCAUUUCU                                                 18

(2) INFORMATION FOR SEQ ID NO:2535:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2535:

AGCAUCUGCC GGGUGGAU                                                 18

(2) INFORMATION FOR SEQ ID NO:2536:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2536:

CAUCUCUGUU UCUCGAUU                                                 18

(2) INFORMATION FOR SEQ ID NO:2537:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2537:

AUUGUCAGUU GAUGCAGG                                                 18

(2) INFORMATION FOR SEQ ID NO:2538:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2538:

UUGUGCUGCU GAUUCGUC                                                 18

(2) INFORMATION FOR SEQ ID NO:2539:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2539:

UGCUGCUGAU UCGUCUUU                                                 18

(2) INFORMATION FOR SEQ ID NO:2540:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2540:

GUCUUCAGAU GUUGAUGA                                              18

(2) INFORMATION FOR SEQ ID NO:2541:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2541:

AACAACUGUC CAAGUCAG                                              18

(2) INFORMATION FOR SEQ ID NO:2542:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2542:

UAUUGCUGCC UUGCCGUU                                              18

(2) INFORMATION FOR SEQ ID NO:2543:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2543:

UGGUGCUGUC UGUCAUUG                                              18

(2) INFORMATION FOR SEQ ID NO:2544:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2544:

AGAACCGGAC UUUAUAUG                                              18

(2) INFORMATION FOR SEQ ID NO:2545:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2545:

CCUUUCAGAC CGGGGCAC                                              18

(2) INFORMATION FOR SEQ ID NO:2546:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2546:

ACAUACAGCU GUGUCGUU                                              18

(2) INFORMATION FOR SEQ ID NO:2547:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2547:

CAAAGCUGAC UUCUCUAC                                              18

(2) INFORMATION FOR SEQ ID NO:2548:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2548:

AUUACCUGCU UUGCUUCC                                              18

(2) INFORMATION FOR SEQ ID NO:2549:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2549:

AAUAACAGUC GUCGUCAU                                              18

(2) INFORMATION FOR SEQ ID NO:2550:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2550:

AGAAGCUGUU UCAGAAGA                                              18

(2) INFORMATION FOR SEQ ID NO:2551:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2551:

AACAACAGCC UUACCUUC                                              18

(2) INFORMATION FOR SEQ ID NO:2552:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2552:

CUGAACAGAC CGUCUUCC                                                              18

(2) INFORMATION FOR SEQ ID NO:2553:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2553:

ACAGACCGUC UUCCUUUA                                                              18

(2) INFORMATION FOR SEQ ID NO:2554:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2554:

CUUCUCUGUC CAUGUGGG                                                              18

(2) INFORMATION FOR SEQ ID NO:2555:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2555:

GCUAGCUGAU CUUUCGGA                                                              18

(2) INFORMATION FOR SEQ ID NO:2556:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2556:

GAGGCCUGCC CUUUUCUG                                                              18

(2) INFORMATION FOR SEQ ID NO:2557:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2557:

GUUACAGCAG AAGAGAAGAC CAGAGAAACA CACGUUGUGG UACAUUACCU GGUA                      54

(2) INFORMATION FOR SEQ ID NO:2558:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2558:

```
CCUGUUACAG AAGCAGAGAC CAGAGAAACA CACGUUGUGG UACAUUACCU GGUA          54

(2) INFORMATION FOR SEQ ID NO:2559:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2559:

CCCCACUCAG AAGUGUGUAC CAGAGAAACA CACGUUGUGG UACAUUACCU GGUA          54

(2) INFORMATION FOR SEQ ID NO:2560:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2560:

CACCAGAGAG AAGGAAGGAC CAGAGAAACA CACGUUGUGG UACAUUACCU GGUA          54

(2) INFORMATION FOR SEQ ID NO:2561:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2561:

UUCAGAGGAG AAGCACCAAC CAGAGAAACA CACGUUGUGG UACAUUACCU GGUA          54

(2) INFORMATION FOR SEQ ID NO:2562:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2562:

CAUGGCAGAG AAGCAGUCAC CAGAGAAACA CACGUUGUGG UACAUUACCU GGUA          54

(2) INFORMATION FOR SEQ ID NO:2563:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2563:

CAGGGUCCAG AAGUCCGAAC CAGAGAAACA CACGUUGUGG UACAUUACCU GGUA          54

(2) INFORMATION FOR SEQ ID NO:2564:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2564:

UGUCCUUGAG AAGAAGAUAC CAGAGAAACA CACGUUGUGG UACAUUACCU GGUA          54
```

(2) INFORMATION FOR SEQ ID NO:2565:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2565:

CAGAAUUCAG AAGGUGGAAC CAGAGAAACA CACGUUGUGG UACAUUACCU GGUA        54

(2) INFORMATION FOR SEQ ID NO:2566:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2566:

UAUAGAUGAG AAGGUCAAAC CAGAGAAACA CACGUUGUGG UACAUUACCU GGUA        54

(2) INFORMATION FOR SEQ ID NO:2567:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2567:

AACAGACAAG AAGAUGGAAC CAGAGAAACA CACGUUGUGG UACAUUACCU GGUA        54

(2) INFORMATION FOR SEQ ID NO:2568:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2568:

GGGAAUGAAG AAGACAAGAC CAGAGAAACA CACGUUGUGG UACAUUACCU GGUA        54

(2) INFORMATION FOR SEQ ID NO:2569:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2569:

CUCGUAACAG AAGGGAAUAC CAGAGAAACA CACGUUGUGG UACAUUACCU GGUA        54

(2) INFORMATION FOR SEQ ID NO:2570:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2570:

AAGAUAAAAG AAGCGUCUAC CAGAGAAACA CACGUUGUGG UACAUUACCU GGUA        54

(2) INFORMATION FOR SEQ ID NO:2571:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2571:

CUGGGGGAAG AAGAGGGUAC CAGAGAAACA CACGUUGUGG UACAUUACCU GGUA        54

(2) INFORMATION FOR SEQ ID NO:2572:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2572:

GGAAUGUGAG AAGGGGGAAC CAGAGAAACA CACGUUGUGG UACAUUACCU GGUA        54

(2) INFORMATION FOR SEQ ID NO:2573:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2573:

GGAAGUACAG AAGUAAUCAC CAGAGAAACA CACGUUGUGG UACAUUACCU GGUA        54

(2) INFORMATION FOR SEQ ID NO:2574:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2574:

UAGAAUUAAG AAGAAAACAC CAGAGAAACA CACGUUGUGG UACAUUACCU GGUA        54

(2) INFORMATION FOR SEQ ID NO:2575:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2575:

AGUUGCGAAG AAGCUUCUAC CAGAGAAACA CACGUUGUGG UACAUUACCU GGUA        54

(2) INFORMATION FOR SEQ ID NO:2576:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2576:

UUUUCUUGAG AAGUUCACAC CAGAGAAACA CACGUUGUGG UACAUUACCU GGUA        54

(2) INFORMATION FOR SEQ ID NO:2577:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2577:

UGGGCUUCAG AAGAUCUUAC CAGAGAAACA CACGUUGUGG UACAUUACCU GGUA        54

(2) INFORMATION FOR SEQ ID NO:2578:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2578:

CUUCUCUGCU GCUGUAAC        18

(2) INFORMATION FOR SEQ ID NO:2579:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2579:

CUCUGCUGCU GUAACAGG        18

(2) INFORMATION FOR SEQ ID NO:2580:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2580:

ACACACGGAU GAGUGGGG        18

(2) INFORMATION FOR SEQ ID NO:2581:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2581:

CCUUCCUGCU CUCUGGUG        18

(2) INFORMATION FOR SEQ ID NO:2582:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2582:

UGGUGCUGCU CCUCUGAA        18

(2) INFORMATION FOR SEQ ID NO:2583:

```
        (i) SEQUENCE CHARACTERISTICS:
              (A) LENGTH:         18 base pairs
              (B) TYPE:           nucleic acid
              (C) STRANDEDNESS:   single
              (D) TOPOLOGY:       linear (xi) SEQUENCE DESCRIPTION: SEQ ID NO:2583:

GACUGCAGAC CUGCCAUG                                                 18

(2) INFORMATION FOR SEQ ID NO:2584:

(i) SEQUENCE CHARACTERISTICS:
              (A) LENGTH:         18 base pairs
              (B) TYPE:           nucleic acid
              (C) STRANDEDNESS:   single
              (D) TOPOLOGY:       linear (xi) SEQUENCE DESCRIPTION: SEQ ID NO:2584:

UCGGACAGUU GGACCCUG                                                 18

(2) INFORMATION FOR SEQ ID NO:2585:

(i) SEQUENCE CHARACTERISTICS:
              (A) LENGTH:         18 base pairs
              (B) TYPE:           nucleic acid
              (C) STRANDEDNESS:   single
              (D) TOPOLOGY:       linear (xi) SEQUENCE DESCRIPTION: SEQ ID NO:2585:

AUCUUCAGAU CAAGGACA                                                 18

(2) INFORMATION FOR SEQ ID NO:2586:

(i) SEQUENCE CHARACTERISTICS:
              (A) LENGTH:         18 base pairs
              (B) TYPE:           nucleic acid
              (C) STRANDEDNESS:   single
              (D) TOPOLOGY:       linear (xi) SEQUENCE DESCRIPTION: SEQ ID NO:2586:

UCCACCAGAU GAAUUCUG                                                 18

(2) INFORMATION FOR SEQ ID NO:2587:

(i) SEQUENCE CHARACTERISTICS:
              (A) LENGTH:         18 base pairs
              (B) TYPE:           nucleic acid
              (C) STRANDEDNESS:   single
              (D) TOPOLOGY:       linear (xi) SEQUENCE DESCRIPTION: SEQ ID NO:2587:

UUGACCUGCU CAUCUAUA                                                 18

(2) INFORMATION FOR SEQ ID NO:2588:

(i) SEQUENCE CHARACTERISTICS:
              (A) LENGTH:         18 base pairs
              (B) TYPE:           nucleic acid
              (C) STRANDEDNESS:   single
              (D) TOPOLOGY:       linear (xi) SEQUENCE DESCRIPTION: SEQ ID NO:2588:

UCCAUCAGCU UGUCUGUU                                                 18

(2) INFORMATION FOR SEQ ID NO:2589:
```

(i) SEQUENCE CHARACTERISTICS:
            (A) LENGTH:         18 base pairs
            (B) TYPE:           nucleic acid
            (C) STRANDEDNESS:   single
            (D) TOPOLOGY:       linear (xi) SEQUENCE DESCRIPTION: SEQ ID NO:2589:

CUUGUCUGUU UCAUUCCC                                                           18

(2) INFORMATION FOR SEQ ID NO:2590:

(i) SEQUENCE CHARACTERISTICS:
            (A) LENGTH:         18 base pairs
            (B) TYPE:           nucleic acid
            (C) STRANDEDNESS:   single
            (D) TOPOLOGY:       linear (xi) SEQUENCE DESCRIPTION: SEQ ID NO:2590:

AUUCCCUGAU GUUACGAG                                                           18

(2) INFORMATION FOR SEQ ID NO:2591:

(i) SEQUENCE CHARACTERISTICS:
            (A) LENGTH:         18 base pairs
            (B) TYPE:           nucleic acid
            (C) STRANDEDNESS:   single
            (D) TOPOLOGY:       linear (xi) SEQUENCE DESCRIPTION: SEQ ID NO:2591:

AGACGCGGCU UUUAUCUU                                                           18

(2) INFORMATION FOR SEQ ID NO:2592:

(i) SEQUENCE CHARACTERISTICS:
            (A) LENGTH:         18 base pairs
            (B) TYPE:           nucleic acid
            (C) STRANDEDNESS:   single
            (D) TOPOLOGY:       linear (xi) SEQUENCE DESCRIPTION: SEQ ID NO:2592:

ACCCUCAGCC UCCCCCAG                                                           18

(2) INFORMATION FOR SEQ ID NO:2593:

(i) SEQUENCE CHARACTERISTICS:
            (A) LENGTH:         18 base pairs
            (B) TYPE:           nucleic acid
            (C) STRANDEDNESS:   single
            (D) TOPOLOGY:       linear (xi) SEQUENCE DESCRIPTION: SEQ ID NO:2593:

UCCCCCAGAC CACAUUCC                                                           18

(2) INFORMATION FOR SEQ ID NO:2594:

(i) SEQUENCE CHARACTERISTICS:
            (A) LENGTH:         18 base pairs
            (B) TYPE:           nucleic acid
            (C) STRANDEDNESS:   single
            (D) TOPOLOGY:       linear (xi) SEQUENCE DESCRIPTION: SEQ ID NO:2594:

GAUUACAGCU GUACUUCC                                                           18

(2) INFORMATION FOR SEQ ID NO:2595:

(i) SEQUENCE CHARACTERISTICS:

```
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO:2595:

GUUUUCUGUC UAAUUCUA                                                  18

(2) INFORMATION FOR SEQ ID NO:2596:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO:2596:

AGAAGCGGCC UCGCAACU                                                  18

(2) INFORMATION FOR SEQ ID NO:2597:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO:2597:

GUGAACAGAC CAAGAAAA                                                  18

(2) INFORMATION FOR SEQ ID NO:2598:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO:2598:

AAGAUCUGAU GAAGCCCA                                                  18

(2) INFORMATION FOR SEQ ID NO:2599:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO:2599:

UCUUACGCAG AAGCUUGCAC CAGAGAAACA CACGUUGUGG UACAUUACCU GGUA           54

(2) INFORMATION FOR SEQ ID NO:2600:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO:2600:

UUGUUCAAAG AAGUGCUGAC CAGAGAAACA CACGUUGUGG UACAUUACCU GGUA           54

(2) INFORMATION FOR SEQ ID NO:2601:

(i) SEQUENCE CHARACTERISTICS:
            (A) LENGTH:           54 base pairs
```

```
            (B) TYPE:          nucleic acid
            (C) STRANDEDNESS:  single
            (D) TOPOLOGY:      linear (xi) SEQUENCE DESCRIPTION: SEQ ID NO:2601:

CUACAGGAAG AAGGUUGUAC CAGAGAAACA CACGUUGUGG UACAUUACCU GGUA        54

(2) INFORMATION FOR SEQ ID NO:2602:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2602:

CAUGGUGCAG AAGGGGUCAC CAGAGAAACA CACGUUGUGG UACAUUACCU GGUA        54

(2) INFORMATION FOR SEQ ID NO:2603:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2603:

AUCAGCAAAG AAGUCACAAC CAGAGAAACA CACGUUGUGG UACAUUACCU GGUA        54

(2) INFORMATION FOR SEQ ID NO:2604:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2604:

CAUCUGAGAG AAGCAAGAAC CAGAGAAACA CACGUUGUGG UACAUUACCU GGUA        54

(2) INFORMATION FOR SEQ ID NO:2605:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2605:

GAAACAGCAG AAGAGAUCAC CAGAGAAACA CACGUUGUGG UACAUUACCU GGUA        54

(2) INFORMATION FOR SEQ ID NO:2606:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2606:

UCCACGGAAG AAGCAUCUAC CAGAGAAACA CACGUUGUGG UACAUUACCU GGUA        54

(2) INFORMATION FOR SEQ ID NO:2607:

(i) SEQUENCE CHARACTERISTICS:
            (A) LENGTH:        54 base pairs
            (B) TYPE:          nucleic acid
```

```
          (C) STRANDEDNESS:    single
          (D) TOPOLOGY:        linear (xi) SEQUENCE DESCRIPTION: SEQ ID NO:2607:

AUGGGCACAG AAGAUAUGAC CAGAGAAACA CACGUUGUGG UACAUUACCU GGUA            54

(2) INFORMATION FOR SEQ ID NO:2608:

(i) SEQUENCE CHARACTERISTICS:
          (A) LENGTH:          54 base pairs
          (B) TYPE:            nucleic acid
          (C) STRANDEDNESS:    single
          (D) TOPOLOGY:        linear (xi) SEQUENCE DESCRIPTION: SEQ ID NO:2608:

UGUCCUUGAG AAGAACAUAC CAGAGAAACA CACGUUGUGG UACAUUACCU GGUA            54

(2) INFORMATION FOR SEQ ID NO:2609:

(i) SEQUENCE CHARACTERISTICS:
          (A) LENGTH:          54 base pairs
          (B) TYPE:            nucleic acid
          (C) STRANDEDNESS:    single
          (D) TOPOLOGY:        linear (xi) SEQUENCE DESCRIPTION: SEQ ID NO:2609:

AGAUACUGAG AAGUUCUGAC CAGAGAAACA CACGUUGUGG UACAUUACCU GGUA            54

(2) INFORMATION FOR SEQ ID NO:2610:

(i) SEQUENCE CHARACTERISTICS:
          (A) LENGTH:          54 base pairs
          (B) TYPE:            nucleic acid
          (C) STRANDEDNESS:    single
          (D) TOPOLOGY:        linear (xi) SEQUENCE DESCRIPTION: SEQ ID NO:2610:

AAGAGAGAAG AAGUUGGAAC CAGAGAAACA CACGUUGUGG UACAUUACCU GGUA            54

(2) INFORMATION FOR SEQ ID NO:2611:

(i) SEQUENCE CHARACTERISTICS:
          (A) LENGTH:          54 base pairs
          (B) TYPE:            nucleic acid
          (C) STRANDEDNESS:    single
          (D) TOPOLOGY:        linear (xi) SEQUENCE DESCRIPTION: SEQ ID NO:2611:

CACACACCAG AAGGGAAUAC CAGAGAAACA CACGUUGUGG UACAUUACCU GGUA            54

(2) INFORMATION FOR SEQ ID NO:2612:

(i) SEQUENCE CHARACTERISTICS:
          (A) LENGTH:          54 base pairs
          (B) TYPE:            nucleic acid
          (C) STRANDEDNESS:    single
          (D) TOPOLOGY:        linear (xi) SEQUENCE DESCRIPTION: SEQ ID NO:2612:

ACACACACAG AAGUCAUAAC CAGAGAAACA CACGUUGUGG UACAUUACCU GGUA            54

(2) INFORMATION FOR SEQ ID NO:2613:

(i) SEQUENCE CHARACTERISTICS:
          (A) LENGTH:          54 base pairs
          (B) TYPE:            nucleic acid
          (C) STRANDEDNESS:    single
```

(D) TOPOLOGY:      linear (xi) SEQUENCE DESCRIPTION: SEQ ID NO:2613:

GUAACUGAAG AAGUAAUCAC CAGAGAAACA CACGUUGUGG UACAUUACCU GGUA        54

(2) INFORMATION FOR SEQ ID NO:2614:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2614:

CAAUGAUGAG AAGCAUCAAC CAGAGAAACA CACGUUGUGG UACAUUACCU GGUA        54

(2) INFORMATION FOR SEQ ID NO:2615:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2615:

GCCUGCUAAG AAGAUUCGAC CAGAGAAACA CACGUUGUGG UACAUUACCU GGUA        54

(2) INFORMATION FOR SEQ ID NO:2616:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2616:

AACUUAGAAG AAGUGUUGAC CAGAGAAACA CACGUUGUGG UACAUUACCU GGUA        54

(2) INFORMATION FOR SEQ ID NO:2617:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2617:

UUCCAAUCAG AAGAGAACAC CAGAGAAACA CACGUUGUGG UACAUUACCU GGUA        54

(2) INFORMATION FOR SEQ ID NO:2618:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear (xi) SEQUENCE DESCRIPTION: SEQ ID NO:2618:

GAAUUCCAAG AAGCUGAGAC CAGAGAAACA CACGUUGUGG UACAUUACCU GGUA        54

(2) INFORMATION FOR SEQ ID NO:2619:

(i) SEQUENCE CHARACTERISTICS:
            (A) LENGTH:        54 base pairs
            (B) TYPE:          nucleic acid
            (C) STRANDEDNESS:  single
            (D) TOPOLOGY:      linear -continued (xi) SEQUENCE DESCRIPTION: SEQ ID NO:2619:

AAUUAUUCAG AAGUAGAAAC CAGAGAAACA CACGUUGUGG UACAUUACCU GGUA        54

(2) INFORMATION FOR SEQ ID NO:2620:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2620:

GCAAGCAGAC GCGUAAGA        18

(2) INFORMATION FOR SEQ ID NO:2621:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2621:

CAGCACGGAC UUGAACAA        18

(2) INFORMATION FOR SEQ ID NO:2622:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2622:

ACAACCAGAC UCCUGUAG        18

(2) INFORMATION FOR SEQ ID NO:2623:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2623:

GACCCCAGAU GCACCAUG        18

(2) INFORMATION FOR SEQ ID NO:2624:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO:2624:

UGUGACAGUC UUGCUGAU        18

(2) INFORMATION FOR SEQ ID NO:2625:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear -continued (xi) SEQUENCE DESCRIPTION: SEQ ID NO:2625:

UCUUGCUGAU CUCAGAUG                                              18

(2) INFORMATION FOR SEQ ID NO:2626:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2626:

GAUCUCAGAU GCUGUUUC                                              18

(2) INFORMATION FOR SEQ ID NO:2627:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2627:

AGAUGCUGUU UCCGUGGA                                              18

(2) INFORMATION FOR SEQ ID NO:2628:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2628:

CAUAUCUGCC GUGCCCAU                                              18

(2) INFORMATION FOR SEQ ID NO:2629:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2629:

AUGUUCAGAU CAAGGACA                                              18

(2) INFORMATION FOR SEQ ID NO:2630:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2630:

CAGAACUGUU CAGUAUCU                                              18

(2) INFORMATION FOR SEQ ID NO:2631:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2631:

UCCAACAGCC UCUCUCUU                                                       18

(2) INFORMATION FOR SEQ ID NO:2632:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO:2632:

AUUCCCGGAU GGUGUGUG                                                       18

(2) INFORMATION FOR SEQ ID NO:2633:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO:2633:

UAUGACCGUU GUGUGUGU                                                       18

(2) INFORMATION FOR SEQ ID NO:2634:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO:2634:

GAUUACAGCU UCAGUUAC                                                       18

(2) INFORMATION FOR SEQ ID NO:2635:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO:2635:

UGAUGCUGCU CAUCAUUG                                                       18

(2) INFORMATION FOR SEQ ID NO:2636:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO:2636:

CGAAUCAGCC UAGCAGGC                                                       18

(2) INFORMATION FOR SEQ ID NO:2637:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO:2637:

CAACACAGCC UCUAAGUU                                                  18

(2) INFORMATION FOR SEQ ID NO:2638:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2638:

GUUCUCAGCU GAUUGGAA                                                  18

(2) INFORMATION FOR SEQ ID NO:2639:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2639:

CUCAGCUGAU UGGAAUUC                                                  18

(2) INFORMATION FOR SEQ ID NO:2640:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2640:

UUCUACAGUU GAAUAAUU                                                  18

(2) INFORMATION FOR SEQ ID NO:2641:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2641:

GACCAGGCAG AAGGACCAAC CAGAGAAACA CACGUUGUGG UACAUUACCU GGUA           54

(2) INFORMATION FOR SEQ ID NO:2642:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2642:

UGAGACCAAG AAGCAGGAAC CAGAGAAACA CACGUUGUGG UACAUUACCU GGUA           54

(2) INFORMATION FOR SEQ ID NO:2643:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2643:

ACUGCAGAAG AAGACGAAAC CAGAGAAACA CACGUUGUGG UACAUUACCU GGUA           54

(2) INFORMATION FOR SEQ ID NO:2644:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2644:

GGUCAGCAAG AAGCCCCAAC CAGAGAAACA CACGUUGUGG UACAUUACCU GGUA        54

(2) INFORMATION FOR SEQ ID NO:2645:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2645:

GGACAGCGAG AAGCAAGCAC CAGAGAAACA CACGUUGUGG UACAUUACCU GGUA        54

(2) INFORMATION FOR SEQ ID NO:2646:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2646:

GGAUGGACAG AAGUCAGCAC CAGAGAAACA CACGUUGUGG UACAUUACCU GGUA        54

(2) INFORMATION FOR SEQ ID NO:2647:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2647:

UCUGGAUGAG AAGCGGUCAC CAGAGAAACA CACGUUGUGG UACAUUACCU GGUA        54

(2) INFORMATION FOR SEQ ID NO:2648:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2648:

GCACAAAGAG AAGCACUGAC CAGAGAAACA CACGUUGUGG UACAUUACCU GGUA        54

(2) INFORMATION FOR SEQ ID NO:2649:

(i) SEQUENCE CHARACTERISTICS:
        (A) LENGTH:       54 base pairs
        (B) TYPE:         nucleic acid
        (C) STRANDEDNESS: single
        (D) TOPOLOGY:     linear (xi) SEQUENCE DESCRIPTION: SEQ ID NO:2649:

CGAGCAUGAG AAGUGCAGAC CAGAGAAACA CACGUUGUGG UACAUUACCU GGUA        54

(2) INFORMATION FOR SEQ ID NO:2650:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2650:

GACCCCAAAG AAGGGCGAAC CAGAGAAACA CACGUUGUGG UACAUUACCU GGUA         54

(2) INFORMATION FOR SEQ ID NO:2651:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2651:

CUGUAGCAAG AAGCUUGAAC CAGAGAAACA CACGUUGUGG UACAUUACCU GGUA         54

(2) INFORMATION FOR SEQ ID NO:2652:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2652:

GCCGACUGAG AAGGGCUCAC CAGAGAAACA CACGUUGUGG UACAUUACCU GGUA         54

(2) INFORMATION FOR SEQ ID NO:2653:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2653:

AAGAAGCCAG AAGGGCAGAC CAGAGAAACA CACGUUGUGG UACAUUACCU GGUA         54

(2) INFORMATION FOR SEQ ID NO:2654:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2654:

GGAGAAGAAG AAGACUGGAC CAGAGAAACA CACGUUGUGG UACAUUACCU GGUA         54

(2) INFORMATION FOR SEQ ID NO:2655:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2655:

UUUUCGAAAG AAGAUGACAC CAGAGAAACA CACGUUGUGG UACAUUACCU GGUA         54

(2) INFORMATION FOR SEQ ID NO:2656:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2656:

CAGACAACAG AAGUCUUGAC CAGAGAAACA CACGUUGUGG UACAUUACCU GGUA          54

(2) INFORMATION FOR SEQ ID NO:2657:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2657:

GGGCUCUCAG AAGAUCCUAC CAGAGAAACA CACGUUGUGG UACAUUACCU GGUA          54

(2) INFORMATION FOR SEQ ID NO:2658:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2658:

GGAUGGCAAG AAGGAUCCAC CAGAGAAACA CACGUUGUGG UACAUUACCU GGUA          54

(2) INFORMATION FOR SEQ ID NO:2659:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2659:

GGAAGAUCAG AAGGAAAAAC CAGAGAAACA CACGUUGUGG UACAUUACCU GGUA          54

(2) INFORMATION FOR SEQ ID NO:2660:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2660:

ACUGGAGCAG AAGUGUUGAC CAGAGAAACA CACGUUGUGG UACAUUACCU GGUA          54

(2) INFORMATION FOR SEQ ID NO:2661:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2661:

UGCACUGGAG AAGCAGUGAC CAGAGAAACA CACGUUGUGG UACAUUACCU GGUA          54

(2) INFORMATION FOR SEQ ID NO:2662:

```
    (i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2662:

CUCUGGCCAG AAGCCUGUAC CAGAGAAACA CACGUUGUGG UACAUUACCU GGUA          54

(2) INFORMATION FOR SEQ ID NO:2663:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2663:

CCUGCAGCAG AAGCACCAAC CAGAGAAACA CACGUUGUGG UACAUUACCU GGUA          54

(2) INFORMATION FOR SEQ ID NO:2664:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2664:

ACCCCUGCAG AAGCAGCAAC CAGAGAAACA CACGUUGUGG UACAUUACCU GGUA          54

(2) INFORMATION FOR SEQ ID NO:2665:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2665:

UGGUCCUGCC GCCUGGUC                                                  18

(2) INFORMATION FOR SEQ ID NO:2666:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2666:

UCCUGCCGCC UGGUCUCA                                                  18

(2) INFORMATION FOR SEQ ID NO:2667:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2667:

UUCGUCUGCC UCUGCAGU                                                  18

(2) INFORMATION FOR SEQ ID NO:2668:
```

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2668:

UGGGGCUGCU UGCUGACC                                               18

(2) INFORMATION FOR SEQ ID NO:2669:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2669:

GCUUGCUGAC CGCUGUCC                                               18

(2) INFORMATION FOR SEQ ID NO:2670:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2670:

GCUGACCGCU GUCCAUCC                                               18

(2) INFORMATION FOR SEQ ID NO:2671:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2671:

GACCGCUGUC CAUCCAGA                                               18

(2) INFORMATION FOR SEQ ID NO:2672:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2672:

CAGUGCUGUU CUUUGUGC                                               18

(2) INFORMATION FOR SEQ ID NO:2673:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2673:

CUGCACCGCU CAUGCUCG                                               18

(2) INFORMATION FOR SEQ ID NO:2674:

(i) SEQUENCE CHARACTERISTICS:

```
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO:2674:

UCGCCCGGCU UUGGGGUC                                                 18

(2) INFORMATION FOR SEQ ID NO:2675:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO:2675:

UCAAGCAGAU UGCUACAG                                                 18

(2) INFORMATION FOR SEQ ID NO:2676:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO:2676:

GAGCCCUGCC CAGUCGGC                                                 18

(2) INFORMATION FOR SEQ ID NO:2677:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO:2677:

CUGCCCAGUC GGCUUCUU                                                 18

(2) INFORMATION FOR SEQ ID NO:2678:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO:2678:

CCAGUCGGCU UCUUCUCC                                                 18

(2) INFORMATION FOR SEQ ID NO:2679:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO:2679:

GUCAUCUGCU UUCGAAAA                                                 18

(2) INFORMATION FOR SEQ ID NO:2680:

(i) SEQUENCE CHARACTERISTICS:
        (A) LENGTH:          18 base pairs
```

```
            (B) TYPE:          nucleic acid
            (C) STRANDEDNESS:  single
            (D) TOPOLOGY:      linear (xi) SEQUENCE DESCRIPTION: SEQ ID NO:2680:

CAAGACUGAU GUUGUCUG                                                    18

(2) INFORMATION FOR SEQ ID NO:2681:

(i) SEQUENCE CHARACTERISTICS:
            (A) LENGTH:        18 base pairs
            (B) TYPE:          nucleic acid
            (C) STRANDEDNESS:  single
            (D) TOPOLOGY:      linear (xi) SEQUENCE DESCRIPTION: SEQ ID NO:2681:

AGGAUCGGCU GAGAGCCC                                                    18

(2) INFORMATION FOR SEQ ID NO:2682:

(i) SEQUENCE CHARACTERISTICS:
            (A) LENGTH:        18 base pairs
            (B) TYPE:          nucleic acid
            (C) STRANDEDNESS:  single
            (D) TOPOLOGY:      linear (xi) SEQUENCE DESCRIPTION: SEQ ID NO:2682:

GGAUCCUGUU UGCCAUCC                                                    18

(2) INFORMATION FOR SEQ ID NO:2683:

(i) SEQUENCE CHARACTERISTICS:
            (A) LENGTH:        18 base pairs
            (B) TYPE:          nucleic acid
            (C) STRANDEDNESS:  single
            (D) TOPOLOGY:      linear (xi) SEQUENCE DESCRIPTION: SEQ ID NO:2683:

UUUUCCCGAC GAUCUUCC                                                    18

(2) INFORMATION FOR SEQ ID NO:2684:

(i) SEQUENCE CHARACTERISTICS:
            (A) LENGTH:        18 base pairs
            (B) TYPE:          nucleic acid
            (C) STRANDEDNESS:  single
            (D) TOPOLOGY:      linear (xi) SEQUENCE DESCRIPTION: SEQ ID NO:2684:

CAACACUGCU GCUCCAGU                                                    18

(2) INFORMATION FOR SEQ ID NO:2685:

(i) SEQUENCE CHARACTERISTICS:
            (A) LENGTH:        18 base pairs
            (B) TYPE:          nucleic acid
            (C) STRANDEDNESS:  single
            (D) TOPOLOGY:      linear (xi) SEQUENCE DESCRIPTION: SEQ ID NO:2685:

CACUGCUGCU CCAGUGCA                                                    18

(2) INFORMATION FOR SEQ ID NO:2686:

(i) SEQUENCE CHARACTERISTICS:
            (A) LENGTH:        18 base pairs
            (B) TYPE:          nucleic acid
```

```
            (C) STRANDEDNESS:    single
            (D) TOPOLOGY:        linear (xi) SEQUENCE DESCRIPTION: SEQ ID NO:2686:

ACAGGCAGUU GGCCAGAG                                                    18

(2) INFORMATION FOR SEQ ID NO:2687:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2687:

UGGUGCUGCU GCUGCAGG                                                    18

(2) INFORMATION FOR SEQ ID NO:2688:

(i) SEQUENCE CHARACTERISTICS:
            (A) LENGTH:          18 base pairs
            (B) TYPE:            nucleic acid
            (C) STRANDEDNESS:    single
            (D) TOPOLOGY:        linear (xi) SEQUENCE DESCRIPTION: SEQ ID NO:2688:

UGCUGCUGCU GCAGGGGU                                                    18

(2) INFORMATION FOR SEQ ID NO:2689:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2689:

GCGCGCACAG AAGAGGCAAC CAGAGAAACA CACGUUGUGG UACAUUACCU GGUA            54

(2) INFORMATION FOR SEQ ID NO:2690:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2690:

UGUCAACAAG AAGCCCCAAC CAGAGAAACA CACGUUGUGG UACAUUACCU GGUA            54

(2) INFORMATION FOR SEQ ID NO:2691:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2691:

CCUAGAUGAG AAGCUGUCAC CAGAGAAACA CACGUUGUGG UACAUUACCU GGUA            54

(2) INFORMATION FOR SEQ ID NO:2692:

(i) SEQUENCE CHARACTERISTICS:
            (A) LENGTH:          54 base pairs
            (B) TYPE:            nucleic acid
            (C) STRANDEDNESS:    single
```

```
            (D) TOPOLOGY:        linear (xi) SEQUENCE DESCRIPTION: SEQ ID NO:2692:

GCUUGUCAAG AAGCUUCCAC CAGAGAAACA CACGUUGUGG UACAUUACCU GGUA          54

(2) INFORMATION FOR SEQ ID NO:2693:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2693:

UUCUCAAGAG AAGUGCAGAC CAGAGAAACA CACGUUGUGG UACAUUACCU GGUA          54

(2) INFORMATION FOR SEQ ID NO:2694:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2694:

UUCCACUGAG AAGAGAAUAC CAGAGAAACA CACGUUGUGG UACAUUACCU GGUA          54

(2) INFORMATION FOR SEQ ID NO:2695:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2695:

CAGGUACAAG AAGUGUCUAC CAGAGAAACA CACGUUGUGG UACAUUACCU GGUA          54

(2) INFORMATION FOR SEQ ID NO:2696:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2696:

GGAUGACAAG AAGUAUCAAC CAGAGAAACA CACGUUGUGG UACAUUACCU GGUA          54

(2) INFORMATION FOR SEQ ID NO:2697:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear (xi) SEQUENCE DESCRIPTION: SEQ ID NO:2697:

GCCGACUGAG AAGGGAUGAC CAGAGAAACA CACGUUGUGG UACAUUACCU GGUA          54

(2) INFORMATION FOR SEQ ID NO:2698:

(i) SEQUENCE CHARACTERISTICS:
            (A) LENGTH:          54 base pairs
            (B) TYPE:            nucleic acid
            (C) STRANDEDNESS:    single
            (D) TOPOLOGY:        linear
```

(xi) SEQUENCE DESCRIPTION: SEQ ID NO:2698:

AAGAAGCCAG AAGGGCAGAC CAGAGAAACA CACGUUGUGG UACAUUACCU GGUA            54

(2) INFORMATION FOR SEQ ID NO:2699:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO:2699:

GGAGAAGAAG AAGACUGGAC CAGAGAAACA CACGUUGUGG UACAUUACCU GGUA            54

(2) INFORMATION FOR SEQ ID NO:2700:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO:2700:

UGACAUUAAG AAGACUCGAC CAGAGAAACA CACGUUGUGG UACAUUACCU GGUA            54

(2) INFORMATION FOR SEQ ID NO:2701:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO:2701:

GGGCUCGCAG AAGGGACUAC CAGAGAAACA CACGUUGUGG UACAUUACCU GGUA            54

(2) INFORMATION FOR SEQ ID NO:2702:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO:2702:

GAAUGACCAG AAGGGCUCAC CAGAGAAACA CACGUUGUGG UACAUUACCU GGUA            54

(2) INFORMATION FOR SEQ ID NO:2703:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO:2703:

CCCAUCACAG AAGGAAUGAC CAGAGAAACA CACGUUGUGG UACAUUACCU GGUA            54

(2) INFORMATION FOR SEQ ID NO:2704:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear -continued (xi) SEQUENCE DESCRIPTION: SEQ ID NO:2704:

UGCCGUCGAG AAGCAGGGAC CAGAGAAACA CACGUUGUGG UACAUUACCU GGUA          54

(2) INFORMATION FOR SEQ ID NO:2705:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2705:

ACUGGAGCAG AAGUGUUAAC CAGAGAAACA CACGUUGUGG UACAUUACCU GGUA          54

(2) INFORMATION FOR SEQ ID NO:2706:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2706:

UGCACUGGAG AAGCGGUGAC CAGAGAAACA CACGUUGUGG UACAUUACCU GGUA          54

(2) INFORMATION FOR SEQ ID NO:2707:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2707:

GUGUGACAAG AAGACACCAC CAGAGAAACA CACGUUGUGG UACAUUACCU GGUA          54

(2) INFORMATION FOR SEQ ID NO:2708:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2708:

CCUCCAAAAG AAGUUCCAAC CAGAGAAACA CACGUUGUGG UACAUUACCU GGUA          54

(2) INFORMATION FOR SEQ ID NO:2709:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2709:

GGUCAGCAAG AAGCCAUCAC CAGAGAAACA CACGUUGUGG UACAUUACCU GGUA          54

(2) INFORMATION FOR SEQ ID NO:2710:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO:2710:

UUCAAAAGAG AAGCAAGCAC CAGAGAAACA CACGUUGUGG UACAUUACCU GGUA    54

(2) INFORMATION FOR SEQ ID NO:2711:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2711:

UGACAGGGAG AAGGCAUGAC CAGAGAAACA CACGUUGUGG UACAUUACCU GGUA    54

(2) INFORMATION FOR SEQ ID NO:2712:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2712:

CGAGCACAAG AAGCGGGCAC CAGAGAAACA CACGUUGUGG UACAUUACCU GGUA    54

(2) INFORMATION FOR SEQ ID NO:2713:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2713:

GUUUUAAAAG AAGUUUCUAC CAGAGAAACA CACGUUGUGG UACAUUACCU GGUA    54

(2) INFORMATION FOR SEQ ID NO:2714:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2714:

CGGGUUUGAG AAGCAAGCAC CAGAGAAACA CACGUUGUGG UACAUUACCU GGUA    54

(2) INFORMATION FOR SEQ ID NO:2715:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2715:

GGAUCAAAAG AAGGUAACAC CAGAGAAACA CACGUUGUGG UACAUUACCU GGUA    54

(2) INFORMATION FOR SEQ ID NO:2716:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO:2716:

```
AAACCCAGAG AAGAUUAAAC CAGAGAAACA CACGUUGUGG UACAUUACCU GGUA          54

(2) INFORMATION FOR SEQ ID NO:2717:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2717:

UGCCUCGGCU GUGCGCGC                                                  18

(2) INFORMATION FOR SEQ ID NO:2718:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2718:

UGGGGCUGCU UGUUGACA                                                  18

(2) INFORMATION FOR SEQ ID NO:2719:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2719:

GACAGCGGUC CAUCUAGG                                                  18

(2) INFORMATION FOR SEQ ID NO:2720:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2720:

GGAAGCCGAC UGACAAGC                                                  18

(2) INFORMATION FOR SEQ ID NO:2721:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2721:

CUGCACAGCU CUUGAGAA                                                  18

(2) INFORMATION FOR SEQ ID NO:2722:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2722:

AUUCUCAGCC CAGUGGAA                                                  18
```

(2) INFORMATION FOR SEQ ID NO:2723:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2723:

AGACACUGUC UGUACCUG                                                  18

(2) INFORMATION FOR SEQ ID NO:2724:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2724:

UGAUACCGUC UGUCAUCC                                                  18

(2) INFORMATION FOR SEQ ID NO:2725:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2725:

CAUCCCUGCC CAGUCGGC                                                  18

(2) INFORMATION FOR SEQ ID NO:2726:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2726:

CUGCCCAGUC GGCUUCUU                                                  18

(2) INFORMATION FOR SEQ ID NO:2727:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2727:

CCAGUCGGCU UCUUCUCC                                                  18

(2) INFORMATION FOR SEQ ID NO:2728:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2728:

CGAGUCAGAC UAAUGUCA                                                  18

(2) INFORMATION FOR SEQ ID NO:2729:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2729:

AGUCCCGGAU GCGAGCCC                                                       18

(2) INFORMATION FOR SEQ ID NO:2730:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2730:

GAGCCCUGCU GGUCAUUC                                                       18

(2) INFORMATION FOR SEQ ID NO:2731:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2731:

CAUUCCUGUC GUGAUGGG                                                       18

(2) INFORMATION FOR SEQ ID NO:2732:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2732:

CCCUGCGGCU CGACGGCA                                                       18

(2) INFORMATION FOR SEQ ID NO:2733:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2733:

UAACACCGCU GCUCCAGU                                                       18

(2) INFORMATION FOR SEQ ID NO:2734:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2734:

CACCGCUGCU CCAGUGCA                                                       18

(2) INFORMATION FOR SEQ ID NO:2735:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2735:

GGUGUCAGCC UGUCACAC                                                        18

(2) INFORMATION FOR SEQ ID NO:2736:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2736:

UGGAACUGCU UUUGGAGG                                                        18

(2) INFORMATION FOR SEQ ID NO:2737:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2737:

GAUGGCUGCU UGCUGACC                                                        18

(2) INFORMATION FOR SEQ ID NO:2738:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2738:

GCUUGCUGAC CUUUUGAA                                                        18

(2) INFORMATION FOR SEQ ID NO:2739:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2739:

CAUGCCUGCC CCCUGUCA                                                        18

(2) INFORMATION FOR SEQ ID NO:2740:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO:2740:

GCCCGCAGCU UGUGCUCG                                                        18

(2) INFORMATION FOR SEQ ID NO:2741:

```
    (i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2741:

AGAAACAGCU UUUAAAAC                                             18

(2) INFORMATION FOR SEQ ID NO:2742:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2742:

GCUUGCUGCC CAAACCCG                                             18

(2) INFORMATION FOR SEQ ID NO:2743:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2743:

GUUACCUGAU UUUGAUCC                                             18

(2) INFORMATION FOR SEQ ID NO:2744:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO:2744:

UUAAUCCGCC CUGGGUUU                                             18

(2) INFORMATION FOR SEQ ID NO:2745:

(i) SEQUENCE CHARACTERISTICS:
        (A) LENGTH:         11 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any
            base. The letter "H" stands
            for A, U, or C.

(xi) SEQUENCE DESCRIPTION: SEQ ID NO:2745:

NNNNUHNNNN N                                                    11

(2) INFORMATION FOR SEQ ID NO:2746:

(i) SEQUENCE CHARACTERISTICS:
        (A) LENGTH:         28 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any
``` base.

(xi) SEQUENCE DESCRIPTION: SEQ ID NO:2746:

NNNNNCUGAN GAGNNNNNNC GAAANNNN                                    28

(2) INFORMATION FOR SEQ ID NO:2747:

(i) SEQUENCE CHARACTERISTICS:
      (A) LENGTH:         15 base pairs
      (B) TYPE:           nucleic acid
      (C) STRANDEDNESS:   single
      (D) TOPOLOGY:       linear (ix) FEATURE:
      (D) OTHER INFORMATION:   The letter "N" stands for any
          base. The leter "Y" stands for
          U or C. The letter "H" stands
          for A, U, or C.

(xi) SEQUENCE DESCRIPTION: SEQ ID NO:2747:

NNNNNNNYNG HYNNN                                                  15

(2) INFORMATION FOR SEQ ID NO:2748:

(i) SEQUENCE CHARACTERISTICS:
      (A) LENGTH:         47 base pairs
      (B) TYPE:           nucleic acid
      (C) STRANDEDNESS:   single
      (D) TOPOLOGY:       linear (ix) FEATURE:
      (D) OTHER INFORMATION:   The letter "N" stands for any
          base.

(xi) SEQUENCE DESCRIPTION: SEQ ID NO:2748:

NNNNGAAGNN NNNNNNNNNA AAHANNNNNN NACAUUACNN NNNNNNN               47

(2) INFORMATION FOR SEQ ID NO:2749:

(i) SEQUENCE CHARACTERISTICS:
      (A) LENGTH:         85 base pairs
      (B) TYPE:           nucleic acid
      (C) STRANDEDNESS:   single
      (D) TOPOLOGY:       linear (xi) SEQUENCE DESCRIPTION: SEQ ID NO:2749:

UGGCCGGCAU GGUCCCAGCC UCCUCGCUGG CGCCGGCUGG GCAACAUUCC GAGGGGACCG    60

UCCCCUCGGU AAUGGCGAAU GGGAC                                        85

(2) INFORMATION FOR SEQ ID NO:2750:

(i) SEQUENCE CHARACTERISTICS:
      (A) LENGTH:         176 base pairs
      (B) TYPE:           nucleic acid
      (C) STRANDEDNESS:   single
      (D) TOPOLOGY:       linear (xi) SEQUENCE DESCRIPTION: SEQ ID NO:2750:

GGGAAAGCUU GCGAAGGGCG UCGUCGCCCC GAGCGGUAGU AAGCAGGGAA CUCACCUCCA    60

AUUUCAGUAC UGAAAUUGUC GUAGCAGUUG ACUACUGUUA UGUGAUUGGU AGAGGCUAAG   120

UGACGGUAUU GGCGUAAGUC AGUAUUGCAG CACAGCACAA GCCCGCUUGC GAGAAU      176

(2) INFORMATION FOR SEQ ID NO:2751:

(i) SEQUENCE CHARACTERISTICS:
      (A) LENGTH:         12 base pairs

```
            (B) TYPE:           nucleic acid
            (C) STRANDEDNESS:   single
            (D) TOPOLOGY:       linear (xi) SEQUENCE DESCRIPTION: SEQ ID NO:2751:

GGCCGAAAGG CC                                                                12
```

US 6,194,150 B1

NUCLEIC ACID BASED INHIBITION OF CD40

RELATED APPLICATIONS

This application is a continuation of Stinchcomb et al., U.S. Ser. No. 08/585,684, filed Jan. 12, 1996, now U.S. Pat. No. 5,877,021, which claims the benefit of Stinchcomb et al., U.S. Ser. No. 60/000,951, filed Jul. 7, 1995 entitled Method and Reagent for the Induction of Graft Tolerance and Reversal of Immune Responses, which is hereby incorporated by reference herein in totality (including drawings and tables).

BACKGROUND OF THE INVENTION

This invention relates to methods for the induction of graft tolerance, treatment of autoimmune diseases, inflammatory disorders and allergies in particular, by inhibition of B7-1, B7-2, B7-3 and CD40.

The following is a discussion of relevant art, none of which is admitted to be prior art to the present invention.

An adaptive immune response requires activation, clonal expansion, and differentiation of a class of cells termed T lymphocytes (T cells). T cell activation is a multi-step process requiring several signalling events between the T cell and an antigen presenting cell. The ensuing discussion details signals that are exchanged between T cells and antigen presenting B cells. Similar pathways are thought to occur between T cells and other antigen presenting cells such as monocytes or follicular dendritic cells.

T cell activation is initiated when the T-cell receptor (TCR) binds to a specific antigen that is associated with the MHC proteins on the surface of an antigen presenting cell. This primary stimulus activates the T cell and induces expression of CD40 ligand (CD40L) on the surface of the T cell. CD40L then interacts with its cognate receptor, CD40, which is constitutively expressed on the surface of B cells; CD40 transduces the signal leading to B cell activation. B cell activations result in the expression of B7-1, B7-2 and/or B7-3, which in turn interacts with constitutively expressed CD28 on the surface of T cells. The interaction generates a secondary co-stimulatory signal that is required to fully activate the T cell. Complete T cell activation via the T cell receptor and CD28 leads to cytokine secretion, clonal expansion, and differentiation. If the T cell receptor is engaged, absence of this secondary co-stimulus mediated by CD28, then the T cell is inactivated, either by clonal anergy (non-responsiveness or reduced reactivity of the immune system to specific antigen(s)) or clonal deletion (Jenkins et al., 1987 *Proc. Natl. Acad. Sci. USA* 84, 5409). Thus, engagement of the TCR without a concomitant costimulatory signal results in a state of tolerance toward the specific antigen recognized by the T cell. This co-stimulatory signal can be mediated by the binding of B7-1 or B7-2 or B7-3, present on activated antigen-presenting cells, to CD28, a receptor that is constitutively expressed on the surface of the T cell (Marshall et al., 1993 *J Clin Immun* 13, 165–174; Linsley, et al., 1991 *J Exp Med* 173, 721; Koulova et al., 1991 *J Exp Med* 173, 759; Harding et al., 1992 *Nature* 356, 607).

Several homologs of B7 (now known as B7-1; Cohen, 1993 *Science* 262, 844) are expressed in activated B cells (Freeman et al., 1993 *Science* 262, 907; Lenschowet al., 1993 *Proc NatlAcad Sci USA* 90, 11054; Azuma et al., 1993 *Nature* 366, 76; Hathcock et al., 1993 *Science* 262, 905; Freeman et al., 1993 *Science* 262, 909). B7-1 and B7-3 are only expressed on the surface of a subset of B cells after 48 hours of contact with T cells. In contrast, B7-2 mRNA is constitutively expressed by unstimulated B cells and increases 4-fold within 4 hours of activation (Freeman et al., 1993 *Science* 262, 909; Boussiotis et al., 1993 *Proc Natl Acad Sci USA* 90, 11059). Since T cells commit to either the anergy or the activation pathway within 12-24 hours of the initial TCR signal, it is thought that B7-2 is the molecule responsible for the primary costimulatory signal. B7-1 and B7-3 may provide a subsequent signal necessary for clonal expansion. Antibodies to B7-2 completely block T cell proliferation in a mixed lymphocyte reaction (Azuma et al., 1993 supra), supporting the central role of B7-2 in T cell activation. These experiments indicate that inhibition of B7-2 expression (for example with a ribozyme) would likely induce anergy. Similarly, inhibition of CD40 expression by a ribozyme would prevent B7-2 upregulation and could induce tolerance to specific antigens.

B7 (B7-1) is a 60 KD modified trans-membrane glycoprotein usually present on the surface of antigen presenting cells (APC). B7 has two ligands—CD28 and CTLA4. Interaction of B7-1 with CD28 and/or CTLA4 causes activation of T cell responses (Janeway and Bottomly, 1994 *Cell* 76, 275).

B7-2 is a 70 KD (34 KD unmodified) trans-membrane glycoprotein found on the surface of APCs. B7-2 encodes a 323 amino-acid protein which is 26% identical to human B7-1 protein. Like B7-1, CD28 and CTLA4 are selectively bound by B7-2. B7-2, unlike B7-1, is expressed on the surface of unstimulated B cells (Freeman et al., 1993 supra).

CD40 is a 45–50 KD surface glycoprotein found on the surface of late pre-B cells in bone marrow, mature B cells, bone marrow-derived dendritic cells and follicular dendritic cells (Clark and Ledbetter, 1994 *Nature* 367, 425).

Successful organ transplantation currently requires suppression of the reipient's immune system in order to prevent graft rejection and maintain good graft function. The available therapies, including cyclosporin A, FK506 and various monoclonal antibodies, all have serious side effects (Caine, 1992 *Transplantation Proceedings* 24,1260; Fuleihan et al., 1994 *J. Clin. Invest.* 93, 1315; Van Gool et al., 1994 *Blood* 83, 176) . In addition, existing therapies result in general immune suppression, leaving the patient susceptible to a variety of opportunistic infections. The ability to induce a state of long-term, antigen-specific tolerance to the donor tissue would revolutionize the field of organ and tissue transplantation. Since organ graft rejection is mediated by T cell effector function, the goal is to block specifically the activation of the subset of T cells that recognize donor antigens. A limitation in the field of transplantation is the supply of donor organs (Nowak 1994 *Science* 266, 1148). The ability to induce donor-specific tolerance would substantially increase the chances of successful allographs, xenographs, thereby greatly increasing the donor pool.

Such transplantation includes grafting of tissues and/or organ ie., implantation or transplantation of tissue and/or organs, from the body of an individual to a different place within the same or different individual. Transplantation also involve grafting of tissues and/or organs from one area of the body to another. Transplantation of tissues and/or organs between genetically dissimilar animals of the same species is termed as allogeneic transplantation. Transplantation of animal organs into humans is termed xenotransplants (for a review see Nowak, 1994 *Science* 266, 1148).

One therapy currently being developed that has similar potential to induce antigen-specific tolerance is treatment with a CTLA4-lg fusion protein. "CTLA4" is a homologue of CD28 that binds B7-1 and B7-2 with high affinity. The engineered, soluble fusion protein, CTLA4-lg, binds B7-1, thereby blocking its interaction with CD28. The results of CTLA4-lg treatment in animal studies are mixed. CTLA4-lg treatment significantly enhanced survival rates and ameliorated the symptoms of graft-versus host disease in a murine bone marrow tranplant model (Blazer et al., 1994 *Blood* 83, 3815). CTLA4-lg induced long-term (>110 days) donor-specific tolerance in pancreatic islet xenografts (Lenschow et al., 1992 *Science* 257, 789). Conversely, in another study CTLA4-lg treatment delayed but did not ultimately prevent cardiac allograft rejection (Turka, et al., 1992 *Proc Nati Acad Sci USA* 89, 11102). Mice immunized with sheep erythrocytes in the presence of CTLA4-lg failed to mount a primary immune response (Linsley, et al., 1992 *Science* 257, 792). A secondary immunization did elicit some response, however, indicating incomplete tolerance. Interestingly, identical results were obtained when CTLA4-lg was administered 2 days after primary immunization, leading the authors to conclude that CTLA4-lg blocked amplification rather than initiation of the immune response. Since CTLA4-lg has been shown to dissociate more raoidly from B7-2 compared with B7-1, this may explain the failure to induce long term tolerance in this model (Linsley et al., 1994 *Immunity* 1, 793).

CTLA4:lg has recently been shown to ameliorate symptoms of spontaneous autoimmune disease in lupus-prone mice (Finck et al., 1994 *Science* 265, 1225).

Linsley et al., WO 92/00092 describe B7 antigen as a ligand for CD28 receptor on T cells. The application states that—

"The B7 antigen, or its fragments or derivatives are reacted with CD28 positive T cells to reglulate T cell interactions with other cells . . . B7 antigen or CD28 receptor may be used to inhibit interaction of cells associated with these molecules, thereby regulating T cell responses."

De Boer and Conroy, WO 94/01547 describe the use of anti-B7 and anti-CD40 antibodies to treat allograft transplant rejection, graft versus host disease and rhematoid arthritis. The application states that—

". . . anti-B7 and anti-CD40 antibodies . . . can be used to prevent or treat an antibody-mediated or immune system disease in a patient."

Since signalling via CD40 precedes induction of B-7, blocking the CD40-CD40L interaction would also have the potential to produce tolerance. According to one report, simultaneous treatment of mice with antibodies to CD40L and sheep red blood cells produced antigen-specific tolerance for up to 3 weeks following cessation of treatment (Foy et al., 1993 *J Exp Med* 178, 1567). Anti-CD40L also produces antigen specific tolerance in a pancreatic islet transplant model (R. Noelle, personal communication). Targeted inhibition of CD40 expression in B cells in addition to B7 would therefore afford double protection against activation of T cells.

Therapeutic agents used to prevent rejection of a transplanted organ are all cytotoxic compounds or antibodies designed to suppress the cell-mediated immune system. The side effects of these agents are those of immunosuppression and infections. The primary approved agents are azathioprine, corticosteroids, cyclosporine; the antibodies are antilymphocyte or antithymocyte globulins. All of these are given to individuals who have been as closely matched as possible to their donors by both major and minor histocompatibility typing. Since the principal problem in transplantation is an antigenic mismatch and the resulting need for cytotoxic therapy, any therapeutic improvement which decreases the local immune response without general immunosuppression should capture the transplant market.

Cyclosporine: At the end of the 1970's and early 1980's the introduction of cyclosporine revolutionized the transplantation field. It is a potent immunosuppressant which can inhibit immunocompetent lymphocytes specifically and reversibly. Its primary mechanism of action appears to be inhibition of the production and release of interleukin-2 by T helper cells. In addition it also interferes with the release of interleukin-1 by macrophages, as well as proliferation of B lymphocytes. It was approved by the FDA in 1983 and by 1989 was almost universally given to transplant recipients. At first it was believed that the toxicity and side effects from cyclosporine were minimal and it was hailed as a "wonder drug." Numerous side effects have been progressively cited, including the appearance of lymphomas, especially in the gastrointestinal tract; acute and chronic nephrotoxicity; hypertension; hepatotoxicity; hirsutism; anemia; neurotoxicity; endocrine and neurological complications; and gastrointestinal distress. It is now widely acknowledged that the non-specific side effects of the drug demand caution and close monitoring of its use. One-year survival rates for cadaver kidney transplants treated with cyclosporine is 80%, much better than the 50–60% rates without the drug. The one-year survival is almost 90% for transplants with related donors and the use of cyclosporine.

Azathioprine: In addition to cyclosporine, azathioprine is used for transplant patients. Azathioprine is one of the mercaptopurine class of drugs and inhibits nucleic acid synthesis. Patients are maintained indefinitely on daily doses of 1 mg/kg or less, with a dosage adjusted in accordance with the white cell count. The drug may cause depression of bone marrow elements and may cause jaundice.

Corticosteroids: Prednisone, used in almost all transplant recipients, is usually given in association with azathioprine and cyclosporine. The dosage must be regulated carefully so as so prevent complications such as infection, development of cushingoid features, and hypertension. Usually the initial maintenance prednisone dosage is 0.5 mglkg/d. This dosage is usually further decreased in the outpatient clinic until maintenance levels of about 10 mg/d for adults are obtained. The exact site of action of corticosteroids on the immune response is not known.

Antithymoblast or antilymphocyte globulin (ALG) and antithymocyte globulin (ATG): These are important adjunctive immunosuppressants. They are effective, particularly in induction of immunosuppressive therapy and in the treatment of corticosteroid-resistant rejection. Both ALG and ATG can be made by immunizing horses, rabbits, or sheep; the main source is horses. Lymphocytes from human peripheral blood, spleen, lymph nodes, or thymus serve as the immunogen.

Tacrolimus: On Apr. 13, 1994 the Food and Drug Administration approved another drug to help prevent the rejection of organ transplants. The drug, tacrolimus, was approved only for use in liver transplant patients. An alternative to cyclosporine, the macrolide immunosuppressant tacrolimus is a powerful and selective anti-T-lymphocyte agent that was discovered in 1984. Tacrolimus, isolated from the fungus *Streptomyces tsukubaensis*, possesses immunodepressant properties similar to but more potent than cyclosporine. It inhibits both cell-mediated and humoral immune responses. Like cyclosporine, tacrolimus demonstrates considerable interindividual variation in its pharmacokinetic profile. Most clinical studies with tacrolimus have neither been published in their entirety nor subjected to extensive peer review; there is also a paucity of published randomized investigations of tacrolimus vs. cyclosporine, particularly in renal transplantation. Despite these drawbacks, tacrolimus has shown notable efficacy as a rescue or primary immunosuppressant therapy when combined with corticosteroids. The potential for reductional withdrawal of corticosteroid therapy with tacrolimus appears to be a distinct advantage compared with the cyclosporine. This benefit may be enhanced by reduced incidence of infectious complications, hypertension and hypercholesterolemia reported by some investigators. In other respects, the tolerability profile of tacrolimus appears to be broadly similar to that of cyclosporine.

In addition to induction of graft tolerance, T cell anergy can be used to reverse autoimmune diseases. Autoimmune diseases represent a broad category of conditions. A few examples include insulin-dependent diabetes mellitus (IDDM), multiple schlerosis (MS), systemic lupus erythematosus (SLE), rheumatoid arthritis (RA), myasthenia gravis (MG), and psoriasis. These seemingly disparate diseases all share the common feature of inappropriate immune response to specific self-antigens. Finck et al. supra have reported that CTLA4lg treatment of mice blocked autoantibody production in a mice model of SLE. In fact, this effect was observed even when the CTLA4lg treatment was initiated during the advanced stages of the disease, suggesting that the autoimmune response was a reversible process.

Chappel., WO 94/11011 describes methods to treat autoimmune diseases by inducing tolerance to cells, tissues and organs. The application states that—

"Cells genetically engineered with DNA encoding a plurality of antigens of a cell, tissue, or organ to which tolerance is to be induced. The cells are free of costimulatory antigens, such as B7 antigen,. Such cells induce T-cell anergy against the proteins encoded by the DNA, and may be administered to a patient in order to prevent the onset of or to treat an autoimmune disease, or to induce tolerance to a tissue or organ prior to transplantation."

Allergic reactions represent an immediate hypersensitivity response to environmental antigens, typically mediated by IgE antibodies. The ability to induce antigen-specific tolerance provides a powerful avenue to alleviate allergies by exposure to the antigen in conjunction with down-regulation of B7-1, B7-2, B7-3 or CD40.

The specific roles of B7-1, B7-2 and B7-3 in T cell activation remains to be determined. Some studies suggest that their functions are essentially redundant (Hathcock et al 1994 *J Exp. Med.* 180, 631), or that the differences observed in the kinetics of expression might simply indicate that B7-2 is important in the initiation of the co-stimulatory signal, while B7-1 plays a role in the amplification of that signal. Other studies point to more specific functions. For example, Kuchroo et al., 1995 *Cell* 80, 707, have reported that blocking B7-1 expression may favor a Th2 response, while blocking B7-2 expression favors a Th1 response. These two helper T cell subpopulations play distinct roles in the immune response and inflammatory disease. Th1 cells are strongly correlated with auto-immune disease. Allergic responses are typically triggered by Th2 response. Therefore, the decision to target B7-1, B7-2, CD40 or a combination of the above will depend to the particular disease application.

SUMMARY OF THE INVENTION

The invention features novel nucleic acid-based techniques [e.g., enzymatic nucleic acid molecules (ribozymes), antisense nucleic acids, 2-5A antisense chimeras, triplex DNA, antisense nucleic acids containing RNA cleaving chemical groups (Cook et al., U.S. Pat. No. 5,359,051)] and methods for their use to induce graft tolerance, to treat autoimmune diseases such as lupus, rheumatoid arthritis, multiple sclerosis and to treatment of allergies.

In a preferred embodiment, the invention features use of one or more of the nucleic acid-based techniques to induce graft tolerance by inhibiting the synthesis of B7-1, B7-2, B7-3 and CD40 proteins.

Those in the art will recognize the other potential targets, for e.g., ICAM-1, VCAM-1, $\beta$1 integrin (VLA4) are also suitable for treatment with the nucleic acid-based techniques described in the present invention.

By "inhibit" is meant that the activity of B7-1, B7-2, B7-3 and/or CD40 or level of mRNAs encoded by B7-1, B7-2, B7-3 and/or CD40 is reduced below that observed in the absence of the nucleic acid. In one embodiment, inhibition with ribozymes preferably is below that level observed in the presence of an enzymatically inactive RNA molecule able to bind to the same site on the mRNA, but unable to cleave that RNA.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention. By "equivalent" RNA to B7-1, B7-2, B7-3 and/or CD40 is meant to include those naturally occurring RNA molecules associated with graft rejection in various animals, including human, mice, rats, rabbits, primates and pigs.

By "antisense nucleic acid" is meant a non-enzymatic nucleic acid molecule that binds to another RNA (target RNA) by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004).

By "2-5A antisense chimera" is meant, an antisense oligonucleotide containing a 5' phosphorylated 2'-5'-linked adenylate residues. These chimeras bind to target RNA in a sequence-specific manner and activate a cellular 2-5A-dependent ribonuclease which in turn cleaves the target RNA (Torrence et al., 1993 *Proc. Natl. Acad. Sci. USA* 90, 1300).

By "triplex DNA" is meant an oligonucleotide that can bind to a double-stranded DNA in a sequence-specific manner to form a triple-strand helix. Triple-helix formation has been shown to inhibit transcription of the targeted gene (Duval-Valentin et al., 1992 *Proc. Natl. Acad. Sci.USA* 89, 504).

By "gene" is meant a nucleic acid that encodes an RNA.

By "complementarity" is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the concentration of ribozyme necessary to affect a therapeutic treatment is lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Ribozymes that cleave the specified sites in B7-1, B7-2, B7-3 and/or CD40 mRNAs represent a novel therapeutic approach to induce graft tolerance and treat autoimmune diseases, allergies and other inflammatory conditions. Applicant indicates that ribozymes are able to inhibit the activity of B7-1, B7-2, B7-3 and/or CD40 and that the catalytic activity of the ribozymes is required for their inhibitory effect. Those of ordinary skill in the art, will find that it is clear from the examples described that other ribozymes that cleave these sites in B7-1, B7-2, B7-3 and/or CD40 mRNAs may be readily designed and are within the invention.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EP0360257, Hampel and Tritz, 1989 *Biochemistiy* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistiy* 32, 2795–2799) and of the Group I intron byt Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of a target mRNAs encoding B7-1, B7-2, B7-3 and/or CD40 proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA/RNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991, *Proc. Natl. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al, 1992 *Proc. Natl. Acad. Sci. USA* 89, 10802–6; Chen et al., 1992 *Nucleic Adids Res.*, 20, 4581–9; Sarver et al., 1990 *Science* 247, 1222–1225). Those skilled in the art realize that any ribozyme can be expressed in eukaryotic cells from the appropriate DNA/RNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856).

Such ribozymes are useful for the prevention of the diseases and conditions discussed above, and any other diseases or conditions that are related to the levels of B7-1, B7-2, B7-3 and/or CD40 activity in a cell or tissue. By "related" is meant that the inhibition of B7-1, B7-2, B7-3 and/or CD40 mRNAs and thus reduction in the level respective protein activity will relieve to some extent the symptoms of the disease or condition.

Ribozymes are added directly, or can be complexed with cationic lipids, packaged within liposomes, or otherwise delivered to target cells. The nucleic acid or nucleic acid complexes can be locally administered to relevant tissues ex vivo, or in vivo through injection, infusion pump or stent, with or without their incorporation in biopolymers. In preferred embodiments, the ribozymes have binding arms which are complementary to the sequences in Tables II, IV, VI, VIII, X, XII, XIV, XV, XVI, XVII, XVIII and XIX. Examples of such ribozymes are shown in Tables III, V, VI, VII, IX, XI, XIII, XIV, XV, XVI, XVII, XVIII and XIX. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit B7-1, B7-2, B7-3 and/or CD40 activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

Figure 2A:
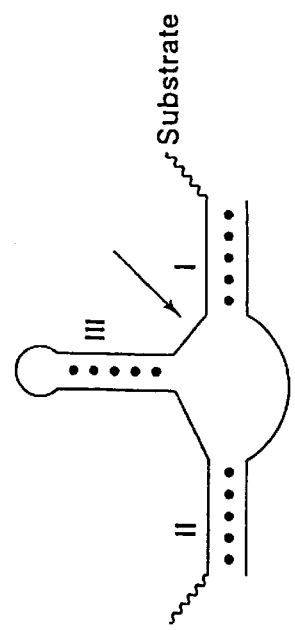
FIG. 2a is a diagrammatic representation of the hammerhead ribozyme domain known in the art.
Figure 2B:
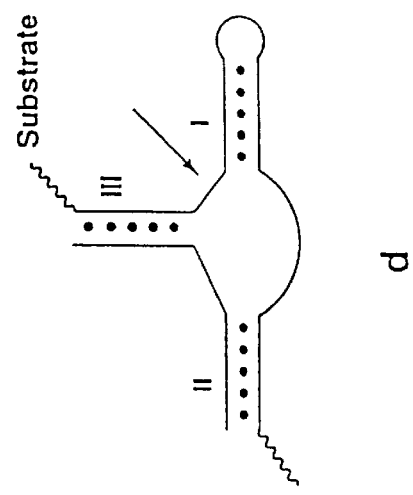
FIG. 2b is a diagrammatic representation of the hammerhead ribozyme as divided by Uhlenbeck (1987, Nature, 327, 596–600) into a substrate and enzyme portion.
Figure 2C:
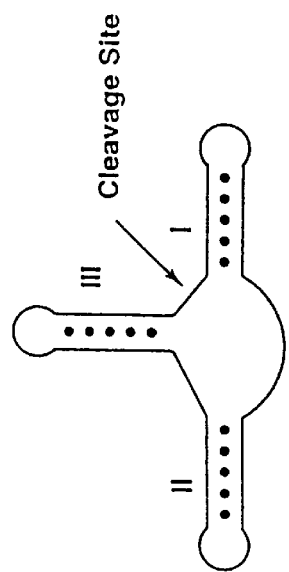
FIG. 2c is a similar diagram showing the hammerhead divided by ,Haseloff and Gerlach (1988, Nature, 334, 585–591) into two portions.
Figure 2D:
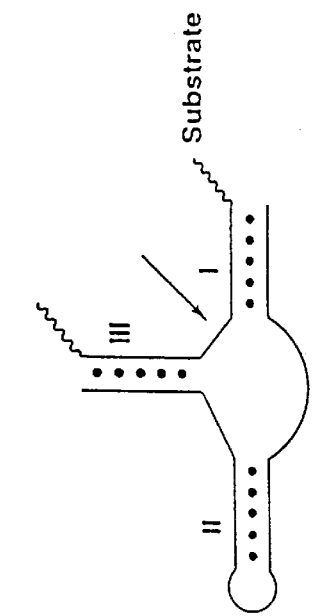

FIG. 2d is a similar diagram showing the hammerhead divided by Jeffries and Symons (1989, Nucl. Acids. Res., 17, 1371–1371) into two portions.

Figure 3:
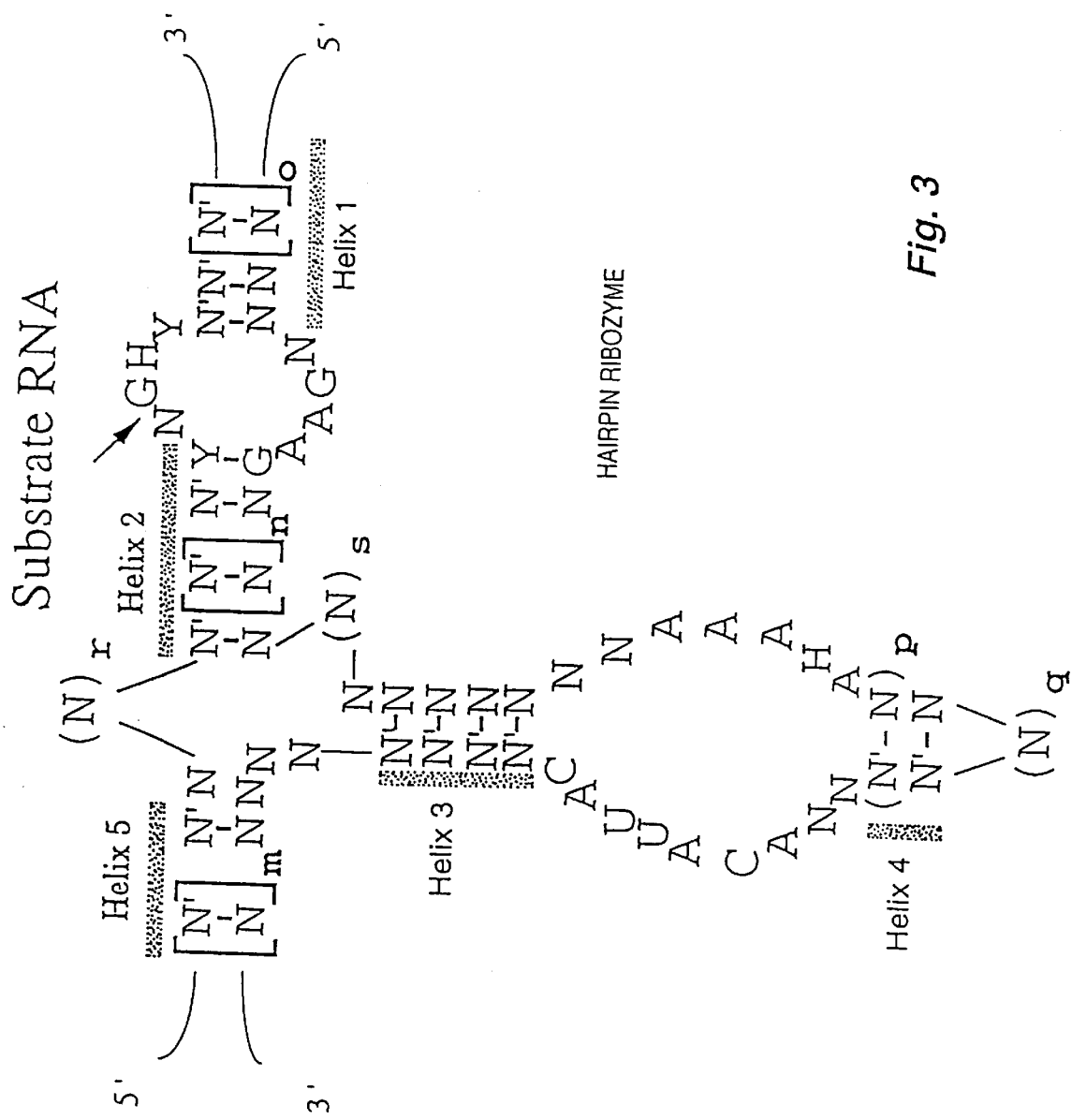

FIG. 3 is a diagrammatic representation of the general structure of a hairpin ribozyme (SEQ ID NO: 2748). Helix 2 (H2) is provided with a least 4 base pairs (i.e., n is 1, 2, 3 or 4) and helix 5 can be optionally provided of length 2 or more bases (preferably 3–20 bases, ie., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (ie., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H, refers to bases A, U or C. Y refers to pyrimidine bases.

Figure 4:
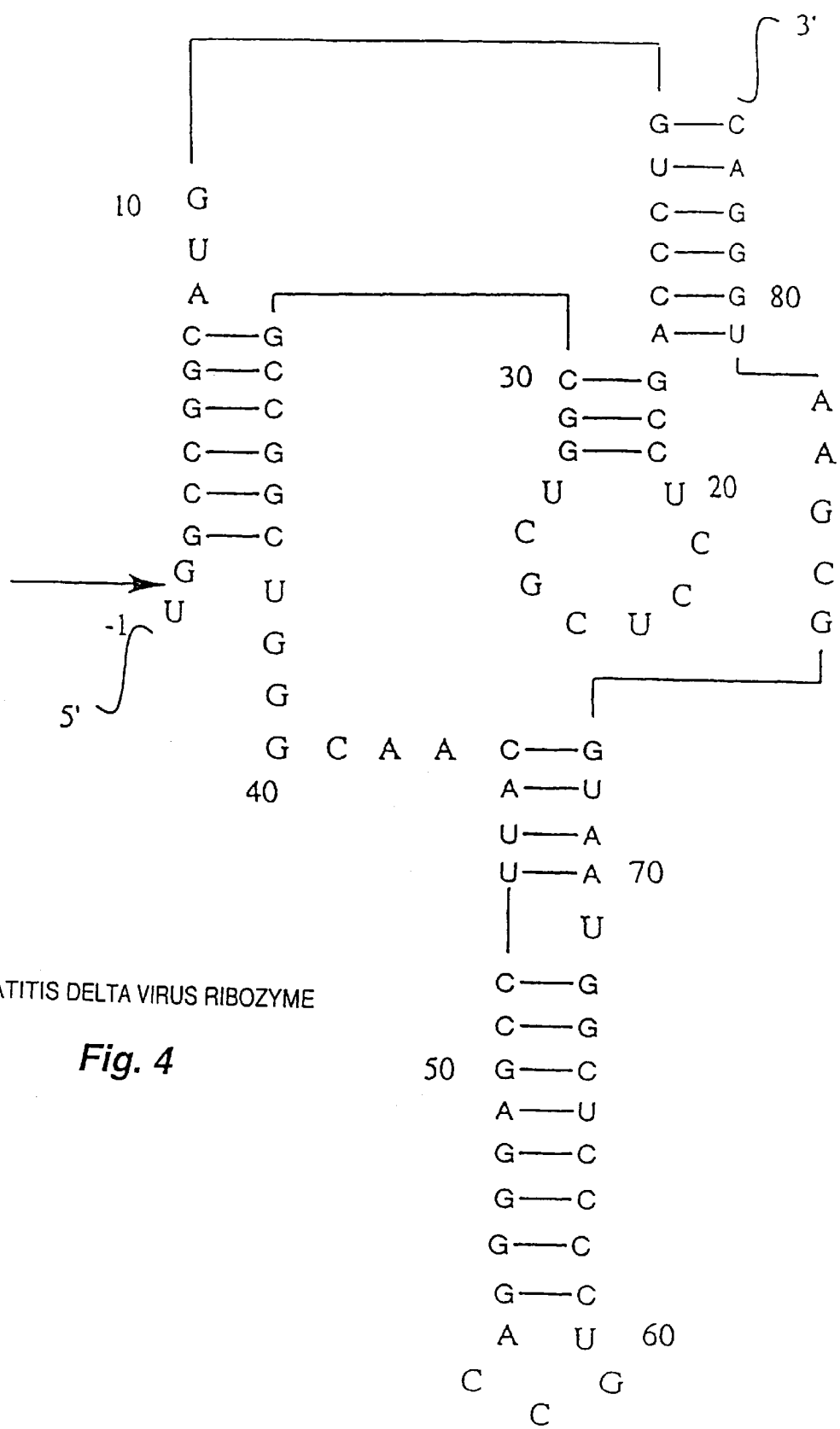

FIG. 4 is a representation of the general structure of the hepatitis delta virus ribozyme domain known in the art (SEQ ID NO: 2749).

Figure 5:
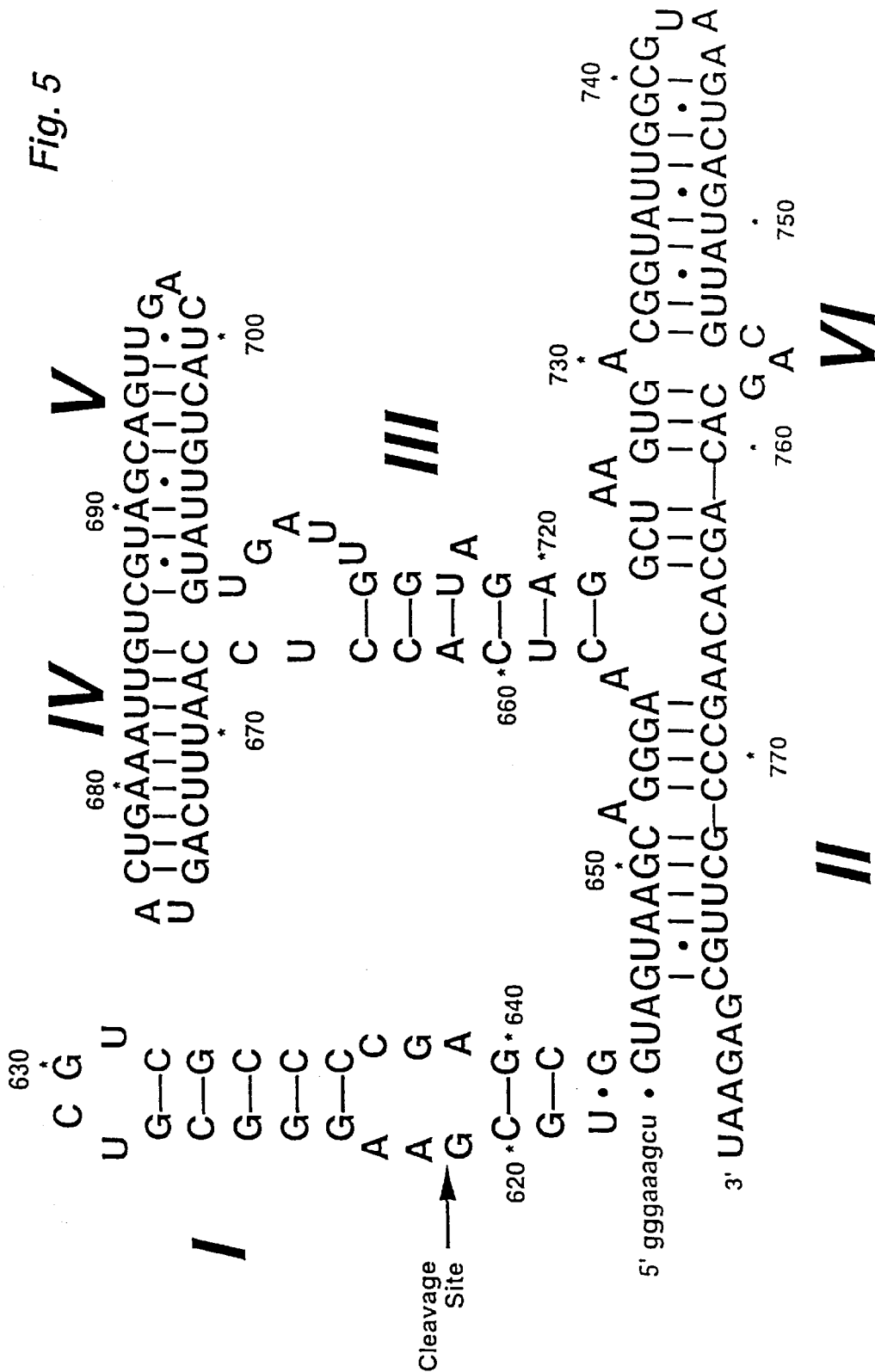

FIG. 5 is a representation of the general structure of the self-cleaving VS RNA ribozyme domain (SEQ ID NO: 2750).

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

RIBOZYMES

Ribozymes of this invention block to some extent B7-1, B7-2, B7-3 and/or CD40 production and can be used to treat disease or diagnose such disease. Ribozymes will be delivered to cells in culture, to cells or tissues in animal models of transplantation, autoimmune diseases and/or allergies and to human cells or tissues ex vivo or in viva. Ribozyme cleavage of B7-1, B7-2 and/or CD40 encoded mRNAs in these systems may alleviate disease symptoms.

Target Sites

Targets for useful ribozymes can be determined as disclosed in Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described.

The sequence of human and mouse B7-1, B7-2, B7-3 and/or CD40 mRNAs were screened for optimal ribozyme target sites using a computer folding algorithm. Hammerhead or hairpin ribozyme cleavage sites were identified. These sites are shown in Tables II, IV, VI, VIII, X, XII, XIV, XV, XVI, XVII, XVIII and XIX (All sequences are 5' to 3' in the tables) The nucleotide base position is noted in the Tables as that site to be cleaved by the designated type of ribozyme. While mouse and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466, mouse targeted ribozymes may be useful to test efficacy of action of the ribozyme prior to testing in humans. The nucleotide base position is noted in the Tables as that site to be cleaved by the designated type of ribozyme.

Hammerhead or hairpin ribozymes were designed that could bind and v-ere individually analyzed by computer folding (Jaeger et al., 1989 Proc. Natl. Acad. Sci. USA, 86, 7706) to assess whether the ribozyme sequences fold into the appropriate secondary structure. Those ribozymes with unfavorable intramolecular interactions between the binding arms and the catalytic core were eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in McSwiggen, U.S. patent application Ser. No. 07/883,849 filed on May 1, 1992, entitled "Assay for ribozyme target site", hereby incorporated by reference herein. Briefly, DNA oligonucleotides representing potential hammerhead or hairpin ribozyme cleavage sites were synthesized. A polymerase chain reaction is used to generate substrates for T7 RNA polymerase transcription from human and mouse B7-1, B7-2 and CD40 cDNA clones. Labeled RNA transcripts are synthesized in vitro from the templates. The oligonucleotides and the labeled transcripts were annealed, RNAseH was added and the mixtures were incubated for the designated times at 37° C. Reactions are stopped and RNA separated on sequencing polyacrylamide gels. The percentage of the substrate cleaved is determined by autoradiographic quantitation using a Phosphorimaging system. From these data, hammerhead or hairpin ribozyme sites are chosen as the most accessible.

Ribozymes of the hammerhead or hairpin motif are designed to anneal to various sites in the mRNA message. The binding arms are complementary to the target site sequences described above. The ribozymes are chemically synthesized. The method of synthesis used follows the procedure for normal RNA synthesis as described in Usman et al., 1987 *J. Am. Chem. Soc.*, 109, 7345 and in Scaringe et al., 1990 *Nucleic Acids Res.*, 18, 5433 and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 *Nucleic Acids Res.*, 20, 3252). Hairpin ribozymes were synthesized in two parts and annealed to reconstruct the active ribozyme (Chowrira and Burke, 1992 *Nucleic Acids Res.*, 20, 2835–2840). Ribozymes were also synthesized from DNA templates using bacteriophage T7 RNA polymerase (Milligan and Uhlenbeck, 1989, *Methods Enzymol.* 180, 51). All ribozymes are modified extensively to enhance stability by modification with nuclease resistant groups, for example, 2'-amino, 2'-C-allyl, 2'-flouro, 2'-O-methyl, 2'-H (for a review see Usman and Cedergren, 1992 TIBS 17, 34). Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

The sequences of the ribozymes that are chemically synthesized, useful in this study, are shown in Tables III, V, VI, VII, IX, XI, XIII, XIV, XV, XVI, XVII, VIII and XIX. Those in the art will recognize that these sequences are representative only of many more such sequences where the enzymatic portion of the ribozyme (all but the binding arms) is altered to affect activity. For example, stem-loop II sequence of hammerhead ribozymes listed in Tables III and V (5'-GGCCGAAAGGCC-3') can be altered (substitution, deletion, and/or insertion) to contain any sequences provided a minimum of two base-paired stem structure can form. Similarly, stem-loop IV sequence of hairpin ribozymes listed in Tables VI and VII (5'-CACGUUGUG-3') can be altered (substitution, deletion, and/or insertion) to contain any sequence, provided a minimum of two base-paired stem structure can form. The sequences listed in Tables III, V, VI, VII, IX, XI, XIII, XIV, XV, XVI, XVII, XVIII and XIX may be formed of ribonucleotides or other nucleotides or non-nucleotides. Such ribozymes are equivalent to the ribozymes described specifically in the Tables.

Optimizing Ribozyme Activity

Ribozyme activity can be optimized as described by Stinchcomb et al, supra. The details will not be repeated here, but include altering the length of tie ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al, 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et ail, International Publication No. WO 91/03162, as well as Usman, N. et al. U.S. patent application Ser. No. 07/829,729, and Sproat, European Patent Application 92110298.4 which describe various chemical modifications that can be made to the sugar moieties of enzymatic RNA molecules). Modifications which enhance their efficacy in cells, and removal of stem II bases to shorten RNA synthesis times and reduce chemical requirements are desired. (All these publications are hereby incorporated by reference herein.), Sullivan, et al., supra, describes the general methods for delivery of enzymatic RNA molecules. Ribozymes may be administered to cells by a variety of methods known to those familiar to the art, including, but not restricted to, encapsulation in liposomes, by lontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

In another preferred embodiment, the ribozyme is administered to the site of B7-1, B7-2, B7-3 and/or CD40 expression (APC) in an appropriate liposomal vesicle. APCs isolated from donor (for example) are treated with the Aribozyme preparation (or other nucleic acid therapeutics) ex vivo and the treated cells are infused into recipient. Alternatively, cells, tissues or organs are directly treated with nucleic acids of the present invention prior to transplantation into a recipient.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase If (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al., 1993 *Proc. Natl. Acad. Sci. U.S.A*, 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves mRNAs encoded by B7-1, B7-2, B7-3 and/or CD40 are inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech.* 3, 533). The adenovirus vector is delivered as recombinant adenoviral particles. The DNA may be delivered alone or complexed with vehicles (as described for RNA above). The recombinant adenovirus or MV particles are locally administered to the site of treatment, e.g., through incubation or inhalation in vivo or by direct application to cells or tissues ex vitro.

B7-1, B7-2, B7-3 and CD40 are attractive ribozyme targets by several criteria. The molecular mechanism of T cell activation is well-established. Efficacy can be tested in well-defined and predictive animal models. The clinical end-point of graft rejection is clear. Since delivery would be ex vivo, treatment of the correct cell population would be assured. Finally, the disease condition is serious and current therapies are inadequate. Whereas protein-based therapies would induce anergy against all antigens encountered during the several week treatment period, ex vivo ribozyme therapy provides a direct and elegant approach to truly donor-specific anergy.

Similarly, autoimmune diseases and allergies can be prevented or treated by reversing the devastating course of immune response to self-antigens. Specifically, nucleic acids of this inventions can dampen the response to naturally occuring antigens.

EXAMPLE 1

: B7-1, B7-2, B7-3 and/or CD40 Hammerhead Ribozymes

By engineering ribozyme motifs we have designed several ribozymes directed against B7-1, B7-2, B7-3 and/or CD40 encoded mRNA sequences. These ribozymes were synthesized with modifications that improve their nuclease resistance. The ability of ribozymes to cleave target sequences in vitro was evaluated.

Several common human cell lines are available that can be induced to express endogenous B7-1, B7-2, B7-3 and/or CD40. Alternatively, murine splenic cells can be isolated and induced, to express B7-1 or B7-2, with IL-4 or recombinant CD40 ligand. B7-1 and B7-2 can be detected easily with monoclonal antibodies. Use of appropriate flourescent reagents and flourescence-activated cell-sorting (FACS) will permit direct quantitation of surface B7-1 and B7-2 on a cell-by-cell basis. Active ribozymes are expected to directly reduce B7-1 or B7-2 expression. Ribozymes targeted to CD40 would prevent induction of B7-2 by CD40 ligand.

Several animal models of transplantation are available—Mouse, rat, Porcine model (Fodor et al., 1994, *Proc. Natl. Acad. Sci. USA* 91, 11153); or Baboon (reviewed by Nowak, 1994 *Science* 266, 1148). B7-1, B7-2, B7-3 and/or CD40 protein levels can be measured clinically or experimentally by FACS analysis. B7-1, B7-2, B7-3 and/or CD40 encoded mRNA levels will be assessed by Northern analysis, RNase-protection, primer extension analysis and/or quantitative RT-PCR. Ribozymes that block the induction of B7-1, B7-2, B7-3 and/or CD40 activity and/or B7-1, B7-2, B7-3 and/or CD40 protein encoding mRNAs by more than 20% in vitro will be identified.

Several animals models of autoimmune disorders are available—allergic encephalomyelitis (EAE) in Lewis rats (Carlson et al., 1993 *Ann. N.Y. Acad. Sci.* 685, 86); animal models of multiple sclerosis (Wekerle et al., 1994 *Ann. Neurol.* 36, s47) and rheumatoid arthritis (van Laar et al., 1994 *Chem. Immunol.* 58, 206).

Several animal models of allergy are available and are reviewed by Kemeny and Diaz-Sanchez, 1990, *Clin. Exp. Immunol.* 82, 423 and Pretolani et al., 1994 *Ann. N.Y.Acad. Sci.* 725, 247).

RNA ribozymes and/or genes encoding them will be delivered by either free delivery, liposome delivery, cationic lipid delivery, adeno-associated virus vector delivery, adenovirus vector delivery, retrovirus vector delivery or plasmid vector delivery in these animal model experiments (see above). One dose of a ribozyme vector that constitutively expresses the ribozyme or one or more doses of a stable anti-B7-1, B7-2, B7-3 and/or CD40 ribozymes or a transiently expressing ribozyme vector to donor APC, followed by infusion into the recipient may reduce the incidence of graft rejection. Alternatively, graft tissues may be treated as described above prior to transplantation.

Diagnostic Uses

Ribozymes of this invention may be used as diagnostic tools to examine genetic drift and mutations within diseased cells or to detect the presence of B7-1, B7-2, B7-3 and/or CD40 RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with B7-1, B7-2, B7-3 and/or CD40 related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (ie., B7-1, B7-2, B7-3 and/or CD40) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.

RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

TABLE I-continued

Characteristics of Ribozymes

Hammerhead Ribozyme

Figure 1:
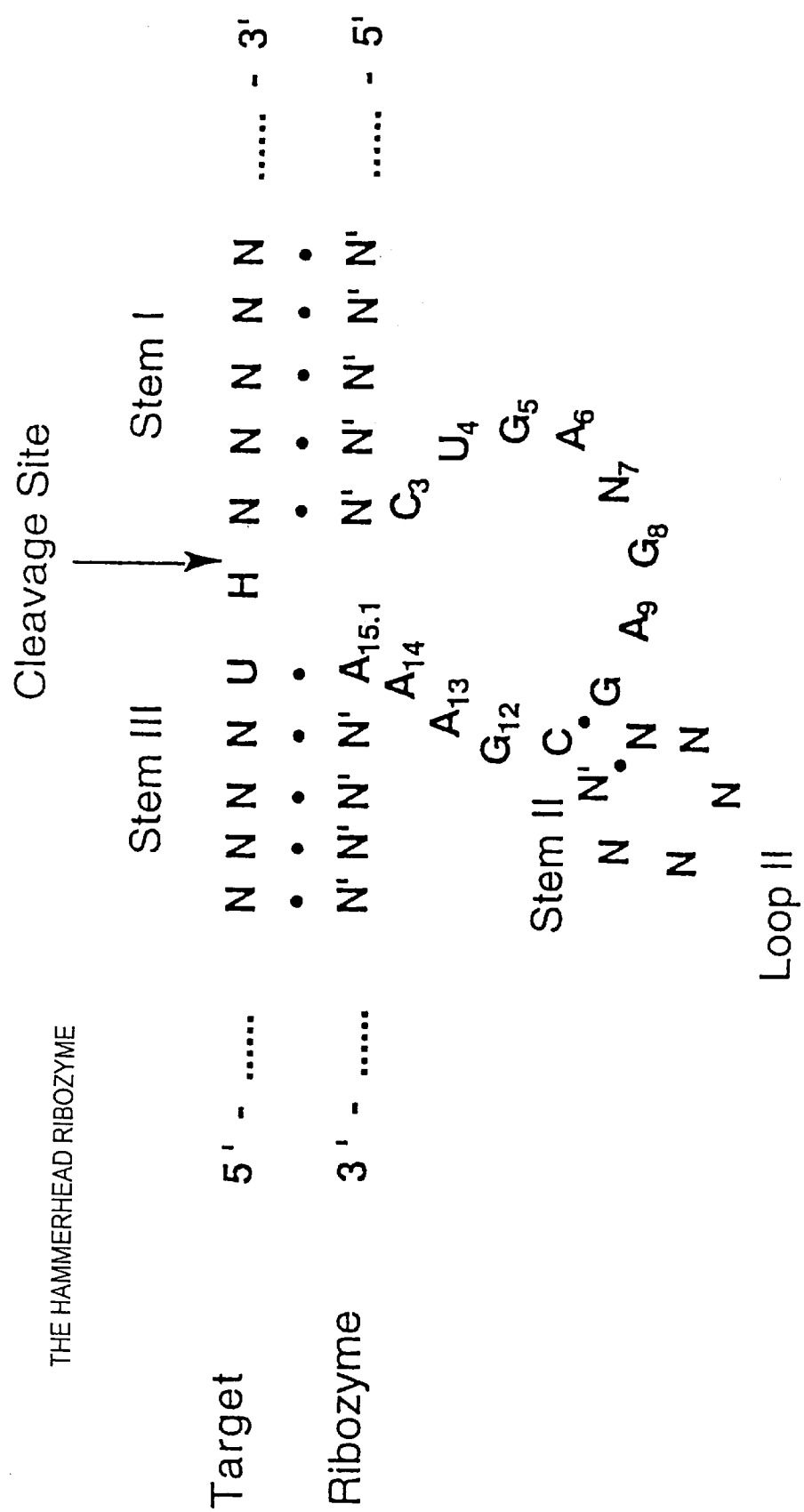
FIG. 1 is a diagrammatic representation of the hammerhead ribozyme domain known in the art (SEQ ID NO: 2746). Stem II can be ≧2 base-pair long.

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)

Hairpin Ribozyme

Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).

Neurospora VS RNA Ribozyme

Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

Human B7-1 Hammerhead Ribozyme Sequences

| nt. Position | HH Target | Sequence | Seq. ID No. | nt. Position | HH Target | Sequence | Seq. ID No. |
|---|---|---|---|---|---|---|---|
| 8 | AAACCCU C | UGUAAAG | 1 | 236 | UGUGUGU U | UUGUAAA | 43 |
| 12 | CCUCUGU A | AAGUAAC | 2 | 237 | GUGUGUU U | UGUAAAC | 44 |
| 17 | GUAAAGU A | ACAGAAG | 3 | 238 | UGUGUUU U | GUAAACA | 45 |
| 26 | CAGAAGU U | AGAAGGG | 4 | 241 | GUUUUGU A | AACAUCA | 46 |
| 27 | AGAAGUU A | GAAGGGG | 5 | 247 | UAAACAU C | ACUGGAG | 47 |
| 41 | GAAAUGU C | GCCUCUC | 6 | 258 | GGAGGGU C | UUCUACG | 48 |
| 46 | GUCGCCU C | UCUGAAG | 7 | 260 | AGGGUCU U | CUACGUG | 49 |
| 48 | CGCCUCU C | UGAAGAU | 8 | 261 | GGGUCUU C | UACGUGA | 50 |
| 56 | UGAAGAU U | ACCCAAA | 9 | 263 | GUCUUCU A | CGUGAGC | 51 |
| 57 | GAAGAUU A | CCCAAAG | 10 | 274 | GAGCAAU U | GGAUUGU | 52 |
| 75 | AAGUGAU U | UGUCAUU | 11 | 279 | AUUGGAU U | GUCAUCA | 53 |
| 76 | AGUGAUU U | GUCAUUG | 12 | 282 | GGAUUGU C | AUCAGCC | 54 |
| 79 | GAUUUGU C | AUUGCUU | 13 | 285 | UUGUCAU C | AGCCCUG | 55 |
| 82 | UUGUCAU U | GCUUUAU | 14 | 298 | UGCCUGU U | UUGCACC | 56 |
| 86 | CAUUGCU U | UAUAGAC | 15 | 299 | GCCUGUU U | UGCACCU | 57 |
| 87 | AUUGCUU U | AUAGACU | 16 | 300 | CCUGUUU U | GCACCUG | 58 |
| 88 | UUGCUUU A | UAGACUG | 17 | 322 | CCCUGGU C | UUACUUG | 59 |

TABLE II-continued

Human B7-1 Hammerhead Ribozyme Sequences

| nt. Position | HH Target Sequence | Seq. ID No. | nt. Position | HH Target Sequence | Seq. ID No. |
|---|---|---|---|---|---|
| 90  | GCUUUAU A GACUGUA | 18  | 324 | CUGGUCU U ACUUGGG | 60  |
| 97  | AGACUGU A AGAAGAG | 19  | 325 | UGGUCUU A CUUGGGU | 61  |
| 110 | AGAACAU C UCAGAAG | 20  | 328 | UCUUACU U GGGUCCA | 62  |
| 112 | AACAUCU C AGAAGUG | 21  | 333 | CUUGGGU C CAAAUUG | 63  |
| 124 | GUGGAGU C UUACCCU | 22  | 339 | UCCAAAU U GUUGGCU | 64  |
| 126 | GGAGUCU U ACCCUGA | 23  | 342 | AAAUUGU U GGCUUUC | 65  |
| 127 | GAGUCUU A CCCUGAA | 24  | 347 | GUUGGCU U UCACUUU | 66  |
| 137 | CUGAAAU C AAAGGAU | 25  | 348 | UUGGCUU U CACUUUU | 67  |
| 145 | AAAGGAU U UAAAGAA | 26  | 349 | UGGCUUU C ACUUUUG | 68  |
| 146 | AAGGAUU U AAAGAAA | 27  | 353 | UUUCACU U UUGACCC | 69  |
| 147 | AGGAUUU A AAGAAAA | 28  | 354 | UUCACUU U UGACCCU | 70  |
| 163 | GUGGAAU U UUUCUUC | 29  | 355 | UCACUUU U GACCCUA | 71  |
| 164 | UGGAAUU U UUCUUCA | 30  | 362 | UGACCCU A AGCAUCU | 72  |
| 165 | GGAAUUU U UCUUCAG | 31  | 368 | UAAGCAU C UGAAGCC | 73  |
| 166 | GAAUUUU U CUUCAGC | 32  | 404 | GGAACAU C ACCAUCC | 74  |
| 167 | AAUUUUU C UUCAGCA | 33  | 410 | UCACCAU C CAAGUGU | 75  |
| 169 | UUUUUCU U CAGCAAG | 34  | 418 | CAAGUGU C CAUACCU | 76  |
| 170 | UUUUCUU C AGCAAGC | 35  | 422 | UGUCCAU A CCUCAAU | 77  |
| 187 | UGAAACU A AAUCCAC | 36  | 426 | CAUACCU C AAUUUCU | 78  |
| 191 | ACUAAAU C CACAACC | 37  | 430 | CCUCAAU U CUUUCAG | 79  |
| 200 | ACAACCU U UGGAGAC | 38  | 431 | CUCAAUU U CUUUCAG | 80  |
| 201 | CAACCUU U GGAGACC | 39  | 432 | UCAAUUU C UUUCAGC | 81  |
| 221 | ACACCCU C CAAUCUC | 40  | 434 | AAUUUCU U UCAGCUC | 82  |
| 226 | CUCCAAU C UCUGUGU | 41  | 435 | AUUUCUU U CAGCUCU | 83  |
| 228 | CCAAUCU C UGUGUGU | 42  | 436 | UUUCUUU C AGCUCUU | 84  |
| 441 | UUCAGCU C UUGGUGC | 85  | 782 | GUGACGU U AUCAGUC | 134 |
| 443 | CAGCUCU U GGUGCUG | 86  | 783 | UGACGUU A UCAGUCA | 135 |
| 457 | GGCUGGU C UUUCUCA | 87  | 785 | ACGUUAU C AGUCAAA | 136 |
| 459 | CUGGUCU U UCUCACU | 88  | 789 | UAUCAGU C AAAGCUG | 137 |
| 460 | UGGUCUU U CUCACUU | 89  | 800 | GCUGACU U CCCUACA | 138 |
| 461 | GGUCUUU C UCACUUC | 90  | 801 | CUGACUU C CCUACAC | 139 |
| 463 | UCUUUCU C ACUUCUG | 91  | 805 | CUUCCCU A CACCUAG | 140 |
| 467 | UCUCACU U CUGUUCA | 92  | 811 | UACACCU A GUAUAUC | 141 |
| 468 | CUCACUU C UGUUCAG | 93  | 814 | ACCUAGU A UAUCUGA | 142 |
| 472 | CUUCUGU U CAGGUGU | 94  | 816 | CUAGUAU A UCUGACU | 143 |
| 473 | UUCUGUU C AGGUGUU | 95  | 818 | AGUAUAU C UGACUUU | 144 |
| 480 | CAGGUGU U AUCCACG | 96  | 824 | UCUGACU U UGAAAUU | 145 |
| 481 | AGGUGUU A UCCACGU | 97  | 825 | CUGACUU U GAAAUUC | 146 |
| 483 | GUGUUAU C CACGUGA | 98  | 831 | UUGAAAU U CCAACUU | 147 |
| 521 | ACGCUGU C CUGUGGU | 99  | 832 | UGAAAUU C CAACUUC | 148 |
| 529 | CUGUGGU C ACAAUGU | 100 | 838 | UCCAACU U CUAAUAU | 149 |
| 537 | ACAAUGU U CUGUUG  | 101 | 839 | CCAACUU C UAAUAUU | 150 |
| 538 | CAAUGUU C UGUUGA  | 102 | 841 | AACUUCU A AUAUUAG | 151 |
| 539 | AAUGUUU C UGUUGAA | 103 | 844 | UUCUAAU A UUAGAAG | 152 |
| 543 | UUUCUGU U GAAGAGC | 104 | 846 | CUAAUAU U AGAAGGA | 153 |
| 562 | ACAAACU U GCAUCUA | 105 | 847 | UAAUAUU A GAAGGAU | 154 |
| 567 | CUCGCAU C UACUGGC | 106 | 855 | GAAGGAU A AUUUGCU | 155 |
| 569 | CGCAUCU A CUGGCAA | 107 | 858 | GGAUAAU U UGCUCAA | 156 |
| 601 | GCUGACU A UGAUGUC | 108 | 859 | GAUAAUU U GCUCAAC | 157 |
| 608 | AUGUGUC C UGGGGAC | 109 | 863 | AUUUGCU C AACUCU  | 158 |
| 622 | CAUGAAU A UAUGGCC | 110 | 869 | UCAACCU C UGGAGGU | 159 |
| 624 | UGAAUAU A UGGCCCG | 111 | 877 | UGGAGGU U UUCCAGA | 160 |
| 635 | CCCGAGU A CAAGAAC | 112 | 878 | GGAGGUU U UCCAGAG | 161 |
| 651 | GGACCAU C UUUGAUA | 113 | 879 | GAGGUUU C CAGAGC  | 162 |
| 653 | ACCAUCU U UGAUAUC | 114 | 880 | AGGUUUU C CAGAGCC | 163 |
| 654 | CCAUCUU U GAUAUCA | 115 | 889 | AGAGCCU C ACCUCUC | 164 |
| 658 | CUUUGAU A UCACUAA | 116 | 894 | CUCACCU C UCCUGGU | 165 |
| 660 | UUGAUAU C ACUAAUA | 117 | 896 | CACCUCU C CUGGUUG | 166 |
| 664 | UAUCACU A AUAACCU | 118 | 902 | UCCUGGU U GGAAAAU | 167 |
| 667 | CACUAAU A ACCUCUC | 119 | 920 | GAAGAAU U AAAUGCC | 168 |
| 672 | AUAACCU C UCCAUUG | 120 | 921 | AAGAAUU A AAUGCCA | 169 |
| 674 | AACCUCU C CAUUGUG | 121 | 930 | AUGCCAU C AACACAA | 170 |
| 678 | UCUCCAU U GUGAUCC | 122 | 942 | CAACAGU U UCCCAAG | 171 |
| 684 | UUGUGAU C CUGGCUC | 123 | 943 | AACAGUU U CCCAAGA | 172 |
| 691 | CCUGGCU C UGCGCCC | 124 | 944 | ACAGUUU C CCAAGAU | 173 |
| 701 | CGCCCAU U UGACGAG | 125 | 952 | CCAAGAU C UGAAAC  | 174 |
| 716 | GGCACAU A CGAGUGU | 126 | 966 | CUGAGCU C UAUGCUG | 175 |
| 726 | AGUGUGU U GUUCUGA | 127 | 968 | GAGCUCU A UGCUGUU | 176 |
| 729 | GUGUUGU U CUGAAGU | 128 | 975 | AUGCUGU U AGCAGCA | 177 |
| 730 | UGUUGUU C UGAAGUA | 129 | 976 | UGCUGUU A GCAGCAA | 178 |
| 737 | CUGAAGU A UGAAAAA | 130 | 991 | ACUGGAU U UCAUAUU | 179 |
| 751 | AGACGCU U UCAAGCG | 131 | 992 | CUGGAUU U CAAUAUG | 180 |
| 752 | GACGCUU U CAAGCGG | 132 | 993 | UGGAUUU C AAUAUGA | 181 |
| 753 | ACGCUUU C AAGCGGG | 133 | 997 | UUUCAAU A UGACAAC | 182 |

TABLE II-continued

Human B7-1 Hammerhead Ribozyme Sequences

| nt. Position | HH Target Sequence | | Seq. ID No. | nt. Position | HH Target Sequence | | Seq. ID No. |
|---|---|---|---|---|---|---|---|
| 1016 | CACAGCU | U CAUGUGU | 183 | 1315 | CAUGGAU | C GUGGGGA | 232 |
| 1017 | ACAGCUU | C AUGUGUC | 184 | 1324 | UGGGGAU | C AUGAGGC | 233 |
| 1024 | CAUGUGU | C UCAUCAA | 185 | 1334 | GAGGCAU | U CUUCCCU | 234 |
| 1026 | UGUGUCU | C AUCAAGU | 186 | 1335 | AGGCAUU | C UUCCCUU | 235 |
| 1029 | GUCUCAU | C AAGUAUG | 187 | 1337 | GCAUUCU | U CCCUUAA | 236 |
| 1034 | AUCAAGU | A UGGACAU | 188 | 1338 | CAUUCUU | C CCUUAAC | 237 |
| 1042 | UGGACAU | U AAGAGUG | 189 | 1342 | CUUCCCU | U AACAAAU | 238 |
| 1043 | GGACAUU | U AAGAGUG | 190 | 1343 | UUCCCUU | A ACAAAUU | 239 |
| 1044 | GACAUUU | A AGAGUGA | 191 | 1350 | AACAAAU | U UAAGCUG | 240 |
| 1054 | AGUGAAU | C AGACCUU | 192 | 1351 | ACAAAUU | U AAGCUGU | 241 |
| 1061 | CAGACCU | U CAACUGG | 193 | 1352 | CAAAUUU | A AGCUGUU | 242 |
| 1062 | AGACCUU | C AACUGGA | 194 | 1359 | AAGCUGU | U UUACCCA | 243 |
| 1072 | CUGGAAU | A CAACCAA | 195 | 1360 | AGCUGUU | U UACCCAC | 244 |
| 1090 | AGAGCAU | U UCCUGA | 196 | 1361 | GCUGUUU | U ACCCACU | 245 |
| 1091 | GAGCAUU | U UCCUGAU | 197 | 1362 | CUGUUUU | A CCCACUA | 246 |
| 1092 | AGCAUUU | U CCUGAUA | 198 | 1369 | ACCCACU | A CCUCACC | 247 |
| 1093 | GCAUUUU | C CUGAUAA | 199 | 1373 | ACUACCU | C ACCUUCU | 248 |
| 1099 | UCCUGAU | A ACCUGCU | 200 | 1378 | CUCACCU | U CUUAAAA | 249 |
| 1107 | ACCUGCU | C CAUCCU | 201 | 1379 | UCACCUU | C UUAAAAA | 250 |
| 1112 | CUCCCAU | C CUGGGCC | 202 | 1381 | ACCUUCU | U AAAAACC | 251 |
| 1122 | GGGCCAU | U ACCUUAA | 203 | 1382 | CCUUCUU | A AAAACCU | 252 |
| 1123 | GGCCAUU | A CCUUAAU | 204 | 1390 | AAAAACCU | C UUUCAGA | 253 |
| 1127 | AUUACCU | U AAUCUCA | 205 | 1392 | AACCUCU | U UCAGAUU | 254 |
| 1128 | UUACCUU | A AUCUCAG | 206 | 1393 | ACCUCUU | U CAGAUUA | 255 |
| 1131 | CCUUAAU | C UCAGUAA | 207 | 1394 | CCUCUUU | C AGAUUAA | 256 |
| 1133 | UUAAUCU | C AGUAAAU | 208 | 1399 | UUCAGAU | U AAGCUGA | 257 |
| 1137 | UCUCAGU | A AAUGGAA | 209 | 1400 | UCAGAUU | A AGCUGAA | 258 |
| 1146 | AUGGAAU | U UUGUGA | 210 | 1412 | GAACAGU | U ACAAGAU | 259 |
| 1147 | UGGAAUU | U UUGUGAU | 211 | 1413 | AACAGUU | A CAAGAUG | 260 |
| 1148 | GGAAUUU | U UGUGAUA | 212 | 1429 | CUGGCAU | C CCUCUCC | 261 |
| 1149 | GAAUUUU | U GUGAUAU | 213 | 1433 | CAUCCCU | C UCCUUUC | 262 |
| 1155 | UUGUGAU | A UGCUGCC | 214 | 1435 | UCCCUCU | C CUUUCUC | 263 |
| 1169 | CUGACCU | A CUGCUUU | 215 | 1438 | CUCUCCU | U UCUCCCC | 264 |
| 1175 | UACUGCU | U UGCCCCA | 216 | 1439 | UCUCCUU | U CUCCCCA | 265 |
| 1176 | ACUGCUU | U GCCCCAA | 217 | 1440 | CUCCUUU | C UCCCCAU | 266 |
| 1214 | GAGAGAU | U GAGAAGG | 218 | 1442 | CCUUUCU | C CCCAUAU | 267 |
| 1230 | AAAGUGU | A CGCCCUG | 219 | 1448 | UCCCCAU | A UGCAAUU | 268 |
| 1239 | GCCCUGU | A UAACAGU | 220 | 1455 | AUGCAAU | U UGCUUAA | 269 |
| 1241 | CCUGUAU | A ACAGUGU | 221 | 1456 | UGCAAUU | U GCUAAAU | 270 |
| 1249 | ACAGUGU | C CGCAGAA | 222 | 1460 | AUUUGCU | U AAUGUAA | 271 |
| 1275 | AAAAGAU | C UGAAGGU | 223 | 1461 | UUUGCUU | A AUGUAAC | 272 |
| 1283 | UGAAGGU | A GCCUCCG | 224 | 1466 | UUAAUGU | A ACCUCUU | 273 |
| 1288 | GUAGCCU | C CGUCAUC | 225 | 1471 | GUAACCU | C UUCUUUU | 274 |
| 1292 | CCUCCGU | C AUCUCUU | 226 | 1473 | AACCUCU | U CUUUUGC | 275 |
| 1295 | CCGUCAU | C UCUUCUG | 227 | 1474 | ACCUCUU | C UUUUGCC | 276 |
| 1297 | GUCAUCU | C UUCUGGG | 228 | 1476 | CUCUCU | U UUGCCAU | 277 |
| 1299 | CAUCUCU | U CUGGGAU | 229 | 1477 | UCUUCUU | U UGCCAUG | 278 |
| 1300 | AUCUCUU | C UGGGAUA | 230 | 1478 | CUUCUUU | U GCCAUGU | 279 |
| 1307 | CUGGGAU | A CAUGGAU | 231 | 1486 | GCCAUGU | U UCCAUUC | 280 |
| 1487 | CCAUGUU | U CCAUUCU | 281 | | | | |
| 1488 | CAUGUUU | C CAUUCUG | 282 | | | | |
| 1492 | UUUCCAU | U CUGCCAU | 283 | | | | |
| 1493 | UUCCAUU | C UGCCAUC | 284 | | | | |
| 1500 | CUGCCAU | C UUGAAUU | 285 | | | | |
| 1502 | GCCAUCU | U GAAUUGU | 286 | | | | |
| 1507 | CUUGAAU | U GUCUUGU | 287 | | | | |
| 1510 | GAAUUGU | C UUGUCAG | 288 | | | | |
| 1512 | AUUGUCU | U GUCAGCC | 289 | | | | |
| 1515 | GUCUUGU | C AGCCAAU | 290 | | | | |
| 1523 | AGCCAAU | U CAUUAUC | 291 | | | | |
| 1524 | GCCAAUU | C AUUAUCU | 292 | | | | |
| 1527 | AAUUCAU | U AUCUAUU | 293 | | | | |
| 1528 | AUUCAUU | A UCUAUUA | 294 | | | | |
| 1530 | UCAUUAU | C UAUUAAA | 295 | | | | |
| 1532 | AUUAUCU | A UUAAACA | 296 | | | | |
| 1534 | UAUCUAU | U AAACACU | 297 | | | | |
| 1535 | AUCUAUU | A AACACUA | 298 | | | | |
| 1542 | AAACACU | A AUUUGAG | 299 | | | | |

TABLE III

Human B7-1 Hammerhead Ribozyme Sequences

| nt. Position | HH Ribozyme Sequence | Seq. ID No. |
|---|---|---|
| 8 | CUUUACA CUGAUGAGGCCGAAAGGCCGAA AGGGUUU | 300 |
| 12 | GUUACUU CUGAUGAGGCCGAAAGGCCGAA ACAGAGG | 301 |
| 17 | CUUCUGU CUGAUGAGGCCGAAAGGCCGAA ACUUUAC | 302 |
| 26 | CCCUUCU CUGAUGAGGCCGAAAGGCCGAA ACUUCUG | 303 |
| 27 | CCCCUUC CUGAUGAGGCCGAAAGGCCGAA AACUUCU | 304 |
| 41 | GAGAGGC CUGAUGAGGCCGAAAGGCCGAA ACAUUUC | 305 |
| 46 | CUUCAGA CUGAUGAGGCCGAAAGGCCGAA AGGCGAC | 306 |
| 48 | AUCUUCA CUGAUGAGGCCGAAAGGCCGAA AGAGGCG | 307 |
| 56 | UUUGGGU CUGAUGAGGCCGAAAGGCCGAA AUCUUCA | 308 |
| 57 | CUUUGGG CUGAUGAGGCCGAAAGGCCGAA AAUCUUC | 309 |
| 75 | AAUGACA CUGAUGAGGCCGAAAGGCCGAA AUCACUU | 310 |
| 76 | CAAUGAC CUGAUGAGGCCGAAAGGCCGAA AAUCACU | 311 |
| 79 | AAGCAAU CUGAUGAGGCCGAAAGGCCGAA ACAAAUC | 312 |
| 82 | AUAAAGC CUGAUGAGGCCGAAAGGCCGAA AUGACAA | 313 |
| 86 | GUCUAUA CUGAUGAGGCCGAAAGGCCGAA AGCAAUG | 314 |
| 87 | AGUCUAU CUGAUGAGGCCGAAAGGCCGAA AAGCAAU | 315 |
| 88 | CAGUCUA CUGAUGAGGCCGAAAGGCCGAA AAAGCAA | 316 |
| 90 | UCUACCU CUGAUGAGGCCGAAAGGCCGAA AUAAAGC | 317 |
| 97 | CUCUUCU CUGAUGAGGCCGAAAGGCCGAA ACAGUCU | 318 |
| 110 | CUUCUGA CUGAUGAGGCCGAAAGGCCGAA AUGUUCU | 319 |
| 112 | CACUUCU CUGAUGAGGCCGAAAGGCCGAA AGAUGUU | 320 |
| 124 | AGGGUAA CUGAUGAGGCCGAAAGGCCGAA ACUCCAC | 321 |
| 126 | UCAGGGU CUGAUGAGGCCGAAAGGCCGAA AGACUCC | 322 |
| 127 | UUCAGGG CUGAUGAGGCCGAAAGGCCGAA AAGACUC | 323 |
| 137 | AUCCUUU CUGAUGAGGCCGAAAGGCCGAA AUUUCAG | 324 |
| 145 | UUCUUUA CUGAUGAGGCCGAAAGGCCGAA AUCCUUU | 325 |
| 146 | UUUCUUU CUGAUGAGGCCGAAAGGCCGAA AAUCCUU | 326 |
| 147 | UUUUCUU CUGAUGAGGCCGAAAGGCCGAA AAAUCCU | 327 |
| 163 | GAAGAAA CUGAUGAGGCCGAAAGGCCGAA AUUCCAC | 328 |
| 164 | UGAAGAA CUGAUGAGGCCGAAAGGCCGAA AAUUCCA | 329 |
| 165 | CUGAAGA CUGAUGAGGCCGAAAGGCCGAA AAAUUCC | 330 |
| 166 | GCUGAAG CUGAUGAGGCCGAAAGGCCGAA AAAAUUC | 331 |
| 167 | UGCUGAA CUGAUGAGGCCGAAAGGCCGAA AAAAAUU | 332 |
| 169 | CUUGCUG CUGAUGAGGCCGAAAGGCCGAA AGAAAAA | 333 |
| 170 | GCUUGCU CUGAUGAGGCCGAAAGGCCGAA AAGAAAA | 334 |
| 187 | GUGGAUU CUGAUGAGGCCGAAAGGCCGAA AGUUUCA | 335 |
| 191 | GGUUGUG CUGAUGAGGCCGAAAGGCCGAA AUUUAGU | 336 |
| 200 | GUCUCCA CUGAUGAGGCCGAAAGGCCGAA AGGUUGU | 337 |
| 201 | GGUCUCC CUGAUGAGGCCGAAAGGCCGAA AAGGUUG | 338 |
| 221 | GAGAUUG CUGAUGAGGCCGAAAGGCCGAA AGGGUGU | 339 |
| 226 | ACACAGA CUGAUGAGGCCGAAAGGCCGAA AUUGGAG | 340 |
| 228 | ACACACA CUGAUGAGGCCGAAAGGCCGAA AGAUUGG | 341 |
| 236 | UUUACAA CUGAUGAGGCCGAAAGGCCGAA ACACACA | 342 |
| 237 | GUUUACA CUGAUGAGGCCGAAAGGCCGAA AACACAC | 343 |
| 238 | UGUUUAC CUGAUGAGGCCGAAAGGCCGAA AAACACA | 344 |
| 241 | UGAUGUU CUGAUGAGGCCGAAAGGCCGAA ACAAAAC | 345 |
| 247 | CUCCAGU CUGAUGAGGCCGAAAGGCCGAA AUGUUUA | 346 |
| 258 | CGUAGAA CUGAUGAGGCCGAAAGGCCGAA ACCCUCC | 347 |
| 260 | CACGUAG CUGAUGAGGCCGAAAGGCCGAA AGACCCU | 348 |
| 261 | UCACGUA CUGAUGAGGCCGAAAGGCCGAA AAGACCC | 349 |
| 263 | GCUCACG CUGAUGAGGCCGAAAGGCCGAA AGAAGAC | 350 |
| 274 | ACAAUCC CUGAUGAGGCCGAAAGGCCGAA AUUGCUC | 351 |
| 279 | UGAUGAC CUGAUGAGGCCGAAAGGCCGAA AUCCAAU | 352 |
| 282 | GGCUGAU CUGAUGAGGCCGAAAGGCCGAA ACAAUCC | 353 |
| 285 | CAGGGCU CUGAUGAGGCCGAAAGGCCGAA AUGACAA | 354 |
| 298 | GGUGCAA CUGAUGAGGCCGAAAGGCCGAA ACAGGCA | 355 |
| 299 | AGGUGCA CUGAUGAGGCCGAAAGGCCGAA AACAGGC | 356 |
| 300 | CAGGUGC CUGAUGAGGCCGAAAGGCCGAA AAACAGG | 357 |
| 322 | CAAGUAA CUGAUGAGGCCGAAAGGCCGAA ACCAGGG | 358 |
| 324 | CCCAAGU CUGAUGAGGCCGAAAGGCCGAA AGACCAG | 359 |
| 325 | ACCCAAG CUGAUGAGGCCGAAAGGCCGAA AAGACCA | 360 |
| 328 | UGGACCC CUGAUGAGGCCGAAAGGCCGAA AGUAAGA | 361 |
| 333 | CAAUUUG CUGAUGAGGCCGAAAGGCCGAA ACCCAAG | 362 |
| 339 | AGCCAAC CUGAUGAGGCCGAAAGGCCGAA AUUUGGA | 363 |
| 342 | GAAAGCC CUGAUGAGGCCGAAAGGCCGAA ACAAUUU | 364 |
| 347 | AAAGUGA CUGAUGAGGCCGAAAGGCCGAA AGCCAAC | 365 |
| 348 | AAAAGUG CUGAUGAGGCCGAAAGGCCGAA AAGCCAA | 366 |
| 349 | CAAAAGU CUGAUGAGGCCGAAAGGCCGAA AAAGCCA | 367 |
| 353 | GGGUCAA CUGAUGAGGCCGAAAGGCCGAA AGUGAAA | 368 |
| 354 | AGGGUCA CUGAUGAGGCCGAAAGGCCGAA AAGUGAA | 369 |
| 355 | UAGGGUC CUGAUGAGGCCGAAAGGCCGAA AAAGUGA | 370 |
| 362 | AGAUGCU CUGAUGAGGCCGAAAGGCCGAA AGGGUCA | 371 |
| 368 | GGCUUCA CUGAUGAGGCCGAAAGGCCGAA AUGCUUA | 372 |
| 404 | GGAUGGU CUGAUGAGGCCGAAAGGCCGAA AUGUUCC | 373 |
| 410 | ACACUUG CUGAUGAGGCCGAAAGGCCGAA AUGGUGA | 374 |

TABLE III-continued

Human B7-1 Hammerhead Ribozyme Sequences

| nt. Position | HH Ribozyme Sequence | Seq. ID No. |
|---|---|---|
| 418 | AGGUAUG CUGAUGAGGCCGAAAGGCCGAA ACACUUG | 375 |
| 422 | AUUGAGG CUGAUGAGGCCGAAAGGCCGAA AUGGACA | 376 |
| 426 | AGAAAUU CUGAUGAGGCCGAAAGGCCGAA AGGUAUG | 377 |
| 430 | UGAAAGA CUGAUGAGGCCGAAAGGCCGAA AUUGAGG | 378 |
| 431 | CUGAAAG CUGAUGAGGCCGAAAGGCCGAA AAUUGAG | 379 |
| 432 | GCUGAAA CUGAUGAGGCCGAAAGGCCGAA AAAUUGA | 380 |
| 434 | GAGCUGA CUGAUGAGGCCGAAAGGCCGAA AGAAAUU | 381 |
| 435 | AGAGCUG CUGAUGAGGCCGAAAGGCCGAA AAGAAAU | 382 |
| 436 | AAGAGCU CUGAUGAGGCCGAAAGGCCGAA AAAGAAA | 383 |
| 441 | GCACCAA CUGAUGAGGCCGAAAGGCCGAA AGCUGAA | 384 |
| 443 | CAGCACC CUGAUGAGGCCGAAAGGCCGAA AGAGCUG | 385 |
| 457 | UGAGAAA CUGAUGAGGCCGAAAGGCCGAA ACCAGCC | 386 |
| 459 | AGUGAGA CUGAUGAGGCCGAAAGGCCGAA AGACCAG | 387 |
| 460 | AAGUGAG CUGAUGAGGCCGAAAGGCCGAA AAGACCA | 388 |
| 461 | GAAGUGA CUGAUGAGGCCGAAAGGCCGAA AAAGACC | 389 |
| 463 | CAGAAGU CUGAUGAGGCCGAAAGGCCGAA AGAAAGA | 390 |
| 467 | UGAACAG CUGAUGAGGCCGAAAGGCCGAA AGUGAGA | 391 |
| 468 | CUGAACA CUGAUGAGGCCGAAAGGCCGAA AAGUGAG | 392 |
| 472 | ACACCUG CUGAUGAGGCCGAAAGGCCGAA ACAGAAG | 393 |
| 473 | AACACCU CUGAUGAGGCCGAAAGGCCGAA AACAGAA | 394 |
| 480 | CGUGGAU CUGAUGAGGCCGAAAGGCCGAA ACACCUG | 395 |
| 481 | ACGUGGA CUGAUGAGGCCGAAAGGCCGAA AACACCU | 396 |
| 483 | UCACGUG CUGAUGAGGCCGAAAGGCCGAA AUAACAC | 397 |
| 521 | ACCACAG CUGAUGAGGCCGAAAGGCCGAA ACAGCGU | 398 |
| 529 | ACAUUGU CUGAUGAGGCCGAAAGGCCGAA ACCACAG | 399 |
| 537 | CAACAGA CUGAUGAGGCCGAAAGGCCGAA ACAUUGU | 400 |
| 538 | UCAACAG CUGAUGAGGCCGAAAGGCCGAA AACAUUG | 401 |
| 539 | UUCAACA CUGAUGAGGCCGAAAGGCCGAA AAACAUU | 402 |
| 543 | GCUCUUC CUGAUGAGGCCGAAAGGCCGAA ACAGAAA | 403 |
| 562 | UAGAUGC CUGAUGAGGCCGAAAGGCCGAA AGUUUGU | 404 |
| 567 | GCCAGUA CUGAUGAGGCCGAAAGGCCGAA AUGCGAG | 405 |
| 569 | UUGCCAG CUGAUGAGGCCGAAAGGCCGAA AGAUGCG | 406 |
| 601 | GACAUCA CUGAUGAGGCCGAAAGGCCGAA AGUCAGC | 407 |
| 608 | GUCCCCA CUGAUGAGGCCGAAAGGCCGAA ACAUCAU | 408 |
| 622 | GGCCAUA CUGAUGAGGCCGAAAGGCCGAA AUUCAUG | 409 |
| 624 | CGGGCCA CUGAUGAGGCCGAAAGGCCGAA AUAUUCA | 410 |
| 635 | GUUCUUG CUGAUGAGGCCGAAAGGCCGAA ACUCGGG | 411 |
| 651 | UAUCAAA CUGAUGAGGCCGAAAGGCCGAA AUGGUCC | 412 |
| 653 | GAUAUCA CUGAUGAGGCCGAAAGGCCGAA AGAUGGU | 413 |
| 654 | UGAUAUC CUGAUGAGGCCGAAAGGCCGAA AAGAUGG | 414 |
| 658 | UUAGUGA CUGAUGAGGCCGAAAGGCCGAA AUCAAAG | 415 |
| 660 | UAUUAGU CUGAUGAGGCCGAAAGGCCGAA AUAUCAA | 416 |
| 664 | AGGUUAU CUGAUGAGGCCGAAAGGCCGAA AGUGAUA | 417 |
| 667 | GAGAGGU CUGAUGAGGCCGAAAGGCCGAA AUUAGUG | 418 |
| 672 | CAAUGGA CUGAUGAGGCCGAAAGGCCGAA AGGUUAU | 419 |
| 674 | CACAAUG CUGAUGAGGCCGAAAGGCCGAA AGAGGUU | 420 |
| 678 | GGAUCAC CUGAUGAGGCCGAAAGGCCGAA AUGGAGA | 421 |
| 684 | GAGCCAG CUGAUGAGGCCGAAAGGCCGAA AUCACAA | 422 |
| 691 | GGGCGCA CUGAUGAGGCCGAAAGGCCGAA AGCCAGG | 423 |
| 701 | CUCGUCA CUGAUGAGGCCGAAAGGCCGAA AUGGGCG | 424 |
| 716 | ACACUCG CUGAUGAGGCCGAAAGGCCGAA AUGUGCC | 425 |
| 726 | UCAGAAC CUGAUGAGGCCGAAAGGCCGAA ACACACU | 426 |
| 729 | ACUUCAG CUGAUGAGGCCGAAAGGCCGAA ACAACAC | 427 |
| 730 | UACUUCA CUGAUGAGGCCGAAAGGCCGAA AACAACA | 428 |
| 737 | UUUUUCA CUGAUGAGGCCGAAAGGCCGAA ACUUCAG | 429 |
| 751 | CGCUUGA CUGAUGAGGCCGAAAGGCCGAA AGCGUCU | 430 |
| 752 | CCGCUUG CUGAUGAGGCCGAAAGGCCGAA AAGCGUC | 431 |
| 753 | CCCGCUU CUGAUGAGGCCGAAAGGCCGAA AAAGCGU | 432 |
| 782 | GACUGAU CUGAUGAGGCCGAAAGGCCGAA ACGUCAC | 433 |
| 783 | UGACUGA CUGAUGAGGCCGAAAGGCCGAA AACGUCA | 434 |
| 785 | UUUGACU CUGAUGAGGCCGAAAGGCCGAA AUAACGU | 435 |
| 789 | CAGCUUU CUGAUGAGGCCGAAAGGCCGAA ACUGAUA | 436 |
| 800 | UGUAGGG CUGAUGAGGCCGAAAGGCCGAA AGUCAGC | 437 |
| 801 | GUGUAGG CUGAUGAGGCCGAAAGGCCGAA AAGUCAG | 438 |
| 805 | CUAGGUG CUGAUGAGGCCGAAAGGCCGAA AGGGAAG | 439 |
| 811 | GAUAUAC CUGAUGAGGCCGAAAGGCCGAA AGGUGUA | 440 |
| 814 | UCAGAUA CUGAUGAGGCCGAAAGGCCGAA ACUAGGU | 441 |
| 816 | AGUCAGA CUGAUGAGGCCGAAAGGCCGAA AUACUAG | 442 |
| 818 | AAAGUCA CUGAUGAGGCCGAAAGGCCGAA AUAUACU | 443 |
| 824 | AAUUUCA CUGAUGAGGCCGAAAGGCCGAA AGUCAGA | 444 |
| 825 | GAAUUUC CUGAUGAGGCCGAAAGGCCGAA AAGUCAG | 445 |
| 831 | AAGUUGG CUGAUGAGGCCGAAAGGCCGAA AUUUCAA | 446 |
| 832 | GAAGUUG CUGAUGAGGCCGAAAGGCCGAA AAUUUCA | 447 |
| 838 | AUAUUAG CUGAUGAGGCCGAAAGGCCGAA AGUUGGA | 448 |
| 839 | AAUAUUA CUGAUGAGGCCGAAAGGCCGAA AAGUUGG | 449 |

TABLE III-continued

Human B7-1 Hammerhead Ribozyme Sequences

| nt. Position | HH Ribozyme Sequence | Seq. ID No. |
|---|---|---|
| 841 | CUAAUAU CUGAUGAGGCCGAAAGGCCGAA AGAAGUU | 450 |
| 844 | CUUCUAA CUGAUGAGGCCGAAAGGCCGAA AUUAGAA | 451 |
| 846 | UCCUUCU CUGAUGAGGCCGAAAGGCCGAA AUAUUAG | 452 |
| 847 | AUCCUUC CUGAUGAGGCCGAAAGGCCGAA AAUAUUA | 453 |
| 855 | AGCAAAU CUGAUGAGGCCGAAAGGCCGAA AUCCUUC | 454 |
| 858 | UUGAGCA CUGAUGAGGCCGAAAGGCCGAA AUUAUCC | 455 |
| 859 | GUUGAGC CUGAUGAGGCCGAAAGGCCGAA AAUUAUC | 456 |
| 863 | AGAGGUU CUGAUGAGGCCGAAAGGCCGAA AGCAAAU | 457 |
| 869 | ACCUCCA CUGAUGAGGCCGAAAGGCCGAA AGGUUGA | 458 |
| 877 | UCUGGAA CUGAUGAGGCCGAAAGGCCGAA ACCUCCA | 459 |
| 878 | CUCUGGA CUGAUGAGGCCGAAAGGCCGAA AACCUCC | 460 |
| 879 | GCUCUGG CUGAUGAGGCCGAAAGGCCGAA AAACCUC | 461 |
| 880 | GGCUCUG CUGAUGAGGCCGAAAGGCCGAA AAAACCU | 462 |
| 889 | GAGAGGU CUGAUGAGGCCGAAAGGCCGAA AGGCUCU | 463 |
| 894 | ACCAGGA CUGAUGAGGCCGAAAGGCCGAA AGGUGAG | 464 |
| 896 | CAACCAG CUGAUGAGGCCGAAAGGCCGAA AGAGGUG | 465 |
| 902 | AUUUUCC CUGAUGAGGCCGAAAGGCCGAA ACCAGGA | 466 |
| 920 | GGCAUUU CUGAUGAGGCCGAAAGGCCGAA AUUCUUC | 467 |
| 921 | UGGCAUU CUGAUGAGGCCGAAAGGCCGAA AAUUCUU | 468 |
| 930 | UUGUGUU CUGAUGAGGCCGAAAGGCCGAA AUGGCAU | 469 |
| 942 | CUUGGGA CUGAUGAGGCCGAAAGGCCGAA ACUGUUG | 470 |
| 943 | UCUUGGG CUGAUGAGGCCGAAAGGCCGAA AACUGUU | 471 |
| 944 | AUCUUGG CUGAUGAGGCCGAAAGGCCGAA AAACUGU | 472 |
| 952 | GUUUCAG CUGAUGAGGCCGAAAGGCCGAA AUCUUGG | 473 |
| 966 | CAGCAUA CUGAUGAGGCCGAAAGGCCGAA AGCUCAG | 474 |
| 968 | AACAGCA CUGAUGAGGCCGAAAGGCCGAA AGAGCUC | 475 |
| 975 | UGCUGCU CUGAUGAGGCCGAAAGGCCGAA ACAGCAU | 476 |
| 976 | UUGCUGC CUGAUGAGGCCGAAAGGCCGAA AACAGCA | 477 |
| 991 | AUAUUGA CUGAUGAGGCCGAAAGGCCGAA AUCCAGU | 478 |
| 992 | CAUAUUG CUGAUGAGGCCGAAAGGCCGAA AAUCCAG | 479 |
| 993 | UCAUAUU CUGAUGAGGCCGAAAGGCCGAA AAAUCCA | 480 |
| 997 | GUUGUCA CUGAUGAGGCCGAAAGGCCGAA AUUGAAA | 481 |
| 1016 | ACACAUG CUGAUGAGGCCGAAAGGCCGAA AGCUGUG | 482 |
| 1017 | GACACAU CUGAUGAGGCCGAAAGGCCGAA AAGCUGU | 483 |
| 1024 | UUGAUGA CUGAUGAGGCCGAAAGGCCGAA ACACAUG | 484 |
| 1026 | ACUUGAU CUGAUGAGGCCGAAAGGCCGAA AGACACA | 485 |
| 1029 | CAUACUU CUGAUGAGGCCGAAAGGCCGAA AUGAGAC | 486 |
| 1034 | AUGUCCA CUGAUGAGGCCGAAAGGCCGAA ACUUGAU | 487 |
| 1042 | ACUCUUA CUGAUGAGGCCGAAAGGCCGAA AUGUCCA | 488 |
| 1043 | CACUCUU CUGAUGAGGCCGAAAGGCCGAA AAUGUCC | 489 |
| 1044 | UCACUCU CUGAUGAGGCCGAAAGGCCGAA AAAUGUC | 490 |
| 1054 | AAGGUCU CUGAUGAGGCCGAAAGGCCGAA AUUCACU | 491 |
| 1061 | CCAGUUG CUGAUGAGGCCGAAAGGCCGAA AGGUCUG | 492 |
| 1062 | UCCAGUU CUGAUGAGGCCGAAAGGCCGAA AAGGUCU | 493 |
| 1072 | UUGGUUG CUGAUGAGGCCGAAAGGCCGAA AUUCCAG | 494 |
| 1090 | UCAGGAA CUGAUGAGGCCGAAAGGCCGAA AUGCUCU | 495 |
| 1091 | AUCAGGA CUGAUGAGGCCGAAAGGCCGAA AAUGCUC | 496 |
| 1092 | UAUCAGG CUGAUGAGGCCGAAAGGCCGAA AAAUGCU | 497 |
| 1093 | UUAUCAG CUGAUGAGGCCGAAAGGCCGAA AAAAUGC | 498 |
| 1099 | AGCAGGU CUGAUGAGGCCGAAAGGCCGAA AUCAGGA | 499 |
| 1107 | AGGAUGG CUGAUHGAGGCCGAAAGGCGAA AGCAGGU | 500 |
| 1112 | GGCCCAG CUGAUGAGGCCGAAAGGCCGAA AUGGGAG | 501 |
| 1122 | UUAAGGU CUGAUGAGGCCGAAAGGCCGAA AUGGCCC | 502 |
| 1123 | AUUAAGG CUGAUGAGGCCGAAAGGCCGAA AAUGGCC | 503 |
| 1127 | UGAGAUU CUGAUGAGGCCGAAAGGCCGAA AGGUAAU | 504 |
| 1128 | CUGAGAU CUGAUGAGGCCGAAAGGCCGAA AAGGUAA | 505 |
| 1131 | UUACUGA CUGAUGAGGCCGAAAGGCCGAA AUUAAGG | 506 |
| 1133 | AUUUACU CUGAUGAGGCCGAAAGGCCGAA AGAUUAA | 507 |
| 1137 | UUCCAUU CUGAUGAGGCCGAAAGGCCGAA ACUGAGA | 508 |
| 1146 | UCACAAA CUGAUGAGGCCGAAAGGCCGAA AUUCCAU | 509 |
| 1147 | AUCACAA CUGAUGAGGCCGAAAGGCCGAA AAUUCCA | 510 |
| 1148 | UAUCACA CUGAUGAGGCCGAAAGGCCGAA AAAUUCC | 511 |
| 1149 | AUAUCAC CUGAUGAGGCCGAAAGGCCGAA AAAAUUC | 512 |
| 1155 | GGCAGCA CUGAUGAGGCCGAAAGGCCGAA AUCACAA | 513 |
| 1169 | AAAGCAG CUGAUGAGGCCGAAAGGCCGAA AGGUCAG | 514 |
| 1175 | UGGGGCA CUGAUGAGGCCGAAAGGCCGAA AGCAGUA | 515 |
| 1176 | UUGGGGC CUGAUGAGGCCGAAAGGCCGAA AAGCAGU | 516 |
| 1214 | CCUUCUC CUGAUGAGGCCGAAAGGCCGAA AUCUCUC | 517 |
| 1230 | CAGGGCG CUGAUGAGGCCGAAAGGCCGAA ACACUUU | 518 |
| 1239 | ACUGUUA CUGAUGAGGCCGAAAGGCCGAA ACAGGGC | 519 |
| 1241 | ACACUGU CUGAUGAGGCCGAAAGGCCGAA AUACAGG | 520 |
| 1249 | UUCUGCG CUGAUGAGGCCGAAAGGCCGAA ACACUGU | 521 |
| 1275 | ACCUUCA CUGAUGAGGCCGAAAGGCCGAA AUCUUUU | 522 |
| 1283 | CGGAGGC CUGAUGAGGCCGAAAGGCCGAA ACCUUCA | 523 |
| 1288 | GAUGACG CUGAUGAGGCCGAAAGGCCGAA AGGCUAC | 524 |

TABLE III-continued

Human B7-1 Hammerhead Ribozyme Sequences

| nt. Position | HH Ribozyme Sequence | Seq. ID No. |
|---|---|---|
| 1292 | AAGAGAU CUGAUGAGGCCGAAAGGCCGAA ACGGAGG | 525 |
| 1295 | CAGAAGA CUGAUGAGGCCGAAAGGCCGAA AUGACGG | 526 |
| 1297 | CCCAGAA CUGAUGAGGCCGAAAGGCCGAA AGAUGAC | 527 |
| 1299 | AUCCCAG CUGAUGAGGCCGAAAGGCCGAA AGAGAUG | 528 |
| 1300 | UAUCCCA CUGAUGAGGCCGAAAGGCCGAA AAGAGAU | 529 |
| 1307 | AUCCAUG CUGAUGAGGCCGAAAGGCCGAA AUCCCAG | 530 |
| 1315 | UCCCCAC CUGAUGAGGCCGAAAGGCCGAA AUCCAUG | 531 |
| 1324 | GCCUCAU CUGAUGAGGCCGAAAGGCCGAA AUCCCCA | 532 |
| 1334 | AGGGAAG CUGAUGAGGCCGAAAGGCCGAA AUGCCUC | 533 |
| 1335 | AAGGGAA CUGAUGAGGCCGAAAGGCCGAA AAUGCCU | 534 |
| 1337 | UUAAGGG CUGAUGAGGCCGAAAGGCCGAA AGAAUGC | 535 |
| 1338 | GUUAAGG CUGAUGAGGCCGAAAGGCCGAA AAGAAUG | 536 |
| 1342 | AUUUGUU CUGAUGAGGCCGAAAGGCCGAA AGGGAAG | 537 |
| 1343 | AAUUUGU CUGAUGAGGCCGAAAGGCCGAA AAGGGAA | 538 |
| 1350 | CAGCUUA CUGAUGAGGCCGAAAGGCCGAA AUUUGUU | 539 |
| 1351 | ACAGCUU CUGAUGAGGCCGAAAGGCCGAA AAUUUGU | 540 |
| 1352 | AACAGCU CUGAUGAGGCCGAAAGGCCGAA AAAUUUG | 541 |
| 1359 | UGGGUAA CUGAUGAGGCCGAAAGGCCGAA ACAGCUU | 542 |
| 1360 | GUGGGUA CUGAUGAGGCCGAAAGGCCGAA AACAGCU | 543 |
| 1361 | AGUGGGU CUGAUGAGGCCGAAAGGCCGAA AAACAGC | 544 |
| 1362 | UAGUGGG CUGAUGAGGCCGAAAGGCCGAA AAAACAG | 545 |
| 1369 | GGUGAGG CUGAUGAGGCCGAAAGGCCGAA AGUGGGU | 546 |
| 1373 | AGAAGGU CUGAUGAGGCCGAAAGGCCGAA AGGUAGU | 547 |
| 1378 | UUUUAAG CUGAUGAGGCCGAAAGGCCGAA AGGUGAG | 548 |
| 1379 | UUUUUAA CUGAUGAGGCCGAAAGGCCGAA AAGGUGA | 549 |
| 1381 | GGUUUUU CUGAUGAGGCCGAAAGGCCGAA AGAAGGU | 550 |
| 1382 | AGGUUUU CUGAUGAGGCCGAAAGGCCGAA AAGAAGG | 551 |
| 1390 | UCUGAAA CUGAUGAGGCCGAAAGGCCGAA AGGUUUU | 552 |
| 1392 | AAUCUGA CUGAUGAGGCCGAAAGGCCGAA AGAGGUU | 553 |
| 1393 | UAAUCUG CUGAUGAGGCCGAAAGGCCGAA AAGAGGU | 554 |
| 1394 | UUAAUCU CUGAUGAGGCCGAAAGGCCGAA AAAGAGG | 555 |
| 1399 | UCAGCUU CUGAUGAGGCCGAAAGGCCGAA AUCUGAA | 556 |
| 1400 | UUCAGCU CUGAUGAGGCCGAAAGGCCGAA AAUCUGA | 557 |
| 1412 | AUCUUGU CUGAUGAGGCCGAAAGGCCGAA ACUGUUC | 558 |
| 1413 | CAUCUUG CUGAUGAGGCCGAAAGGCCGAA AACUGUU | 559 |
| 1429 | GGAGAGG CUGAUGAGGCCGAAAGGCCGAA AUGCCAG | 560 |
| 1433 | GAAAGGA CUGAUGAGGCCGAAAGGCCGAA AGGGAUG | 561 |
| 1435 | GAGAAAG CUGAUGAGGCCGAAAGGCCGAA AGAGGGA | 562 |
| 1438 | GGGGAGA CUGAUGAGGCCGAAAGGCCGAA AGGAGAG | 563 |
| 1439 | UGGGGAG CUGAUGAGGCCGAAAGGCCGAA AAGGAGA | 564 |
| 1440 | AUGGGGA CUGAUGAGGCCGAAAGGCCGAA AAAGGAG | 565 |
| 1442 | AUAUGGG CUGAUGAGGCCGAAAGGCCGAA AGAAAGG | 566 |
| 1448 | AAUUGCA CUGAUGAGGCCGAAAGGCCGAA AUGGGGA | 567 |
| 1455 | UUAAGCA CUGAUGAGGCCGAAAGGCCGAA AUUGCAU | 568 |
| 1456 | AUUAAGC CUGAUGAGGCCGAAAGGCCGAA AAUUGCA | 569 |
| 1460 | UUACAUU CUGAUGAGGCCGAAAGGCCGAA AGCAAAU | 570 |
| 1461 | GUUACAU CUGAUGAGGCCGAAAGGCCGAA AAGCAAA | 571 |
| 1466 | AAGAGGU CUGAUGAGGCCGAAAGGCCGAA ACAUUAA | 572 |
| 1471 | AAAAGAA CUGAUGAGGCCGAAAGGCCGAA AGGUUAC | 573 |
| 1473 | GCAAAAG CUGAUGAGGCCGAAAGGCCGAA AGAGGUU | 574 |
| 1474 | GGCAAAA CUGAUGAGGCCGAAAGGCCGAA AAGAGGU | 575 |
| 1476 | AUGGCAA CUGAUGAGGCCGAAAGGCCGAA AGAAGAG | 576 |
| 1477 | CAUGGCA CUGAUGAGGCCGAAAGGCCGAA AAGAAGA | 577 |
| 1478 | ACAUGGC CUGAUGAGGCCGAAAGGCCGAA AAAGAAG | 578 |
| 1486 | GAAUGGA CUGAUGAGGCCGAAAGGCCGAA ACAUGGC | 579 |
| 1487 | AGAAUGG CUGAUGAGGCCGAAAGGCCGAA AACAUGG | 580 |
| 1488 | CAGAAUG CUGAUGAGGCCGAAAGGCCGAA AAACAUG | 581 |
| 1492 | AUGGCAG CUGAUGAGGCCGAAAGGCCGAA AUGGAAA | 582 |
| 1493 | GAUGGCA CUGAUGAGGCCGAAAGGCCGAA AAUGGAA | 583 |
| 1500 | AAUUCAA CUGAUGAGGCCGAAAGGCCGAA AUGGCAG | 584 |
| 1502 | ACAAUUC CUGAUGAGGCCGAAAGGCCGAA AGAUGGC | 585 |
| 1507 | ACAAGAC CUGAUGAGGCCGAAAGGCCGAA AUUCAAG | 586 |
| 1510 | CUGACAA CUGAUGAGGCCGAAAGGCCGAA ACAAUUC | 587 |
| 1512 | GGCUGAC CUGAUGAGGCCGAAAGGCCGAA AGACAAU | 588 |
| 1515 | AUUGGCU CUGAUGAGGCCGAAAGGCCGAA ACAAGAC | 589 |
| 1523 | GAUAAUG CUGAUGAGGCCGAAAGGCCGAA AUUGGCU | 590 |
| 1524 | AGAUAAU CUGAUGAGGCCGAAAGGCCGAA AAUUGGC | 591 |
| 1527 | AAUAGAU CUGAUGAGGCCGAAAGGCCGAA AUGAAUU | 592 |
| 1528 | UAAUAGA CUGAUGAGGCCGAAAGGCCGAA AAUGAAU | 593 |
| 1530 | UUUAAUA CUGAUGAGGCCGAAAGGCCGAA AUAAUGA | 594 |
| 1532 | UGUUUAA CUGAUGAGGCCGAAAGGCCGAA AGAUAAU | 595 |
| 1534 | AGUGUUU CUGAUGAGGCCGAAAGGCCGAA AUAGAUA | 596 |
| 1535 | UAGUGUU CUGAUGAGGCCGAAAGGCCGAA AAUAGAU | 597 |
| 1542 | CUCAAAU CUGAUGAGGCCGAAAGGCCGAA AGUGUUU | 598 |

TABLE 1V

Mouse B7-1 Hammerhead Ribozyme Target Sequences

| nt. Position | HH Target Sequence | Seq. ID No. | nt. Position | HH Target Sequence | Seq. ID No. |
|---|---|---|---|---|---|
| 8 | GaGUuUU a UACcUcA | 599 | 108 | CaUcUUU a GCAuCUG | 641 |
| 10 | guUuuAU A CCUcCAAU | 600 | 108 | CAUcUUU a gcaUCUG | 642 |
| 10 | GUuUUaU a ccuCAAU | 601 | 131 | aUGCCAU C caGgcUU | 643 |
| 14 | uAUacCU c aAUAGAC | 602 | 142 | gCUuCUU U uUCuaCA | 644 |
| 18 | CcucAAU A gaCUCUu | 603 | 142 | gCuUCUU u UUcUaCa | 645 |
| 18 | CCUCaaU a gaCUCUU | 604 | 143 | CUuCUUU U UCuaCAU | 646 |
| 18 | CcUcAAU a GaCUcUU | 605 | 143 | CuUcUuU u uCuAcAU | 647 |
| 23 | AuaGaCU c uUACuaG | 606 | 143 | CUUCUUU U uCuAcaU | 648 |
| 25 | AGACuCU U aCuAGuu | 607 | 143 | cUUCuUU u UCUAcau | 649 |
| 26 | GACuCUU a CuAGuuu | 608 | 144 | UuCuUuU U cUaCAuC | 650 |
| 29 | UCUUACU a GuuUCuc | 609 | 144 | UuCuuuU u cUAcAUC | 651 |
| 29 | UcUuACU a gUuuCuC | 610 | 144 | UUCuUUU u cuaCAUC | 652 |
| 29 | UCUUaCU a guUUCUc | 611 | 147 | uUUUuCU a cAuCUCU | 653 |
| 29 | UCuuaCU a gUUUCUC | 612 | 153 | uAcAuCU C ugUUUCU | 654 |
| 34 | CUaGUuU c UCUuuuU | 613 | 165 | uCUCgAU U UuUgUgA | 655 |
| 34 | CUAGUuU c UCUuuuU | 614 | 165 | uCUcgAU u UuuGUgA | 656 |
| 34 | cUAgUuU c uCuUuUU | 615 | 165 | ucucgAU U UUUGUGA | 657 |
| 40 | ucuCUuU U UCAGgUU | 616 | 166 | CUCgAUU U uUgUgAG | 658 |
| 41 | cUCUuUU u caGGuUg | 617 | 167 | uCgAUuU U UGUGaGc | 659 |
| 41 | cuCUuUU U CAGgUUg | 618 | 167 | ucGauUU U UGUgAgC | 660 |
| 42 | uCUuUUU C AGgUUgu | 619 | 167 | UCgAUUU u UgUgAGC | 661 |
| 56 | UGAAACU c AAcCuuC | 620 | 168 | cGAUuUU u gUgAGCC | 662 |
| 56 | UGAAAcU C aAcCUuC | 621 | 168 | cgAUUUU U GUGAgcc | 663 |
| 62 | uCAACCU U caaAGAC | 622 | 197 | GCUccAU u GgCUcUA | 664 |
| 62 | UCaAcCU U CaAAgAc | 623 | 202 | aUUGGCU c UagaUUc | 665 |
| 62 | UCAACCU u caaAGac | 624 | 208 | UCuAgAU U ccUGGCU | 666 |
| 63 | CAACCUU u aaAGACa | 625 | 216 | CCUGGCU U UcCcCau | 667 |
| 73 | aGAcAcU c UGuUcCA | 626 | 217 | cUGGCUU U CcCcaUc | 668 |
| 77 | acUCUgU u cCAuUUC | 627 | 217 | cUgGCuU U CccCAUC | 669 |
| 78 | CucUGUU u CauUUCU | 628 | 217 | CUGGCUu u CCCcauC | 670 |
| 83 | UucCAuU U CUGUggA | 629 | 218 | UGGCuUU c ccCaUCA | 671 |
| 93 | GUggAcU A AuAGGau | 630 | 218 | UGGCUUU C cCcaUca | 672 |
| 93 | gUgGacU a AUAGgaU | 631 | 218 | UGgCuUU c CCcaUCA | 673 |
| 93 | gUGGacU a AuAGGAU | 632 | 218 | ugGcUUU c CCCAucA | 674 |
| 96 | GAcuAAU a GGAUcaU | 633 | 224 | UCcCCAU c aUGuUCu | 675 |
| 96 | gacuAAU a gGAucAU | 634 | 224 | UccCCAU c aUGuucU | 676 |
| 101 | AUaGGAU c aUCuUuA | 635 | 230 | UCAugUU C UccAAAg | 677 |
| 104 | GGAuCAU C uuuAgCa | 636 | 232 | AuGUUcu C CAaAGCa | 678 |
| 104 | GGAuCAU C UUUagcA | 637 | 232 | AUGuUcU C caaAGCA | 679 |
| 106 | AuCAUCU U UagcAUC | 638 | 232 | AugUUCU c cAAAgCa | 680 |
| 107 | UcAuCuU u AGCAUCU | 639 | 241 | AAAGcAU C UgAAGcu | 681 |
| 107 | uCaUCUU u AgcAuCU | 640 | 241 | aAAGCAU C UGAAGCu | 682 |
| 241 | AAAgcAU C UGaAgCU | 683 | 556 | ACCuACU c uCUUAuC | 732 |
| 249 | UGAAgcU A UGGCuuG | 684 | 556 | AcCUAcU c ucUUAUC | 733 |
| 264 | CAAuUgU c AGuUGaU | 685 | 560 | AcUcUCU U aUCAuCC | 734 |
| 287 | CAccaCU c CUcaagU | 686 | 561 | cUCuCUU a UcAuCCU | 735 |
| 295 | CUCaAgU u UCcaUGU | 687 | 561 | cuCUcuU a uCAUCCU | 736 |
| 295 | cuCAaGU U UCCaUgu | 688 | 561 | CUCUCUU u UCauCCu | 737 |
| 296 | uCAAgUU u ccAUGUc | 689 | 566 | UUaUcAU C CUGGgcC | 738 |
| 297 | CAAGUuU C CAUguCc | 690 | 566 | uUauCAU C CUGGGCC | 739 |
| 297 | CAaGuuU c cAUGuCC | 691 | 581 | UGGuCcU U UcAGAcc | 740 |
| 314 | GGCUcaU u cUUCUCU | 692 | 583 | gucCUUU C AgaCcGg | 741 |
| 314 | GgcuCAU U CUUCuCU | 693 | 583 | GuCcUUU C AGAccGg | 742 |
| 315 | GcuCAUU c UuCUcuU | 694 | 598 | GGCACAU A CagcUGU | 743 |
| 315 | gcuCAUU C UUCuCUU | 695 | 608 | gcUGUGU c GUUCaaA | 744 |
| 317 | uCAUUCU U CuCUUug | 696 | 611 | GUGUcgU u CAaaaGA | 745 |
| 318 | CAUUCUU c uCUUugu | 697 | 611 | GUGUcGU U CaaAAGa | 746 |
| 318 | CAUuCUU C UCuUUgu | 698 | 612 | UGUcGUU C aaAAGaA | 747 |
| 320 | uUCUUCU c uuUGuGC | 699 | 641 | aUGaAGU u aaACaCU | 748 |
| 320 | UUCUuCU C UUuuGuGC | 700 | 649 | AAAcacU U GGCUUUa | 749 |
| 322 | CuuCUCU U uGUGCUG | 701 | 649 | AaaCAcU U gGCUUUA | 750 |
| 322 | CUucuCU u UgUGCUG | 702 | 655 | UUggcuU u AGUAAAg | 751 |
| 323 | UUcuCUU u gUGcugC | 703 | 656 | UGgcUUU a GUAAAgu | 752 |
| 336 | gcUGAUU c GUCuUuc | 704 | 659 | CuUuaGU A AAGUugu | 753 |
| 341 | uUCGuCU u UCacAAG | 705 | 664 | GUaAaGU U gUCcaUC | 754 |
| 341 | UUCgucU u UcAcAAG | 706 | 667 | AaGUUgU C caUCAAA | 755 |
| 342 | UcGUCUU U CaCAagU | 707 | 671 | UgUCcaU C AAAGCUG | 756 |
| 343 | cgucUuU C AcAAGUG | 708 | 682 | gCUgAcU u CuCuACC | 757 |
| 343 | cGuCUUU C AcaAGUG | 709 | 682 | GCUGACU U CuCUACc | 758 |
| 352 | caAGUGU C uuCAGAu | 710 | 682 | GCUGacU U cuCUAcc | 759 |
| 355 | gUgUcUU U AGaUGUU | 711 | 683 | CUGACUU C uCUACcC | 760 |
| 382 | UCcaAGU c AgUGaAA | 712 | 683 | CUGACUU c ucuAccC | 761 |
| 408 | gCUGCcU U GCCguuA | 713 | 685 | gACUuCU U UaCCCCc | 762 |
| 414 | UUGccgU U aCAACUc | 714 | 685 | gaCUucU c UACCCcC | 763 |

TABLE 1V-continued

Mouse B7-1 Hammerhead Ribozyme Target Sequences

| nt. Position | HH Target Sequence | | | Seq. ID No. | nt. Position | HH Target Sequence | | | Seq. ID No. |
|---|---|---|---|---|---|---|---|---|---|
| 414 | UUgCCgU | u | ACAAcUc | 715 | 687 | CUUCuCU | A | CcCCcAa | 764 |
| 421 | UaCAAcU | c | UCcUcAU | 716 | 698 | ccAACAU | A | ACUGagu | 765 |
| 426 | CUCuCCU | c | aUgAAgA | 717 | 698 | CCaacAU | A | ACuGaGU | 766 |
| 439 | GaUGAgU | c | UGAaGaC | 718 | 718 | AAcCCaU | C | UGcAgAc | 767 |
| 452 | acCGaAU | C | UACUGGC | 719 | 718 | aaCCCAU | c | UGCAgac | 768 |
| 454 | CGaAUCU | A | CUGGCAA | 720 | 729 | AGACacU | A | AaAgGAu | 769 |
| 484 | GUGCUgU | c | UGucaUU | 721 | 729 | agAcAcU | A | aAAGGAU | 770 |
| 484 | GugCUGU | c | UgucAuU | 722 | 729 | agAcAcU | A | AaAgGAU | 771 |
| 488 | ugUcUGU | C | AUUGCUg | 723 | 737 | aAAGGAU | u | AccUGCU | 772 |
| 503 | gGAAacU | A | aAAGuGu | 724 | 737 | aAAGgAU | U | AccUGCu | 773 |
| 503 | ggAAAcU | a | AAAgUGU | 725 | 737 | aaagGAU | u | ACCUGCU | 774 |
| 520 | CCCGAGU | A | uAAGAAC | 726 | 745 | aCCUGcU | U | UGCuuCc | 775 |
| 535 | cGGAcUU | U | aUaUGAc | 727 | 745 | accUGcU | u | UGCUuuCC | 776 |
| 536 | GGAcUUU | U | aUaUGAcA | 728 | 759 | cGggGgU | U | uCCCAAA | 777 |
| 538 | AcUuUAU | a | UGACaac | 729 | 759 | cGggGGU | u | UcCcAaa | 778 |
| 553 | acuACCU | a | cUCUcUU | 730 | 759 | cGGGGGU | U | UcCCAaA | 779 |
| 553 | AcUaCcU | a | cUCUcUU | 731 | 760 | GggGgUU | u | CCCAAAG | 780 |
| 760 | gGGgUU | u | cCCAaag | 781 | 1060 | aAAUgcU | u | cUGUaAG | 830 |
| 760 | GggGGUU | U | cCCAaag | 782 | 1060 | AAAugCU | u | cUgUaAG | 831 |
| 761 | GgGGUUU | c | CCAaAGC | 783 | 1061 | AAUGcUU | C | UGUaagc | 832 |
| 771 | aAAgccU | U | GCuUCUC | 784 | 1080 | Aagcugu | u | UCAGAAG | 833 |
| 771 | AaAGCCU | C | gCuUCUC | 785 | 1080 | AAGCUGU | U | UcAgaag | 834 |
| 776 | CUCgCUU | C | UcUUggu | 786 | 1081 | AgCuGUU | U | CAgaAga | 835 |
| 776 | CUCgCuU | C | UcUUGGU | 787 | 1121 | acAGcCU | U | ACCuUcg | 836 |
| 778 | CgCuUCU | C | uUGGUUG | 788 | 1121 | AcAgCCU | U | aCCuUcG | 837 |
| 784 | UCuUGGU | U | GGAAAAU | 789 | 1121 | ACagCCU | u | ACCUUCg | 838 |
| 803 | GAGaaUU | A | CCugGcA | 790 | 1122 | CaGcCuU | a | cCUUCgG | 839 |
| 803 | gAGAAUU | A | ccUggCA | 791 | 1126 | CUuACCU | u | CgGgccU | 840 |
| 803 | gagAaUU | a | CCUggcA | 792 | 1127 | UUaCcUU | c | ggGcCUG | 841 |
| 812 | cUGgCAU | C | AAuACgA | 793 | 1127 | UuACcUU | c | GggCCUg | 842 |
| 812 | CUGGcAU | c | aAuaCgA | 794 | 1144 | GaagCAU | U | AgCUgAA | 843 |
| 816 | caUCAAU | A | cGACAaU | 795 | 1144 | gaAGcAU | u | AGCUGAA | 844 |
| 816 | cAUCaAU | a | cgACAaU | 796 | 1145 | aAgcAUU | a | GCUgAAC | 845 |
| 824 | CgACAaU | U | UCCCAgG | 797 | 1160 | AGAcCgU | c | UUCCUuu | 846 |
| 825 | gACAaUU | U | CCCAgGA | 798 | 1162 | AcCgUCU | u | CcUUuaG | 847 |
| 826 | ACAaUUU | C | CCAgGAU | 799 | 1163 | ccGUCUU | c | CUUuaGU | 848 |
| 834 | CCAgGAU | C | CUGAAuC | 800 | 1167 | cUUCcUU | u | AGuUCUU | 849 |
| 841 | CcUGaaU | C | ugAAUUG | 801 | 1177 | uUCUUCU | c | UguCCAU | 850 |
| 841 | cCUGaaU | C | UGAAuUg | 802 | 1181 | UCuCugU | C | CAuGUGg | 851 |
| 850 | gAAuUGU | A | CaCCAuU | 803 | 1181 | ucUCUGU | c | CAuGUGg | 852 |
| 869 | gccAaCU | a | gAUuUCA | 804 | 1192 | gUGGGAU | A | CAUGGua | 853 |
| 869 | GCCAaCU | a | GAUuUCA | 805 | 1199 | aCaUGGU | a | UUAugUG | 854 |
| 869 | GCCAACU | a | gaUuUCa | 806 | 1201 | AuGgUaU | u | aUGUGGc | 855 |
| 873 | acUaGAU | u | UCAaUAc | 807 | 1210 | ugUGGcU | C | aUGaGGu | 856 |
| 873 | ACUaGAU | U | UCAAUAc | 808 | 1210 | UGuGGcU | C | AUGAGGu | 857 |
| 874 | CUaGAUU | U | CAAUAcG | 809 | 1223 | GUacAAU | U | UUUCUUu | 858 |
| 875 | UaGAUUU | C | AAUAcGA | 810 | 1225 | ACAAUcU | U | UCUuUca | 859 |
| 885 | UAcgACU | c | gcAACCa | 811 | 1225 | ACAAucU | u | uCuUucA | 860 |
| 899 | ACACCaU | u | aAgUgUC | 812 | 1226 | caAuCUU | u | cUuUCAG | 861 |
| 899 | ACAccaU | u | AaGUGUC | 813 | 1227 | aAucUUU | u | uUUCAGC | 862 |
| 906 | UaaGUGU | c | UcaUUAA | 814 | 1227 | AAucuUU | C | UUUCAGc | 863 |
| 906 | uAaGUGU | c | UcAUuAA | 815 | 1227 | AAuCUUU | c | uUUcaGC | 864 |
| 908 | aGUGUCU | C | AUuAAaU | 816 | 1229 | ucUUUCU | U | UCAGCaC | 865 |
| 911 | GUCUCAU | u | AAaUAUG | 817 | 1230 | cUUUCUU | U | CAGCaCc | 866 |
| 916 | AUuAaaU | a | UGGaGAu | 818 | 1252 | cUgAUCU | u | UcggACA | 867 |
| 916 | AUuAAaU | A | UGGAgAU | 819 | 1274 | acaAGAU | a | gAGuUaA | 868 |
| 943 | gAGgaCU | U | CAcCUGG | 820 | 1310 | UGAggAU | u | uCuUuCc | 869 |
| 944 | AGgaCUU | C | AcCUGGg | 821 | 1312 | aGgAUUU | U | UuUcCAu | 870 |
| 1001 | UGCUcUU | u | GggGCAg | 822 | 1314 | gAUUUcU | u | UcCAuCA | 871 |
| 1034 | CAGucGU | c | gUCaucG | 823 | 1316 | UUUcUuU | c | CAuCAgG | 872 |
| 1037 | UcGUCgU | C | AuCguUG | 824 | 1320 | UUUccaU | C | AGgAAGC | 873 |
| 1043 | uCAUCgU | U | GucAUCA | 825 | 1320 | UUUCcaU | c | aggaAGC | 874 |
| 1046 | ucgUUGU | c | AuCAUCA | 826 | 1339 | GgCAagU | u | UgCUGGG | 875 |
| 1049 | uUgucaU | c | AuCAAAU | 827 | 1355 | cUuUgAU | U | GCUUgAU | 876 |
| 1060 | aAAUgcU | U | CUGUaag | 828 | 1437 | gUGguaU | A | aGAAAAA | 877 |
| 1060 | AAaUgCU | u | cUgUaAG | 829 | 1437 | gUggUAU | a | AGAAaaA | 878 |
| 1475 | gCCUAGU | c | UuaCUGc | 879 | | | | | |
| 1477 | CUaGUCU | U | ACUgCaa | 880 | | | | | |
| 1487 | ugCAaCU | U | gAUaUGU | 881 | | | | | |
| 1491 | ACuUGAU | U | UGUCAUg | 882 | | | | | |
| 1491 | aCUUgaU | a | UguCAUG | 883 | | | | | |
| 1505 | gUUUGgU | U | ggUGUcu | 884 | | | | | |
| 1530 | uGCCcUU | u | uCUgAAg | 885 | | | | | |
| 1531 | GcccUUU | u | CUGAagA | 886 | | | | | |

TABLE 1V-continued

Mouse B7-1 Hammerhead Ribozyme Target Sequences

| nt. Position | HH Target Sequence | Seq. ID No. | nt. Position | HH Target Sequence | Seq. ID No. |
|---|---|---|---|---|---|
| 1532 | CcCuUuU C UGAAGAg | 887 | | | |
| 1644 | CcCuuuU C UGAaGAG | 888 | | | |
| 1652 | CUaUGGU u gggAUGU | 889 | | | |
| 1652 | ggGAuGU a AaAAcGG | 890 | | | |
| 1670 | GgGAugU a aAaAcGG | 891 | | | |
| 1674 | aUaAUAU a AaUAuUA | 892 | | | |
| 1676 | uAuAAAU a UuAaaUa | 893 | | | |
| 1677 | UaAaUAU u aAaUAAA | 894 | | | |
| 1677 | AAauAUU a AAuaAAA | 895 | | | |
| 1694 | AaaUAUU A AAuAaaA | 896 | | | |

TABLE V

Mouse B7-1 Hammerhead Ribozyme Sequences

| nt. Position | HH Ribozyme Sequences | Seq. ID No. |
|---|---|---|
| 8 | UGAGGUA CUGAUGAGGCCGAAAGGCCGAA AAAACUC | 898 |
| 10 | AUUGAGG CUGAUGAGGCCGAAAGGCCGAA AUAAAAC | 899 |
| 10 | AUUGAGG CUGAUGAGGCCGAAAGGCCGAA AUAAAAC | 900 |
| 14 | GUCUAUU CUGAUGAGGCCGAAAGGCCGAA AGGUAUA | 901 |
| 18 | AAGAGUC CUGAUGAGGCCGAAAGGCCGAA AUUGAGG | 902 |
| 18 | AAGAGUC CUGAUGAGGCCGAAAGGCCGAA AUUGAGG | 903 |
| 18 | AAGAGUC CUGAUGAGGCCGAAAGGCCGAA AUUGAGG | 904 |
| 23 | CUAGUAA CUGAUGAGGCCGAAAGGCCGAA AGUCUAU | 905 |
| 25 | AACUAGU CUGAUGAGGCCGAAAGGCCGAA AGAGUCU | 906 |
| 26 | AAACUAG CUGAUGAGGCCGAAAGGCCGAA AAGAGUC | 907 |
| 29 | GAGAAAC CUGAUGAGGCCGAAAGGCCGAA AGUAAGA | 908 |
| 29 | GAGAAAC CUGAUGAGGCCGAAAGGCCGAA AGUAAGA | 909 |
| 29 | GAGAAAC CUGAUGAGGCCGAAAGGCCGAA AGUAAGA | 910 |
| 29 | GAGAAAC CUGAUGAGGCCGAAAGGCCGAA AGUAAGA | 911 |
| 34 | AAAAAGA CUGAUGAGGCCGAAAGGCCGAA AAACUAG | 912 |
| 34 | AAAAAGA CUGAUGAGGCCGAAAGGCCGAA AAACUAG | 913 |
| 34 | AAAAAGA CUGAUGAGGCCGAAAGGCCGAA AAACUAG | 914 |
| 40 | AACCUGA CUGAUGAGGCCGAAAGGCCGAA AAAGAGA | 915 |
| 41 | CAACCUG CUGAUGAGGCCGAAAGGCCGAA AAAAGAG | 916 |
| 41 | CAACCUG CUGAUGAGGCCGAAAGGCCGAA AAAAGAG | 917 |
| 42 | ACAACCU CUGAUGAGGCCGAAAGGCCGAA AAAAAGA | 918 |
| 56 | GAAGGUU CUGAUGAGGCCGAAAGGCCGAA AGUUUCA | 919 |
| 56 | GAAGGUU CUGAUGAGGCCGAAAGGCCGAA AGUUUCA | 920 |
| 62 | GUCUUUG CUGAUGAGGCCGAAAGGCCGAA AGGUUGA | 921 |
| 62 | GUCUUUG CUGAUGAGGCCGAAAGGCCGAA AGGUUGA | 922 |
| 62 | GUCUUUG CUGAUGAGGCCGAAAGGCCGAA AGGUUGA | 923 |
| 63 | UGUCUUU CUGAUGAGGCCGAAAGGCCGAA AAGGUUG | 924 |

TABLE V-continued

Mouse B7-1 Hammerhead Ribozyme Sequences

| nt. Position | HH Ribozyme Sequences | Seq. ID No. |
|---|---|---|
| 73 | UGGAACA CUGAUGAGGCCGAAAGGCCGAA AGUGUCU | 925 |
| 77 | GAAAUGG CUGAUGAGGCCGAAAGGCCGAA ACAGAGU | 926 |
| 78 | AGAAAUG CUGAUGAGGCCGAAAGGCCGAA AACAGAG | 927 |
| 83 | UCCACAG CUGAUGAGGCCGAAAGGCCGAA AAUGGAA | 928 |
| 93 | AUCCUAU CUGAUGAGGCCGAAAGGCCGAA AGUCCAC | 929 |
| 93 | AUCCUAU CUGAUGAGGCCGAAAGGCCGAA AGUCCAC | 930 |
| 93 | AUCCUAU CUGAUGAGGCCGAAAGGCCGAA AGUCCAC | 931 |
| 96 | AUGAUCC CUGAUGAGGCCGAAAGGCCGAA AUUAGUC | 932 |
| 96 | AUGAUCC CUGAUGAGGCCGAAAGGCCGAA AUUAGUC | 933 |
| 101 | UAAAGAU CUGAUGAGGCCGAAAGGCCGAA AUCCUAU | 934 |
| 104 | UGCUAAA CUGAUGAGGCCGAAAGGCCGAA AUGAUCC | 935 |
| 104 | UGCUAAA CUGAUGAGGCCGAAAGGCCGAA AUGAUCC | 936 |
| 106 | GAUGCUA CUGAUGAGGCCGAAAGGCCGAA AGAUGAU | 937 |
| 107 | AGAUGCU CUGAUGAGGCCGAAAGGCCGAA AAGAUGA | 938 |
| 107 | AGAUGCU CUGAUGAGGCCGAAAGGCCGAA AAGAUGA | 939 |
| 108 | CAGAUGC CUGAUGAGGCCGAAAGGCCGAA AAAGAUG | 940 |
| 108 | CAGAUGC CUGAUGAGGCCGAAAGGCCGAA AAAGAUG | 941 |
| 131 | AAGCCUG CUGAUGAGGCCGAAAGGCCGAA AUGGCAU | 942 |
| 142 | UGUAGAA CUGAUGAGGCCGAAAGGCCGAA AAGAAGC | 943 |
| 142 | UGUAGAA CUGAUGAGGCCGAAAGGCCGAA AAGAAGC | 944 |
| 143 | AUGUAGA CUGAUGAGGCCGAAAGGCCGAA AAAGAAG | 945 |
| 143 | AUGUAGA CUGAUGAGGCCGAAAGGCCGAA AAAGAAG | 946 |
| 143 | AUGUAGA CUGAUGAGGCCGAAAGGCCGAA AAAGAAG | 947 |
| 143 | AUGUAGA CUGAUGAGGCCGAAAGGCCGAA AAAGAAG | 948 |
| 144 | GAUGUAG CUGAUGAGGCCGAAAGGCCGAA AAAAGAA | 949 |
| 144 | GAUGUAG CUGAUGAGGCCGAAAGGCCGAA AAAAGAA | 950 |
| 144 | GAUGUAG CUGAUGAGGCCGAAAGGCCGAA AAAAGAA | 951 |
| 147 | AGAGAUG CUGAUGAGGCCGAAAGGCCGAA AGAAAAA | 952 |
| 153 | AGAAACA CUGAUGAGGCCGAAAGGCCGAA AGAUGUA | 953 |
| 165 | UCACAAA CUGAUGAGGCCGAAAGGCCGAA AUCGAGA | 954 |
| 165 | UCACAAA CUGAUGAGGCCGAAAGGCCGAA AUCGAGA | 955 |
| 165 | UCACAAA CUGAUGAGGCCGAAAGGCCGAA AUCGAGA | 956 |
| 166 | CUCACAA CUGAUGAGGCCGAAAGGCCGAA AAUCGAG | 957 |
| 167 | GCUCACA CUGAUGAGGCCGAAAGGCCGAA AAAUCGA | 958 |
| 167 | GCUCACA CUGAUGAGGCCGAAAGGCCGAA AAAUCGA | 959 |
| 167 | GCUCACA CUGAUGAGGCCGAAAGGCCGAA AAAUCGA | 960 |
| 168 | GGCUCAC CUGAUGAGGCCGAAAGGCCGAA AAAAUCG | 961 |

TABLE V-continued

Mouse B7-1 Hammerhead Ribozyme Sequences

| nt. Position | HH Ribozyme Sequences | Seq. ID No. |
|---|---|---|
| 168 | GGCUCAC CUGAUGAGGCCGAAAGGCCGAA AAAAUCG | 962 |
| 197 | UAGAGCC CUGAUGAGGCCGAAAGGCCGAA AUGGAGC | 963 |
| 202 | GAAUCUA CUGAUGAGGCCGAAAGGCCGAA AGCCAAU | 964 |
| 208 | AGCCAGG CUGAUGAGGCCGAAAGGCCGAA AUCUAGA | 965 |
| 216 | AUGGGGA CUGAUGAGGCCGAAAGGCCGAA AGCCAGG | 966 |
| 217 | GAUGGGG CUGAUGAGGCCGAAAGGCCGAA AAGCCAG | 967 |
| 217 | GAUGGGG CUGAUGAGGCCGAAAGGCCGAA AAGCCAG | 968 |
| 217 | GAUGGGG CUGAUGAGGCCGAAAGGCCGAA AAGCCAG | 969 |
| 218 | UGAUGGG CUGAUGAGGCCGAAAGGCCGAA AAAGCCA | 970 |
| 218 | UGAUGGG CUGAUGAGGCCGAAAGGCCGAA AAAGCCA | 971 |
| 218 | UGAUGGG CUGAUGAGGCCGAAAGGCCGAA AAAGCGA | 972 |
| 218 | UGAUGGG CUGAUGAGGCCGAAAGGCCGAA AAAGCCA | 973 |
| 224 | AGAACAU CUGAUGAGGCCGAAAGGCCGAA AUGGGGA | 974 |
| 224 | AGAACAU UGAUGAGGCCGAAAGGCCGAAA AUGGGGA | 975 |
| 230 | CUUUGGA CUGAUGAGGCCGAAAGGCCGAA AACAUGA | 976 |
| 232 | UGCUUUG CUGAUGAGGCCGAAAGGCCGAA AGAACAU | 977 |
| 232 | UGCUUUG CUGAUGAGGCCGAAAGGCCGAA AGAACAU | 978 |
| 232 | UGCUUUG CUGAUGAGGCCGAAAGGCCGAA AGAACAU | 979 |
| 241 | AGCUUCA CUGAUGAGGCCGAAAGGCCGAA AUGCUUU | 980 |
| 241 | AGCUUCA CUGAUGAGGCCGAAAGGCCGAA AUGCUUU | 981 |
| 241 | AGCUUCA CUGAUGAGGCCGAAAGGCCGAA AUGCUUU | 982 |
| 249 | CAAGCCA CUGAUGAGGCCGAAAGGCCGAA AGCUUCA | 983 |
| 264 | AUCAACU CUGAUGAGGCCGAAAGGCCGAA ACAAUUG | 984 |
| 287 | ACUUGAG CUGAUGAGGCCGAAAGGCCGAA AGUGGUG | 985 |
| 295 | ACAUGGA CUGAUGAGGCCGAAAGGCCGAA ACUUGAG | 966 |
| 295 | ACAUGGA CUGAUGAGGCCGAAAGGCCGAA ACUUGAG | 987 |
| 296 | GACAUGG CUGAUGAGGCCGAAAGGCCGAA AACUUGA | 988 |
| 297 | GGACAUG CUGAUGAGGCCGAAAGGCCGAA AAACUUG | 989 |
| 297 | GGACAUG CUGAUGAGGCCGAAAGGCCGAA AAACUUG | 990 |
| 314 | AGAGAAG CUGAUGAGGCCGAAAGGCCGAA AUGAGCC | 991 |
| 314 | AGAGAAG CUGAUGAGGCCGAAAGGCCGAA AUGAGCC | 992 |
| 315 | AAGAGAA CUGAUGAGGCCGAAAGGCCGAA AAUGAGC | 993 |
| 315 | AAGAGAA CUGAUGAGGCCGAAAGGCCGAA AAUGAGC | 994 |
| 317 | CAAAGAG CUGAUGAGGCCGAAAGGCCGAA AGAAUGA | 995 |
| 318 | ACAAAGA CUGAUGAGGCCGAAAGGCCGAA AAGAAUG | 996 |
| 318 | ACAAAGA CUGAUGAGGCCGAAAGGCCGAA AAGAAUG | 997 |
| 320 | GCACAAA CUGAUGAGGCCGAAAGGCCGAA AGAAGAA | 998 |

TABLE V-continued

Mouse B7-1 Hammerhead Ribozyme Sequences

| nt. Position | HH Ribozyme Sequences | Seq. ID No. |
|---|---|---|
| 320 | GCACAAA CUGAUGAGGCCGAAAGGCCGAA AGAAGAA | 999 |
| 322 | CAGCACA CUGAUGAGGCCGAAAGGCCGAA AGAGAAG | 1000 |
| 322 | CAGCACA CUGAUGAGGCCGAAAGGCCGAA AGAGAAG | 1001 |
| 323 | GCAGCAC CUGAUGAGGCCGAAAGGCCGAA AAGAGAA | 1002 |
| 336 | GAAAGAC CUGAUGAGGCCGAAAGGCCGAA AAUCAGC | 1003 |
| 341 | CUUGUGA CUGAUGAGGCCGAAAGGCCGAA AGACGAA | 1004 |
| 341 | CUUGUGA CUGAUGAGGCCGAAAGGCCGAA AGACGAA | 1005 |
| 342 | ACUUGUG CUGAUGAGGCCGAAAGGCCGAA AAGACGA | 1006 |
| 343 | CACUUGU CUGAUGAGGCCGAAAGGCCGAA AAAGACG | 1007 |
| 343 | CACUUGU CUGAUGAGGCCGAAAGGCCGAA AAAGACG | 1008 |
| 352 | AUCUGAA CUGAUGAGGCCGAAAGGCCGAA ACACUUG | 1009 |
| 355 | AACAUCU CUGAUGAGGCCGAAAGGCCGAA AAGACAC | 1010 |
| 382 | UUUCACU CUGAUGAGGCCGAAAGGCCGAA ACUUGGA | 1011 |
| 408 | UAACGGC CUGAUGAGGCCGAAAGGCCGAA AGGCAGC | 1012 |
| 414 | GAGUUGU CUGAUGAGGCCGAAAGGCCGAA ACGGCAA | 1013 |
| 414 | GAGUUGU CUGAUGAGGCCGAAAGGCCGAA ACGGCAA | 1014 |
| 421 | AUGAGGA CUGAUGAGGCCGAAAGGCCGAA AGUUGUA | 1015 |
| 426 | UCUUCAU CUGAUGAGGCCGAAAGGCCGAA AGGAGAG | 1016 |
| 439 | GUCUUCA CUGAUGAGGCCGAAAGGCCGAA ACUCAUC | 1017 |
| 452 | GCCAGUA CUGAUGAGGCCGAAAGGCCGAA AUUCGGU | 1018 |
| 454 | UUGCCAG CUGAUGAGGCCGAAAGGCCGAA AGAUUCG | 1019 |
| 484 | AAUGACA CUGAUGAGGCCGAAAGGCCGAA ACAGCAC | 1020 |
| 484 | AAUGACA CUGAUGAGGCCGAAAGGCCGAA ACAGCAC | 1021 |
| 488 | CAGCAAU CUGAUGAGGCCGAAAGGCCGAA ACAGACA | 1022 |
| 503 | ACACUUU CUGAUGAGGCCGAAAGGCCGAA AGUUUCC | 1023 |
| 503 | ACACUUU CUGAUGAGGCCGAAAGGCCGAA AGUUUCC | 1024 |
| 520 | GUUCUUA CUGAUGAGGCCGAAAGGCCGAA ACUCGGG | 1025 |
| 535 | GUCAUAU CUGAUGAGGCCGAAAGGCCGAA AAGUCCG | 1026 |
| 536 | UGUCAUA CUGAUGAGGCCGAAAGGCCGAA AAAGUCC | 1027 |
| 538 | GUUGUCA CUGAUGAGGCCGAAAGGCCGAA AUAAAGU | 1028 |
| 553 | AAGAGAG CUGAUGAGGCCGAAAGGCCGAA AGGUAGU | 1029 |
| 553 | AAGAGAG CUGAUGAGGCCGAAAGGCCGAA AGGUAGU | 1030 |
| 556 | GAUAAGA CUGAUGAGGCCGAAAGGCCGAA AGUAGGU | 1031 |
| 556 | GAUAAGA CUGAUGAGGCCGAAAGGCCGAA AGUAGGU | 1032 |
| 560 | GGAUGAU CUGAUGAGGCCGAAAGGCCGAA AGAGAGU | 1033 |
| 561 | AGGAUGA CUGAUGAGGCCGAAAGGCCGAA AAGAGAG | 1034 |
| 561 | AGGAUGA CUGAUGAGGCCGAAAGGCCGAA AAGAGAG | 1035 |

TABLE V-continued

Mouse B7-1 Hammerhead Ribozyme Sequences

| nt. Position | HH Ribozyme Sequences | Seq. ID No. |
|---|---|---|
| 561 | AGGAUGA CUGAUGAGGCCGAAAGGCCGAA AAGAGAG | 1036 |
| 566 | GGCCCAG CUGAUGAGGCCGAAAGGCCGAA AUGAUAA | 1037 |
| 566 | GGCCCAG CUGAUGAGGCCGAAAGGCCGAA AUGAUAA | 1038 |
| 581 | GGUCUGA CUGAUGAGGCCGAAAGGCCGAA AGGACCA | 1039 |
| 583 | CCGGUCU CUGAUGAGGCCGAAAGGCCGAA AAAGGAC | 1040 |
| 583 | CCGGUCU CUGAUGAGGCCGAAAGGCCGAA AAAGGAC | 1041 |
| 598 | ACAGCUG CUGAUGAGGCCGAAAGGCCGAA AUGUGCC | 1042 |
| 608 | UUUGAAC CUGAUGAGGCCGAAAGGCCGAA ACACAGC | 1043 |
| 611 | UCUUUUG CUGAUGAGGCCGAAAGGCCGAA ACGACAC | 1044 |
| 611 | UCUUUUG CUGAUGAGGCCGAAAGGCCGAA ACGACAC | 1045 |
| 612 | UUCUUUU CUGAUGAGGCCGAAAGGCCGAA AACGACA | 1046 |
| 641 | AGUGUUU CUGAUGAGGCCGAAAGGCCGAA ACUUCAU | 1047 |
| 649 | UAAAGCC CUGAUGAGGCCGAAAGGCCGAA AGUGUUU | 1048 |
| 649 | UAAAGCC CUGAUGAGGCCGAAAGGCCGAA AGUGUUU | 1049 |
| 655 | CUUUACU CUGAUGAGGCCGAAAGGCCdAA AAGCCAA | 1050 |
| 656 | ACUUUAC CUGAUGAGGCCGAAAGGCCGAA AAAGCCA | 1051 |
| 659 | ACAACUU CUGAUGAGGCCGAAAGGCCGAA ACUAAAG | 1052 |
| 664 | GAUGGAC CUGAUGAGGCCGAAAGGCCGAA ACUUUAC | 1053 |
| 667 | UUUGAUG CUGAUGAGGCCGAAAGGCCGAA ACAACUU | 1054 |
| 671 | CAGCUUU CUGAUGAGGCCGAAAGGCCGAA AUGGACA | 1055 |
| 682 | GGUAGAG CUGAUGAGGCCGAAAGGCCGAA AGUCAGC | 1056 |
| 682 | GGUAGAG CUGAUGAGGCCGAAAGGCCGAA AGUCAGC | 1057 |
| 682 | GGUAGAG CUGAUGAGGCCGAAAGGCCGAA AGUCAGC | 1058 |
| 683 | GGGUAGA CUGAUGAGGCCGAAAGGCCGAA AAGUCAG | 1059 |
| 683 | GGGUAGA CUGAUGAGGCCGAAAGGCCGAA AAGUCAG | 1060 |
| 685 | GGGGGUA CUGAUGAGGCCGAAAGGCCGAA AGAAGUC | 1061 |
| 685 | GGGGGUA CUGAUGAGGCCGAAAGGCCGAA AGAAGUC | 1062 |
| 687 | UUGGGGG CUGAUGAGGCCGAAAGGCCGAA AGAGAAG | 1063 |
| 698 | ACUCAGU CUGAUGAGGCCGAAAGGCCGAA AUGUUGG | 1064 |
| 698 | ACUCAGU CUGAUGAGGCCGAAAGGCCGAA AUGUUGG | 1065 |
| 718 | GUCUGCA CUGAUGAGGCCGAAAGGCCGAA AUGGGUU | 1066 |
| 718 | GUCUGCA CUGAUGAGGCCGAAAGGCCGAA AUGGGUU | 1067 |
| 729 | AUCCUUU CUGAUGAGGCCGAAAGGCCGAA AGUGUCU | 1068 |
| 729 | AUCCUUU CUGAUGAGGCCGAAAGGCCGAA AGUGUCU | 1069 |
| 729 | AUCCUUU CUGAUGAGGCCGAAAGGCCGAA AGUGUCU | 1070 |
| 737 | AGCAGGU CUGAUGAGGCCGAAAGGCCGAA AUCCUUU | 1071 |
| 737 | AGCAGGU CUGAUGAGGCCGAAAGGCCGAA AUCCUUU | 1072 |

TABLE V-continued

Mouse B7-1 Hammerhead Ribozyme Sequences

| nt. Position | HH Ribozyme Sequences | Seq. ID No. |
|---|---|---|
| 737 | AGCAGGU CUGAUGAGGCCGAAAGGCCGAA AUCCUUU | 1073 |
| 745 | GGAAGCA CUGAUGAGGCCGAAAGGCCGAA AGCAGGU | 1074 |
| 745 | GGAAGCA CUGAUGAGGCCGAAAGGCCGAA AGCAGGU | 1075 |
| 759 | UUUGGGA CUGAUGAGGCCGAAAGGCCGAA ACCCCCG | 1076 |
| 759 | UUUGGGA CUGAUGAGGCCGAAAGGCCGAA ACCCCCG | 1077 |
| 759 | UUUGGGA CUGAUGAGGCCGAAAGGCCGAA ACCCCCG | 1078 |
| 760 | CUUUGGG CUGAUGAGGCCGAAAGGCCGAA AACCCCC | 1079 |
| 760 | CUUUGGG CUGAUGAGGCCGAAAGGCCGAA AACCCCC | 1080 |
| 760 | CUUUGGG CUGAUGAGGCCGAAAGGCCGAA AACCCCC | 1081 |
| 761 | GCUUUGG CUGAUGAGGCCGAAAGGCCGAA AAACCCC | 1082 |
| 771 | GAGAAGC CUGAUGAGGCCGAAAGGCCGAA AGGCUUU | 1083 |
| 771 | GAGAAGC CUGAUGAGGCCGAAAGGCCGAA AGGCUUU | 1084 |
| 776 | ACCAAGA CUGAUGAGGCCGAAAGGCCGAA AAGCGAG | 1085 |
| 776 | ACCAAGA CUGAUGAGGCCGAAAGGCCGAA AAGCGAG | 1086 |
| 778 | CAACCAA CUGAUGAGGCCGAAAGGCCGAA AGAAGCG | 1087 |
| 784 | AUUUCC CUGAUGAGGCCGAAAGGCCGAA ACCAAGA | 1088 |
| 803 | UGCCAGG CUGAUGAGGCCGAAAGGCCGAA AAUUCUC | 1089 |
| 803 | UGCCAGG CUGAUGAGGCCGAAAGGCCGAA AAUUCUC | 1090 |
| 803 | UGCCAGG CUGAUGAGGCCGAAAGGCCGAA AAUUCUC | 1091 |
| 812 | UCGUAUU CUGAUGAGGCCGAAAGGCCGAA AUGCCAG | 1092 |
| 812 | UCGUAUU CUGAUGAGGCCGAAAGGCCGAA AUGCCAG | 1093 |
| 816 | AUUGUCG CUGAUGAGGCCGAAAGGCCGAA AUUGAUG | 1094 |
| 816 | AUUGUCG CUGAUGAGGCCGAAAGGCCGAA AUUGAUG | 1095 |
| 824 | CCUGGGA CUGAUGAGGCCGAAAGGCCGAA AUUGUCG | 1096 |
| 825 | UCCUGGG CUGAUGAGGCCGAAAGGCCGAA AAUUGUC | 1097 |
| 826 | AUCCUGG CUGAUGAGGCCGAAAGGCCGAA AAAUUGU | 1098 |
| 834 | GAUUCAG CUGAUGAGGCCGAAAGGCCGAA AUCCUGG | 1099 |
| 841 | CAAUUCA CUGAUGAGGCCGAAAGGCCGAA AUUCAGG | 1100 |
| 841 | CAAUUCA CUGAUGAGGCCGAAAGGCCGAA AUUCAGG | 1101 |
| 850 | AAUGGUG CUGAUGAGGCCGAAAGGCCGAA ACAAUUC | 1102 |
| 869 | UGAAAUC CUGAUGAGGCCGAAAGGCCGAA AGUUGGC | 1103 |
| 869 | UGAAAUC CUGAUGAGGCCGAAAGGCCGAA AGUUGGC | 1104 |
| 869 | UGAAAUC CUGAUGAGGCCGAAAGGCCGAA AGUUGGC | 1105 |
| 873 | GUAUUGA CUGAUGAGGCCGAAAGGCCGAA AUCUAGU | 1106 |
| 873 | GUAUUGA CUGAUGAGGCCGAAAGGCCGAA AUCUAGU | 1107 |
| 874 | CGUAUUG CUGAUGAGGCCGAAAGGCCGAA AAUCUAG | 1108 |
| 875 | UCGUAUU CUGAUGAGGCCGAAAGGCCGAA AAAUCUA | 1109 |

TABLE V-continued

Mouse B7-1 Hammerhead Ribozyme Sequences

| nt. Position | HH Ribozyme Sequences | Seq. ID No. |
|---|---|---|
| 885 | UGGUUGC CUGAUGAGGCCGAAAGGCCGAA AGUCGUA | 1110 |
| 899 | GACACUU CUGAUGAGGCCGAAAGGCCGAA AUGGUGU | 1111 |
| 899 | GACACUU CUGAUGAGGCCGAAAGGCCGAA AUGGUGU | 1112 |
| 906 | UUAAUGA CUGAUGAGGCCGAAAGGCCGAA ACACUUA | 1113 |
| 906 | UUAAUGA CUGAUGAGGCCGAAAGGCCGAA ACACUUA | 1114 |
| 908 | AUUUAAU CUGAUGAGGCCGAAAGGCCGAA AGACACU | 1115 |
| 911 | CAUAUUU CUGAUGAGGCCGAAAGGCCGAA AUGAGAC | 1116 |
| 916 | AUCUCCA CUGAUGAGGCCGAAAGGCCGAA AUUUAAU | 1117 |
| 916 | AUCUCCA CUGAUGAGGCCGAAAGGCCGAA AUUUAAU | 1118 |
| 943 | CCAGGUG CUGAUGAGGCCGAAAGGCCGAA AGUCCUC | 1119 |
| 944 | CCCAGGU CUGAUGAGGCCGAAAGGCCGAA AAGUCCU | 1120 |
| 1001 | CUGCCCC CUGAUGAGGCCGAAAGGCCGAA AAGAGCA | 1121 |
| 1034 | CGAUGAC CUGAUGAGGCCGAAAGGCCGAA ACGACUG | 1122 |
| 1037 | CAACGAU CUGAUGAGGCCGAAAGGCCGAA ACGACGA | 1123 |
| 1043 | UGAUGAC CUGAUGAGGCCGAAAGGCCGAA ACGAUGA | 1124 |
| 1046 | UGAUGAU CUGAUGAGGCCGAAAGGCCGAA ACAACGA | 1125 |
| 1049 | AUUUGAU CUGAUGAGGCCGAAAGGCCGAA AUGACAA | 1126 |
| 1060 | CUUACAG CUGAUGAGGCCGAAAGGCCGAA AGCAUUU | 1127 |
| 1060 | CUUACAG CUGAUGAGGCCGAAAGGCCGAA AGCAUUU | 1128 |
| 1060 | CUUACAG CUGAUGAGGCCGAAAGGCCGAA AGCAUUU | 1129 |
| 1060 | CUUACAG CUGAUGAGGCCGAAAGGCCGAA AGCAUUU | 1130 |
| 1061 | GCUUACA CUGAUGAGGCCGAAAGGCCGAA AAGCAUU | 1131 |
| 1080 | CUUCUGA CUGAUGAGGCCGAAAGGCCGAA ACAGCUU | 1132 |
| 1080 | CUUCUGA CUGAUGAGGCCGAAAGGCCGAA ACAGCUU | 1133 |
| 1081 | UCUUCUG CUGAUGAGGCCGAAAGGCCGAA AACAGCU | 1134 |
| 1121 | CGAAGGU CUGAUGAGGCCGAAAGGCCGAA AGGCUGU | 1135 |
| 1121 | CGAAGGU CUGAUGAGGCCGAAAGGCCGAA AGGCUGU | 1136 |
| 1121 | CGAAGGU CUGAUGAGGCCGAAAGGCCGAA AGGCUGU | 1137 |
| 1122 | CCGAAGG CUGAUGAGGCCGAAAGGCCGAA AAGGCUG | 1138 |
| 1126 | AGGCCCG CUGAUGAGGCCGAAAGGCCGAA AGGUAAG | 1139 |
| 1127 | CAGGCCC CUGAUGAGGCCGAAAGGCCGAA AAGGUAA | 1140 |
| 1127 | CAGGCCC CUGAUGAGGCCGAAAGGCCGAA AAGGUAA | 1141 |
| 1144 | UUCAGCU CUGAUGAGGCCGAAAGGCCGAA AUGCUUC | 1142 |
| 1144 | UUCAGCU CUGAUGAGGCCGAAAGGCCGAA AUGCUUC | 1143 |
| 1145 | GUUCAGC CUGAUGAGGCCGAAAGGCCGAA AAUGCUU | 1144 |
| 1160 | AAAGGAA CUGAUGAGGCCGAAAGGCCGAA ACGGUCU | 1145 |
| 1162 | CUAAAGG CUGAUGAGGCCGAAAGGCCGAA AGACGGU | 1146 |

TABLE V-continued

Mouse B7-1 Hammerhead Ribozyme Sequences

| nt. Position | HH Ribozyme Sequences | Seq. ID No. |
|---|---|---|
| 1163 | ACUAAAG CUGAUGAGGCCGAAAGGCCGAA AAGACGG | 1147 |
| 1167 | AAGAACU CUGAUGAGGCCGAAAGGCCGAA AAGGAAG | 1148 |
| 1177 | AUGGACA CUGAUGAGGCCGAAAGGCCGAA AGAAGAA | 1149 |
| 1181 | CCACAUG CUGAUGAGGCCGAAAGGCCGAA ACAGAGA | 1150 |
| 1181 | CCACAUG CUGAUGAGGCCGAAAGGCCGAA ACAGAGA | 1151 |
| 1192 | UACCAUG CUGAUGAGGCCGAAAGGCCGAA AUCCCAC | 1152 |
| 1199 | CACAUAA CUGAUGAGGCCGAAAGGCCGAA ACCAUGU | 1153 |
| 1201 | GCCAGAU CUGAUGAGGCCGAAAGGCCGAA AUACCAU | 1154 |
| 1210 | ACCUCAU CUGAUGAGGCCGAAAGGCCGAA AGCCACA | 1155 |
| 1210 | ACCUCAU CUGAUGAGGCCGAAAGGCCGAA AGCCACA | 1156 |
| 1223 | AAAGAAA CUGAUGAGGCCGAAAGGCCGAA AUUGUAC | 1157 |
| 1225 | UGAAAGA CUGAUGAGGCCGAAAGGCCGAA AGAUUGU | 1158 |
| 1225 | UGAAAGA CUGAUGAGGCCGAAAGGCCGAA AGAUUGU | 1159 |
| 1226 | CUGAAAG CUGAUGAGGCCGAAAGGCCGAA AAGAUUG | 1160 |
| 1227 | GCUGAAA CUGAUGAGGCCGAAAGGCCGAA AAAGAUU | 1161 |
| 1227 | GCUGAAA CUGAUGAGGCCGAAAGGCCGAA AAAGAUU | 1162 |
| 1227 | GCUGAAA CUGAUGAGGCCGAAAGGCCGAA AAAGAUU | 1163 |
| 1229 | GUGCUGA CUGAUGAGGCCGAAAGGCCGAA AGAAAGA | 1164 |
| 1230 | GGUGCUG CUGAUGAGGCCGAAAGGCCGAA AAGAAAG | 1165 |
| 1252 | UGUCCGA CUGAUGAGGCCGAAAGGCCGAA AGAUCAG | 1166 |
| 1274 | UUAACUC CUGAUGAGGCCGAAAGGCCGAA AUCUUGU | 1167 |
| 1310 | GGAAAGA CUGAUGAGGCCGAAAGGCCGAA AUCCUCA | 1168 |
| 1312 | AUGGAAA CUGAUGAGGCCGAAAGGCCGAA AAAUCCU | 1169 |
| 1314 | UGAUGGA CUGAUGAGGCCGAAAGGCCGAA AGAAAUC | 1170 |
| 1316 | CCUGAUG CUGAUGAGGCCGAAAGGCCGAA AAAGAAA | 1171 |
| 1320 | GCUUCCU CUGAUGAGGCCGAAAGGCCGAA AUGGAAA | 1172 |
| 1320 | GCUUCCU CUGAUGAGGCCGAAAGGCCGAA AUGGAAA | 1173 |
| 1339 | CCCAGCA CUGAUGAGGCCGAAAGGCCGAA ACUUGCC | 1174 |
| 1355 | AUCAAGC CUGAUGAGGCCGAAAGGCCGAA AUCAAAG | 1175 |
| 1437 | UUUUUCU CUGAUGAGGCCGAAAGGCCGAA AUACCAC | 1176 |
| 1437 | UUUUUCU CUGAUGAGGCCGAAAGGCCGAA AUACCAC | 1177 |
| 1475 | GCAGUAA CUGAUGAGGCCGAAAGGCCGAA ACUAGGC | 1178 |
| 1477 | UUGCAGU CUGAUGAGGCCGAAAGGCCGAA AGACUAG | 1179 |
| 1487 | ACAUAUC CUGAUGAGGCCGAAAGGCCGAA AGUUGCA | 1180 |
| 1491 | CAUGACA CUGAUGAGGCCGAAAGGCCGAA AUCAAGU | 1181 |
| 1491 | CAUGACA CUGAUGAGGCCGAAAGGCCGAA AUCAAGU | 1182 |
| 1505 | AGACACC CUGAUGAGGCCGAAAGGCCGAA ACCAAAC | 1183 |

TABLE V-continued

Mouse B7-1 Hammerhead Ribozyme Sequences

| nt. Position | HH Ribozyme Sequences | Seq. ID No. |
|---|---|---|
| 1530 | CUUCAGA CUGAUGAGGCCGAAAGGCCGAA AAGGGCA | 1184 |
| 1531 | UCUUCAG CUGAUGAGGCCGAAAGGCCGAA AAAGGGC | 1185 |
| 1532 | CUCUUCA CUGAUGAGGCCGAAAGGCCGAA AAAAGGG | 1186 |
| 1532 | CUCUUCA CUGAUGAGGCCGAAAGGCCGAA AAAAGGG | 1187 |
| 1644 | ACAUCCC CUGAUGAGGCCGAAAGGCCGAA ACCAUAG | 1188 |
| 1652 | CCGUUUU CUGAUGAGGCCGAAAGGCCGAA ACAUCCC | 1189 |
| 1652 | CCGUUUU CUGAUGAGGCCGAAAGGCCGAA ACAUCCC | 1190 |
| 1670 | UAAUAUU CUGAUGAGGCCGAAAGGCCGAA AUAUUAU | 1191 |
| 1674 | UAUUUAA CUGAUGAGGCCGAAAGGCCGAA AUUUAUA | 1192 |
| 1676 | UUUAUUU CUGAUGAGGCCGAAAGGCCGAA AUAUUUA | 1193 |
| 1677 | UUUUAUU CUGAUGAGGCCGAAAGGCCGAA AAUAUUU | 1194 |
| 1677 | UUUUAUU CUGAUGAGGCCGAAAGGCCGAA AAUAUUU | 1195 |
| 1694 | UUUGCUC CUGAUGAGGCCGAAAGGCCGAA AUACUCU | 1196 |

TABLE VI

Human B7-2 Hammerhead Ribozyme Sequences

| nt. Position | HH Target Sequence | Seq. ID No. | nt. Position | HH Target Sequence | Seq. ID No. |
|---|---|---|---|---|---|
| 16 | GAAAGCU U UGCUUCU | 1197 | 271 | UAGUAGU A UUUUGGC | 1239 |
| 17 | AAAGCUU U GCUUCUC | 1198 | 273 | GUAGUAU U UUGGCAG | 1240 |
| 21 | CUUUGCU U CUCUGCU | 1199 | 274 | UAGUAUU U UGGCAGG | 1241 |
| 22 | UUUGCUU C UCUGCUG | 1206 | 275 | AGUAUUU U GGCAGGA | 1242 |
| 24 | UGCUUCU C UGCUGCU | 1201 | 294 | GAAAACU U GGUUCUG | 1243 |
| 34 | CUGCUGU A ACAGGGA | 1202 | 298 | ACUUGGU U CUGAAUG | 1244 |
| 44 | AGGGACU A GCACAGA | 1203 | 299 | CUUGGUU C UGAAUGA | 1245 |
| 70 | GUGGGGU C AUUUCCA | 1204 | 310 | AUGAGGU A UACUUAG | 1246 |
| 73 | GGGUCAU U UCCAGAU | 1205 | 312 | GAGGUAU A CUUAGGC | 1247 |
| 74 | GGUCAUU U CCAGAUA | 1206 | 315 | GUAUACU U AGGCAAA | 1248 |
| 75 | GUCAUUU C CAGAUAU | 1207 | 316 | UAUACUU A GGCAAAG | 1249 |
| 81 | UCCAGAU A UUAGGUC | 1208 | 330 | GAGAAAU U UGACAGU | 1250 |
| 83 | CAGAUAU U AGGUCAC | 1209 | 331 | AGAAAUU U GACAGUG | 1251 |
| 84 | AGAUAUU A GGUCACA | 1210 | 340 | ACAGUGU U CAUUCCA | 1252 |
| 88 | AUUAGGU C ACAGCAG | 1211 | 341 | CAGUGUU C AUUCCAA | 1253 |
| 113 | AAUGGAU C CCCAGUG | 1212 | 344 | UGUUCAU U CCAAGUA | 1254 |
| 125 | GUGCACU A UGGGACU | 1213 | 345 | GUUCAUU C CAAGUAU | 1255 |
| 137 | ACUGAGU A ACAUUCU | 1214 | 351 | UCCAAGU A UAUGGGC | 1256 |
| 142 | GUAACAU U CUCUUUG | 1215 | 353 | CAAGUAU A UGGGCCG | 1257 |

TABLE VI-continued

Human B7-2 Hammerhead Ribozyme Sequences

| nt. Position | HH Target Sequence | Seq. ID No. | nt. Position | HH Target Sequence | Seq. ID No. |
|---|---|---|---|---|---|
| 143 | UAACAUU C UCUUUGU | 1216 | 368 | CACAAGU U UUGAUUC | 1258 |
| 145 | ACAUUCU C UUUGUGA | 1217 | 369 | ACAAGUU U UGAUUCG | 1259 |
| 147 | AUUCUCU U UGUGAUG | 1218 | 370 | CAAGUUU U GAUUCGG | 1260 |
| 148 | UUCUCUU U GUGAUGG | 1219 | 374 | UUUUGAU U CGGACAG | 1261 |
| 159 | AUGGCCU U CCUGCUC | 1220 | 375 | UUUGAUU C GGACAGU | 1262 |
| 160 | UGGCCUU C CUGCUCU | 1221 | 383 | GGACAGU U GGACCCU | 1263 |
| 166 | UCCUGCU C UCUGGUG | 1222 | 397 | UGAGACU U CACAAUC | 1264 |
| 168 | CUGCUCU C UGGUGCU | 1223 | 398 | GAGACUU C ACAAUCU | 1265 |
| 179 | UGCUGCU C CUCUGAA | 1224 | 404 | UCACAAU C UUCAGAU | 1266 |
| 182 | UGCUCCU C UGAAGAU | 1225 | 406 | ACAAUCU U CAGAUCA | 1267 |
| 190 | UGAAGAU U CAAGCUU | 1226 | 407 | CAAUCUU C AGAUCAA | 1268 |
| 191 | GAAGAUU C AAGCUUA | 1227 | 412 | UUCAGAU C AAGGACA | 1269 |
| 197 | UCAAGCU U AUUUCAA | 1228 | 426 | AAGGGCU U GUAUCAA | 1270 |
| 198 | CAAGCUU A UUUCAAU | 1229 | 429 | GGCUUGU A UCAAUGU | 1271 |
| 200 | AGCUUAU U UCAAUGA | 1230 | 431 | CUUGUAU C AAUGUAU | 1272 |
| 201 | GCUUAUU U CAAUGAG | 1231 | 437 | UCAAUGU A UCAUCCA | 1273 |
| 202 | CUUAUUU C AAUGAGA | 1232 | 439 | AAUGUAU C AUCCAUC | 1274 |
| 231 | UGCCAAU U UGCAAAC | 1233 | 442 | GUAUCAU C CAUCACA | 1275 |
| 232 | GCCAAUU U GCAAACU | 1234 | 446 | CAUCCAU C ACAAAAA | 1276 |
| 240 | GCAAACU C UCAAAAC | 1235 | 469 | GAAUGAU U CGCAUCC | 1277 |
| 242 | AAACUCU C AAAACCA | 1236 | 470 | AAUGAUU C GCAUCCA | 1278 |
| 265 | GUGAGCU A GUAGUAU | 1237 | 475 | UUCGCAU C CACCAGA | 1279 |
| 268 | AGCUAGU A GUAUUUU | 1238 | 488 | GAUGAAU U CUGAACU | 1280 |
| 489 | AUGAAUU C UGAACUG | 1281 | 721 | UGUCUGU U UCAUUCC | 1330 |
| 498 | GAACUGU C AGUGCUU | 1282 | 722 | GUCUGUU U CAUUCCC | 1331 |
| 505 | CAGUGCU U GCUAACU | 1283 | 723 | UCUGUUU C AUUCCCU | 1332 |
| 509 | GCUUGCU A ACUUCAG | 1284 | 726 | GUUUCAU U CCCUGAU | 1333 |
| 513 | GCUAACU U CAGUCAA | 1285 | 727 | UUUCAUU C CCUGAUG | 1334 |
| 514 | CUAACUU C AGUCAAC | 1286 | 736 | CUGAUGU U ACGAGCA | 1335 |
| 518 | CUUCAGU C AACCUGA | 1287 | 737 | UGAUGUU A CGAGCAA | 1336 |
| 529 | CUGAAAU A GUACCAA | 1288 | 746 | GAGCAAU A UGACCAU | 1337 |
| 532 | AAAUAGU A CCAAUUU | 1289 | 754 | UGACCAU C UUCUGUA | 1338 |
| 538 | UACCAAU U UCUAAUA | 1290 | 756 | ACCAUCU U CUGUAUU | 1339 |
| 539 | ACCAAUU U CUAAUAU | 1291 | 757 | CCAUCUU C UGUAUUC | 1340 |
| 540 | CCAAUUU C UAAUAUA | 1292 | 761 | CUUCUGU A UUCUGGA | 1341 |
| 542 | AAUUUCU A AUAUAAC | 1293 | 763 | UCUGUAU U CUGGAAA | 1342 |
| 545 | UUCUAAU A UAACAGA | 1294 | 764 | CUGUAUU C UGGAAAC | 1343 |

TABLE VI-continued

Human B7-2 Hammerhead Ribozyme Sequences

| nt. Position | HH Target Sequence | Seq. ID No. | nt. Position | HH Target Sequence | Seq. ID No. |
|---|---|---|---|---|---|
| 547 | CUAAUAU A ACAGAAA | 1235 | 787 | CGCGGCU U UUAUCUU | 1344 |
| 561 | AAUGUGU A CAUAAAU | 1296 | 788 | GCGGCUU U UAUCUUC | 1345 |
| 565 | UGUACAU A AAUUUGA | 1297 | 789 | CGGCUUU U AUCUUCA | 1346 |
| 569 | CAUAAAU U UGACCUG | 1298 | 790 | GGCUUUU A UCUUCAC | 1347 |
| 570 | AUAAAUU U GACCUGC | 1299 | 792 | CUUUUAU C UUCACCU | 1348 |
| 579 | ACCUGCU C AUCUAUA | 1300 | 794 | UUUAUCU U CACCUUU | 1349 |
| 582 | UGCUCAU C UAUACAC | 1301 | 795 | UUAUCUU C ACCUUUC | 1350 |
| 584 | CUCAUCU A UACACGG | 1302 | 800 | UUCACCU U UCUCUAU | 1351 |
| 586 | CAUCUAU A CACCGUU | 1303 | 801 | UCACCUU U CUCUAUA | 1352 |
| 593 | ACACGGU U ACCCAGA | 1304 | 802 | CACCUUU C UCUAUAG | 1353 |
| 594 | CACGGUU A CCCAGAA | 1305 | 804 | CCUUUCU C UAUAGAG | 1354 |
| 605 | AGAACCU A AGAAGAU | 1306 | 806 | UUUCUCU A UAGAGCU | 1355 |
| 619 | UGAGUGU U UUGCUAA | 1307 | 808 | UCUCUAU A GAGCUUG | 1356 |
| 620 | GAGUGUU U UGCUAAG | 1308 | 814 | UAGAGCU U GAGGACC | 1357 |
| 621 | AGUGUUU U GCUAAGA | 1309 | 824 | GGACCCU C AGCCUCC | 1358 |
| 625 | UUUUGCU A AGAACCA | 1310 | 830 | UCAGCCU C CCCAGA | 1359 |
| 638 | CAAGAAU U CAACUAU | 1311 | 844 | ACCACAU U CCUUGGA | 1360 |
| 639 | AAGAAUU C AACUAUC | 1312 | 845 | CCACAUU C CUUGGAU | 1361 |
| 644 | UUCAACU A UCGAGUA | 1313 | 848 | CAUUCCU U GGAUUAC | 1362 |
| 646 | CAACUAU C GAGUAUG | 1314 | 853 | CUUGGAU U ACAGCUG | 1363 |
| 651 | AUCGAGU A UGAUGGU | 1315 | 854 | UUGGAUU A CAGCUGU | 1364 |
| 659 | UGAUGGU A UUAUGCA | 1316 | 862 | CAGCUGU A CUUCCAA | 1365 |
| 661 | AUGGUAU U AUGCAGA | 1317 | 865 | CUGUACU U CCAACAG | 1366 |
| 662 | UGGUAUU A UGCAGAA | 1318 | 866 | UGUACUU C CAACAGU | 1367 |
| 672 | CAGAAAU C UCAAGAU | 1319 | 874 | CAACAGU U AUUAUAU | 1368 |
| 674 | GAAAUCU C AAGAUAA | 1320 | 875 | AACAGUU A UUAUAUG | 1369 |
| 680 | UCAAGAU A AUGUCAC | 1321 | 877 | CAGUUAU U AUAUGUG | 1370 |
| 685 | AUAAUGU C ACAGAAC | 1322 | 878 | AGUUAUU A UAUGUGU | 1371 |
| 696 | GAACUGU A CGACGUU | 1323 | 880 | UUAUUAU A UGUGUGA | 1372 |
| 703 | ACGACGU U UCCAUCA | 1324 | 892 | UGAUGGU U UUCUGUC | 1373 |
| 704 | CGACGUU U CCAUCAG | 1325 | 893 | GAUGGUU U UCUGUCU | 1374 |
| 705 | GACGUUU C CAUCAGC | 1326 | 894 | AUGGUUU U CUGUCUA | 1375 |
| 709 | UUUCCAU C AGCUUGU | 1327 | 895 | UGGUUUU C UGUCUAA | 1376 |
| 714 | AUCAGCU U GUCUGUU | 1328 | 899 | UUUCUGU C UAAUUCU | 1377 |
| 717 | AGCUUGU C UGUUUCA | 1329 | 901 | UCUGUCU A AUUCUAU | 1378 |
| 904 | GUCUAAU U CUAUGGA | 1379 | | | |
| 905 | UCUAAUU C UAUGGAA | 1380 | | | |

TABLE VI-continued

Human B7-2 Hammerhead Ribozyme Sequences

| nt. Position | HH Target Sequence | Seq. ID No. | nt. Position | HH Target Sequence | Seq. ID No. |
|---|---|---|---|---|---|
| 907 | UAAUUCU A UGGAAAU | 1381 | | | |
| 935 | GCGGCCU C GCAACUC | 1382 | | | |
| 942 | CGCAACU C UUAUAAA | 1383 | | | |
| 944 | CAACUCU U AUAAAUG | 1384 | | | |
| 945 | AACUCUU A UAAAUGU | 1385 | | | |
| 947 | CUCUUAU A AAUGUGG | 1386 | | | |
| 1009 | AAAAAAU C CAUAUAC | 1387 | | | |
| 1013 | AAUCCAU A UACCUGA | 1388 | | | |
| 1015 | UCCAUAU A CCUGAAA | 1389 | | | |
| 1026 | GAAAGAU U GAUGAA | 1390 | | | |
| 1045 | AGCGUGU U UUUAAAA | 1391 | | | |
| 1046 | GCGUGUU U UUAAAAG | 1392 | | | |
| 1047 | CGUGUUU U UAAAAGU | 1393 | | | |
| 1048 | GUGUUUU U AAAAGUU | 1394 | | | |
| 1049 | UGUUUUU A AAAGUUC | 1395 | | | |
| 1055 | UAAAAGU U CGAAGAC | 1396 | | | |
| 1056 | AAAAGUU C GAAGACA | 1397 | | | |
| 1065 | AAGACAU C UUCAUGC | 1398 | | | |
| 1067 | GACAUCU U CAUGCGA | 1399 | | | |
| 1068 | ACAUCUU C AUGCGAC | 1400 | | | |
| 1085 | AAGUGAU A CAUGUUU | 1401 | | | |
| 1091 | UACAUGU U UUUAAUU | 1402 | | | |
| 1092 | ACAUGUU U UUAAUUA | 1403 | | | |
| 1093 | CAUGUUU U UAAUUAA | 1404 | | | |
| 1094 | AUGUUUU U AAUUAAA | 1405 | | | |
| 1095 | UGUUUUU A AUUAAAG | 1406 | | | |
| 1098 | UUUUAAU U AAAGAGU | 1407 | | | |
| 1099 | UUUAAUU A AAGAGUA | 1408 | | | |

TABLE VII

Human B7-2 Hammerhead Ribozyme Sequences

| nt. Position | HH Ribozyme Sequences | Seq. Id No. |
|---|---|---|
| 16 | AGAAGCA CUGAUGAGGCCGAAAGGCCGAA AGCUUUC | 1409 |
| 17 | GAGAAGC CUGAUGAGGCCGAAAGGCCGAA AAGCUUU | 1410 |
| 21 | AGCAGAG CUGAUGAGGCCGAAAGGCCGAA AGCAAAG | 1411 |
| 22 | CAGCAGA CUGAUGAGGCCGAAAGGCCGAA AAGCAAA | 1412 |

TABLE VII-continued

Human B7-2 Hammerhead Ribozyme Sequences

| nt. Position | HH Ribozyme Sequences | Seq. Id No. |
|---|---|---|
| 24 | AGCAGCA CUGAUGAGGCCGAAAGGCCGAA AGAAGCA | 1413 |
| 34 | UCCCUGU CUGAUGAGGCCGAAAGGCCGAA ACAGCAG | 1414 |
| 44 | UCUGUGC CUGAUGAGGCCGAAAGGCCGAA AGUCCCU | 1415 |
| 70 | UGGAAAU CUGAUGAGGCCGAAAGGCCGAA ACCCCAC | 1416 |
| 73 | AUCUGGA CUGAUGAGGCCGAAAGGCCGAA AUGACCC | 1417 |
| 74 | UAUCUGG CUGAUGAGGCCGAAAGGCCGAA AAUGACC | 1418 |
| 75 | AUAUCUG CUGAUGAGGCCGAAAGGCCGAA AAAUGAC | 1419 |
| 81 | GACCUAA CUGAUGAGGCCGAAAGGCCGAA AUCUGGA | 1420 |
| 83 | GUGACCU CUGAUGAGGCCGAAAGGCCGAA AUAUCUG | 1421 |
| 84 | UGUGACC CUGAUGAGGCCGAAAGGCCGAA AAUAUCU | 1422 |
| 88 | CUGCUGU CUGAUGAGGCCGAAAGGCCGAA ACCUAAU | 1423 |
| 113 | CACUGGG CUGAUGAGGCCGAAAGGCCGAA AUCCAUU | 1424 |
| 125 | AGUCCCA CUGAUGAGGCCGAAAGGCCGAA AGUGCAC | 1425 |
| 137 | AGAAUGU CUGAUGAGGCCGAAAGGCCGAA ACUCAGU | 1426 |
| 142 | CAAAGAG CUGAUGAGGCCGAAAGGCCGAA AUGUUAC | 1427 |
| 143 | ACAAAGA CUGAUGAGGCCGAAAGGCCGAA AAUGUUA | 1428 |
| 145 | UCACAAA CUGAUGAGGCCGAAAGGCCGAA AGAAUGU | 1429 |
| 147 | CAUCACA CUGAUGAGGCCGAAAGGCCGAA AGAGAAU | 1430 |
| 148 | CCAUCAC CUGAUGAGGCCGAAAGGCCGAA AAGAGAA | 1431 |
| 159 | GAGCAGG CUGAUGAGGCCGAAAGGCCGAA AGGCCAU | 1432 |
| 166 | AGAGCAG CUGAUGAGGCCGAAAGGCCGAA AAGGCCA | 1433 |
| 166 | CACCAGA CUGAUGAGGCCGAAAGGCCGAA AGCAGGA | 1434 |
| 168 | AGCACCA CUGAUGAGGCCGAAAGGCCGAA AGAGCAG | 1435 |
| 179 | UUCAGAG CUGAUGAGGCCGAAAGGCCGAA AGCAGCA | 1436 |
| 182 | AUCUUCA CUGAUGAGGCCGAAAGGCCGAA AGGAGCA | 1437 |
| 190 | AAGCUUG CUGAUGAGGCCGAAAGGCCGAA AUCUUCA | 1438 |
| 191 | UAAGCUU CUGAUGAGGCCGAAAGGCCGAA AAUCUUC | 1439 |
| 197 | UUGAAAU CUGAUGAGGCCGAAAGGCCGAA AGCUUGA | 1440 |
| 198 | AUUGAAA CUGAUGAGGCCGAAAGGCCGAA AAGCUUG | 1441 |
| 200 | UCAUUGA CUGAUGAGGCCGAAAGGCCGAA AUAAGCU | 1442 |
| 201 | CUCAUUG CUGAUGAGGCCGAAAGGCCGAA AAUAAGC | 1443 |
| 202 | UCUCAUU CUGAUGAGGCCGAAAGGCCGAA AAAUAAG | 1444 |
| 231 | GUUUGCA CUGAUGAGGCCGAAAGGCCGAA AUUGGCA | 1445 |
| 232 | AGUUUGC CUGAUGAGGCCGAAAGGCCGAA AAUUGGC | 1446 |
| 240 | GUUUUGA CUGAUGAGGCCGAAAGGCCGAA AGUUUGC | 1447 |
| 242 | UGGUUUU CUGAUGAGGCCGAAAGGCCGAA AGAGUUU | 1448 |
| 265 | AUACUAC CUGAUGAGGCCGAAAGGCCGAA AGCUCAC | 1449 |

TABLE VII-continued

Human B7-2 Hammerhead Ribozyme Sequences

| nt. Position | HH Ribozyme Sequences | Seq. Id No. |
|---|---|---|
| 268 | AAAAUAC CUGAUGAGGCCGAAAGGCCGAA ACUAGCU | 1450 |
| 271 | GCCAAAA CUGAUGAGGCCGAAAGGCCGAA ACUACUA | 1451 |
| 273 | CUGCCAA CUGAUGAGGCCGAAAGGCCGAA AUACUAC | 1452 |
| 274 | CCUGCCA CUGAUGAGGCCGAAAGGC&GAA AAUACUA | 1453 |
| 275 | UCCUGCC CUGAUGAGGCCGAAAGGCCGAA AAAUACU | 1454 |
| 294 | CAGAACC CUGAUGAGGCCGAAAGGCCGAA AGUUUUC | 1455 |
| 298 | CAUUCAG CUGAUGAGGCCGAAAGGCCGAA ACCAAGU | 1456 |
| 299 | UCAUUCA CUGAUGAGGCCGAAAGGCCGAA AACCAAG | 1457 |
| 310 | CUAAGUA CUGAUGAGGCCGAAAGGCCGAA ACCUCAU | 1458 |
| 312 | GCCUAAG CUGAUGAGGCCGAAAGGCCGAA AUACCUC | 1459 |
| 315 | UUUGCCU CUGAUGAGGCCGAAAGGCCGAA AGUAUAC | 1460 |
| 316 | CUUUGCC CUGAUGAGGCCGAAAGGCCGAA AAGUAUA | 1461 |
| 330 | ACUGUCA CUGAUGAGGCCGAAAGGCCGAA AUUUCUC | 1462 |
| 331 | CACUGUC CUGAUGAGGCCGAAAGGCCGAA AAUUUCU | 1463 |
| 340 | UGGAAUG CUGAUGAGGCCGAAAGGCCGAA ACACUGU | 1464 |
| 341 | UUGGAAU CUGAUGAGGCCGAAAGGCCGAA AACACUG | 1465 |
| 344 | UACUUGG CUGAUGAGGCCGAAAGGCCGAA AUGAACA | 1466 |
| 345 | AUACUUG CUGAUGAGGCCGAAAGGCCGAA AAUGAAC | 1467 |
| 351 | GCCCAUA CUGAUGAGGCCGAAAGGCCGAA ACUUGGA | 1468 |
| 353 | CGGCCCA CUGAUGAGGCCGAAAGGCCGAA AUACUUG | 1469 |
| 368 | GAAUCAA CUGAUGAGGCCGAAAGGCCGAA ACUUGUG | 1470 |
| 369 | CGAAUCA CUGAUGAGGCCGAAAGGCCGAA AACUUGU | 1471 |
| 370 | CCGAAUC CUGAUGAGGCCGAAAGGCCGAA AAACUUG | 1472 |
| 374 | CUGUCCG CUGAUGAGGCCGAAAGGCCGAA AUCAAAA | 1473 |
| 375 | ACUGUCC CUGAUGAGGCCGAAAGGCCGAA AAUCAAA | 1474 |
| 383 | AGGGUCC CUGAUGAGGCGAAAGGCCGAAA ACUGUCC | 1475 |
| 397 | GAUUGUG CUGAUGAGGCCGAAAGGCCGAA AGUCUCA | 1476 |
| 398 | AGAUUGU CUGAUGAGGCCGAAAGGCCGAA AAGUCUC | 1477 |
| 404 | AUCUGAA CUGAUGAGGCCGAAAGGCCGAA AUUGUGA | 1478 |
| 406 | UGAUCUG CUGAUGAGGCCGAAAGGCCGAA AGAUUGU | 1479 |
| 407 | UUGAUCU CUGAUGAGGCCGAAAGGCCGAA AAGAUUG | 1480 |
| 412 | UGUCCUU CUGAUGAGGCCGAAAGGCCGAA AUCUGAA | 1481 |
| 426 | UUGAUAC CUGAUGAGGCCGAAAGGCCGAA AGCCCUU | 1482 |
| 429 | ACAUUGA CUGAUGAGGCCGAAAGGCCGAA ACAAGCC | 1483 |
| 431 | AUACAUU CUGAUGAGGCCGAAAGGCCGAA AUACAAG | 1484 |
| 437 | UGGAUGA CUGAUGAGGCCGAAAGGCCGAA ACAUUGA | 1485 |
| 439 | GAUGGAU CUGAUGAGGCCGAAAGGCCGAA AUACAUU | 1486 |

TABLE VII-continued

Human B7-2 Hammerhead Ribozyme Sequences

| nt. Position | HH Ribozyme Sequences | Seq. Id No. |
|---|---|---|
| 442 | UGUGAUG CUGAUGAGGCCGAAAGGCCGAA AUGAUAC | 1487 |
| 446 | UUUUUGU CUGAUGAGGCCGAAAGGCCGAA AUGGAUG | 1488 |
| 469 | GGAUGCG CUGAUGAGGCCGAAAGGCCGAA AUCAUUC | 1489 |
| 470 | UGGAUGC CUGAUGAGGCCGAAAGGCCGAA AAUCAUU | 1490 |
| 475 | UCUGGUG CUGAUGAGGCCGAAAGGCCGAA AUGCGAA | 1491 |
| 488 | AGUUCAG CUGAUGAGGCCGAAAGGCCGAA AUUCAUC | 1492 |
| 489 | CAGUUCA CUGAUGAGGCCGAAAGGCCGAA AAUUCAU | 1493 |
| 498 | AAGCACU CUGAUGAGGCCGAAAGGCCGAA ACAGUUC | 1494 |
| 505 | AGUUAGC CUGAUGAGGCCGAAAGGCCGAA AGCACUG | 1495 |
| 509 | CUGAAGU CUGAUGAGGCCGAAAGGCCGAA AGCAAGC | 1496 |
| 513 | UUGACUG CUGAUGAGGCCGAAAGGCCGAA AGUUAGC | 1497 |
| 514 | GUUGACU CUGAUGAGGCCGAAAGGCCGAA AAGUUAG | 1498 |
| 518 | UCAGGUU CUGAUGAGGCCGAAAGGCCGAA ACUGAAG | 1499 |
| 529 | UUGGUAC CUGAUGAGGCCGAAAGGCCGAA AUUUCAG | 1500 |
| 532 | AAAUUGG CUGAUGAGGCCGAAAGGCCGAA ACUAUUU | 1501 |
| 538 | UAUUAGA CUGAUGAGGCCGAAAGGCCGAA AUUGGUA | 1502 |
| 539 | AUAUUAG CUGAUGAGGCCGAAAGGCCGAA AAUUGGU | 1503 |
| 540 | UAUAUUA CUGAUGAGGCCGAAAGGCCGAA AAAUUGG | 1504 |
| 542 | GUUAUAU CUGAUGAGGCCGAAAGGCCGAA AGAAAUU | 1505 |
| 545 | UCUGUUA CUGAUGAGGCCGAAAGGCCGAA AUUAGAA | 1506 |
| 547 | UUUCUGU CUGAUGAGGCCGAAAGGCCGAA AUAUUAG | 1507 |
| 561 | AUUUAUG CUGAUGAGGCCGAAAGGCCGAA ACACAUU | 1508 |
| 565 | UCAAAUU CUGAUGAGGCCGAAAGGCCGAA AUGUACA | 1509 |
| 569 | CAGGUCA CUGAUGAGGCCGAAAGGCCGAA AUUUAUG | 1510 |
| 570 | GCAGGUC CUGAUGAGGCCGAAAGGCCGAA AAUUUAU | 1511 |
| 579 | UAUAGAU CUGAUGAGGCCGAAAGGCCGAA AGCAGGU | 1512 |
| 582 | GUGUAUA CUGAUGAGGCCGAAAGGCCGAA AUGAGCA | 1513 |
| 584 | CCGUGUA CUGAUGAGGCCGAAAGGCCGAA AGAUGAG | 1514 |
| 586 | AACCGUG CUGAUGAGGCCGAAAGGCCGAA AUAGAUG | 1515 |
| 593 | UCUGGGU CUGAUGAGGCCGAAAGGCCGAA ACCGUGU | 1516 |
| 594 | UUCUGGG CUGAUGAGGCCGAAAGGCCGAA AACCGUG | 1517 |
| 605 | AUCUUCU CUGAUGAGGCCGAAAGGCCGAA AGGUUCU | 1518 |
| 619 | UUAGCAA CUGAUGAGGCCGAAAGGCCGAA ACACUCA | 1519 |
| 620 | CUUAGCA CUGAUGAGGCCGAAAGGCCGAA AACACUC | 1520 |
| 621 | UCUUAGC CUGAUGAGGCCGAAAGGCCGAA AAACACU | 1521 |
| 625 | UGGUUCU CUGAUGAGGCCGAAAGGCCGAA AGCAAAA | 1522 |
| 638 | AUAGUUG CUGAUGAGGCCGAAAGGCCGAA AUUCUUG | 1523 |

TABLE VII-continued

Human B7-2 Hammerhead Ribozyme Sequences

| nt. Position | HH Ribozyme Sequences | Seq. Id No. |
|---|---|---|
| 639 | GAUAGUU CUGAUGAGGCCGAAAGGCCGAA AAUUCUU | 1524 |
| 644 | UACUCGA CUGAUGAGG6CGAAAGGCCGAA AGUUGAA | 1525 |
| 646 | CAUACUC CUGAUGAGGCCGAAAGGCCGAA AUAGUUG | 1526 |
| 651 | ACCAUCA CUGAUGAGGCCGAAAGGCCGAA ACUCGAU | 1527 |
| 659 | UGCAUAA CUGAUGAGGCCGAAAGGCCGAA ACCAUCA | 1528 |
| 661 | UCUGCAU CUGAUGAGGCCGAAAGGCCGAA AUACCAU | 1529 |
| 662 | UUCUGCA CUGAUGAGGCCGAAAGGCCGAA AAUACCA | 1530 |
| 672 | AUCUUGA CUGAUGAGGCCGAAAGGCCGAA AUUUCUG | 1531 |
| 674 | UUAUCUU CUGAUGAGGCCGAAAGGCCGAA AGAUUUC | 1532 |
| 680 | GUGACAU CUGAUGAGGCCGAAAGGCCGAA AUCUUGA | 1533 |
| 685 | GUUCUGU CUGAUGAGGCCGAAAGGCCGAA ACAUUAU | 1534 |
| 696 | AACGUCG CUGAUGAGGCCGAAAGGCCGAA ACAGUUC | 1535 |
| 703 | UGAUGGA CUGAUGAGGCCGAAAGGCCGAA ACGUCGU | 1536 |
| 704 | CUGAUGG CUGAUGAGGCCGAAAGGCCGAA AACGUCG | 1537 |
| 705 | GCUGAUG CUGAUGAGGCCGAAAGGCCGAA AAACGUC | 1538 |
| 709 | ACAAGCU CUGAUGAGGCCGAAAGGCCGAA AUGGAAA | 1539 |
| 714 | AACAGAC CUGAUGAGGCCGAAAGGCCGAA AGCUGAU | 1540 |
| 717 | UGAAACA CUGAUGAGGCCGAAAGGCCGAA ACAAGCU | 1541 |
| 721 | GGAAUGA CUGAUGAGGCCGAAAGGCCGAA ACAGACA | 1542 |
| 722 | GGGAAUG CUGAUGAGGCCGAAAGGCCGAA AACAGAC | 1543 |
| 723 | AGGGAAU CUGAUGAGGCCGAAAGGCCGAA AAACAGA | 1544 |
| 726 | AUCAGGG CUGAUGAGGCCGAAAGGCCGAA AUGAAAC | 1545 |
| 727 | CAUCAGG CUGAUGAGGCCGAAAGGCCGAA AAUGAAA | 1546 |
| 736 | UGCUCGU CUGAWGAGGCCGAAAGG&CGAA ACAUCAG | 1547 |
| 737 | UUGCUCG CUGAUGAGGCCGAAAGGCCGAA AACAUCA | 1548 |
| 746 | AUGGUCA CUGAUGAGGCCGAAAGGCCGAA AUUGCUC | 1549 |
| 754 | UACAGAA CUGAUGAGGCCGAAAGGCCGAA AUGGUCA | 1550 |
| 756 | AAUACAG CUGAUGAGGCCGAAAGGCCGAA AGAUGGU | 1551 |
| 757 | GAAUACA CUGAUGAGGCCGAAAGGCCGAA AAGAUGG | 1552 |
| 761 | UCCAGAA CUGAUGAGGCCGAAAGGCCGAA ACAGAAG | 1553 |
| 763 | UUUCCAG CUGAUGAGGCCGAAAGGCCGAA AUACAGA | 1554 |
| 764 | GUUUCCA CUGAUGAGGCCGAAAGGCCGAA AAUACAG | 1555 |
| 787 | AAGAUAA CUGAUGAGGCCGAAAGGCCGAA AGCCGCG | 1556 |
| 788 | GAAGAUA CUGAUGAGGCCGAAAGGCCGAA AAGCCGC | 1557 |
| 789 | UGAAGAU CUGAUGAGGCCGAAAGGCCGAA AAAGCCG | 1558 |
| 790 | GUGAAGA CUGAUGAGGCCGAAAGGCCGAA AAAAGCC | 1559 |
| 792 | AGGUGAA CUGAUGAGGCCGAAAGGCCGAA AUAAAAG | 1560 |

TABLE VII-continued

Human B7-2 Hammerhead Ribozyme Sequences

| nt. Position | HH Ribozyme Sequences | Seq. Id No. |
|---|---|---|
| 794 | AAAGGUG CUGAUGAGGCCGAAAGGCCGAA AGAUAAA | 1561 |
| 795 | GAAAGGU CUGAUGAGGCCGAAAGGCCGAA AAGAUAA | 1562 |
| 800 | AUAGAGA CUGAUGAGGCCGAAAGGCCGAA AGGUGAA | 1563 |
| 801 | UAUAGAG CUGAUGAGGCCGAAAGGCCGAA AAGGUGA | 1564 |
| 802 | CUAUAGA CUGAUGAGGCCGAAAGGCCGAA AAAGGUG | 1565 |
| 804 | CUCUAUA CUGAUGAGGCCGAAAGGCCGAA AGAAAGG | 1566 |
| 806 | AGCUCUA CUGAUGAGGCCGAAAGGCCGAA AGAGAAA | 1567 |
| 808 | CAAGCUC CUGAUGAGGCCGAAAGGCCGAA AUAGAGA | 1568 |
| 814 | GGUCCUC CUGAUGAGGCCGAAAGGCCGAA AGCUCUA | 1569 |
| 824 | GGAGGCU CUGAUGAGGCCGAAAGGCCGAA AGGGUCC | 1570 |
| 830 | UCUGGGG CUGAUGAGGCCGAAAGGCCGAA AGGCUGA | 1571 |
| 844 | UCCAAGG CUGAUGAGGCCGAAAGGCCGAA AUGUGGU | 1572 |
| 845 | AUCCAAG CUGAUGAGGCCGAAAGGCCGAA AAUGUGG | 1573 |
| 848 | GUAAUCC CUGAUGAGGCCGAAAGGCCGAA AGGAAUG | 1574 |
| 853 | CAGCUGU CUGAUGAGGCCGAAAGGCCGAA AUCCAAG | 1575 |
| 854 | ACAGCUG CUGAUGAGGCCGAAAGGCCGAA AAUCCAA | 1576 |
| 862 | UUGGAAG CUGAUaAGGCCGAAAGGCCGAA ACAGCUG | 1577 |
| 865 | CUGUUGG CUGAUGAGGCCGAAAGGCCGAA AGUACAG | 1578 |
| 866 | ACUGUUG CUGAUGAGGCCGAAAGGCCGAA AAGUACA | 1579 |
| 874 | AUAUAAU CUGAUGAGGCCGAAAGGCCGAA ACUGUUG | 1580 |
| 875 | CAUAUAA CUGAUGAGGCCGAAAGGCCGAA AACUGUU | 1581 |
| 877 | CACAUAU CUGAUGAGGCCGAAAGGCCGAA AUAACUG | 1582 |
| 878 | ACACAUA CUGAUGAGGCCGAAAGGCCGAA AAUAACU | 1583 |
| 880 | UCACACA CUGAUGAGGCCGAAAGGCCGAA AUAAUAA | 1584 |
| 892 | GACAGAA CUGAUGAGGCCGAAAGGCCGAA ACCAUCA | 1585 |
| 893 | AGACAGA CUGAUGAGGCCGAAAGGCCGAA AACCAUC | 1586 |
| 894 | UAGACAG CUGAUGAGGCCGAAAGGdCGAA AAACCAU | 1587 |
| 895 | UUAGACA CUGAUGAGGCCGAAAGGCCGAA AAAACCA | 1588 |
| 899 | AGAAUUA CUGAUGAGGCCGAAAGGCCGAA ACAGAAA | 1589 |
| 901 | AUAGAAU CUGAUGAGGCCGAAAGGCCGAA AGACAGA | 1590 |
| 904 | UCCAUAG CUGAUGAGGCCGAAAGGCCGAA AUUAGAC | 1591 |
| 905 | UUCCAUA CUGAUGAGGCCGAAAGGCCGAA AAUUAGA | 1592 |
| 907 | AUUUCCA CUGAUGAGGCCGAAAGGCCGAA AGAAUUA | 1593 |
| 935 | GAGUUGC CUGAUGAGGCCGAAAGGCCGAA AGGCCGC | 1594 |
| 942 | UUUAUAA CUGAUGAGGCCGAAAGGCCGAA AGUUGCG | 1595 |
| 944 | CAUUUAU CUGAUGAGGCCGAAAGGCCGAA AGAGUUG | 1596 |
| 945 | ACAUUUA CUGAUGAGGCCGAAAGGCCGAA AAGAGUU | 1597 |

TABLE VII-continued

Human B7-2 Hammerhead Ribozyme Sequences

| nt. Position | HH Ribozyme Sequences | Seq. Id No. |
| --- | --- | --- |
| 947 | CCACAUU CUGAUGAGGCCGAAAGGCCGAA AUAAGAG | 1598 |
| 1009 | GUAUAUG CUGAUGAGGCCGAAAGGCCGAA AUUUUUU | 1599 |
| 1013 | UCAGGUA CUGAUGAGGCCGAAAGGCCGAA AUGGAUU | 1600 |
| 1015 | UUUCAGG CUGAUGAGGCCGAAAGGCCGAA AUAUGGA | 1601 |
| 1026 | UUCAUCA CUGAUGAGGCCGAAAGGCCGAA AUCUUUC | 1602 |
| 1045 | UUUUAAA CUGAUGAGGCCGAAAGGCCGAA ACACGCU | 1603 |
| 1046 | CUUUUAA CUGAUGAGGCCGAAAGGCCGAA AACACGC | 1604 |
| 1047 | ACUUUUA CUGAUGAGGCCGAAAGGCCGAA AAACACG | 1605 |
| 1048 | AACUUUU CUGAUGAGGCCGAAAGGCCGAA AAAACAC | 1606 |
| 1049 | GAACUUU CUGAUGAGGCCGAAAGGCCGAA AAAAACA | 1607 |
| 1055 | GUCUUCG CUGAUGAGGCCGAAAGGCCGAA ACUUUUA | 1608 |
| 1056 | UGUCUUC CUGAUGAGGCCGAAAGGCCGAA AACUUUU | 1609 |
| 1065 | GCAUGAA CUGAUGAGGCCGAAAGGCCGAA AUGUCUU | 1610 |
| 1067 | UCGCAUG CUGAUGAGGCCGAAAGGCCGAA AGAUGUC | 1611 |
| 1068 | GUCGCAU CUGAUGAGGCCGAAAGGCCGAA AAGAUGU | 1612 |
| 1085 | AAACAUG CUGAUGAGGCCGAAAGGCCGAA AUCACUU | 1613 |
| 1091 | AAUUAAA CUGAUGAGGCCGAAAGGCCGAA ACAUGUA | 1614 |
| 1092 | UAAUUAA CUGAUGAGGCCGAAAGGCCGAA AACAUGU | 1615 |
| 1093 | UUAAUUA CUGAUGAGGCCGAAAGGCCGAA AAACAUG | 1616 |
| 1094 | UUUAAUU CUGAUGAGGCCGAAAGGCCGAA AAAACAU | 1617 |
| 1095 | CUUUAAU CUGAUGAGGCCGAAAGGCCGAA AAAAACA | 1618 |
| 1098 | ACUCUUU CUGAUGAGGCCGAAAGGCCGAA AUUAAAA | 1619 |
| 1099 | UACUCUU CUGAUGAGGCCGAAAGGCCGAA AAUUAAA | 1620 |

TABLE VII

Mouse B7-2 Hammerhead Ribozyme Target Sequences

| nt. Position | HH Target Sequence | Seq. ID No. |
| --- | --- | --- |
| 47 | AcGGACU u GaACAac | 1621 |
| 47 | aCggACU u gaAcAAC | 1622 |
| 66 | CUccUgU a gAcGUgU | 1623 |
| 66 | CUCcUgU A gAcGUGu | 1624 |
| 74 | gAcGUGU u CcagAAc | 1625 |
| 83 | CaGaACU U aCggaAG | 1626 |
| 134 | caAuCcU U aUCUUUG | 1627 |
| 134 | CaauccU U AUCUUUg | 1628 |
| 134 | caAUCcU u AuCUUUg | 1629 |
| 134 | CAaUccU U AUcUuUG | 1630 |
| 134 | CAAucCU U AUcuuUG | 1631 |
| 135 | aAuCcUU a UCUUUGU | 1632 |
| 135 | AauCcUU a UCUuUgu | 1633 |
| 135 | AaUccUU A UcUuUGU | 1634 |
| 135 | aAUccUU a UCUuUgU | 1635 |
| 137 | uCcUUaU C UUUGUGA | 1636 |

TABLE VII-continued

Mouse B7-2 Hammerhead Ribozyme Target Sequences

| nt. Position | HH Target Sequence | Seq. ID No. |
|---|---|---|
| 137 | UccUUAU c UuUGUGA | 1637 |
| 137 | UCCuUAU c uuUGugA | 1638 |
| 139 | cUUaUCU U UGUGAca | 1639 |
| 140 | UUaUCUU U GUGAcaG | 1640 |
| 140 | UUaUcuU U guGACAG | 1641 |
| 149 | UGAcaGU c UUGCUgA | 1642 |
| 151 | AcAGucU U GCUgaUC | 1643 |
| 151 | AcaGuCU U gCUGaUC | 1644 |
| 158 | UgCuGAU U UcAGaUg | 1645 |
| 158 | UgCUGaU C UCaGaUG | 1646 |
| 158 | UGcUgAU U uCAgaUg | 1647 |
| 158 | UgCugAU c UCagAUg | 1648 |
| 160 | CUGaUCU C aGaUGCU | 1649 |
| 160 | cUGaUcU c AgAuGcU | 1650 |
| 170 | AUGcuGU u UcCgUgG | 1651 |
| 171 | UGCUGuU u CcgUGgA | 1652 |
| 172 | gCUgUuU C cgUgGAG | 1653 |
| 189 | GcaaGcU u AUUUCaA | 1654 |
| 189 | gCAAGCU U AUUUCAA | 1655 |
| 189 | GCaaGCU u AuUUCAa | 1656 |
| 190 | CAAGCUU A UUUCAAU | 1657 |
| 190 | CaAgcUU a uUUcaAU | 1658 |
| 192 | AGCUUAU U UCAAUGg | 1659 |
| 192 | aGCUUaU u UCAAUGg | 1660 |
| 193 | GCUUAUU U CAAUGgG | 1661 |
| 193 | GcuUAuU U CaAUGGg | 1662 |
| 194 | CUUAUUU C AAUGgGA | 1663 |
| 194 | cuUAuUU C aAUGGgA | 1664 |
| 208 | acUGCaU a UCUGCCcG | 1665 |
| 210 | UGCaUaU U UGCcGUg | 1666 |
| 223 | UGCCcAU U UaCAAAg | 1667 |
| 223 | UGCCcAU u UAcAaAg | 1668 |
| 224 | GCCcAUU U aCAAAgg | 1669 |
| 225 | ccCAUUU a CAaAggc | 1670 |
| 225 | CccaUUU a cAAAgGc | 1671 |
| 242 | AAaACAU a agCcUGa | 1672 |
| 260 | AGCUggU A GUAUUUU | 1673 |
| 260 | aGCuGgU a gUAUuUU | 1674 |
| 263 | UgGUAGU A UUUUGGC | 1675 |
| 263 | UGgUaGU a UUuUGgC | 1676 |
| 265 | GUAGUAU U UUGGCAG | 1677 |
| 265 | guAGUAU u UuGGCaG | 1678 |
| 266 | UAGUAUU U UGGCAGG | 1679 |
| 266 | uAGUaUU U UGgcAgG | 1680 |
| 266 | UAgUaUU u UGGcAgg | 1681 |
| 267 | AGUAUUU U GGCAGGA | 1682 |
| 267 | AGUaUUU U GgcAgGA | 1683 |
| 286 | cAAAAgU U GGUUCUG | 1684 |
| 286 | CAAaagU U GgUUCuG | 1685 |
| 290 | AgUUGGU U CUGuAcG | 1686 |
| 291 | gUUGGUU C UGuAcGA | 1687 |
| 295 | GUUCugU a CgAGcAc | 1688 |
| 304 | GAGcacU A uUUgGGC | 1689 |
| 307 | cacUAUU u GGGcACA | 1690 |
| 323 | AGAAAcU U GAuAGUG | 1691 |
| 343 | gCCAAGU A ccUGGGC | 1692 |
| 343 | gCCAagU a CCUgGGc | 1693 |
| 361 | ACgAGcU U UGAcagG | 1694 |
| 381 | cUGgACU c UacGACU | 1695 |
| 383 | GgACUcU A CGACuUc | 1696 |
| 383 | GGACuCU a cGaCUuC | 1697 |
| 389 | uAcGacU u CaCAaUG | 1698 |
| 389 | UacGACU U CACAAUg | 1699 |
| 390 | acGACUU C ACAAUgU | 1700 |
| 390 | ACgAcUU c acAAUgU | 1701 |
| 398 | ACAaUGU U CAgauCA | 1702 |
| 398 | ACAAUgU U CAGAUCA | 1703 |
| 398 | ACaAuGU U cagAUCA | 1704 |
| 399 | CAaUGUU C AgauCAA | 1705 |
| 399 | CAAUgUU C AGAUCAA | 1706 |
| 399 | CaAuGUU c agAUCAa | 1707 |
| 399 | caAUGUU c aGAuCAA | 1708 |
| 399 | CAaUguU c aGAUcAa | 1709 |
| 399 | cAAuGuU C aGAUcAA | 1710 |

TABLE VII-continued

Mouse B7-2 Hammerhead Ribozyme Target Sequences

| nt. Position | HH Target Sequence | Seq. ID No. |
|---|---|---|
| 399 | CAaugUU c agAUcAA | 1711 |
| 404 | UUCAGAU C AAGGACA | 1712 |
| 404 | UucAGaU c aAGGACa | 1713 |
| 418 | aUGgGCU c GUAugAU | 1714 |
| 418 | AuGGGCU c GUAUgAu | 1715 |
| 418 | AUggGCU c GUaUGaU | 1716 |
| 421 | gGCUCgU a UGAuugU | 1717 |
| 421 | ggcUCgU A UgAuUGU | 1718 |
| 429 | UgAuUGU u UuAUaCA | 1719 |
| 429 | UGAUuGU u UUUAuACA | 1720 |
| 431 | AuUgUuU u AUaCAa | 1721 |
| 431 | AUuGUuU U AUaCAaA | 1722 |
| 432 | UuGUuUU A UaCAaAA | 1723 |
| 432 | UuGUUUU a UacaaAA | 1724 |
| 432 | uUGUUUU a uAcaAAA | 1725 |
| 461 | gAUcaAU u AUCCucC | 1726 |
| 462 | AucaAUU u uCcUCCA | 1727 |
| 464 | CAauUaU c CUcCaAc | 1728 |
| 467 | uUAUCcU C CAaCAgA | 1729 |
| 467 | UUauCcU C CAaCAGA | 1730 |
| 467 | UUaUccU c cAACAGA | 1731 |
| 467 | UuAuCCU C CaaCAGA | 1732 |
| 490 | GAACUGU C AGUGaUc | 1733 |
| 497 | CAGUGaU c GCcAACU | 1734 |
| 505 | GCcAACU U CAGUgAA | 1735 |
| 506 | CcAACUU C AGUgAAC | 1736 |
| 506 | CCAaCUU c aGUgaaC | 1737 |
| 521 | CUGAAAU A aaACugg | 1738 |
| 531 | ACUGgcU c AgAaUgU | 1739 |
| 539 | agaaUGU A ACAGGaA | 1740 |
| 550 | GgAaAuU c uGGCAuA | 1741 |
| 550 | ggAAaUU C UggcAUA | 1742 |
| 557 | cuggCAU A AAUUUGA | 1743 |
| 561 | CAUAAAU U UGACCUG | 1744 |
| 562 | AUAAAUU U GACCUGC | 1745 |
| 576 | CaCgUCU A agCAaGG | 1746 |
| 585 | gCAaGGU c ACCCgaA | 1747 |
| 597 | gaAACCU A AGAAGAU | 1748 |
| 607 | AaGaUgU a uUuUCUg | 1749 |
| 611 | UGUaUUU u cUgAUAa | 1750 |
| 625 | AcuAAUU C AACUAau | 1751 |
| 630 | UUCAACU A auGAGUA | 1752 |
| 630 | UUcAAcU A AuGAGUA | 1753 |
| 637 | AauGAGU A UGgUGaU | 1754 |
| 656 | uGCAgaU a UcAcAAg | 1755 |
| 658 | CAGAUAU c AcaagAu | 1756 |
| 658 | CAgauAU C ACAAgAu | 1757 |
| 658 | CAGAuAU C aCAAGAU | 1758 |
| 658 | CaGAuaU c ACaAGau | 1759 |
| 666 | aCAAGAU A AUGUCAC | 1760 |
| 666 | ACAagaU a AUGucAC | 1761 |
| 671 | AUaAuGU C ACAGaAc | 1762 |
| 671 | aUAAUgU C ACAGAAc | 1763 |
| 671 | AUAAUGU C ACAGAAC | 1764 |
| 682 | gAACUgU u cAGUAUc | 1765 |
| 683 | aAcUGuU c aGuAUCu | 1766 |
| 683 | AAcUGuU c agUaUcU | 1767 |
| 691 | aguaUcU C CAaCAGC | 1768 |
| 691 | agUAUCU C CAaCagc | 1769 |
| 691 | aGUAucU C CAACAGc | 1770 |
| 701 | aCaGCcU c UcUCUUu | 1771 |
| 701 | acagCCU c UCUCUuU | 1772 |
| 703 | AGCcUcU C UcUUUCA | 1773 |
| 703 | aGCcUcU c UCUUuca | 1774 |
| 707 | UcUCUcU U UCAUUCC | 1775 |
| 707 | UcUCUcU u UcAUUCc | 1776 |
| 708 | cUCUcUU U CAUUCCC | 1777 |
| 709 | UCUcUUU C AUCCCCg | 1778 |
| 709 | UCUCUuU c auuCccG | 1779 |
| 709 | UCUcUuU c AUUCccg | 1780 |
| 712 | CUUUcaU U CcCgGaU | 1781 |
| 712 | cuuUCAU U cCCgGAU | 1782 |
| 712 | CuUucAU u CcCGGaU | 1783 |
| 712 | cUUUCAU U CCCgGAU | 1784 |

TABLE VII-continued

Mouse B7-2 Hammerhead Ribozyme Target Sequences

| nt. Position | HH Target Sequence | Seq. ID No. |
|---|---|---|
| 712 | CUUUcAU u ccCggaU | 1785 |
| 713 | uuUCAUU c CCgGAUg | 1786 |
| 713 | UUUCAUU C CCgGAUG | 1787 |
| 732 | GuGgcAU a UGACcGU | 1788 |
| 732 | GuGgcAU A UGACCgU | 1789 |
| 740 | UGACCgU u gUgUGUg | 1790 |
| 749 | UgUGUgU U CUGGAAA | 1791 |
| 749 | uGuGUGU U cUggAAA | 1792 |
| 750 | gUGUgUU C UGGAAAC | 1793 |
| 750 | GuGUGUU c UggAAAc | 1794 |
| 773 | ugAAGaU U UcCUcCa | 1795 |
| 778 | aUUUcCU c caAACCu | 1796 |
| 788 | AAcCUCU C AAuuuCA | 1797 |
| 798 | UUUCaCU c aAGAGuU | 1798 |
| 805 | CAagAGU U UccAUcu | 1799 |
| 805 | CAAgAGU U uccAUcU | 1800 |
| 806 | AAgAGUU u ccAUcUc | 1801 |
| 811 | UUUCCAU C ucCUcaa | 1802 |
| 811 | uUUCcaU C UcCUcaA | 1803 |
| 813 | uCCAUCU c CUcaAac | 1804 |
| 836 | aGgAGAU U acAGCUU | 1805 |
| 836 | aggaGAU U ACAGCUU | 1806 |
| 837 | GgAGAUU a cAGCUUC | 1807 |
| 848 | CUUCAGU u AcugUGg | 1808 |
| 860 | UGGCCcU C CUcCUug | 1809 |
| 860 | UggCCcU c CUCcuUg | 1810 |
| 878 | ugCUGCU C AUCauUg | 1811 |
| 951 | GCGGgaU a GuAACgC | 1812 |
| 974 | AgaCuAU c aACCUGA | 1813 |
| 989 | aGgAAcU U GaACCCc | 1814 |
| 1006 | auUgCUU c aGCAAAa | 1815 |
| 1055 | AAAgAGU u aaAAaUU | 1816 |
| 1056 | AaGAgUU a aaAAuUG | 1817 |
| 1062 | uAAAAAU u gcUuUgC | 1818 |
| 1092 | CAgaGUU u CuCAGAA | 1819 |
| 1095 | aGUUUcU c AgAaUUC | 1820 |
| 1101 | UCAgAAU u caaAaAU | 1821 |
| 1101 | ucAGAAU U CAAaaAU | 1822 |
| 1101 | UcAgAaU U CaAAaAu | 1823 |
| 1111 | aAaAUGU U cUcAgcU | 1824 |
| 1112 | AaAUGUU c UcAgcUg | 1825 |
| 1128 | UUgGAaU u cuACAGU | 1826 |
| 1128 | UUGGAaU u CuaCaGU | 1827 |
| 1131 | GAAuUCU a cAGuUgA | 1828 |
| 1131 | GAauUCU a CAguuGA | 1829 |
| 1141 | GuUGAAU a aUuAAag | 1830 |
| 1144 | gaaUAAU U AAAGAac | 1831 |
| 1145 | AAuAaUU a aAgaACA | 1832 |

TABLE IX

Mouse B7-2 Hammerhead Ribozyme Sequences

| nt. Position | HH Ribozyme Sequences | Seq. ID No. |
|---|---|---|
| 47 | GUUGUUC CUGAUGAGGCCGAAAGGCCGAA AGUCCGU | 1833 |
| 47 | GUUGUUC CUGAUGAGGCCGAAAGGCCGAA AGUCCGU | 1834 |
| 66 | ACACGUC CUGAUGAGGCCGAAAGGCCGAA ACAGGAG | 1835 |
| 66 | ACACGUC CUGAUGAGGCCGAAAGGCCGAA ACAGGAG | 1836 |

TABLE IX-continued

Mouse B7-2 Hammerhead Ribozyme Sequences

| nt. Position | HH Ribozyme Sequences | Seq. ID No. |
|---|---|---|
| 74 | GUUCUGG CUGAUGAGGCCGAAAGGCCGAA ACACGUC | 1837 |
| 83 | CUUCCGU CUGAUGAGGCCGAAAGGCCGAA AGUUCUG | 1838 |
| 134 | CAAAGAU CUGAUGAGGCCGAAAGGCCGAA AGGAUUG | 1839 |
| 134 | CAAAGAU CUGAUGAGGCCGAAAGGCCGAA AGGAUUG | 1840 |
| 134 | CAAAGAU CUGAUGAGGCCGAAAGGCCGAA AGGAUUG | 1841 |
| 134 | CAAAGAU CUGAUGAGGCCGAAAGGCCGAA AGGAUUG | 1842 |
| 134 | CAAAGAU CUGAUGAGGCCGAAAGGCCGAA AGGAUUG | 1843 |
| 135 | ACAAAGA CUGAUGAGGCCGAAAGGCCGAA AAGGAUU | 1844 |
| 135 | ACAAAGA CUGAUGAGGCCGAAAGGCCGAA AAGGAUU | 1845 |
| 135 | ACAAAGA CUGAUGAGGCCGAAAGGCCGAA AAGGAUU | 1846 |
| 135 | ACAAAGA CUGAUGAGGCCGAAAGGCCGAA AAGGAUU | 1847 |
| 137 | UCACAAA CUGAUGAGGCCGAAAGGCCGAA AUAAGGA | 1848 |
| 137 | UCACAAA CUGAUGAGGCCGAAAGGCCGAA AUAAGGA | 1849 |
| 137 | UCACAAA CUGAUGAGGCCGAAAGGCCGAA AUAAGGA | 1850 |
| 139 | UGUCACA CUGAUGAGGCCGAAAGGCCGAA AGAUAAG | 1851 |
| 140 | CUGUCAC CUGAUGAGGCCGAAAGGCCGAA AAGAUAA | 1852 |
| 140 | CUGUCAC CUGAUGAGGCCGAAAGGCCGAA AAGAUAA | 1853 |
| 149 | UCAGCAA CUGAUGAGGCCGAAAGGCCGAA ACUGUCA | 1854 |
| 151 | GAUCAGC CUGAUGAGGCCGAAAGGCCGAA AGACUGU | 1855 |
| 151 | GAUCAGC CUGAUGAGGCCGAAAGGCCGAA AGACUGU | 1856 |
| 158 | CAUCUGA CUGAUGAGGCCGAAAGGCCGAA AUCAGCA | 1857 |
| 158 | CAUCUGA CUGAUGAGGCCGAAAGGCCGAA AUCAGCA | 1858 |
| 158 | CAUCUGA CUGAUGAGGCCGAAAGGCCGAA AUCAGCA | 1859 |
| 158 | CAUCUGA CUGAUGAGGCCGAAAGGCCGAA AUCAGCA | 1860 |
| 160 | AGCAUCU CUGAUGAGGCCGAAAGGCCGAA AGAUCAG | 1861 |
| 160 | AGCAUCU CUGAUGAGGCCGAAAGGCCGAA AGAUCAG | 1862 |
| 170 | CCACGGA CUGAUGAGGCCGAAAGGCCGAA ACAGCAU | 1863 |
| 171 | UCCACGG CUGAUGAGGCCGAAAGGCCGAA AACAGCA | 1864 |
| 172 | CUCCACG CUGAUGAGGCCGAAAGGCCGAA AAACAGC | 1865 |
| 189 | UUGAAAU CUGAUGAGGCCGAAAGGCCGAA AGCUUGC | 1866 |
| 189 | UUGAAAU CUGAUGAGGCCGAAAGGCCGAA AGCUUGC | 1867 |
| 189 | UUGAAAU CUGAUGAGGCCGAAAGGCCGAA AGCUUGC | 1868 |
| 190 | AUUGAAA CUGAUGAGGCCGAAAGGCCGAA AAGCUUG | 1869 |
| 190 | AUUGAAA CUGAUGAGGCCGAAAGGCCGAA AAGCUUG | 1870 |
| 192 | CCAUUGA CUGAUGAGGCCGAAAGGCCGAA AUAAGCU | 1871 |
| 192 | CCAUUGA CUGAUGAGGCCGAAAGGCCGAA AUAAGCU | 1872 |
| 193 | CCCAUUG CUGAUGAGGCCGAAAGGCCGAA AAUAAGC | 1873 |
| 193 | CCCAUUG CUGAUGAGGCCGAAAGGCCGAA AAUAAGC | 1874 |

TABLE IX-continued

Mouse B7-2 Hammerhead Ribozyme Sequences

| nt. Position | HH Ribozyme Sequences | Seq. ID No. |
|---|---|---|
| 194 | UCCCAUU CUGAUGAGGCCGAAAGGCCGAA AAAUAAG | 1875 |
| 194 | UCCCAUU CUGAUGAGGCCGAAAGGCCGAA AAAUAAG | 1876 |
| 208 | CGGCAGA CUGAUGAGGCCGAAAGGCCGAA AUGCAGU | 1877 |
| 210 | CACGGCA CUGAUGAGGCCGAAAGGCCGAA AUAUGCA | 1878 |
| 223 | CUUUGUA CUGAUGAGGCCGAAAGGCCGAA AUGGGCA | 1879 |
| 223 | CUUUGUA CUGAUGAGGCCGAAAGGCCGAA AUGGGCA | 1880 |
| 224 | CCUUUGU CUGAUGAGGCCGAAAGGCCGAA AAUGGGC | 1881 |
| 225 | GCCUUUG CUGAUGAGGCCGAAAGGCCGAA AAAUGGG | 1882 |
| 225 | GCCUUUG CUGAUGAGGCCGAAAGGCCGAA AAAUGGG | 1883 |
| 242 | UCAGGCU CUGAUGAGGCCGAAAGGCCGAA AUGUUUU | 1884 |
| 260 | AAAAUAC CUGAUGAGGCCGAAAGGCCGAA ACCAGCU | 1885 |
| 260 | AAAAUAC CUGAUGAGGCCGAAAGGCCGAA ACCAGCU | 1886 |
| 263 | GCCAAAA CUGAUGAGGCCGAAAGGCCGAA ACUACCA | 1887 |
| 263 | GCCAAAA CUGAUGAGGCCGAAAGGCCGAA ACUACCA | 1888 |
| 265 | CUGCCAA CUGAUGAGGCCGAAAGGCCGAA AUACUAC | 1889 |
| 265 | CUGCCAA CUGAUGAGGCCGAAAGGCCGAA AUACUAC | 1890 |
| 266 | CCUGCCA CUGAUGAGGCCGAAAGGCCGAA AAUACUA | 1891 |
| 266 | CCUGCCA CUGAUGAGGCCGAAAGGCCGAA AAUACUA | 1892 |
| 266 | CCUGCCA CUGAUGAGGCCGAAAGGCCGAA AAUACUA | 1893 |
| 267 | UCCUGCC CUGAUGAGGCCGAAAGGCCGAA AAAUACU | 1894 |
| 267 | UCCUGCC CUGAUGAGGCCGAAAGGCCGAA AAAUACU | 1895 |
| 286 | CAGAACC CUGAUGAGGCCGAAAGGCCGAA ACUUUUG | 1896 |
| 286 | CAGAACC CUGAUGAGGCCGAAAGGCCGAA ACUUUUG | 1897 |
| 290 | CGUACAG CUGAUGAGGCCGAAAGGCCGAA ACCAACU | 1898 |
| 291 | UCGUACA CUGAUGAGGCCGAAAGGCCGAA AACCAAC | 1899 |
| 295 | GUGCUCG CUGAUGAGGCCGAAAGGCCGAA ACAGAAC | 1900 |
| 304 | GCCCAAA CUGAUGAGGCCGAAAGGCCGAA AGUGCUC | 1901 |
| 307 | UGUGCCC CUGAUGAGGCCGAAAGGCCGAA AAUAGUG | 1902 |
| 323 | CACUAUC CUGAUGAGGCCGAAAGGCCGAA AGUUUCU | 1903 |
| 343 | GCCCAGG CUGAUGAGGCCGAAAGGCCGAA ACUUGGC | 1904 |
| 343 | GCCCAGG CUGAUGAGGCCGAAAGGCCGAA ACUUGGC | 1905 |
| 361 | CCUGUCA CUGAUGAGGCCGAAAGGCCGAA AGCUCGU | 1906 |
| 381 | AGUCGUA CUGAUGAGGCCGAAAGGCCGAA AGUCCAG | 1907 |
| 383 | GAAGUCG CUGAUGAGGCCGAAAGGCCGAA AGAGUCC | 1908 |
| 383 | GAAGUCG CUGAUGAGGCCGAAAGGCCGAA AGAGUCC | 1909 |
| 389 | CAUUGUG CUGAUGAGGCCGAAAGGCCGAA AGUCGUA | 1910 |
| 389 | CAUUGUG CUGAUGAGGCCGAAAGGCCGAA AGUCGUA | 1911 |

TABLE IX-continued

Mouse B7-2 Hammerhead Ribozyme Sequences

| nt. Position | HH Ribozyme Sequences | Seq. ID No. |
|---|---|---|
| 390 | ACAUUGU CUGAUGAGGCCGAAAGGCCGAA AAGUCGU | 1912 |
| 390 | ACAUUGU CUGAUGAGGCCGAAAGGCCGAA AAGUCGU | 1913 |
| 398 | UGAUCUG CUGAUGAGGCCGAAAGGCCGAA ACAUUGU | 1914 |
| 398 | UGAUCUG CUGAUGAGGCCGAAAGGCCGAA ACAUUGU | 1915 |
| 398 | UGAUCUG CUGAUGAGGCCGAAAGGCCGAA ACAUUGU | 1916 |
| 399 | UUGAUCU CUGAUGAGGCCGAAAGGCCGAA AACAUUG | 1917 |
| 399 | UUGAUCU CUGAUGAGGCCGAAAGGCCGAA AACAUUG | 1918 |
| 399 | UUGAUCU CUGAUGAGGCCGAAAGGCCGAA AACAUUG | 1919 |
| 399 | UUGAUCU CUGAUGAGGCCGAAAGGCCGAA AACAUUG | 1920 |
| 399 | UUGAUCU CUGAUGAGGCCGAAAGGCCGAA AACAUUG | 1921 |
| 399 | UUGAUCU CUGAUGAGGCCGAAAGGCCGAA AACAUUG | 1922 |
| 399 | UUGAUCU CUGAUGAGGCCGAAAGGCCGAA AACAUUG | 1923 |
| 404 | UGUCCUU CUGAUGAGGCCGAAAGGCCGAA AUCUGAA | 1924 |
| 404 | UGUCCUU CUGAUGAGGCCGAAAGGCCGAA AUCUGAA | 1925 |
| 418 | AUCAUAC CUGAUGAGGCCGAAAGGCCGAA AGCCCAU | 1926 |
| 418 | AUCAUAC CUGAUGAGGCCGAAAGGCCGAA AGCCCAU | 1927 |
| 418 | AUCAUAC CUGAUGAGGCCGAAAGGCCGAA AGCCCAU | 1928 |
| 421 | ACAAUCA CUGAUGAGGCCGAAAGGCCGAA ACGAGCC | 1929 |
| 421 | ACAAUCA CUGAUGAGGCCGAAAGGCCGAA ACGAGCC | 1930 |
| 429 | UGUAUAA CUGAUGAGGCCGAAAGGCCGAA ACAAUCA | 1931 |
| 429 | UGUAUAA CUGAUGAGGCCGAAAGGCCGAA ACAAUCA | 1932 |
| 431 | UUUGUAU CUGAUGAGGCCGAAAGGCCGAA AAACAAU | 1933 |
| 431 | UUUGUAU CUGAUGAGGCCGAAAGGCCGAA AAACAAU | 1934 |
| 432 | UUUUGUA CUGAUGAGGCCGAAAGGCCGAA AAAACAA | 1935 |
| 432 | UUUUGUA CUGAUGAGGCCGAAAGGCCGAA AAAACAA | 1936 |
| 432 | UUUUGUA CUGAUGAGGCCGAAAGGCCGAA AAAACAA | 1937 |
| 461 | GGAGGAU CUGAUGAGGCCGAAAGGCCGAA AUUGAUC | 1938 |
| 462 | UGGAGGA CUGAUGAGGCCGAAAGGCCGAA AAUUGAU | 1939 |
| 464 | GUUGGAG CUGAUGAGGCCGAAAGGCCGAA AUAAUUG | 1940 |
| 467 | UCUGUUG CUGAUGAGGCCGAAAGGCCGAA AGGAUAA | 1941 |
| 467 | UCUGUUG CUGAUGAGGCCGAAAGGCCGAA AGGAUAA | 1942 |
| 467 | UCUGUUG CUGAUGAGGCCGAAAGGCCGAA AGGAUAA | 1943 |
| 467 | UCUGUUG CUGAUGAGGCCGAAAGGCCGAA AGGAUAA | 1944 |
| 490 | GAUCACU CUGAUGAGGCCGAAAGGCCGAA ACAGUUC | 1945 |
| 497 | AGUUGGC CUGAUGAGGCCGAAAGGCCGAA AUCACUG | 1946 |
| 505 | UUCACUG CUGAUGAGGCCGAAAGGCCGAA AGUUGGC | 1947 |
| 506 | GUUCACU CUGAUGAGGCCGAAAGGCCGAA AAGUUGG | 1948 |
| 506 | GUUCACU CUGAUGAGGCCGAAAGGCCGAA AAGUUGG | 1949 |

TABLE IX-continued

Mouse B7-2 Hammerhead Ribozyme Sequences

| nt. Position | HH Ribozyme Sequences | Seq. ID No. |
|---|---|---|
| 521 | CCAGUUU CUGAUGAGGCCGAAAGGCCGAA AUUUCAG | 1950 |
| 531 | ACAUUCU CUGAUGAGGCCGAAAGGCCGAA AGCCAGU | 1951 |
| 539 | UUCCUGU CUGAUGAGGCCGAAAGGCCGAA ACAUUCU | 1952 |
| 550 | UAUGCCA CUGAUGAGGCCGAAAGGCCGAA AAUUUCC | 1953 |
| 550 | UAUGCCA CUGAUGAGGCCGAAAGGCCGAA AAUUUCC | 1954 |
| 557 | UCAAAUU CUGAUGAGGCCGAAAGGCCGAA AUGCCAG | 1955 |
| 561 | CAGGUCA CUGAUGAGGCCGAAAGGCCGAA AUUUAUG | 1956 |
| 562 | GCAGGUC CUGAUGAGGCCGAAAGGCCGAA AAUUUAU | 1957 |
| 576 | CCUUGCU CUGAUGAGGCCGAAAGGCCGAA AGACGUG | 1958 |
| 585 | UUCGGGU CUGAUGAGGCCGAAAGGCCGAA ACCUUGC | 1959 |
| 597 | AUCUUCU CUGAUGAGGCCGAAAGGCCGAA AGGUUUC | 1960 |
| 607 | CAGAAAA CUGAUGAGGCCGAAAGGCCGAA ACAUCUU | 1961 |
| 611 | UUAUCAG CUGAUGAGGCCGAAAGGCCGAA AAAUACA | 1962 |
| 625 | AUUAGUU CUGAUGAGGCCGAAAGGCCGAA AAUUAGU | 1963 |
| 630 | UACUCAU CUGAUGAGGCCGAAAGGCCGAA AGUUGAA | 1964 |
| 630 | UACUCAU CUGAUGAGGCCGAAAGGCCGAA AGUUGAA | 1965 |
| 637 | AUCACCA CUGAUGAGGCCGAAAGGCCGAA ACUCAUU | 1966 |
| 656 | CUUGUGA CUGAUGAGGCCGAAAGGCCGAA AUCUGCA | 1967 |
| 658 | AUCUUGU CUGAUGAGGCCGAAAGGCCGAA AUAUCUG | 1968 |
| 658 | AUCUUGU CUGAUGAGGCCGAAAGGCCGAA AUAUCUG | 1969 |
| 658 | AUCUUGU CUGAUGAGGCCGAAAGGCCGAA AUAUCUG | 1970 |
| 658 | AUCUUGU CUGAUGAGGCCGAAAGGCCGAA AUAUCUG | 1971 |
| 666 | GUGACAU CUGAUGAGGCCGAAAGGCCGAA AUCUUGU | 1972 |
| 666 | GUGACAU CUGAUGAGGCCGAAAGGCCGAA AUCUUGU | 1973 |
| 671 | GUUCUGU CUGAUGAGGCCGAAAGGCCGAA ACAUUAU | 1974 |
| 671 | GUUCUGU CUGAUGAGGCCGAAAGGCCGAA ACAUUAU | 1975 |
| 671 | GUUCUGU CUGAUGAGGCCGAAAGGCCGAA ACAUUAU | 1976 |
| 682 | GAUACUG CUGAUGAGGCCGAAAGGCCGAA ACAGUUC | 1977 |
| 683 | AGAUACU CUGAUGAGGCCGAAAGGCCGAA AACAGUU | 1978 |
| 683 | AGAUACU CUGAUGAGGCCGAAAGGCCGAA AACAGUU | 1979 |
| 691 | GCUGUUG CUGAUGAGGCCGAAAGGCCGAA AGAUACU | 1980 |
| 691 | GCUGUUG CUGAUGAGGCCGAAAGGCCGAA AGAUACU | 1981 |
| 691 | GCUGUUG CUGAUGAGGCCGAAAGGCCGAA AGAUACU | 1982 |
| 701 | AAAGAGA CUGAUGAGGCCGAAAGGCCGAA AGGCUGU | 1983 |
| 701 | AAAGAGA CUGAUGAGGCCGAAAGGCCGAA AGGCUGU | 1984 |
| 703 | UGAAAGA CUGAUGAGGCCGAAAGGCCGAA AGAGGCU | 1985 |
| 703 | UGAAAGA CUGAUGAGGCCGAAAGGCCGAA AGAGGCU | 1986 |

TABLE IX-continued

Mouse B7-2 Hammerhead Ribozyme Sequences

| nt. Position | HH Ribozyme Sequences | Seq. ID No. |
|---|---|---|
| 707 | GGAAUGA CUGAUGAGGCCGAAAGGCCGAA AGAGAGA | 1987 |
| 707 | GGAAUGA CUGAUGAGGCCGAAAGGCCGAA AGAGAGA | 1988 |
| 708 | GGGAAUG CUGAUGAGGCCGAAAGGCCGAA AAGAGAG | 1989 |
| 709 | CGGGAAU CUGAUGAGGCCGAAAGGCCGAA AAAGAGA | 1990 |
| 709 | CGGGAAU CUGAUGAGGCCGAAAGGCCGAA AAAGAGA | 1991 |
| 709 | CGGGAAU CUGAUGAGGCCGAAAGGCCGAA AAAGAGA | 1992 |
| 712 | AUCCGGG CUGAUGAGGCCGAAAGGCCGAA AUGAAAG | 1993 |
| 712 | AUCCGGG CUGAUGAGGCCGAAAGGCCGAA AUGAAAG | 1994 |
| 712 | AUCCGGG CUGAUGAGGCCGAAAGGCCGAA AUGAAAG | 1995 |
| 712 | AUCCGGG CUGAUGAGGCCGAAAGGCCGAA AUGAAAG | 1996 |
| 712 | AUCCGGG CUGAUGAGGCCGAAAGGCCGAA AUGAAAG | 1997 |
| 713 | CAUCCGG CUGAUGAGGCCGAAAGGCCGAA AAUGAAA | 1998 |
| 713 | CAUCCGG CUGAUGAGGCCGAAAGGCCGAA AAUGAAA | 1999 |
| 732 | ACGGUCA CUGAUGAGGCCGAAAGGCCGAA AUGCCAC | 2000 |
| 732 | ACGGUCA CUGAUGAGGCCGAAAGGCCGAA AUGCCAC | 2001 |
| 740 | CACACAC CUGAUGAGGCCGAAAGGCCGAA ACGGUCA | 2002 |
| 749 | UUUCCAG CUGAUGAGGCCGAAAGGCCGAA ACACACA | 2003 |
| 749 | UUUCCAG CUGAUGAGGCCGAAAGGCCGAA ACACACA | 2004 |
| 750 | GUUUCCA CUGAUGAGGCCGAAAGGCCGAA AACACAC | 2005 |
| 750 | GUUUCCA CUGAUGAGGCCGAAAGGCCGAA AACACAC | 2006 |
| 773 | UGGAGGA CUGAUGAGGCCGAAAGGCCGAA AUCUUCA | 2007 |
| 778 | AGGUUUC CUGAUGAGGCCGAAAGGCCGAA AGGAAAU | 2008 |
| 788 | UGAAAUU CUGAUGAGGCCGAAAGGCCGAA AGAGGUU | 2009 |
| 798 | AACUCUU CUGAUGAGGCCGAAAGGCCGAA AGUGAAA | 2010 |
| 805 | AGAUGGA CUGAUGAGGCCGAAAGGCCGAA ACUCUUG | 2011 |
| 805 | AGAUGGA CUGAUGAGGCCGAAAGGCCGAA ACUCUUG | 2012 |
| 806 | GAGAUGG CUGAUGAGGCCGAAAGGCCGAA AACUCUU | 2013 |
| 811 | UUGAGGA CUGAUGAGGCCGAAAGGCCGAA AUGGAAA | 2014 |
| 811 | UUGAGGA CUGAUGAGGCCGAAAGGCCGAA AUGGAAA | 2015 |
| 813 | GUUUGAG CUGAUGAGGCCGAAAGGCCGAA AGAUGGA | 2016 |
| 836 | AAGCUGU CUGAUGAGGCCGAAAGGCCGAA AUCUCCU | 2017 |
| 836 | AAGCUGU CUGAUGAGGCCGAAAGGCCGAA AUCUCCU | 2018 |
| 837 | GAAGCUG CUGAUGAGGCCGAAAGGCCGAA AAUCUCC | 2019 |
| 848 | CCACAGU CUGAUGAGGCCGAAAGGCCGAA ACUGAAG | 2020 |
| 860 | CAAGGAG CUGAUGAGGCCGAAAGGCCGAA AGGGCCA | 2021 |
| 860 | CAAGGAG CUGAUGAGGCCGAAAGGCCGAA AGGGCCA | 2022 |
| 878 | CAAUGAU CUGAUGAGGCCGAAAGGCCGAA AGCAGCA | 2023 |
| 951 | GCGUUAC CUGAUGAGGCCGAAAGGCCGAA AUCCCGC | 2024 |

TABLE IX-continued

Mouse B7-2 Hammerhead Ribozyme Sequences

| nt. Position | HH Ribozyme Sequences | Seq. ID No. |
|---|---|---|
| 974 | UCAGGUU CUGAUGAGGCCGAAAGGCCGAA AUAGUCU | 2025 |
| 989 | GGGGUUC CUGAUGAGGCCGAAAGGCCGAA AGUUCCU | 2026 |
| 1006 | UUUUGCU CUGAUGAGGCCGAAAGGCCGAA AAGCAAU | 2027 |
| 1055 | AAUUUUU CUGAUGAGGCCGAAAGGCCGAA ACUCUUU | 2028 |
| 1056 | CAAUUUU CUGAUGAGGCCGAAAGGCCGAA AACUCUU | 2029 |
| 1062 | GCAAAGC CUGAUGAGGCCGAAAGGCCGAA AUUUUUA | 2030 |
| 1092 | UUCUGAG CUGAUGAGGCCGAAAGGCCGAA AACUCUG | 2031 |
| 1095 | GAAUUCU CUGAUGAGGCCGAAAGGCCGAA AGAAACU | 2032 |
| 1101 | AUUUUUG CUGAUGAGGCCGAAAGGCCGAA AUUCUGA | 2033 |
| 1101 | AUUUUUG CUGAUGAGGCCGAAAGGCCGAA AUUCUGA | 2034 |
| 1101 | AUUUUUG CUGAUGAGGCCGAAAGGCCGAA AUUCUGA | 2035 |
| 1111 | AGCUGAG CUGAUGAGGCCGAAAGGCCGAA ACAUUUU | 2036 |
| 1112 | CAGCUGA CUGAUGAGGCCGAAAGGCCGAA AACAUUU | 2037 |
| 1128 | ACUGUAG CUGAUGAGGCCGAAAGGCCGAA AUUCCAA | 2038 |
| 1128 | ACUGUAG CUGAUGAGGCCGAAAGGCCGAA AUUCCAA | 2039 |
| 1131 | UCAACUG CUGAUGAGGCCGAAAGGCCGAA AGAAUUC | 2040 |
| 1131 | UCAACUG CUGAUGAGGCCGAAAGGCCGAA AGAAUUC | 2041 |
| 1141 | CUUUAAU CUGAUGAGGCCGAAAGGCCGAA AUUCAAC | 2042 |
| 1144 | GUUCUUU CUGAUGAGGCCGAAAGGCCGAA AUUAUUC | 2043 |
| 1145 | UGUUCUU CUGAUGAGGCCGAAAGGCCGAA AAUUAUU | 2044 |

TABLE X

Human CD40 Hammerhead Ribozyme Target Sequences

| nt. Position | HH Target Sequence | Seq. ID No. |
|---|---|---|
| 9 | CCUCGCU C GGGCGCC | 2045 |
| 24 | CAGUGGU C CUGCCGC | 2046 |
| 37 | GCCUGGU C UCACCUC | 2047 |
| 39 | CUGGUCU C ACCUCGC | 2048 |
| 44 | CUCACCU C GCCAUGG | 2049 |
| 53 | CCAUGGU U CGUCUGC | 2050 |
| 54 | CAUGGUU C GUCUGCC | 2051 |
| 57 | GGUUCGU C UGCCUCU | 2052 |
| 63 | UCUGCCU C UGCAGUG | 2053 |
| 74 | AGUCGCU C CUCUGGG | 2054 |
| 77 | GCGUCCU C UGGGGCU | 2055 |
| 88 | GGCUGCU U GCUGACC | 2056 |
| 101 | CCGCUGU C CAUCCAG | 2057 |
| 105 | UGUCCAU C CAGAACC | 2058 |
| 139 | AAACAGU A CCUAAUA | 2059 |
| 143 | AGUACCU A AUAAACA | 2060 |
| 146 | ACCUAAU A AACAGUC | 2061 |
| 153 | AAACAGU C AGUGCUG | 2062 |
| 162 | GUGCUGU U CUUUGUG | 2063 |
| 163 | UGCUGUU C UUUGUGC | 2064 |
| 165 | CUGUUCU U UGUGCCA | 2065 |
| 166 | UGUUCUU U GUGCCAG | 2066 |
| 208 | ACAGAGU U CACUGAA | 2067 |

TABLE X-continued

Human CD40 Hammerhead Ribozyme Target Sequences

| nt. Position | HH Target Sequence | Seq. ID No. |
|---|---|---|
| 209 | CAGAGUU C ACUGAAA | 2068 |
| 227 | AAUGCCU U CCUUGCG | 2069 |
| 228 | AUGCCUU C CUUGCGG | 2070 |
| 231 | CCUUCCU U GCGGUGA | 2071 |
| 247 | AGCGAAU U CCUAGAC | 2072 |
| 248 | GCGAAUU C CUAGACA | 2073 |
| 251 | AAUUCCU A GACACCU | 2074 |
| 292 | CACAAAU A CUGCGAC | 2075 |
| 308 | CCAACCU A GGGCUUC | 2076 |
| 314 | UAGGGCU U CGGGUCC | 2077 |
| 315 | AGGGCUU C GGGUCCA | 2078 |
| 320 | UUCGGGU C CAGCAGA | 2079 |
| 337 | GGCACCU C AGAAACA | 2080 |
| 353 | ACACCAU C UGCACCU | 2081 |
| 381 | GCACUGU A CGAGUGA | 2082 |
| 407 | GCUGUGU C CUGCACC | 2083 |
| 418 | CACCGCU C AUGCUCG | 2084 |
| 424 | UCAUGCU C GCCCGGC | 2085 |
| 433 | CCCGGCU U UGGGGUC | 2086 |
| 434 | CCGGCUU U GGGGUCA | 2087 |
| 440 | UUGGGGU C AAGCAGA | 2088 |
| 449 | AGCAGAU U GCUACAG | 2089 |
| 453 | GAUUGCU A CAGGGGU | 2090 |
| 461 | CAGGGGU U UCUGAUA | 2091 |
| 462 | AGGGGUU U CUGAUAC | 2092 |
| 463 | GGGGUUU C UGAUACC | 2093 |
| 468 | UUCUGAU A CCAUCUG | 2094 |
| 473 | AUACCAU C UGCGAGC | 2095 |
| 491 | GCCCAGU C GGCUUCU | 2096 |
| 496 | GUCGGCU U CUUCUCC | 2097 |
| 497 | UCGGCUU C UUCUCCA | 2098 |
| 499 | GGCUUCU U CUCCAAU | 2099 |
| 500 | GCUUCUU C UCCAAUG | 2100 |
| 502 | UUCUUCU C CAAUGUG | 2101 |
| 511 | AAUGUGU C AUCUGCU | 2102 |
| 514 | GUGUCAU C UGCUUUC | 2103 |
| 519 | AUCUGCU U UCGAAAA | 2104 |
| 520 | UCUGCUU U CGAAAAA | 2105 |
| 521 | CUGCUUU C GAAAAAU | 2106 |
| 531 | AAAAUGU C ACCCUUG | 2107 |
| 537 | UCACCCU U GGACAAG | 2108 |
| 566 | ACCUGGU U GUGCAAC | 2109 |
| 599 | CUGAUGU U GUCUGUG | 2110 |
| 602 | AUGUUGU C UGUGGUC | 2111 |
| 609 | CUGUGGU C CCCAGGA | 2112 |
| 618 | CCAGGAU C GGCUGAG | 2113 |
| 641 | UGGUGAU C CCCAUCA | 2114 |
| 647 | UCCCCAU C AUCUUCG | 2115 |
| 650 | CCAUCAU C UUCGGGA | 2116 |
| 652 | AUCAUCU U CGGGAUC | 2117 |
| 653 | UCAUCUU C GGGAUCC | 2118 |
| 659 | UCGGGAU C CUGUUUG | 2119 |
| 664 | AUCCUGU U UGCCAUC | 2120 |
| 665 | UCCUGUU U GCCAUCC | 2121 |
| 671 | UUGCCAU C CUCUUGG | 2122 |
| 674 | CCAUCCU C UUGGUGC | 2123 |
| 676 | AUCCUCU U GGUGCUG | 2124 |
| 686 | UGCUGGU C UUUAUCA | 2125 |
| 688 | CUGGUCU U UAUCAAA | 2126 |
| 689 | UGGUCUU U AUCAAAA | 2127 |
| 690 | GGUCUUU A UCAAAAA | 2128 |
| 692 | UCUUUAU C AAAAGG | 2129 |
| 720 | AACCAAU A AGGCCCC | 2130 |
| 755 | AGGAGAU C AAUUUUC | 2131 |
| 759 | GAUCAAU U UUCCCGA | 2132 |
| 760 | AUCAAUU U UCCCGAC | 2133 |
| 761 | UCAAUUU U CCCGACG | 2134 |
| 762 | CAAUUUU C CCGACGA | 2135 |
| 771 | CGACGAU C UUCCUGG | 2136 |
| 773 | ACGAUCU U CCUGGCU | 2137 |
| 774 | CGAUCUU C CUGGCUC | 2138 |
| 781 | CCUGGCU C CAACACU | 2139 |
| 795 | UGCUGCU C CAGUGCA | 2140 |
| 810 | GGAGACU U ACAUGG | 2141 |

TABLE X-continued

Human CD40 Hammerhead Ribozyme Target Sequences

| nt. Position | HH Target Sequence | Seq. ID No. |
|---|---|---|
| 811 | GAGACUU U ACAUGGA | 2142 |
| 812 | AGACUUU A CAUGGAU | 2143 |
| 830 | AACCGGU C ACCCAGG | 2144 |
| 855 | AGAGAGU C GCAUCUC | 2145 |
| 860 | GUCGCAU C UCAGUGC | 2146 |
| 862 | CGCAUCU C AGUGCAG | 2147 |
| 927 | AGGCAGU U GGCCAGA | 2148 |
| 981 | GGGAGCU A UGCCCAG | 2149 |
| 990 | GCCCAGU C AGUGCCA | 2150 |

TABLE XI

Human CD40 Hammerhead Ribozyme Sequences

| nt. Position | HH Ribozyme Sequences | Seq. ID No. |
|---|---|---|
| 9 | GGCGCCC CUGAUGAGGCCGAAAGGCCGAA AGCGAGG | 2151 |
| 24 | GCGGCAG CUGAUGAGGCCGAAAGGCCGAA ACCACUG | 2152 |
| 37 | GAGGUGA CUGAUGAGGCCGAAAGGCCGAA ACCAGGC | 2153 |
| 39 | GCGAGGU CUGAUGAGGCCGAAAGGCCGAA AGACCAG | 2154 |
| 44 | CCAUGGC CUGAUGAGGCCGAAAGGCCGAA AGGUGAG | 2155 |
| 53 | GCAGACG CUGAUGAGGCCGAAAGGCCGAA ACCAUGG | 2156 |
| 54 | GGCAGAC CUGAUGAGGCCGAAAGGCCGAA AACCAUG | 2157 |
| 57 | AGAGGCA CUGAUGAGGCCGAAAGGCCGAA ACGAACC | 2158 |
| 63 | CACUGCA CUGAUGAGGCCGAAAGGCCGAA AGGCAGA | 2159 |
| 74 | CCCAGAG CUGAUGAGGCCGAAAGGCCGAA ACGCACU | 2160 |
| 77 | AGCCCCA CUGAUGAGGCCGAAAGGCCGAA AGGACGC | 2161 |
| 88 | GGUCAGC CUGAUGAGGCCGAAAGGCCGAA AGCAGCC | 2162 |
| 101 | CUGGAUG CUGAUGAGGCCGAAAGGCCGAA ACAGCGG | 2163 |
| 105 | GGUUCUG CUGAUGAGGCCGAAAGGCCGAA AUGGACA | 2164 |
| 139 | UAUUAGG CUGAUGAGGCCGAAAGGCCGAA ACUGUUU | 2165 |
| 143 | UGUUUAU CUGAUGAGGCCGAAAGGCCGAA AGGUACU | 2166 |
| 146 | GACUGUU CUGAUGAGGCCGAAAGGCCGAA AUUAGGU | 2167 |
| 153 | CAGCACU CUGAUGAGGCCGAAAGGCCGAA ACUGUUU | 2168 |
| 162 | CACAAAG CUGAUGAGGCCGAAAGGCCGAA ACAGCAC | 2169 |
| 163 | GCACAAA CUGAUGAGGCCGAAAGGCCGAA AACAGCA | 2170 |
| 165 | UGGCACA CUGAUGAGGCCGAAAGGCCGAA AGAACAG | 2171 |
| 166 | CUGGCAC CUGAUGAGGCCGAAAGGCCGAA AAGAACA | 2172 |
| 208 | UUCAGUG CUGAUGAGGCCGAAAGGCCGAA ACUCUGU | 2173 |
| 209 | UUUCAGU CUGAUGAGGCCGAAAGGCCGAA AACUCUG | 2174 |

TABLE XI-continued

Human CD40 Hammerhead Ribozyme Sequences

| nt. Position | HH Ribozyme Sequences | Seq. ID No. |
|---|---|---|
| 227 | CGCAAGG CUGAUGAGGCCGAAAGGCCGAA AGGCAUU | 2175 |
| 228 | CCGCAAG CUGAUGAGGCCGAAAGGCCGAA AAGGCAU | 2176 |
| 231 | UCACCGC CUGAUGAGGCCGAAAGGCCGAA AGGAAGG | 2177 |
| 247 | GUCUAGG CUGAUGAGGCCGAAAGGCCGAA AUUCGCU | 2178 |
| 248 | UGUCUAG CUGAUGAGGCCGAAAGGCCGAA AAUUCGC | 2179 |
| 251 | AGGUGUC CUGAUGAGGCCGAAAGGCCGAA AGGAAUU | 2180 |
| 292 | GUCGCAG CUGAUGAGGCCGAAAGGCCGAA AUUUGUG | 2181 |
| 308 | GAAGCCC CUGAUGAGGCCGAAAGGCCGAA AGGUUGG | 2182 |
| 314 | GGACCCG CUGAUGAGGCCGAAAGGCCGAA AGCCCUA | 2183 |
| 315 | UGGACCC CUGAUGAGGCCGAAAGGCCGAA AAGCCCU | 2184 |
| 320 | UCUGCUG CUGAUGAGGCCGAAAGGCCGAA ACCCGAA | 2185 |
| 337 | UGUUUCU CUGAUGAGGCCGAAAGGCCGAA AGGUGCC | 2186 |
| 353 | AGGUGCA CUGAUGAGGCCGAAAGGCCGAA AUGGUGU | 2187 |
| 381 | UCACUCG CUGAUGAGGCCGAAAGGCCGAA ACAGUGC | 2188 |
| 407 | GGUGCAG CUGAUGAGGCCGAAAGGCCGAA ACACAGC | 2189 |
| 418 | CGAGCAU CUGAUGAGGCCGAAAGGCCGAA AGCGGUG | 2190 |
| 424 | GCCGGGC CUGAUGAGGCCGAAAGGCCGAA AGCAUGA | 2191 |
| 433 | GACCCCA CUGAUGAGGCCGAAAGGCCGAA AGCCGGG | 2192 |
| 434 | UGACCCC CUGAUGAGGCCGAAAGGCCGAA AAGCCGG | 2193 |
| 440 | UCUGCUU CUGAUGAGGCCGAAAGGCCGAA ACCCCAA | 2194 |
| 449 | CUGUAGC CUGAUGAGGCCGAAAGGCCGAA AUCUGCU | 2195 |
| 453 | ACCCCUG CUGAUGAGGCCGAAAGGCCGAA AGCAAUC | 2196 |
| 461 | UAUCAGA CUGAUGAGGCCGAAAGGCCGAA ACCCCUG | 2197 |
| 462 | GUAUCAG CUGAUGAGGCCGAAAGGCCGAA AACCCCU | 2198 |
| 463 | GGUAUCA CUGAUGAGGCCGAAAGGCCGAA AAACCCC | 2199 |
| 468 | CAGAUGG CUGAUGAGGCCGAAAGGCCGAA AUCAGAA | 2200 |
| 473 | GCUCGCA CUGAUGAGGCCGAAAGGCCGAA AUGGUAU | 2201 |
| 491 | AGAAGCC CUGAUGAGGCCGAAAGGCCGAA ACUGGGC | 2202 |
| 496 | GGAGAAG CUGAUGAGGCCGAAAGGCCGAA AGCCGAC | 2203 |
| 497 | UGGAGAA CUGAUGAGGCCGAAAGGCCGAA AAGCCGA | 2204 |
| 499 | AUUGGAG CUGAUGAGGCCGAAAGGCCGAA AGAAGCC | 2205 |
| 500 | CAUUGGA CUGAUGAGGCCGAAAGGCCGAA AAGAAGC | 2206 |
| 502 | CACAUUG CUGAUGAGGCCGAAAGGCCGAA AGAAGAA | 2207 |
| 511 | AGCAGAU CUGAUGAGGCCGAAAGGCCGAA ACACAUU | 2208 |
| 514 | GAAAGCA CUGAUGAGGCCGAAAGGCCGAA AUGACAC | 2209 |
| 519 | UUUUCGA CUGAUGAGGCCGAAAGGCCGAA AGCAGAU | 2210 |
| 520 | UUUUUCG CUGAUGAGGCCGAAAGGCCGAA AAGCAGA | 2211 |

TABLE XI-continued

Human CD40 Hammerhead Ribozyme Sequences

| nt. Position | HH Ribozyme Sequences | Seq. ID No. |
|---|---|---|
| 521 | AUUUUUC CUGAUGAGGCCGAAAGGCCGAA AAAGCAG | 2212 |
| 531 | CAAGGGU CUGAUGAGGCCGAAAGGCCGAA ACAUUUU | 2213 |
| 537 | CUUGUCC CUGAUGAGGCCGAAAGGCCGAA AGGGUGA | 2214 |
| 566 | GUUGCAC CUGAUGAGGCCGAAAGGCCGAA ACCAGGU | 2215 |
| 599 | CACAGAC CUGAUGAGGCCGAAAGGCCGAA ACAUCAG | 2216 |
| 602 | GACCACA CUGAUGAGGCCGAAAGGCCGAA ACAACAU | 2217 |
| 609 | UCCUGGG CUGAUGAGGCCGAAAGGCCGAA ACCACAG | 2218 |
| 618 | CUCAGCC CUGAUGAGGCCGAAAGGCCGAA AUCCUGG | 2219 |
| 641 | UGAUGGG CUGAUGAGGCCGAAAGGCCGAA AUCACCA | 2220 |
| 647 | CGAAGAU CUGAUGAGGCCGAAAGGCCGAA AUGGGGA | 2221 |
| 650 | UCCCGAA CUGAUGAGGCCGAAAGGCCGAA AUGAUGG | 2222 |
| 652 | GAUCCCG CUGAUGAGGCCGAAAGGCCGAA AGAUGAU | 2223 |
| 653 | GGAUCCC CUGAUGAGGCCGAAAGGCCGAA AAGAUGA | 2224 |
| 659 | CAAACAG CUGAUGAGGCCGAAAGGCCGAA AUCCCGA | 2225 |
| 664 | GAUGGCA CUGAUGAGGCCGAAAGGCCGAA ACAGGAU | 2226 |
| 665 | GGAUGGC CUGAUGAGGCCGAAAGGCCGAA AACAGGA | 2227 |
| 671 | CCAAGAG CUGAUGAGGCCGAAAGGCCGAA AUGGCAA | 2228 |
| 674 | GCACCAA CUGAUGAGGCCGAAAGGCCGAA AGGAUGG | 2229 |
| 676 | CAGCACC CUGAUGAGGCCGAAAGGCCGAA AGAGGAU | 2230 |
| 686 | UGAUAAA CUGAUGAGGCCGAAAGGCCGAA ACCAGCA | 2231 |
| 688 | UUUGAUA CUGAUGAGGCCGAAAGGCCGAA AGACCAG | 2232 |
| 689 | UUUUGAU CUGAUGAGGCCGAAAGGCCGAA AAGACCA | 2233 |
| 690 | UUUUUGA CUGAUGAGGCCGAAAGGCCGAA AAAGACC | 2234 |
| 692 | CCUUUUU CUGAUGAGGCCGAAAGGCCGAA AUAAAGA | 2235 |
| 720 | GGGGCCU CUGAUGAGGCCGAAAGGCCGAA AUUGGUU | 2236 |
| 755 | GAAAAUU CUGAUGAGGCCGAAAGGCCGAA AUCUCCU | 2237 |
| 759 | UCGGGAA CUGAUGAGGCCGAAAGGCCGAA AUUGAUC | 2238 |
| 760 | GUCGGGA CUGAUGAGGCCGAAAGGCCGAA AAUUGAU | 2239 |
| 761 | CGUCGGG CUGAUGAGGCCGAAAGGCCGAA AAAUUGA | 2240 |
| 762 | UCGUCGG CUGAUGAGGCCGAAAGGCCGAA AAAAUUG | 2241 |
| 771 | CCAGGAA CUGAUGAGGCCGAAAGGCCGAA AUCGUCG | 2242 |
| 773 | AGCCAGG CUGAUGAGGCCGAAAGGCCGAA AGAUCGU | 2243 |
| 774 | GAGCCAG CUGAUGAGGCCGAAAGGCCGAA AAGAUCG | 2244 |
| 781 | AGUGUUG CUGAUGAGGCCGAAAGGCCGAA AGCCAGG | 2245 |
| 795 | UGCACUG CUGAUGAGGCCGAAAGGCCGAA AGCAGCA | 2246 |
| 810 | CCAUGUA CUGAUGAGGCCGAAAGGCCGAA AGUCUCC | 2247 |
| 811 | UCCAUGU CUGAUGAGGCCGAAAGGCCGAA AAGUCUC | 2248 |
| 812 | AUCCAUG CUGAUGAGGCCGAAAGGCCGAA AAAGUCU | 2249 |

TABLE XI-continued

Human CD40 Hammerhead Ribozyme Sequences

| nt. Position | HH Ribozyme Sequences | Seq. ID No. |
|---|---|---|
| 830 | CCUGGGU CUGAUGAGGCCGAAAGGCCGAA ACCGGUU | 2250 |
| 855 | GAGAUGC CUGAUGAGGCCGAAAGGCCGAA ACUCUCU | 2251 |
| 860 | GCACUGA CUGAUGAGGCCGAAAGGCCGAA AUGCGAC | 2252 |
| 862 | CUGCACU CUGAUGAGGCCGAAAGGCCGAA AGAUGCG | 2253 |
| 927 | UCUGGCC CUGAUGAGGCCGAAAGGCCGAA ACUGCCU | 2254 |
| 981 | CUGGGCA CUGAUGAGGCCGAAAGGCCGAA AGCUCCC | 2255 |
| 990 | UGGCACU CUGAUGAGGCCGAAAGGCCGAA ACUGGGC | 2256 |

TABLE XII

Mouse CD40 Hammerhead Ribozyme Target Sequences

| nt. Position | HH Target Sequence | Seq. ID No. |
|---|---|---|
| 18 | GGUgucU u UGCCUCg | 2257 |
| 18 | GGuguCU u UGCCUcG | 2258 |
| 24 | UuUGCCU C gGCuGUG | 2259 |
| 38 | GCGcgCU a UGGGGCU | 2260 |
| 62 | CagcGGU c CaUCUag | 2261 |
| 62 | CaGCgGU C CAUCuAG | 2262 |
| 66 | gGUCCAU C uAGggCa | 2263 |
| 80 | AGUGuGU u acgUGca | 2264 |
| 80 | AgUGUGU u AcgUGCa | 2265 |
| 81 | gUGugUU a CgUGCaG | 2266 |
| 100 | AAACAGU A CCUccac | 2267 |
| 126 | CUGUgaU U UGUGCCA | 2268 |
| 127 | UGUgaUU U GUGCCAG | 2269 |
| 170 | CAgcUcU u gaGAaGA | 2270 |
| 208 | gGCGAAU U CucAGcC | 2271 |
| 209 | GCGAAUU C ucAGcCc | 2272 |
| 233 | gGGAGAU u cgcUgUC | 2273 |
| 267 | ACCcAAU c AAggGcu | 2274 |
| 267 | AcCCAAU c AaGggCu | 2275 |
| 275 | aAGGGCU U CGGGUua | 2276 |
| 275 | AaGGGcU U CgGgUua | 2277 |
| 276 | AGGGCUU C GGGUuaA | 2278 |
| 281 | UUCGGGU u aAGaAGg | 2279 |
| 281 | UUcGGGU u AAGaAGg | 2280 |
| 314 | ACACugU C UGuACCU | 2281 |
| 354 | caAgGaU u GCgaGGC | 2282 |
| 386 | cCugUaU c CCUGGCU | 2283 |
| 394 | CCUgGCU u uGGaGuu | 2284 |
| 394 | CCuGGCU U UGGaGUu | 2285 |
| 395 | CuGGCUU U GGaGUuA | 2286 |
| 429 | caCUGAU A CCgUCUG | 2287 |
| 434 | AUACCgU C UGucAuC | 2288 |
| 434 | AUaCcGU c UGuCAUC | 2289 |
| 441 | CugUCaU C CcuGCcC | 2290 |
| 452 | GCCCAGU C GGCUUCU | 2291 |
| 452 | GCCCAGU C gGcuuCu | 2292 |
| 457 | GUCGGCU U CUUCUCC | 2293 |
| 458 | UCGGCUU C UUCUCCA | 2294 |
| 460 | GGCUUCU U CUCCAAU | 2295 |
| 461 | GCUUCUU C UCCAAUc | 2296 |
| 463 | UUCUUCU C CAAUcaG | 2297 |
| 472 | AAuCAGU C AucaCUu | 2298 |
| 472 | AAUcaGU c auCACuU | 2299 |
| 479 | cAUCAcU U UUCgaaA | 2300 |
| 480 | AUCacUU U UCGAAAA | 2301 |
| 481 | UCacUUU U CGAAAAg | 2302 |
| 481 | UCACuUU U cGAaAAG | 2303 |
| 492 | AAAgUGU u AuCCcUG | 2304 |
| 560 | CUaAUGU c aUCUGUG | 2305 |

TABLE XII-continued

Mouse CD40 Hammerhead Ribozyme Target Sequences

| nt. Position | HH Target Sequence | Seq. ID No. |
|---|---|---|
| 563 | AUGUcaU C UGUGGUu | 2306 |
| 572 | gUGGUuU a AagUCcC | 2307 |
| 572 | GuGGUUU a aagUcCC | 2308 |
| 577 | UuAAagU c CCgGAuG | 2309 |
| 620 | UGGgcAU C CuCAUCA | 2310 |
| 626 | UCCuCAU C AcCaUuu | 2311 |
| 632 | uCAcCAU u UUCGGGg | 2312 |
| 632 | UcaCCAU u uUCggGG | 2313 |
| 634 | AcCAUuU U CGGGgUg | 2314 |
| 635 | CCaUuuU c GgGGUGu | 2315 |
| 635 | cCAUuUU C GGGgUgu | 2316 |
| 635 | CCAUuuU C ggGGUGu | 2317 |
| 647 | UGuUucU C UaUAUCA | 2318 |
| 649 | uUucUCU a UAUCAAA | 2319 |
| 651 | ucUCUaU A UCAAAAA | 2320 |
| 653 | UCUaUAU C AAAAAGG | 2321 |
| 735 | gGAaGAU u aUCCcGG | 2322 |
| 759 | cGCUGCU C CAGUGCA | 2323 |
| 794 | AgCCuGU C ACaCAGG | 2324 |
| 794 | AGcCuGU c acaCAGg | 2325 |
| 819 | AGAGAGU GCAUCUC | 2326 |
| 824 | GUCGCAU C UCAGUGC | 2327 |
| 826 | CGCAUCU C AGUGCAG | 2328 |
| 876 | cCCUGGU C UgAaCcC | 2329 |
| 913 | GGCUGCU U GCUGACC | 2330 |
| 997 | CUCAaCU u GCuuUuu | 2331 |
| 1003 | uUGCUUU u uAAggAU | 2332 |
| 1003 | uugCUUU u uAaGGAU | 2333 |
| 1023 | gaAAgCU c GGGCaUC | 2334 |
| 1048 | CAGuGaU U UCUaccA | 2335 |
| 1052 | gAUauCU a CCaaGuG | 2336 |
| 1081 | CCAGagU u GuCUugc | 2337 |
| 1084 | gAGUuGU C uUGCuGC | 2338 |
| 1086 | gUugUCU U GcUGCgG | 2339 |
| 1097 | gCgGcGU U CACUGuA | 2340 |

TABLE XII-continued

Mouse CD40 Hammerhead Ribozyme Target Sequences

| nt. Position | HH Target Sequence | Seq. ID No. |
|---|---|---|
| 1098 | CgGcGUU C ACUGuAA | 2341 |
| 1118 | cgUgGCU A CAGGaGU | 2342 |
| 118 | CgUGGCU a CaggAgU | 2343 |
| 1141 | CgCaGCU u gUGCUCG | 2344 |
| 1164 | aCCUGgU U GCCAUCa | 2345 |
| 1202 | UGuaaUU a UUUaUaC | 2346 |
| 1220 | gGcAuCU c AgAAACu | 2347 |
| 1220 | GGCAuCU C AGAAACu | 2348 |
| 1228 | aGAaACU c UAgcaGG | 2349 |
| 1253 | AaCaGGU a GUGgAAu | 2350 |
| 1331 | AGgAGCU U GCUgCcc | 2351 |
| 1362 | uUuUGaU C CCugGGA | 2352 |
| 1373 | gGGaCUU c AUgguAA | 2353 |
| 1373 | GgGACUU c AugguaA | 2354 |
| 1413 | uUGUCAU u UGaccUC | 2355 |
| 1443 | GUaaUGU a CcccGUG | 2356 |
| 1470 | CACAuAU c CUaaaAu | 2357 |
| 1492 | GugGUGU a uUGuAga | 2358 |
| 1497 | GuAuUGU A gaAaUuA | 2359 |
| 1508 | auUauUU a aUCcGCC | 2360 |
| 1508 | AUuAuUU a auCCGcC | 2361 |
| 1523 | cuGGGuU u CUaccUG | 2362 |

TABLE XIII

Mouse CD40 Hammerhead Ribozyme Sequences

| nt. Position | HH Ribozyme Sequence | Seq. ID No. |
|---|---|---|
| 18 | CGAGGCA CUGAUGAGGCCGAAAGGCCGAA AGACACC | 2363 |
| 18 | CGAGGCA CUGAUGAGGCCGAAAGGCCGAA AGACACC | 2364 |
| 24 | CACAGCC CUGAUGAGGCCGAAAGGCCGAA AGGCAAA | 2365 |
| 38 | AGCCCCA CUGAUGAGGCCGAAAGGCCGAA AGCGCGC | 2366 |
| 62 | CUAGAUG CUGAUGAGGCCGAAAGGCCGAA ACCGCUG | 2367 |
| 62 | CUAGAUG CUGAUGAGGCCGAAAGGCCGAA ACCGCUG | 2368 |
| 66 | UGCCCUA CUGAUGAGGCCGAAAGGCCGAA AUGGACC | 2369 |
| 80 | UGCACGU CUGAUGAGGCCGAAAGGCCGAA ACACACU | 2370 |
| 80 | UGCACGU CUGAUGAGGCCGAAAGGCCGAA ACACACU | 2371 |
| 81 | CUGCACG CUGAUGAGGCCGAAAGGCCGAA AACACAC | 2372 |
| 100 | GUGGAGG CUGAUGAGGCCGAAAGGCCGAA ACUGUUU | 2373 |
| 126 | UGGCACA CUGAUGAGGCCGAAAGGCCGAA AUCACAG | 2374 |
| 127 | CUGGCAC CUGAUGAGGCCGAAAGGCCGAA AAUCACA | 2375 |
| 170 | UCUUCUC CUGAUGAGGCCGAAAGGCCGAA AGAGCUG | 2376 |
| 208 | GGCUGAG CUGAUGAGGCCGAAAGGCCGAA AUUCGCC | 2377 |
| 209 | GGGCUGA CUGAUGAGGCCGAAAGGCCGAA AAUUCGC | 2378 |
| 233 | GACAGCG CUGAUGAGGCCGAAAGGCCGAA AUCUCCC | 2379 |
| 267 | AGCCCUU CUGAUGAGGCCGAAAGGCCGAA AUUGGGU | 2380 |
| 267 | AGCCCUU CUGAUGAGGCCGAAAGGCCGAA AUUGGGU | 2381 |
| 275 | UAACCCG CUGAUGAGGCCGAAAGGCCGAA AGCCCUU | 2382 |
| 275 | UAACCCG CUGAUGAGGCCGAAAGGCCGAA AGCCCUU | 2383 |
| 276 | UUAACCC CUGAUGAGGCCGAAAGGCCGAA AAGCCCU | 2384 |
| 281 | CCUUCUU CUGAUGAGGCCGAAAGGCCGAA ACCCGAA | 2385 |
| 281 | CCUUCUU CUGAUGAGGCCGAAAGGCCGAA ACCCGAA | 2386 |
| 314 | AGGUACA CUGAUGAGGCCGAAAGGCCGAA ACAGUGU | 2387 |
| 354 | GCCUCGC CUGAUGAGGCCGAAAGGCCGAA AUCCUUG | 2388 |
| 386 | AGCCAGG CUGAUGAGGCCGAAAGGCCGAA AUACAGG | 2389 |
| 394 | AACUCCA CUGAUGAGGCCGAAAGGCCGAA AGCCAGG | 2390 |
| 394 | AACUCCA CUGAUGAGGCCGAAAGGCCGAA AGCCAGG | 2391 |
| 395 | UAACUCC CUGAUGAGGCCGAAAGGCCGAA AAGCCAG | 2392 |
| 429 | CAGACGG CUGAUGAGGCCGAAAGGCCGAA AUCAGUG | 2393 |
| 434 | GAUGACA CUGAUGAGGCCGAAAGGCCGAA ACGGUAU | 2394 |
| 434 | GAUGACA CUGAUGAGGCCGAAAGGCCGAA ACGGUAU | 2395 |
| 441 | GGGCAGG CUGAUGAGGCCGAAAGGCCGAA AUGACAG | 2396 |
| 452 | AGAAGCC CUGAUGAGGCCGAAAGGCCGAA ACUGGGC | 2397 |
| 452 | AGAAGCC CUGAUGAGGCCGAAAGGCCGAA ACUGGGC | 2398 |
| 457 | GGAGAAG CUGAUGAGGCCGAAAGGCCGAA AGCCGAC | 2399 |
| 458 | UGGAGAA CUGAUGAGGCCGAAAGGCCGAA AAGCCGA | 2400 |

TABLE XIII-continued

Mouse CD40 Hammerhead Ribozyme Sequences

| nt. Position | HH Ribozyme Sequence | Seq. ID No. |
|---|---|---|
| 460 | AUUGGAG CUGAUGAGGCCGAAAGGCCGAA AGAAGCC | 2401 |
| 461 | GAUUGGA CUGAUGAGGCCGAAAGGCCGAA AAGAAGC | 2402 |
| 463 | CUGAUUG CUGAUGAGGCCGAAAGGCCGAA AGAAGAA | 2403 |
| 472 | AAGUGAU CUGAUGAGGCCGAAAGGCCGAA ACUGAUU | 2404 |
| 472 | AAGUGAU CUGAUGAGGCCGAAAGGCCGAA ACUGAUU | 2405 |
| 479 | UUUCGAA CUGAUGAGGCCGAAAGGCCGAA AGUGAUG | 2406 |
| 480 | UUUUCGA CUGAUGAGGCCGAAAGGCCGAA AAGUGAU | 2407 |
| 481 | CUUUUCG CUGAUGAGGCCGAAAGGCCGAA AAAGUGA | 2408 |
| 481 | CUUUUCG CUGAUGAGGCCGAAAGGCCGAA AAAGUGA | 2409 |
| 492 | CAGGGAU CUGAUGAGGCCGAAAGGCCGAA ACACUUU | 2410 |
| 560 | CACAGAU CUGAUGAGGCCGAAAGGCCGAA ACAUUAG | 2411 |
| 563 | AACCACA CUGAUGAGGCCGAAAGGCCGAA AUGACAU | 2412 |
| 572 | GGGACUU CUGAUGAGGCCGAAAGGCCGAA AAACCAC | 2413 |
| 572 | GGGACUU CUGAUGAGGCCGAAAGGCCGAA AAACCAC | 2414 |
| 577 | CAUCCGG CUGAUGAGGCCGAAAGGCCGAA ACUUUAA | 2415 |
| 620 | UGAUGAG CUGAUGAGGCCGAAAGGCCGAA AUGCCCA | 2416 |
| 626 | AAAUGGU CUGAUGAGGCCGAAAGGCCGAA AUGAGGA | 2417 |
| 632 | CCCCGAA CUGAUGAGGCCGAAAGGCCGAA AUGGUGA | 2418 |
| 632 | CCCCGAA CUGAUGAGGCCGAAAGGCCGAA AUGGUGA | 2419 |
| 634 | CACCCCG CUGAUGAGGCCGAAAGGCCGAA AAAUGGU | 2420 |
| 635 | ACACCCC CUGAUGAGGCCGAAAGGCCGAA AAAAUGG | 2421 |
| 635 | ACACCCC CUGAUGAGGCCGAAAGGCCGAA AAAAUGG | 2422 |
| 635 | ACACCCC CUGAUGAGGCCGAAAGGCCGAA AAAAUGG | 2423 |
| 647 | UGAUAUA CUGAUGAGGCCGAAAGGCCGAA AGAAACA | 2424 |
| 649 | UUUGAUA CUGAUGAGGCCGAAAGGCCGAA AGAGAAA | 2425 |
| 651 | UUUUUGA CUGAUGAGGCCGAAAGGCCGAA AUAGAGA | 2426 |
| 653 | CCUUUUU CUGAUGAGGCCGAAAGGCCGAA AUAUAGA | 2427 |
| 735 | CCGGGAU CUGAUGAGGCCGAAAGGCCGAA AUCUUCC | 2428 |
| 759 | UGCACUG CUGAUGAGGCCGAAAGGCCGAA AGCAGCG | 2429 |
| 794 | CCUGUGU CUGAUGAGGCCGAAAGGCCGAA ACAGGCU | 2430 |
| 794 | CCUGUGU CUGAUGAGGCCGAAAGGCCGAA ACAGGCU | 2431 |
| 819 | GAGAUGC CUGAUGAGGCCGAAAGGCCGAA ACUCUCU | 2432 |
| 824 | GCACUGA CUGAUGAGGCCGAAAGGCCGAA AUGCGAC | 2433 |
| 826 | CUGCACU CUGAUGAGGCCGAAAGGCCGAA AGAUGCG | 2434 |
| 876 | GGGUUCA CUGAUGAGGCCGAAAGGCCGAA ACCAGGG | 2435 |
| 913 | GGUCAGC CUGAUGAGGCCGAAAGGCCGAA AGCAGCC | 2436 |
| 997 | AAAAAGC CUGAUGAGGCCGAAAGGCCGAA AGUUGAG | 2437 |

TABLE XIII-continued

Mouse CD40 Hammerhead Ribozyme Sequences

| nt. Position | HH Ribozyme Sequence | Seq. ID No. |
| --- | --- | --- |
| 1003 | AUCCUUA CUGAUGAGGCCGAAAGGCCGAA AAAGCAA | 2438 |
| 1003 | AUCCUUA CUGAUGAGGCCGAAAGGCCGAA AAAGCAA | 2439 |
| 1023 | GAUGCCC CUGAUGAGGCCGAAAGGCCGAA AGCUUUC | 2440 |
| 1048 | UGGUAGA CUGAUGAGGCCGAAAGGCCGAA AUCACUG | 2441 |
| 1052 | CACUUGG CUGAUGAGGCCGAAAGGCCGAA AGAUAUC | 2442 |
| 1081 | GCAAGAC CUGAUGAGGCCGAAAGGCCGAA ACUCUGG | 2443 |
| 1084 | GCAGCAA CUGAUGAGGCCGAAAGGCCGAA ACAACUC | 2444 |
| 1086 | CCGCAGC CUGAUGAGGCCGAAAGGCCGAA AGACAAC | 2445 |
| 1097 | UACAGUG CUGAUGAGGCCGAAAGGCCGAA ACGCCGC | 2446 |
| 1098 | UUACAGU CUGAUGAGGCCGAAAGGCCGAA AACGCCG | 2447 |
| 1118 | ACUCCUG CUGAUGAGGCCGAAAGGCCGAA AGCCACG | 2448 |
| 1118 | ACUCCUG CUGAUGAGGCCGAAAGGCCGAA AGCCACG | 2449 |
| 1141 | CGAGCAC CUGAUGAGGCCGAAAGGCCGAA AGCUGCG | 2450 |
| 1164 | UGAUGGC CUGAUGAGGCCGAAAGGCCGAA ACCAGGU | 2451 |
| 1202 | GUAUAAA CUGAUGAGGCCGAAAGGCCGAA AAUUACA | 2452 |
| 1220 | AGUUUCU CUGAUGAGGCCGAAAGGCCGAA AGAUGCC | 2453 |
| 1220 | AGUUUCU CUGAUGAGGCCGAAAGGCCGAA AGAUGCC | 2454 |
| 1228 | CCUGCUA CUGAUGAGGCCGAAAGGCCGAA AGUUUCU | 2455 |
| 1253 | AUUCCAC CUGAUGAGGCCGAAAGGCCGAA ACCUGUU | 2456 |
| 1331 | GGGCAGC CUGAUGAGGCCGAAAGGCCGAA AGCUCCU | 2457 |
| 1362 | UCCCAGG CUGAUGAGGCCGAAAGGCCGAA AUCAAAA | 2458 |
| 1373 | UUACCAU CUGAUGAGGCCGAAAGGCCGAA AAGUCCC | 2459 |
| 1373 | UUACCAU CUGAUGAGGCCGAAAGGCCGAA AAGUCCC | 2460 |
| 1413 | GAGGUCA CUGAUGAGGCCGAAAGGCCGAA AUGACAA | 2461 |
| 1443 | CACGGGG CUGAUGAGGCCGAAAGGCCGAA ACAUUAC | 2462 |
| 1470 | AUUUUAG CUGAUGAGGCCGAAAGGCCGAA AUAUGUG | 2463 |
| 1492 | UCUACAA CUGAUGAGGCCGAAAGGCCGAA ACACCAC | 2464 |
| 1497 | UAAUUUC CUGAUGAGGCCGAAAGGCCGAA ACAAUAC | 2465 |
| 1508 | GGCGGAU CUGAUGAGGCCGAAAGGCCGAA AAAUAAU | 2466 |
| 1508 | GGCGGAU CUGAUGAGGCCGAAAGGCCGAA AAAUAAU | 2467 |
| 1523 | CAGGUAG CUGAUGAGGCCGAAAGGCCGAA AACCCAG | 2468 |

TABLE XIV

Human B7 Hairpin Ribozyme and Target Sequence

| nt. Position | Hairpin Ribozyme Sequence | Seq. ID No. | Substrate | Seq. ID No. |
| --- | --- | --- | --- | --- |
| 286 | ACAGGCAG AGAA GAUGAC ACCAGAGAAACACACGUUGUGGUACAUUACCUGGUA | 2469 | GUCAUCA GCC CUGCCUGU | 2490 |
| 291 | GCAAACA AGAA GGGCUG ACCAGAGAAACACACGUUGUGGUACAUUACCUGGUA | 2470 | CAGCCCU GCC UGUUUUGC | 2491 |
| 295 | AGGUGCAA AGAA GGCAGG ACCAGAGAAACACACGUUGUGGUACAUUACCUGGUA | 2471 | CCUGCCU GUU UUGCACCU | 2492 |

TABLE XIV-continued

Human B7 Hairpin Ribozyme and Target Sequence

| nt. Position | Hairpin Ribozyme Sequence | Seq. ID No. | Substrate | Seq. ID No. |
|---|---|---|---|---|
| 437 | GCACCAAG AGAA GAAAGA ACCAGAGAAACACACGUUGUGGUACAUUACCUGGUA | 2472 | UCUUUCA GCU CUUGGUGC | 2493 |
| 469 | AACACCUG AGAA GAAGUG ACCAGAGAAACACACGUUGUGGUACAUUACCUGGUA | 2473 | CACUUCU GUU CAGGUGUU | 2494 |
| 518 | GACCACAG AGAA GCGUUG ACCAGAGAAACACACGUUGUGGUACAUUACCUGGUA | 2474 | CAACGCU GUC CUGUGGUC | 2495 |
| 540 | AGCUCUUC AGAA GAAACA ACCAGAGAAACACACGUUGUGGUACAUUACCUGGUA | 2475 | UGUUUCU GUU GAAGAGCU | 2496 |
| 596 | ACAUCAUA AGAA GCACCA ACCAGAGAAACACACGUUGUGGUACAUUACCUGGUA | 2476 | UGGUGCU GAC UAUGAUGU | 2497 |
| 644 | CAAAGAUG AGAA GGUUCU ACCAGAGAAACACACGUUGUGGUACAUUACCUGGUA | 2477 | AGAACCG GAC CAUCUUUG | 2498 |
| 702 | GUGCCCUC AGAA GAUGGd ACCAGAGAAACACACGUUGUGGUACAUUACCUGGUA | 2478 | CCCAUCU GAC GAGGGCAC | 2499 |
| 795 | GUAGGGAA AGAA GCUUUg ACCAGAGAAACACACGUUGUGGUACAUUACCUGGUA | 2479 | CAAAGCU GAC UUCCCUAC | 2500 |
| 819 | AUUUCAAA AGAA GAUAUA ACCAGAGAAACACACGUUGUGGUACAUUACCUGGUA | 2480 | UAUAUCU GAC UUUGAAAU | 2501 |
| 939 | UCUUGGGA AGAA GUUGUU ACCAGAGAAACACACGUUGUGGUACAUUACCUGGUA | 2481 | CACACAA GUU UCCCAAGA | 2502 |
| 1012 | ACACAUGA AGAA GUGGUU ACCAGAGAAACACACGUUGUGGUACAUUACCUGGUA | 2482 | AACCACA GCU UCAUGUGU | 2503 |
| 1055 | AGUUGAAG AGAA GAUUCA ACCAGAGAAACACACGUUGUGGUACAUUACCUGGUA | 2483 | UGAAUCA GAC CUUCAACU | 2504 |
| 1103 | AGGAUGGG AGAA GGUUAU ACCAGAGAAACACACGUUGUGGUACAUUACCUGGUA | 2484 | AUAACCU GCU CCCAUCCU | 2505 |
| 1159 | GUAGGUCA AGAA GCAUAU ACCAGAGAAACACACGUUGUGGUACAUUACCUGGUA | 2485 | AUAUGCU GCC UGACCUAC | 2506 |
| 1163 | AGdAGUAG AGAA GGCAGC ACCAGAGAAACACACGUUGUGGUACAUUACCUGGUA | 2486 | GCUGCCU GAC CUACUGCU | 2507 |
| 1171 | UGGGGCAA AGAA GUAGGU ACCAGAGAAACACACGUUGUGGUACAUUACCUGGUA | 2487 | ACCUACU GCU UUGCCCCA | 2508 |
| 1356 | GUGGGUAA AGAA GCUUAA ACCAGAGAAACACACGUUGUGGUACAUUACCUGGUA | 2488 | UUAAGCU GUU UUACCCAC | 2509 |
| 1395 | UCAdCUUA AGAA GAAAGA ACCAGAGAAACACACGUUGUGGUACAUUACCUGGUA | 2489 | UCUUUCA GAU UAAGCUGA | 2510 |

TABLE XV

Mouse B7 Hairpin Ribozyme and Target Sequence

| nt. Position | Hairpin Ribozyme Sequence | Seq. ID No. | Substrate | Seq. ID No. |
|---|---|---|---|---|
| 74 | AGAAAUGG AGAA GAGUGU ACCAGAGAAACACACGUUGUGGUACAUUACCUGGUA | 2511 | ACACUCU GUU CCAUUUCU | 2534 |
| 114 | AUCCACCC AGAA GAUGCU ACCAGAGAAACACACGUUGUGGUACAUUACCUGGUA | 2512 | AGCAUCU GCC GGGUGGAU | 2535 |
| 154 | AAUCGAGA AGAA GAGAUG ACCAGAGAAACACACGUUGUGGUACAUUACCUGGUA | 2513 | CAUCUCU GUU UCUCGAUU | 2536 |
| 265 | CCUGCAUC AGAA GACAAU ACCAGAGAAACACACGUUGUGGUACAUUACCUGGUA | 2514 | AUUGCA GUU GAUGCAGG | 2537 |
| 328 | GACGAAUC AGAA GCACAA ACCAGAGAAACACACGUUGUGGUACAUUACCUGGUA | 2515 | UUGUGCU GCU GAUUCGUC | 2538 |
| 331 | AAAGACGA AGAA GCAGCA ACCAdAGAAACACACGUUGUGGUACAUUACCUGGUA | 2516 | UGCUGCU GAU UCGUCUUU | 2539 |
| 356 | UCAUCAAC AGAA GAAGAC ACCAGAGAAACACACGUUGUGGUACAUUACCUGGUA2 | 5 1 7 GUCUUCA GAU GUUGAUGA | | 2540 |
| 373 | CUGACUUG AGAA GUUGUU ACCAGAGAAACACACGUUGUGGUACAUUACCUGGUA | 2518 | AACAACU GUC CAAGUCAG | 2541 |
| 403 | AACGGCAA AGAA GCAAUA ACCAdAGAAACACACGUUGUGGUACAUUACCUGGUA | 2519 | UAUUGCU GCC UUGCCGUU | 2542 |
| 481 | CAAUGACA AGAA GCACCA ACCAGAGAAACACACGUUGUGGUACAUUACCUGGUA | 2520 | UGGUGCU GUC UGUCAUUG | 2543 |
| 529 | CAUAUAAA AGAA GGUUCU ACCAGAGAAACACACGUUGUGGUACAUUACCUGGUA | 2521 | AGAACCU GAC UUUAUAUG | 2544 |
| 584 | GUGCCCCG AGAA GAAAGG ACCAGAGAAACACACGUUGUGGUACAUUACCUGGUA | 2522 | CCUUUCA GAC CGGGGCAC | 2545 |
| 600 | AACGACAC AGAA GUAUGU ACCAGAGAAACACACGUUGUGGUACAUUACCUGGUA | 2523 | ACAUACA GCU GUGUCGUU | 2546 |
| 677 | GUAGAAA AGAA GCUUUG ACCAGAGAAACACACGUUGUGGUACAUUACCUGGUA | 2524 | CAAAGCU GAC UUCUCUAC | 2547 |
| 741 | GGAAGCAA AGAA GGUAAU ACCAGAGAAACACACGUUGUGGUACAUUACCUGGUA | 2525 | AUUACCU GCU UUGCUUCC | 2548 |
| 1028 | AUGACGAC AGAA GUUAUU ACCAGAGAAACACACGUUGUGGUACAUUACCUGGUA | 2526 | AAUAACA GUC GUCGUCAU | 2549 |
| 1077 | UCUUCUGA AGAA GCUUCU ACCAGAGAAACACACGUUGUGGUACAUUACCUGGUA | 2527 | AGAAGCU GUU UCAGAAGA | 2550 |
| 1116 | GAAGGUAA AGAA GUUGUU ACCAGA9AAACACACGUUGUGGUACAUUACCUGGUA | 2528 | AACAACA GCC UUACCUUC 2551 | |
| 1153 | GGAAGACG AGAA GUUCAG ACCAGAGAAACACACGUUGUGGUACAUUACCUGGUA | 2529 | CUGAACA GAC CGUCUUCC | 2552 |
| 1157 | UAAAGGAA AGAA GUCUGU ACCAGAGAAACACACGUUGUGGUACAUUACCUGGUA | 2530 | ACAGACC GUC UUCCUUUA | 2553 |
| 1178 | CCCACAUG AGAA GAGAAG ACCAGAGAAACACACGUUGUGGUACAUUACCUGGUA | 2531 | CUUCUCU GUC CAUGUGGG | 2554 |
| 1246 | UCCGAAAG AGAA GCUAGC ACCAGAGAAACACACGUUGUGGUACAUUACCUGGUA | 2532 | GCUAGCU GAU CUUUCGGA | 2555 |
| 1523 | CAGAAAAG AGAA GGCCUC ACCAGAGAAACACACGUUGUGGUACAUUACCUGGUA | 2533 | GAGGCCU GCC CUUUUCUG | 2556 |

TABLE XVI

Human B7-2 Hairpin Ribozyme and Target Sequences

| nt. Position | HP Ribozyme Sequences | Seq. ID No. | Substrate | Seq. ID No. |
|---|---|---|---|---|
| 25 | GUUACAGC AGAA GAGAAG ACCAGAGAAACACACGUUGUGGUACAUUACCUGGUA | 2557 | CUUCUCU GCU GCUGUAAC | 2578 |
| 28 | CCUGUUAC AGAA GCAGAG ACCAGAGAAACACACGUUGUGGUACAUUACCUGGUA | 2558 | CUCUGCU GCU GUAACAGG | 2579 |
| 57 | CCCCACUC AGAA GUGUGU ACCAGAGAAACACACGUUGUGGUACAUUACCUGGUA | 2559 | ACACACG GAU GAGUGGGG | 2580 |
| 162 | CACCGAGG AGAA GGAAGG ACCAGAGAAACACACGUUGUGGUACAUUACCUGGUA | 2560 | CCUUCCU GCU CUCUGGUG | 2581 |
| 175 | UUCAGAGG AGAA GCACCA ACCAGAGAAACACACGUUGUGGUACAUUACCUGGUA | 2561 | UGGUGCU GCU CCUCUGAA | 2582 |
| 214 | CAUGGCAG AGAA GCAGUC ACCAGAGAAACACACGUUGUGGUACAUUACCUGGUA | 2562 | GACUGCG GAC CUGCCAUG | 2583 |
| 380 | CAGGGUCC AGAA GUCCGA ACCAGAGAAACACACGUUGUGGUACAUUACCUGGUA | 2563 | UCGGACA GUU GGACCCUG | 2584 |
| 408 | UGUCCUUG AGAA GAAGAU ACCAGAGAAACACACGUUGUGGUACAUUACCUGGUA | 2564 | AUCUUCA GAU CAAGGACA | 2585 |
| 480 | CAGAAUUC AGAA GQUGGA ACCAGAGAAACACACGUUGUGGUACAUUACCUGGUA | 2565 | UCCACCA GAU GAAUUCUG | 2586 |
| 575 | UAUAGAUG AGAA GGUCAA ACCAGAGAAACACACGUUGUGGUACAUUACCUGGUA | 2566 | UUGACCU GCU CAUCUAUA | 2587 |
| 710 | AACAGACA AGAA GAUGGA ACCAGAGAAACACACGUUGUGGUACAUUACCUGGUA | 2567 | UCCAUCA GCU UGUCUGUU | 2588 |
| 718 | GGGAAUGA AGAA GACAAG ACCAGAGAAACACACGUUGUGGUACAUUACCUGGUA | 2568 | CUUGUCU GUU UCAUUCCC | 2589 |
| 730 | CUCGUAAC AGAA GGGAAU ACCAGAGAAACACACGUUGUGGUACAUUACCUGGUA | 2569 | AUUCCCU GAU GUUACGAG | 2590 |
| 783 | AAGAUAAA AGAA GCGUCU ACCAGAGAAACACACGUUGUGGUACAUUACCUGGUA | 2570 | AGACGCG GCU UUUAUCUU | 2591 |
| 825 | CUGGGGGA AGAA GAGGGU ACCAGAGAAACACACGUUGUGGUACAUUACCUGGUA | 2571 | ACCCUCA GCC UCCCCCAG | 2592 |
| 835 | GGAAUGUG AGAA GGGGGA ACCAGAGAAACACACGUUGUGGUACAUUACCUGGUA | 2572 | UCCCCCA GAC CACAUUCC | 2593 |
| 856 | GGAAGUAC AGAA GUAAUC ACCAGAGAAACACACGUUGUGGUACAUUACCUGGUA | 2573 | GAUUACA GCU GUACUUCC | 2594 |
| 896 | UAGAAUUA AGAA GAAAAC ACCAGAGAAACACACGUUGUGGUACAUUACCUGGUA | 2574 | GUUUUCU GUC UAAUUCUA | 2595 |
| 930 | AGUUGCGA AGAA GCUUCU ACCAGAGAAACACACGUUGUGGUACAUUACCUGGUA | 2575 | AGAAGCG GCC UCGCAACU | 2596 |
| 987 | UUUUCUUG AGAA GUUCAC ACCAGAGAAACACACGUUGUGGUACAUUACCUGGUA | 2576 | GUGAACA GAC CAAGAAAA | 2597 |
| 1027 | UGGGCUUC AGAA GAUCUU ACCAGAGAAACACACGUUGUGGUACAUUACCUGGUA | 2577 | AAGAUCU GAU GAAGCCCA | 2598 |

TABLE XVII

Mouse B7-2 Hairpin Ribozyme and Target Sequences

| nt. Position | HP Ribozyme Sequences | Seq. ID No. | Substrate | Seq. ID No. |
|---|---|---|---|---|
| 10 | UCUUACGC AGAA GCUUGCACCAGAGAAACACACGUUGUGGUACAUUACCUGGUA | 2599 | GCAAGCA GAC GCGUAAGA | 2620 |
| 42 | UUGUUCAA AGAA GUGCUG ACCAGAGAAACACACGUUGUGGUACAUUACCUGGUA | 2600 | CAGCACG GAC UUGAACAA | 2621 |
| 56 | CUACAGGA AGAA GGUUGU ACCAGAGAAACACACGUUGUGGUACAUUACGUGGUA | 2601 | ACAACCA GAC UCCUGUAG | 2622 |
| 108 | CAUGGUGC AGAA GGGGUC ACCAGAGAAACACACGUUGUGGUACAUUACCUGGUA | 2602 | GACCCCA GAU GCACCAUG | 2623 |
| 146 | AUCAGCAA AGAA GUCACA ACCAGAGAAACACACGUUGUGGUACAUUACCUGGUA | 2603 | UGUGACA GUC UUGCUGAU | 2624 |
| 154 | CAUCUGAG AGAA GCAAGA ACCAGAGAAACACACGUUGUGGUACAUUACCUGGUA | 2604 | UCUUGCU GAU CUCAGAUG | 2625 |
| 161 | GAAACAGC AGAA GAGAUC ACCAGAGAAACACACGUUGUGGUACAUUACCUGGUA | 2665 | GAUCUCA GAU GCUGUUUC | 2626 |
| 167 | UCCACGGA AGAA GCAUCU AGCAGAGAAACACACGUUGUGGUACAUUACCUGGUA | 2606 | AGAUGCU GUU UCCGUGGA | 2627 |
| 211 | AUGGGCAC AGAA GAUAUG ACCAGAGAAACACACGUUGUGGUACAUUACCUGGUA | 2607 | CAUAUCU GCC GUGCCCAU | 2628 |
| 400 | UGCCUUUG AGAA GAACAU ACCAGAGAAACACACAGAUUGUGGUACAUUACCUGGUA | 2608 | AUGUUCA GAU CAAGGACA | 2629 |
| 679 | AGAUACUG AGAA GUUCUG ACCAGAGAAACACACGUUGUGGUACAUUACCUGGUA | 2609 | CAGAACU GUU CAGUAUCU | 2630 |
| 696 | AAGAGAGA AGAA GUUGGA ACCAGAGAAACACACGUUGUGGUACAUUACCUGGUA | 2610 | UCCAACA GCC UGUGUCUU | 2631 |
| 716 | CACACACC AGAA GGGAAU ACCAGAGAAACACACGUUGUGGUACAUUACCUGGUA | 2611 | AUCCCG GAU GGUGUGUG | 2632 |
| 737 | ACACACAC AGAA GCAAGA ACCAGAGAAACACACGUUGUGGUACAUUACCUGGUA | 2612 | UAUGACA GUU GUGUGUGU | 2633 |
| 839 | GUAACUGA AGAA GUAAUC ACCAGAGAAACACACGUUGUGGUACAUUACCUGGUA | 2613 | GAUUACA GCU UCAGUUAC | 2634 |
| 874 | CAAUGAUG AGAA GCAUCA ACCAGAGAAACACdGUUGUGGUACAUUACCUGGUA | 2614 | UGAUGCU GCU CAUCAUUG | 2635 |
| 907 | GCCUGCUA AGAA GAUUCG ACCAGAGAAACACACGUUGUGGUACAUUACCUGGUA | 2615 | CGAAUCA GCC UAGCAGGC | 2636 |
| 929 | AACUUAGA AGAA GUGUUG ACCAGAGAAACACACGUUGUGGUACAUUACCUGGUA | 2616 | GAACACA GCC UCUAAGUU | 2637 |
| 1115 | UUCCAAUC AGAA GAGAAC ACCAGAGAAACACACGUUGUGGUACAUUACCUGGUA | 2617 | GUUCUCA GCU GAUUGGAA | 2638 |
| 1118 | GAAUUCCA AGAA GCUGAG ACCAGAGAAACACACGUUGUGGUACAUUACCUGGUA | 2618 | CUGAGCU GAU UGGAAUUC | 2639 |
| 1133 | AAUUAUUC AGAA GUAGAA ACCAGAGAAACACdGUUGUGGUACAUUACCUGGUA | 2619 | UUCUACA GUU GAAUAAUU | 2640 |

TABLE XVIII

Human CD40 Hairpin Ribozyme and Target Sequences

| nt. Position | Hairpin Ribozyme Sequences | Seq. ID No. | Substrate | Seq. ID No. |
|---|---|---|---|---|
| 26 | GACCAGGC AGAA GGACCA ACCAGAGAAACACACGUUGUGGUACAUUACCUGGUA | 2641 | UGGUCCU GCC GCCUGGUC | 2665 |
| 29 | UGAGACCA AGAA GCAGGA ACCAGAGAAACACACGUUGUGGUACAUUACCUGGUA | 2642 | UCCUGCC GCC UGGUCUCA | 2666 |
| 58 | ACUGCAGA AGAA GACGAA ACCAGAGAAACACACGUUGUGGUACAUUACCUGGUA | 2643 | UUCGUCU GCC UCUGCAGU | 2667 |
| 84 | GGUCAGCA AGAA GCCCCA ACCAGAGAAACACACGUUGU9GUACAUUACCUGGUA | 2644 | UGGGGCU GCU UGCUGACC | 2668 |
| 91 | GGACACGC AGAA GCAAGC ACCAGAGAAACACACGUUGUGGUACAUUACCUGdUA | 2645 | GCUUGCC GAC CGCUGUCC | 2669 |
| 95 | GGAUGGAC AGAA GUCAGC ACCAGAGAAACACACGUUGUGGUACAUUACCUGGUA | 2646 | GCUGACC GCU UCCAUCC | 2670 |
| 98 | UCUGGAUG AGAA GCGGUC ACCAGAGAAACACACGUUGUGGUACAUUACCUGGUA | 2647 | GACCGCU GUC CAUCCAGA | 2671 |
| 159 | GCACAAAG AGAA GCACUG ACCAGAGAAACACACGUUGUGGUACAUUACCUGGUA | 2648 | CAGUGCU GUU CUUUGUGC | 2672 |
| 414 | CGAGCAUG AGAA GUGCAG ACCAGAGAAACACACGUUGUGGUACAUUACCUGGUA | 2649 | CUGCACC GCU CAUGCUCG | 2673 |
| 429 | GACCCCAA AGAA GGGCGA ACCAGAGAAACACACGUUGUGGUACAUUACCUGGUA | 2650 | UCGCCCG GCU UUGGGGUC | 2674 |
| 445 | CUGUAGCA AGAA GCUUGA ACCAGAGAAACACACGUUGUGGUACAUUACCUGGUA | 2651 | UCAAGCA GAU UGCUACAG | 2675 |
| 483 | GCCGACUG AGAA GGGCUC ACCAGAGAAACACACGUUGUGGUACAUUACCUGGUA | 2652 | GAGCCCU GCC CAGUCGGC | 2676 |
| 488 | AAGAAGCC AGAA GGGCAG ACCAGAGAAACACACGUUGUGGUACAUUACCUGGUA | 2653 | CUGCCCA GUC GGCUUCUU | 2677 |
| 492 | GGAGAAGA AGAA GACUGG ACCAGAGAAACACACGUUGUGGUACAUUACCUGGUA | 2654 | CCAGUCG GCU UCUUCUCC | 2678 |
| 515 | UUUUCGAA AGAA GAUGAC ACCAGAGAAACACACGUUGUGGUACAUUACCUGGUA | 2655 | GUCAUCU GCU UUCGAAAA | 2679 |
| 593 | CAGACAAC AGAA GUCUUG ACCAGAGAAACACACGUUGUGGUACAUUACCUGGUA | 2656 | CAAGACU GAU GUUGUCUG | 2680 |
| 619 | GGGCUCUC AGAA GAUCCU ACCAGAGAAACACACGUUGUGGUACAUUACCUGGUA | 2657 | AGGAUCG GCU GAGAGCCC | 2681 |
| 661 | GGAUGGCA AGAA GGAUCC ACCAGAGAAACACACGUUGUGGUACAUUACCUGGUA | 2658 | GGAUCCU GUU UGCCAUCC | 2682 |
| 764 | GGAAGAUC AGAA GGAAAA ACCAGAGAAACACACGUUQUGGUACAUUACCUGGUA | 2659 | UUUUCCC GAC GAUCUUCC | 2683 |
| 788 | ACUGGAGC AGAA GUGUUG ACCAQAGAAACACACGUUGUGGUACAUUACCUGGUA | 2660 | CAACACU GCU GCUCCAGU | 2684 |
| 791 | UGCACUGG AGAA GCAGUG ACCAGAGAAACACACGUUGUGGUACAUUACCUGGUA | 2661 | CACUGCU GCU CCAGUGCA | 2685 |
| 924 | CUCUGGCC AGAA GCCGUU ACCAGAGAAACACACGUUGUGGUACAUUACCUGGUA | 2662 | ACAGGCA GUU GGCCAGAG | 2686 |
| 946 | CCUGCAGC AGAA GCACCA ACCAGAGAAACACACGUUGUGGUACAUUACCUGGUA | 2663 | UGGUGCU GCU GCUGCAGG | 2687 |
| 949 | ACCCCUGC AGAA GCAGCA ACCAGAGAAACACACGUUGUGGUACAUUACCUGGUA | 2664 | UGCUGCU GCU GCAGGGGU | 2688 |

TABLE XIX

Mouse CD40 Hairpin Ribozyme and Substrate Sequences

| nt. Position | HP Ribozyme Sequences | Seq. ID No. | Substrate | Seq. ID No. |
|---|---|---|---|---|
| 25 | GCGCGCAC AGAA GAGGCA ACCAGAGAAACACACGUUGUGGUACAUUACCUGGUA | 2689 | UGCCUCG GCU GUGCGCGC | 2717 |
| 45 | UGUCAACA AGAA GCCCCA ACCAGAGAAACACACGUUGUGGUACAUUACCUGGUA | 2690 | UGGGGCU GCU UGUUGACA | 2718 |
| 59 | CCUAGAUG AGAA GCUGUC ACCAGAGAAACACACGUUGUGGUACAUUACCUGGUA | 2691 | GACAGCG GUC CAUCUAGG | 2719 |
| 144 | GCUUGUCA AGAA GCUUCC ACCAGAGAAACACACGUUGUGGUACAUUACCUGGUA | 2692 | GGAAGCC GAC UGACAAGC | 2720 |
| 164 | UUCUCAAG AGAA GUGCAG ACCAGAGAAACACACGUUGUGGUACAUUACCUGGUA | 2693 | CUGCACA GCU CUUGAGAA | 2721 |
| 212 | UUCCACUG AGAA GAGAAU ACCAGAGAAACACACGUUGUGGUACAUUACCUGGUA | 2694 | AUUCUCA GCC CAGUGGAA | 2722 |
| 311 | CAGGUACA AGAA GUGUCU ACCAGAGAAACACACGUUGUGGUACAUUACCUGGUA | 2695 | AGACACU GUC UGUACCUG | 2723 |
| 431 | GGAUGACA AGAA GUAUCA ACCAGAGAAACACACGUUGUGGUACAUUACCUGGUA | 2696 | UGAUACC GUC UGUCAUCC | 2724 |
| 444 | GCCGACUG AGAA GGGAUG ACCAGAGAAACACACGUUGUGGUACAUUACCUGGUA | 2697 | CAUCCCU GCC CAGUCGGC | 2725 |
| 449 | AAGAAGCC AGAA GGGCAG ACCAGAGAAACACACGUUGUGGUACAUUACCUGGUA | 2698 | CUGCCCA GUC GGCUUCUU | 2726 |
| 453 | GGAGAAGA AGAA GACUGG ACCAGAGAAACACACGUUGUGGUACAUUACCUGGUA | 2699 | CCAGUCG GCU UCUUCUCC | 2727 |
| 550 | UGACAUUA AGAA GACUCG AGCAGAGAAACACACGUUGUGGUACAUUACCUGGUA | 2700 | CGAGUCA GAC UAAUGUCA | 2728 |
| 580 | GGGCUCGC AGAA GGGACU ACCAGAGAAACACACGUUGUGGUACAUUACCUGGUA | 2701 | AGUCCG GAU GCGAGCCC | 2729 |
| 592 | GAAUGACC AGAA GGGCUC ACCAGAGAAACACACGUUGUGGUACAUUACCUGGUA | 2702 | GAGCCCU GCU GGUCAUUC | 2730 |
| 605 | CCCAUCAC AGAA GGAAUG ACCAGAGAAACACACGUUGUGGUACAUUACCUGGUA | 2703 | CAUUCCU GUC GUGAUGGG | 2731 |
| 701 | UGCCGUCG AGAA GCAGGG ACCAGAGAAACACACGUUGUGGUACAUUACCUGGUA | 2704 | CCCUGCG GCU CGACGGCA | 2732 |
| 752 | ACUGGAGC AGAA GUGUUA ACCAGAGAAACACACGUUGUGGUACAUUACCUGGUA | 2705 | UAACACC GCU GCUCCAGU | 2733 |
| 755 | UGCACUGG AGAA GCGGUG ACCAGAGAAACACACGUUGUGGUACAUUACCUGGUA | 2706 | CACCGCU GCU CCAGUGCA | 2734 |
| 787 | GUGUGACA AGAA GACACC ACCAGAGAAACACACGUUGUGGUACAUUACCUGGUA | 2707 | GGUGUCA GCC UGUGACAC | 2735 |
| 890 | CCUCCAAA AGAA GUUCCA ACCAGAGAAACACACGUUGUGGUACAUUACCUGGUA | 2708 | UGGAACU GCU UUGGAGG | 2736 |
| 909 | GGUCAGCA AGAA GCCAUC ACCAGAGAAACACACGUUGUGGUACAUUACCUGGUA | 2709 | GAUGGCU GCU UGCUGACC | 2737 |
| 916 | UUCAAAAG AGAA GCAAGC ACCAGAGAAACACACGUUGUGGUACAUUACCUGGUA | 2710 | GCUUGCU GAC CUUUUGAA | 2738 |
| 975 | UGACAGGG AGAA GGCAUG ACCAGAGAAACACACGUUGUGGUACAUUACCUGGUA | 2711 | CAUGCCU GCC CCCUGUCA | 2739 |
| 1137 | CGAGCACA AGAA GCGGGC ACCAGAGAAACACACGUUGUGGUACAUUACCUGGUA | 2712 | GCCCGCA GCU UGUGCUCG | 2740 |
| 1276 | GUUUUAAA AGAA GUUUCU ACCAGAGAAACACACGUUGUGGUACAUUACCUGGUA | 2713 | AGAAACA GCU UUAAAAC | 2741 |
| 1334 | CGGGUUUG AGAA GCAAGC ACCAGAGAAACACACGUUGUGGUACAUUACCUGGUA | 2714 | GCUUGCC GCC CAAACCCG | 2742 |
| 1352 | GGAUCAAA AGAA GGUAAC ACCAGAGAAACACACGUUGUGGUACAUUACCUGGUA | 2715 | GUUACCU GAU UUUGAUCC | 2743 |
| 1512 | AAACCCAG AGAA GAUUAA ACCAGAGAAACACACGUUGUGGUACAUUACCUGGUA | 2716 | UUAAUCC GCC CUGGGUUU | 2744 |

What is claimed is:

1. A nucleic acid molecule which specifically blocks expression of a transcript encoding human or mouse CD40, wherein said nucleic acid molecule is selected from the group consisting of an antisense nucleic acid molecule and an enzymatic nucleic acid molecule.

2. The nucleic acid molecule of claim 1, wherein said nucleic acid molecule is an enzymatic nucleic acid molecule.

3. The nucleic acid molecule of claim 2, wherein, the binding arms of said enzymatic nucleic acid molecule comprise sequences complementary to any of nucleotide base sequences in Tables X and XII.

4. The nucleic acid molecule of claim 2, wherein said enzymatic nucleic acid molecule is in a hammerhead motif.

5. The nucleic acid molecule of claim 2, wherein said enzymatic nucleic acid molecule is in a hairpin, hepatitis Delta virus, group I intron, VS nucleic acid or RNaseP nucleic acid motif.

6. The nucleic acid molecule of claim 2, wherein said enzymatic nucleic acid molecule comprises between 12 and 100 bases complementary to a portion of RNA encoding said CD40.

7. The nucleic acid molecule of claim 6, wherein said enzymatic nucleic acid molecule comprises between 14 and 24 bases complementary to the RNA.

8. A mammalian cell in vitro including a nucleic acid molecule of claim 1.

9. The mammalian cell of claim 8, wherein said mammalian cell is a human cell.

10. An expression vector comprising a nucleic acid sequence encoding the nucleic acid molecule of claim 1, in a manner which allows expression and/or delivery of said nucleic acid molecule.

11. A mammalian cell in vitro including the expression vector of claim 10.

12. The mammalian cell of claim 11, wherein said mammalian cell is a human cell.

13. The nucleic acid molecule of claim 4, wherein said hammerhead motif comprises any of nucleotide sequence shown in Tables XI and XIII.

14. The nucleic acid molecule of claim 2, wherein, the binding arms of said enzymatic nucleic acid molecule comprise sequences complementary to any of substrate nucleotide base sequences in Tables XVIII and XIX.

15. The nucleic acid molecule of claim 1, wherein said nucleic acid molecule is an antisense nucleic acid molecule.

16. The nucleic acid molecule of claim 15, wherein, said antisense nucleic acid molecule is complementary to any of nucleotide sequence in Tables X and XII.

17. The nucleic acid molecule of claim 1, wherein said nucleic acid molecule comprises a chemical modification.

18. The nucleic acid molecule of claim 17, wherein said chemical modification is a sugar modification.

19. The nucleic acid molecule of claim 18, wherein said sugar modification is 2'-O-methyl or 2'H or a combination of 2'-O-methyl and 2'H.

20. The nucleic acid molecule of claim 17, wherein said chemical modification is a nucleotide base modification.

21. The nucleic acid molecule of claim 17, wherein said chemical modification is a phosphodiester backbone modification.

22. The nucleic acid molecule of claim 17, wherein said phosphodiester backbone modification is phosphorothioate.

23. The nucleic acid molecule of claim 2, wherein said enzymatic nucleic acid molecule is able to specifically cleave RNA encoded by said gene.

24. A method of blocking the expression of CD40 gene in vitro, comprising the step of contacting RNA encoded by said CD40 gene with the nucleic acid molecule of claim 1 under conditions suitable for said blocking.

25. The method of claim 23, wherein said nucleic acid molecule is an enzymatic nucleic acid molecule.

26. The method of claim 23, wherein said nucleic acid molecule is an antisense nucleic acid molecule.

* * * * *